(12) United States Patent
Hosaka

(10) Patent No.: US 10,249,483 B2
(45) Date of Patent: Apr. 2, 2019

(54) ULTRA-COMPACT MASS ANALYSIS DEVICE AND ULTRA-COMPACT PARTICLE ACCELERATION DEVICE

(71) Applicant: Takashi Hosaka, Tokyo (JP)

(72) Inventor: Takashi Hosaka, Tokyo (JP)

( * ) Notice: Subject to any disclaimer, the term of this patent is extended or adjusted under 35 U.S.C. 154(b) by 60 days.

(21) Appl. No.: 15/329,153

(22) PCT Filed: Jul. 29, 2015

(86) PCT No.: PCT/JP2015/071538
§ 371 (c)(1),
(2) Date: Jun. 27, 2017

(87) PCT Pub. No.: WO2016/017712
PCT Pub. Date: Feb. 4, 2016

(65) Prior Publication Data
US 2017/0330739 A1    Nov. 16, 2017

(30) Foreign Application Priority Data

Jul. 29, 2014   (JP) ................................. 2014-154005

(51) Int. Cl.
*H01J 49/06*     (2006.01)
*H01J 49/20*     (2006.01)
(Continued)

(52) U.S. Cl.
CPC .............. *H01J 49/06* (2013.01); *G01N 27/62* (2013.01); *H01J 49/0018* (2013.01);
(Continued)

(58) Field of Classification Search
CPC .. H01J 49/06; H01J 49/20; H01J 49/22; H01J 49/4205; H01J 49/08; H01J 49/10; H01J 49/26; H01J 49/28
(Continued)

(56) References Cited

U.S. PATENT DOCUMENTS 5,386,115 A    1/1995  Freidhoff et al.
7,057,170 B2 *  6/2006  Freidhoff ................ H01J 41/10
                                                       250/281
(Continued)

FOREIGN PATENT DOCUMENTS

JP    H04116351 U    10/1992
JP    H10512996 A    12/1998
(Continued)

*Primary Examiner* — Nicole Ippolito
(74) *Attorney, Agent, or Firm* — Harness, Dickey & Pierce, P.L.C.

(57) ABSTRACT

A mass analyzer includes a main substrate, an upper substrate adhered to the main substrate, and a lower substrate. A mass analysis room (cavity) is formed in the main substrate and penetrates from an upper surface of the first main substrate to a lower surface of the first main substrate. A vertical direction (Z direction) to the main substrate by the upper substrate, both sides of the lower substrate, a travelling direction (X direction) of charged particles and a right angle to the Z direction by the main substrate, and both sides of a right-angled direction (Y to Z direction) and the X direction by a side surface of the main substrate are surrounded. A central hole is open in the side plate of the main substrate that the charged particles enter. The charged particles enter the mass analysis room through the central hole formed in the first main substrate.

18 Claims, 45 Drawing Sheets

(51) Int. Cl.
   *H01J 49/22* (2006.01)
   *H01J 49/42* (2006.01)
   *G01N 27/62* (2006.01)
   *H05H 5/03* (2006.01)
   *H05H 7/04* (2006.01)
   *H05H 7/22* (2006.01)
   *H05H 9/00* (2006.01)
   *H05H 13/04* (2006.01)
   *H01J 49/00* (2006.01)
   *H01J 49/32* (2006.01)
   *H01J 49/38* (2006.01)

(52) U.S. Cl.
   CPC .............. *H01J 49/20* (2013.01); *H01J 49/22* (2013.01); *H01J 49/326* (2013.01); *H01J 49/38* (2013.01); *H01J 49/4205* (2013.01); *H01J 49/4215* (2013.01); *H05H 5/03* (2013.01); *H05H 7/04* (2013.01); *H05H 7/22* (2013.01); *H05H 9/00* (2013.01); *H05H 13/04* (2013.01)

(58) Field of Classification Search
   USPC ............ 250/281, 282, 283, 288, 423 R, 424, 250/492.1, 492.3; 315/500, 501, 502, 315/503, 504, 505, 506, 507
   See application file for complete search history.

(56) References Cited

U.S. PATENT DOCUMENTS

| | | |
|---|---|---|
| 2008/0067342 A1 | 3/2008 | Ding |
| 2009/0253117 A1* | 10/2009 | Cerda ...................... C12Q 1/34 435/4 |
| 2010/0090103 A1 | 4/2010 | Mueller et al. |
| 2011/0198494 A1 | 8/2011 | Huq et al. |
| 2012/0077260 A1* | 3/2012 | Sharon ............. B01L 3/502738 435/287.2 |
| 2012/0175515 A1* | 7/2012 | Hori ...................... G01N 27/622 250/282 |

FOREIGN PATENT DOCUMENTS

| | | |
|---|---|---|
| JP | 2002015699 A | 1/2002 |
| JP | 2003-036996 A | 2/2003 |
| JP | 2008502097 A | 1/2008 |
| JP | 2010519687 A | 6/2010 |
| JP | 2012505495 A | 3/2012 |
| WO | WO-2007055756 A2 | 5/2007 |

* cited by examiner

ULTRA-COMPACT MASS ANALYSIS DEVICE AND ULTRA-COMPACT PARTICLE ACCELERATION DEVICE

CROSS REFERENCE TO RELATED APPLICATIONS

This application is a U.S. National Phase Application under 35 U.S.C. 371 of International Application No. PCT/JP2015/071538 filed on Jul. 29, 2015 and published in Japanese as WO 2016/017712 A1 on Feb. 4, 2016. This application claims the benefit of priority from Japanese Patent Application No. 2014-154005 filed Jul. 29, 2015. The entire disclosures of all of the above applications are incorporated herein by reference.

TECHNICAL FIELD

This invention is regarding an ultracompact mass spectroscope and an ultra small particle accelerator.

BACKGROUND ART

A particle accelerator is utilized in various fields such as a mass analysis, an atom smashing and molecular breakdown, and a generation of a radiation light. However, since high vacuum is needed in movement of particles, and a magnetic field generator and a electric field generator to generate large magnetic field or large electric field is needed, a particle accelerator is very large in size and very high in cost.

SUMMARY OF THE INVENTION

Problems to be Resolved by the Invention

If a particle accelerator becomes very smaller, it can be carried by oneself and it becomes very lower in cost. Also, since in-situ analysis and in-situ particle acceleration can be achieved, rapid analysis and accelerated particle can be used.

Means of Solving the Problems

In this invention, top and bottom of penetrated cavities (or rooms) (called first penetrated room) formed in a semiconductor substrate such as a silicon substrate, and an insulating substrate, etc. are closed with an insulating substrate such as a glass substrate and a quarts substrate, etc., and the penetrated rooms become a orbital of charged particles such as accelerated ions, etc., and requirements for the accelerator and the mass spectroscope, for example, an extraction electrode, an acceleration electrode, an acceleration cavity, quadrupole electrodes, a quadrupole trap, etc., are formed using LSI process. In particular, this invention has the following characteristics.

(1) The present invention is a mass spectroscope which is constructed from plural substrates which include a first main substrate, a first upper substrate attached on a top surface of the first main substrate and a first lower substrate attached on a bottom surface of the first main substrate, wherein a room of mass analysis is a cavity that penetrates the first main substrate from the top surface of the first main substrate to the bottom surface of the first main substrate and the room of mass analysis is surrounded by the first upper substrate and the first lower substrate in the vertical direction (Z direction) to the surface of the first main substrate, and both sides of the room of mass analysis in right angle direction (X direction) to Z direction and in traveling direction (X direction) of charged particles are surrounded by the sides of the first main substrate, and both sides of the room of mass analysis in right angle direction (Y direction) to Z direction and X direction are surrounded by the sides of the first main substrate, wherein the hole is formed in the center of the side of the first main substrate in X direction in the room of mass analysis, which is a central hole, the charged particles are incident into the room of mass analysis from the central hole, wherein the first main substrate is a insulating substrate, a semiconductor substrate, a conductive substrate, or a laminated substrate of these substrates, wherein the first upper substrate and the first lower substrate are a glass substrate, a quartz substrate, a plastic substrate, an alumina substrate, a AlN substrate, a ceramics substrate, a polymer substrate, or a laminated substrate of these substrates, wherein in the case that the first main substrate is the insulating substrate, the first main substrate is a glass substrate, a quartz substrate, a plastic substrate, an alumina substrate, a AlN substrate, a ceramics substrate, a polymer substrate, or a laminated substrate of these substrates, wherein in the case that the first main substrate is the semiconductor substrate, the first main substrate is Si substrate, SiC substrate, C substrate, GaAs substrate, InP substrate, GaN substrate, CdS substrate, a binary compound semiconductor, a ternary compound semiconductor, or a laminated substrate of these substrates, wherein in the case that the first main substrate is the conductive substrate, the first main substrate is Cu, Al, Ti, Zn, Fe, an alloy containing these metals, or a laminated substrate of these substrates.

(2) In the present invention, the room of mass analysis is a room of a quadrupole mass spectrometer (QMS), wherein the room of mass analysis has two quadrupole electrodes that are formed or adhered to the bottom surface of the first upper substrate and has two quadrupole electrodes that are formed or adhered to the top surface of the first lower substrate, wherein the mass spectroscope has a contact wiring (called a upper substrate contact wiring), which is formed on a top surface of the first upper substrate, connected to the said two quadrupole electrodes put underneath the bottom surface of the first upper substrate, and an electrode (called a top surface electrode of a upper substrate), which is formed on the top surface of the first upper substrate, connected to the upper substrate contact wiring, and a contact wiring (called a lower substrate contact wiring), which is formed underneath a bottom surface of the first lower substrate, connected to the said two quadrupole electrodes put on the top surface of the first lower substrate, and an electrode (called a bottom surface electrode of a lower substrate), which is formed underneath the bottom surface of the first lower substrate, connected to the lower substrate contact wiring, wherein high-frequency voltage and direct voltage are applied through the top surface electrode of the upper substrate and/or the bottom surface electrode of the lower substrate, wherein distances between non-adjacent two quadrupole electrodes in each other in the said two quadrupole electrodes put under the bottom surface of the first upper substrate and the said two quadrupole electrodes put on the top surface of the first lower substrate are nearly equal, and middle points between them almost coincide each other. distances between adjacent two quadrupole electrodes in each other in the said two quadrupole electrodes put under the bottom surface of the first upper substrate and the said two quadrupole electrodes put on the top surface of the first lower substrate are nearly equal.

(3) In the present invention, second main substrate is attached on or above the first upper substrate, and second upper substrate is attached on the second main substrate, and a penetrated room (called second penetrated room) penetrating from a bottom surface of the second upper substrate to the top surface of the first upper substrate is formed above the said first penetrated room in the second main substrate, and a opening portion is formed in a part of the first upper substrate between the first penetrated room and the second penetrated room, and the said opening portion is formed between two quadrupole electrodes put underneath the bottom surface of the first upper substrate, a electrode and wiring, which is formed on the first upper substrate, connecting to the quadrupole electrode put underneath the bottom surface of the first upper substrate connects to a wiring (called second wiring) formed on the side of the second penetrated room, and the second wiring connects to an electrode and wiring formed underneath the bottom surface of the second upper substrate, and the electrode and wiring formed underneath the bottom surface of the second upper substrate connects to a contact wiring (called a contact wiring of the second upper substrate) formed in the second upper substrate, and the contact wiring of the second upper substrate connects to an electrode and wiring (called second upper electrode and wiring) formed on the top surface of the second upper substrate, wherein third main substrate is attached underneath or below the first lower substrate, and second lower substrate is attached underneath the bottom surface of the third main substrate, and a penetrated room (called third penetrated room) penetrating from a top surface of the second lower substrate to the bottom surface of the first lower substrate is formed below the said first penetrated room in the third main substrate, and a opening portion is formed in a part of the first lower substrate between the first penetrated room and the third penetrated room, and the said opening portion is formed between two quadrupole electrodes put on the top surface of the first lower substrate, a electrode and wiring, which is formed on the first lower substrate, connecting to the quadrupole electrode put on the top surface of the first lower substrate connects to a wiring (called third wiring) formed on the side of the third penetrated room, and the third wiring connects to an electrode and wiring formed on the top surface of the second lower substrate, and the electrode and wiring formed on the top surface of the second lower substrate connects to a contact wiring (called a contact wiring of the second lower substrate) formed in the second lower substrate, and the contact wiring of the second lower substrate connects to an electrode and wiring (called second lower electrode and wiring) formed on the bottom surface of the second upper substrate, wherein high-frequency voltage and direct voltage are applied through the said second upper electrode and wiring and the second lower electrode and wiring, wherein the second upper substrate and the second lower substrate are a glass substrate, a quartz substrate, a plastic substrate, an alumina substrate, a AlN substrate, a ceramics substrate, a polymer substrate, or a laminated substrate of these substrates, wherein in the case that the second main substrate and the third main substrate are the insulating substrate, the first main substrate and the third main substrate are a glass substrate, a quartz substrate, a plastic substrate, an alumina substrate, a AlN substrate, a ceramics substrate, a polymer substrate, or a laminated substrate of these substrates, wherein in the case that the second main substrate and the third main substrate are the semiconductor substrate, the first main substrate is Si substrate, SiC substrate, C substrate, GaAs substrate, InP substrate, GaN substrate, CdS substrate, a binary compound semiconductor, a ternary compound semiconductor, or a laminated substrate of these substrates, wherein in the case that the second main substrate and the third main substrate are the conductive substrate, the first main substrate is Cu, Al, Ti, Zn, Fe, an alloy containing these metals, or a laminated substrate of these substrates.

(4) In the present invention, the mass analysis room is the quadrupole mass analysis room, one quadrupole electrode is arranged on the upper surface of upper substrate adhered the upper portion of the mass analysis room, one quadrupole electrode is arranged on the lower surface of lower substrate adhered the lower portion of the mass analysis room, one quadrupole electrode is arranged respectively in two penetrated room in the right side and the left side of the mass analysis room formed in the main substrate. The side wall plate exists between the penetrated room formed in the right side and the left side neighbor the mass analysis room, and the mass analysis room, the quadrupole electrodes are rod shapes, and the rod portions are adhered to the given portions of the upper substrate, the lower substrate and the main substrate, and the quadrupole electrodes are the conductive film deposited and patterned at the given shape using CVD, PVD, plating, electrocasting, screen printing, squeezing, spincoating, dispensing, or these combinations, and the mass analysis room is the quadrupole electrodes mass analysis room, two quadrupole electrodes are adhered to the lower surface of the upper substrate adhered to the upper portion of the mass analysis room and the surface of the side of the mass analysis room, and the quadrupole electrodes are adhered to the upper surface of the lower substrate adhered to the lower portion of the mass analysis room and the surface of the side of the mass analysis room, and the penetrated room (the second penetrated room) is formed on the upper side of the upper substrate (first upper substrate) adhering two quadrupole electrodes, the second upper substrate is adhered to the upper portion of the second penetrated room, a part of the first upper substrate between the mass analysis room (the first penetrated room) and the second penetrated room are removed, and the pressure of the first penetrated room and the second penetrated room is almost same, and furthermore the penetrated room (the third penetrated room) is formed on the lower side of the lower substrate (the first lower substrate) adhering two quadrupole electrodes, and the second lower substrate is adhered in the lower portion of the third penetrated room, a part of the first lower substrate between the mass analysis room (the first penetrated room) and the third penetrated room are removed, and the pressure of the first penetrated room and the third penetrated room is almost same.

(5) The mass analysis room of the present invention contains one quadrupole electrode (the first quadrupole electrode) adhered to or formed in the lower surface of the upper substrate, one quadrupole electrode (the second quadrupole electrode) adhered to or formed in the upper surface of the lower substrate, and a part of the substrate of one side surface of the mass analysis room extend to Y direction in the mass analysis room and one quadrupole electrode (the third quadrupole electrode) adhered to or formed in the upper or lower surface of the extended side substrate, and a part of the substrate of the other side surface of the mass analysis room extend to Y direction in the mass analysis room and one quadrupole electrode (the forth quadrupole electrode) adhered to or formed in the upper or lower surface of the extended side substrate, and the upper substrate has the contact wiring (the first upper substrate contact wiring) connecting to the first quadrupole electrode and the electrode wiring (the first upper substrate electrode wiring)

connecting to the first upper substrate contact wiring, and the lower substrate has the contact wiring (the first lower substrate contact wiring) connecting to the second quadrupole electrode and the electrode wiring (the first lower substrate electrode wiring) connecting to the first lower substrate contact wiring, and the side surface substrate adhered to or formed in the third quadrupole electrode having the wiring connecting to the third quadrupole electrode, the wiring connects to the wiring formed on the side surface of the main substrate, furthermore the wiring connects to the contact wiring formed in the upper substrate or the lower substrate (the second upper substrate contact wiring or the second lower substrate contact wiring), furthermore the second upper substrate contact wiring or the second lower substrate contact wiring connects to the electrode wiring (the second upper substrate electrode wiring or the second lower substrate electrode wiring.

(6) In the present invention, additionally a penetrated room (second penetrated room) is formed on the upper side of the upper substrate (the first upper substrate), second upper substrate is adhered to the upper portion of the second penetrated room, a part of the first upper substrate between the mass analysis room (the first penetrated room) and the second penetrated room is removed, the pressure of the first penetrated room and the second penetrated room is almost the same, and additionally a penetrated room (third penetrated room) is formed on the lower side of the lower substrate (the first lower substrate), second lower substrate is adhered to the lower portion of the third penetrated room, a part of the first lower substrate between the mass analysis room (the first penetrated room) and the third penetrated room is removed, the pressure of the first penetrated room and the third penetrated room is almost the same, and the mass analysis room is the quadrupole electrode mass analysis room, the mass analysis room has, one quadrupole electrode (first quadrupole electrode) adhered to or formed in the lower surface of the upper substrate, and one quadrupole electrode (third quadrupole electrode) adhered to or formed in the upper surface of the lower substrate and contact wiring (upper substrate contact wiring) formed in the upper substrate connecting to the quadrupole electrode (the first quadrupole electrode) arranged in the lower surface of the upper substrate, and electrode wiring (upper substrate upper surface electrode wiring) formed in upper substrate upper surface connecting to the upper substrate contact wiring, and contact wiring (lower substrate contact wiring) formed in lower substrate connecting to the quadrupole electrode (the third quadrupole electrode), and electrode wiring (lower substrate lower surface electrode wiring) formed in lower surface of the lower substrate connecting to the lower substrate contact wiring, and the mass analysis room has 2 quadrupole electrodes (second quadrupole electrode and four quadrupole electrode) formed in two side surfaces in Y direction of the main substrate, the second quadrupole electrode and the four quadrupole electrode has contact wiring formed in the upper substrate and/or the lower substrate, and electrode wiring (upper substrate upper surface electrode wiring and/or lower substrate lower surface electrode wiring), and high-frequency voltage and/or direct voltage are applied from the upper substrate upper surface electrode wiring and/or the lower substrate lower surface electrode wiring.

(7) In the present invention, the second quadrupole electrode and the four quadrupole electrode are conductive films deposited in the penetrated room formed in the main substrate, and a part of the conductive film is a plating film, and the mass analysis room is a type to apply magnetic field, and one or plural coils are arranged on the upper side of the upper substrate adhered to the upper portion of the main substrate, and uses the method to make an orbital of charged particle change by generating vertical magnetic field to the substrate surface of the main substrate using one or plural coils arranged on the lower side of the lower substrate adhered to the lower portion of the main substrate where the mass analysis room is formed, and the mass analysis room is a type to apply magnetic field, and uses the method to make an orbital of charged particle change by generating vertical magnetic field to the substrate surface of the main substrate using electric magnets arrange on the upper side of the upper substrate adhered to the upper portion of the main substrate where the mass analysis is formed and/or on the lower side of the lower substrate adhered to the lower portion of the main substrate where the mass analysis is formed, and the said one or plural coils arranged on the upper side of the upper substrate and/or on the lower side of the lower substrate are formed br depositing in the second main substrate, and the charged particles go out of a room to extract the charged particles (charged particle extraction room) or a room to accelerate the charged particles (charged particle acceleration room) and enter the mass analysis room, and at least one substrate side wall plate (front substrate side wall plate) having a central hole is arranged between the charged particle extraction room or the charged particle acceleration room and the mass analysis room, and the charged particles enter the mass analysis room thorough the central hole of the front substrate side wall plate, and the charged particles ejected from the mass analysis room enter a room to detect ions (ion detection room), and the charged particles are identified in the ion detection room, and the ion detection room is the penetrated room formed in the main substrate, and at least one substrate side wall plate (back substrate side wall plate) having a central hole is arranged between the mass analysis room and the ion detection room, and the charged particles enter the ion detection room through the central hole of the back substrate side wall plate, and the charged particles are curved in the range of zero degree to 360 degree in the detection room (first ion detection room) by magnetic field and the first detection room has plural ion detection rooms (second detection rooms) and the ions are detected in the second detection rooms.

(8) In the present invention, the mass analysis room is a double-focusing type adding a applied electric field type additionally, and an area where charged particles in the applied electric field type pass is formed in the main substrate, an upper surface (Z direction) is surrounded by the upper substrate, and a lower surface (Z direction) is surrounded by the lower substrate, and side surfaces (Y direction) are surrounded by the side substrate of the main substrate, the mass analysis room is the penetrated room (the applied electric field type penetrated room) including the sectorial penetrated room (sectorial area penetrated room), and X direction of the applied electric field type penetrated room is surrounded by the side wall plate having the central hole, and the charged particles enter the applied electric field type penetrated room from the central hole of the side wall plate in the one side and the orbital of the charged particles is curved in the applied electric field type penetrated room, and the charged particles go out of the central hole of the side wall plate in the other side, and in the applied electric field type penetrated room, the central orbital is $R0$ in radius and a in central angle, electrode is formed on both side surfaces of the main substrate facing with distance $d0$ from the central orbital, and the charge particles are curved by the electric field generating by the voltage applied to the electrode formed on the both side surface, and the electrodes of both side surface (side surface electrodes) is a conductive film deposited using CVD method or PVD method, a plating film deposited on it, and the contact wiring connecting to the side surface electrodes is formed on the upper substrate adhered to the upper surface of the applied electric field type penetrated room, and connects to the electrode wiring formed on the upper surface of the upper substrate, and/or is formed in the lower substrate adhered to the lower surface of the applied electric field type penetrated room, and connects to the electrode wiring formed in the lower surface of the lower substrate.

(9) The penetrated room (ICR room) where the charged particles enter and practice cyclotron motion is surrounded by the substrate side wall plate (the extraction electrode side wall plate) having the central hole that is an ingress of the charged particles from ion surface, and the substrate side wall plate (the trap electrode substrate side wall plate), which is arranged in the travelling direction of the charged particle and faces the extraction electrode side wall plate and impacted by the charged particles of the cyclotron motion, the upper substrate adhered to the upper portion of ICR room, the lower substrate adhered to the lower portion of ICR room and 2 substrate side wall (receiver electrode substrate side wall) almost parallel to the travelling direction of the charged particles, and On the extraction electrode side wall plate) the conductive film electrode, which becomes the extraction electrode drawing the charged particles from the central hole to ICR room, is formed, and on the trap electrode substrate side wall plate the conductive film electrode applying the voltage trapping the charged particles is formed, and the conductive film electrode applying the voltage exciting the charged particles on the upper substrate and the lower substrate, and in ICR room parallel magnetic field to the direction travelling from the extraction electrode to the trap electrode is applied, and coil wiring generating the magnetic field is formed adhering to the substrate and the lower substrate, and support pole substrate is adhered to the lower substrate, and second lower substrate is adhered on the support pole substrate, the coil wiring generating the magnetic field is formed adhering to the substrate and the lower substrate, and is formed adhering to the outside side surface of the main substrate, and electrode wiring connecting with the extraction in ICR room, trap electrode, 2 ion exciting electrode facing each other, and 2 receiver electrode is formed on the upper substrate and/or the lower substrate, and the electrode wiring exists in the space surrounding by the upper substrate, support pole substrate, and the second upper substrate, and/or exists in the space surrounding by the lower substrate, support pole substrate, and the second lower substrate, and their electrode wiring connects electrode wiring formed on the second upper substrate and/or the second lower substrate, and the electrode connecting to the coil connects with the electrode wiring formed on the second upper substrate and/or the second lower substrate.

(10) Charged particles generation room to generate the charged particles includes 2 penetrated rooms (charged particles generation room 1, 2) formed in the main substrate where the lower portion is adhered to the lower substrate and the upper portion is adhered to the upper substrate, and the 2 penetrated rooms (charged particles generation room 1, 2) are the adjacent penetrated rooms partitioned by substrate side wall plate (first substrate side wall plate), and sample plate inserted from opening portion opened in the upper substrate is arranged in the charged particles generation room 1, laser beam is irradiated to sample adhered to the sample plate from the opening portion opened in the upper substrate, and the sample is dissolved to particles by the irradiation, and the dissolved particles enter the charged particles generation room 2 through the central hole of the substrate side wall plate, and the charged particles generate by irradiation, wherein one ionized beam selected from laser, electron beam, synchrotron emission light, and X-ray is irradiated to the dissolved particles that exist in the charged particles generation room 2, and an extraction electrode acceleration room is arranged next to the charged particles generation room 2 and partitioned by substrate side wall plate (second substrate side wall plate) having the central hole, and the extraction electrode acceleration room is the penetrated room formed in the main substrate where the upper portion is adhered to the upper substrate and the lower portion is adhered to the lower substrate, and in the charged particles generation room 2, conductive film electrode is formed on the side surface of the upper substrate and the lower substrate, and/or the first substrate side wall plate, and/or on the side surface of the second substrate side wall plate, and/or on the side surface of the other 2 substrate side wall, and the conductive film electrode connects to contact wiring formed on the upper substrate and/or the lower substrate, and the contact wiring connects to conductive film electrode wiring formed on the outside surface of the upper substrate and/or the lower substrate, and the charge particles having the same charge as the voltage applied to the conductive film electrode are drawn to the extraction electrode acceleration room through the central hole of the second substrate side wall plate by the extraction electrode arrange in the extraction electrode acceleration room, and the charged particles entering the extraction electrode acceleration room go out of the extraction electrode acceleration room and enter the mass analysis room, and in the charged particles generation room 1, the back side of the sample is arranged closely attached on the side surface of the side wall, and central hole is formed in the substrate side wall, and the central holes connects to a cavity formed in the thickness of the main substrate direction, and the cavity connects to the upper substrate or the lower substrate, and the sample plate is stuck on the side surface of the substrate side wall by vacuumizing from the opening portion of the upper substrate or the lower substrate.

In the mass analyzer of the present invention, charged particles generation room to generate the charged particles includes 2 penetrated rooms (charged particles generation room 1, 2) formed in the main substrate where the lower portion is adhered to the lower substrate and the upper portion is adhered to the upper substrate, and the 2 penetrated rooms (charged particles generation room 1, 2) are the adjacent penetrated rooms partitioned by substrate side wall plate (first substrate side wall plate), and sample plate inserted from opening portion opened in the upper substrate is arranged in the charged particles generation room 1, in the charged particles generation room 1, the back side of the sample is arranged closely attached on the side surface of the side wall, and central hole is formed in the substrate side wall, and the central holes connects to a cavity formed in the thickness of the main substrate direction, and the cavity connects to the upper substrate or the lower substrate, and the sample plate is stuck on the side surface of the substrate side wall by vacuumizing from the opening portion of the upper substrate or the lower substrate. Conductive film is formed on the side surface of the substrate side wall, the conductive film formed on the side surface of the substrate side wall connects to conductive film formed on the surface of the side of the charged particles generation room 1 in the upper substrate and/or the lower substrate, and the conductive film connects to contact wiring formed in the upper substrate and/or the lower substrate, and the contact wiring connects to conductive film electrode wiring formed on the outside surface of the upper substrate and/or the lower substrate, and voltage is applied to the sample plate of the conductive material from the conductive film electrode wiring, and laser beam is irradiated to sample adhered to the sample plate from the opening portion opened in the upper substrate and/or the lower substrate, and the sample is dissolved to particles and the charged particles generates by the laser irradiation, and the charged particles having the same charge as the sample plate fly out from the sample plate, and substrate side wall plate (third substrate side wall plate) having central hole is arranged in the direction facing the sample plate, and conductive film is formed on the surface of the third substrate side wall plate, the conductive film formed on the surface of the third substrate side wall plate connects to the conductive film formed on the surface of the side of the charged particle generation room 1 in the upper substrate and/or the lower substrate, and the conductive film connects to the contact wiring formed in the upper substrate and/or the lower substrate, and the contact wiring connects to conductive film electrode wiring formed on the outside surface of the upper substrate and/or the lower substrate, and the reverse voltage to the voltage applied to the sample plate is applied to the conductive film formed on the third substrate side wall plate surface conductor from the conductive film electrode wiring, and the charged particles flying out of the sample plate are extracted, and the charged particles pass the central hole formed in the third substrate side wall plate, and enter the charged particle generation room 2 through the central hole of the first substrate side wall plate, and in the inner surface of the charged particle generation room 2, conductive film electrode is formed on the side surface of the upper substrate and the lower substrate, and/or the first substrate side wall plate, and/or on the side surface of the second substrate side wall plate, and/or on the side surface of the other 2 substrate side wall, and the conductive film electrode connects to contact wiring formed on the upper substrate and/or the lower substrate, and the contact wiring connects to conductive film electrode wiring formed on the outside surface of the upper substrate and/or the lower substrate, and voltage applied to the conductive film electrode has the same charge as the charged particles, and the charged particles are focused by adjusting the voltage and enter the mext room through the central hole where the substrate side wall plate (second substrate wall plate) partitioned between the charged particle generation room 2 and the next room, and the charged particles through the central hole that the second substrate wall plate has enter the mass analysis room.

(12) The present invention is relating to ionization method. The upper substrate is adhered on the upper surface of the main substrate, and the lower substrate is adhered on the lower surface of the main substrate, and the penetrated room formed in the main substrate is the ionization room, having the central hole connecting to the ionization room, the central hole connects to a longitudinal hole (vertical direction to the substrate surface), which connects to the opening portion (sample inlet opening portion) of the upper substrate or the lower substrate, formed in the main substrate, and the conductive film (second conductive film) is formed on the inner surface of the central hole, and the conductive film (first conductive film) is formed on the inner surface of the ionization room, and the first conductive film and the second conductive film are connected by conductive film formed on the side surface of the main substrate in the ionization room, and the first conductive film connects to outside electrode formed on the upper substrate and/or the lower substrate through the contact wiring formed on the upper substrate and/or the lower substrate, sample solution or sample gas is inlet from the sample inlet opening portion, and is introduced to the ionization room as spray gas in exit to the ionization room, voltage is applied to conductive film formed on the inner surface of the central hole by applying the voltage from the outside electrode formed on the upper substrate and/or the lower substrate, and gas (spray gas) spouted at the exit portion of the ionization room is ionized.

(13) The present invention is relating to ionization method. The upper substrate is adhered on the upper surface of the main substrate, and the lower substrate is adhered on the lower surface of the main substrate, and the penetrated room formed in the main substrate is the ionization room, having the central hole connecting to the ionization room, the central hole connects to a longitudinal hole (vertical direction to the substrate surface), which connects to the opening portion (sample inlet opening portion) of the upper substrate or the lower substrate, formed in the main substrate, and parallel plate conductive film electrode is formed in the upper portion and in the lower portion in inner surface of the central hole, or parallel plate conductive film electrode is formed in two side surfaces in inner surface of the central hole, the respective parallel plate conductive film electrode connects to conductive film formed on the upper substrate and the lower substrate in the ionization room through conductive film formed on the side surface in the ionization room, and the respective parallel plate conductive film electrode connects to conductive film formed on the upper substrate and the lower substrate through contact wiring formed on the side surface in the ionization room, and sample solution or sample gas is inlet from the sample inlet opening portion, and is introduced to the ionization room as spray gas in exit to the ionization room through the longitudinal hole and the central hole, high-frequency voltage is applied to conductive film formed on the inner surface of the central hole by applying the high-frequency voltage from the outside electrode formed on the upper substrate and/or the lower substrate, and gas (spray gas) spouted at the exit portion of the ionization room is ionized.

(14) The present invention is relating to the mass analyzer. The present invention is relating to ionization method. Concave portions and opening portion surrounding a part of circumference of an ionization room are formed in the main substrate and the upper substrate and/or lower substrate, the ionization room and/or the central hole are cooled or heated by flowing cooling media or heating media through the concave portion, and heating the ionization room using a part of the conductive film formed in the upper substrate and/or the lower substrate, and heating the ionization room using a part of the conductive film formed in the central hole, and the ions are pushed out to the extraction electrode by making the conductive film electrode on the substrate side wall plate facing the extraction electrode or on the substrate side wall plate and applying the voltage having the same charge as the ions to the conductive film electrode.

(15) The present invention is relating to the ionization method. The upper substrate is adhered on the upper surface of the main substrate, and the lower substrate is adhered to the lower surface of the main substrate, one penetrated room formed in the main substrate is the ionization room, and the heating room, which is the penetrated room formed in the main substrate, is made in the neighbor of the ionization room, and the ionization room and the heating room are separated by the substrate side wall plate having the central hole (the second central hole), or they are the same penetrated room and they do not have the substrate side wall plate partitioned, and the central hole (first central hole) connecting to the heating room is formed in the main substrate, and the first central hole connects to the longitudinal hole (vertical direction to the substrate surface) formed in the main substrate, where the longitudinal hole connects to the opening portion (sample inlet opening portion) of the upper portion or the lower substrate, and the conductive film (second conductive film) is formed in the inner surface of the central hole, and the conductive film (first conductive film) is formed in the surface of the heating room, and the first conductive film and the second conductive film are connected by the conductive formed on the side surface of the main substrate in the heating room, and the first conductive film connects to the outside electrode formed in the upper substrate and/or the lower substrate, sample solution or sample gas is inlet from the sample inlet opening portion, and is introduced to the ionization room as spray gas in exit to the heating room through the longitudinal hole and the central hole, voltage is applied from the outside electrode formed on the upper substrate and/or the lower substrate, the heating room is heated by flowing the current to the first conductive film and heating the first conductive film, and steeple electrodes are arranged in the upper substrate and/or the lower substrate, the steeple electrodes connect to the outside electrode formed on the upper substrate and/or the lower substrate, through the contact wiring formed in the upper substrate and/or the lower substrate, and the spray gas heated is ionized by applying the voltage to the outside electrode and discharging with the steeple electrode.

(16) The present invention is relating to the mass analyzer. The present invention is relating to ionization method. Concave portions and opening portion surrounding a part of circumference of an ionization room are formed in the main substrate and the upper substrate and/or lower substrate, the ionization room and/or the central hole are cooled or heated by flowing cooling media or heating media through the concave portion, and heating the ionization room using a part of the conductive film formed in the upper substrate and/or the lower substrate, and heating the ionization room using a part of the conductive film formed in the central hole, and the ions are pushed out to the extraction electrode by making the conductive film electrode on the substrate side wall plate facing the extraction electrode or on the substrate side wall plate and applying the voltage having the same charge as the ions to the conductive film electrode.

(17) The present invention is relating to the ionization method. The upper substrate is adhered on the upper surface of the main substrate, and the lower substrate is adhered to the lower surface of the main substrate, penetrated room formed in the main substrate is the ionization room, and the central hole (first central hole) connecting to the heating room is formed in the main substrate, and the first central hole connects to the longitudinal hole (vertical direction to the substrate surface) formed in the main substrate, where the longitudinal hole connects to the opening portion (sample inlet opening portion) of the upper portion or the lower substrate, and the sample solution is introduced from the sample inlet opening portion, and matrix is formed in exit to the ionization room through the longitudinal hole and the central hole, and laser or high speed atomic beam is irradiated to the matrix from outside through the opening portion formed in the upper substrate or the lower substrate, thus molecules in the matrix are ionized, and the upper substrate is adhered on the upper surface of the main substrate, and the lower substrate is adhered to the lower surface of the main substrate, penetrated room formed in the main substrate is the ionization room, and the central hole (first central hole) connecting to the heating room is formed in the main substrate, and the first central hole connects to the longitudinal hole (vertical direction to the substrate surface) formed in the main substrate, where the longitudinal hole connects to the opening portion (sample inlet opening portion) of the upper portion or the lower substrate, and the sample solution is introduced from the sample inlet opening portion, and matrix is formed in exit to the ionization room through the longitudinal hole and the central hole, and laser or high speed atomic beam room is arranged in the neighbor of the ionization room, and laser or high speed atomic beam is irradiated to the matrix from the laser or high speed atomic beam room, thus molecules in the matrix are ionized.

(18) The penetrated room formed in the main substrate adjacent to the ionization room is the extraction electrode room, and the extraction electrode room and the ionization room are separated by the substrate side wall plate having the central hole (second central hole), and the conductive film is formed in the side surface of the substrate side wall facing the substrate side wall plate, and the voltage having the same charge as the ions is applied to the conductive film, and the ions generated are pushed out by the conductive film electrode and the ions are ejected to the extraction electrode room through the second central hole, the concave portion and the opening portion surrounding a part of circumference of the ionization room are formed in the main substrate and the upper substrate and/or the lower substrate, and the ionization room and/or the central hole are cooled or heated by flowing cooling media or heating media in the concave portion, and the conductive film is formed on the inner surface of the ionization room and/or the inner surface of the penetrated room, and the central hole and/or the penetrated room are heated by flowing the current in the conductive film and heating them.

(19) The present invention is relating the ion trapping type mass analyzer. The upper substrate is adhered on the upper surface of the main substrate, and the lower substrate is adhered to the lower surface of the main substrate, and ring electrode is formed in the main substrate, and the penetrated room formed in the center of the ring electrode is an ion trap room, and upper electrode (ion trap upper electrode) formed in the upper substrate is arranged in the upper portion of the ion trap room, and lower electrode (ion trap lower electrode) formed in the lower substrate is arranged in the lower portion of the ion trap room, and ring conductive film electrode connects to outside electrode formed in the upper substrate and/or the lower substrate through contact wiring formed in the upper substrate and/or the lower substrate, and The ion trap upper electrode and the ion trap lower electrode connect to outside electrode formed in the upper substrate and/or the lower substrate through contact wiring formed in the upper substrate and/or the lower substrate, and the ring electrode is the main substrate having the central hole and is arranged between the ion trap room and the extraction electrode acceleration electrode room or the ionization room, which is one penetrated room arranged in the neighbor of the ion trap room, and the ring electrode is arranged between the ion trap room and the ion detection room, which is the other penetrated room arranged in the neighbor of the ion trap room, and one central hole connects to the ion trap room from the ionization room, and the other central hole connects to the ion detection room from the ion trap room, and the ions entering the ion trap room through the central hole connecting to the ion trep room from the ionization or the extraction electrode acceleration electrode room are trapped in the ion trap room by applying the given voltage to the ring conductive film electrode, the ion trap upper electrode, and the ion trap lower electrode, and the trapped ions go out of the ion trap room and enter the ion detection room through the central hole connecting to the ion detection room, thus the ion are detected.

(20) The present invention is relating the ion trapping type mass analyzer. The upper substrate is adhered on the upper surface of the main substrate, ring electrode is formed in the main substrate, and the penetrated room is formed in the central of the ring electrode is the ion trap room, and the upper electrode (the ion trap upper electrode) formed in the upper substrate is arranged in the upper portion of the ion trap room, and the lower electrode (the ion trap lower electrode) formed in the lower substrate is arranged in the lower portion of the ion trap room, and in the ring electrode, the conductive film (ring conductive film electrode) is formed with ring shape in the main substrate, and the ring conductive film electrode connects to the outside electrode formed in the upper substrate and/or the lower substrate through the contact wiring formed in the upper substrate and/or the lower substrate, and the ion trap upper electrode and the ion trap lower electrode connect to the outside electrode formed in the upper substrate and the lower substrate through the contact wiring formed in the upper substrate and the lower substrate, and the ring electrode is the main substrate having the central hole and the ling electrode is arranged between the ion trap room and the extraction electrode acceleration electrode room or the ionization room, which is one penetrated room arranged in the upper portion of the ion trap room, and the ring electrode is arranged between the ion trap room and the ion detection room, which is the other penetrated room arranged in the neighbor of the ion trap room, and one central hole connects to the ion trap room from the ionization room, and the other central hole connects to the ion detection room from the ion trap room, the ions entering the ion trap room through the central hole connecting to the ion trap room from the ionization or the extraction electrode acceleration electrode room are trapped in the ion trap room by applying the given voltage to the ring conductive film electrode, the ion trap upper electrode, and the ion trap lower electrode, and the trapped ions go out of the ion trap room and enter the ion detection room through the central hole connecting to the ion detection room, thus the ion are detected.

(21) The present invention is an accelerator including a main substrate having plural penetrated rooms penetrating from upper surface to lower surface, upper substrate adhered to the upper surface of the main substrate, lower substrate adhered to the lower surface of the main substrate, substrate side wall plates having central hole partitioning penetrated rooms, and charged particles pass the penetrated rooms and the central hole of the substrate side wall plates, and the accelerator includes charged particle generation system and linear acceleration system, and the particle generation system and the linear acceleration system are formed in the penetrated room, electrode and wiring are conductive films deposited using one or plural methods selected from CVD method, PVD method, plating method, or electrode casting method, and the electrode and wiring connect to outside electrode formed in the upper and/or lower substrates through contact wiring formed in the upper and/or lower substrates, and the linear acceleration system is consisted of plural electrodes (substrate side wall plate electrodes) on which the conductive film is formed on the substrate side wall plates having the central hole, and the charged particles are accelerated or decelerated or focused by applying static voltage or hi-frequency voltage to the substrate side wall plate electrodes, and the accelerator has further deceleration or focusing system, and the deceleration or focusing system is consisted of plural electrodes (substrate side wall plate electrodes) on which the conductive film is formed on the substrate side wall plates having the central hole, and the charged particles are decelerated or focused by applying reverse voltage to the charged particles to the substrate side wall plate electrodes.

(22) The present invention has further deceleration or focusing system, and the deceleration or focusing system uses quadrupole magnets, in the quadrupole magnets, electric magnets are arranged in upper and lower direction in longitudinal direction (vertical direction to the surface of the main substrate) in outside of the main substrate having the penetrated room, which is a passage where the charged particles travel, made in the main substrate, and electric magnets are arranged in both side in horizontal direction (right angle direction to the vertical direction) in outside of the main substrate having the penetrated room, which is a passage where the charged particles travel, made in the main substrate, and when the electric magnets are arranged in the horizontal direction, areas of the main substrate in portions where the magnets are arranged are opened, and the electric magnets are arranged in the opening portions, and opening method is laser dicing or high pressure liquid jet dicing, and the electric magnets (coils) are arranged in the main substrate in both side of the penetrated room, and for the coils, conductive film (penetrated hole wiring) is formed in the penetrated holes penetrating from the upper and lower substrates and the main substrate, and coil wiring is formed by forming the coil wiring binding the penetrated hole wiring in the upper and lower substrates, and both end electrodes of the coils are formed in the upper substrate and/or the lower substrate.

(23) The penetrated rooms (the coil arrangement penetrated room) are formed in both side of (the charged particle focusing penetrated room), and the coils are inserted into the coil arrangement penetrated room, and the coils are arranged in the both side of the charged particle focusing penetrated room, and the coils are arranged on the upper portion and in the lower portion of the coil arrangement penetrated room (or the penetrated room where the charged particles travel), and the coils are arranged tightly or closely, and the coils are arranged by adhering the substrate where the coils are formed (coil formation substrate) to the upper substrate and the lower substrate.

Advantageous Effect of the Invention

Since necessary features for the mass spectroscope and the particle accelerator of the present invention are formed at a blow in the substrate, the position between each feature portion, for example, an acceleration electrode, is formed very precisely. Furthermore since a distance between electrodes and a size of a path which charged particles run through can be formed precisely on the order of mm or µm, the mass spectroscope and the particle accelerator gets very small in size. For example, since the electric field strength becomes large if the distance between electrodes becomes small, acceleration or deceleration of charged particle can be effectively controlled. Also, since frequency of high-frequency wave can become higher, larger acceleration can be achieved in a shorter distance. Furthermore, since each functional component can be made at a blow, the production cost can be dramatically reduced.

In the mass spectroscope of the present invention, sample supply section (or room), ionization section (or room), extraction electrode and acceleration section (or room), electric field section (or room), magnetic field section (or room), and ion detection section (or room), which are called functional portions, can be made using a substrate which is 4 inches to 8 inches in size. (Diameter is 100 mm-200 mm. Thickness is less than or equal to 3 mm. (For example, main substrate is 2 mm Si substrate, and upper substrate and lower substrate are 0.3 mm glass substrate.) Of course, a substrate more than 8 inches in size can be used. Shape of the substrate may be rectangle, triangle, or polygonal except circle.) In addition, these functional portions can be formed by connected in one substrate, and can be made with same process. The above contents are not reported in any literature, and ideas such as patents have been not found. Furthermore, since there are not any reports that these functional portions are made in one substrate, the present inventions have a novelty and an inventive step Since the mass spectroscope of the present invention is very small in size, for example, main body size is less than and equal to 6 inches, main body volume is less than and equal to 50 cm3, main body weight is less than and equal to 130 g, and a manufacturing process of these functional portions is same, the manufacturing cost can be less than 100,000 yen in the case of 6 inches wafer. Size of conventional mass spectroscope is more than 50 cm×50 cm×50 cm, and its weight is mare than 20 kg. Accordingly, the mass spectroscope of the present invention is less than 1/2500 in size (or volume) and less than 1/100 in weight, and less than 1/20 in cost compared to the conventional product. Since each functional portions can be made together and with high dimensional accuracy (less than 1 μm), the mass spectroscope of the present invention can be made much accurately and detection accuracy of the mass spectroscope of the present invention excellent compared to the conventional product. Also, since the mass spectroscope of the present invention is very small and light, it can be carried by oneself and in-situ analyses is available using the mass spectroscope of the present invention.

Furthermore, coils made using a substrate are used in the magnetic room in the mass spectroscope of the present invention. Since the coils are arranged by aligning between two substrates, alignment accuracy is less than 10 μm and very good. In addition, since the coil is 1 mm-10 mm-50 mm and small in size, the total size of the mass spectroscope of the present invention can be very small.

BRIEF DESCRIPTION OF THE DAWINGS

Figure 8:
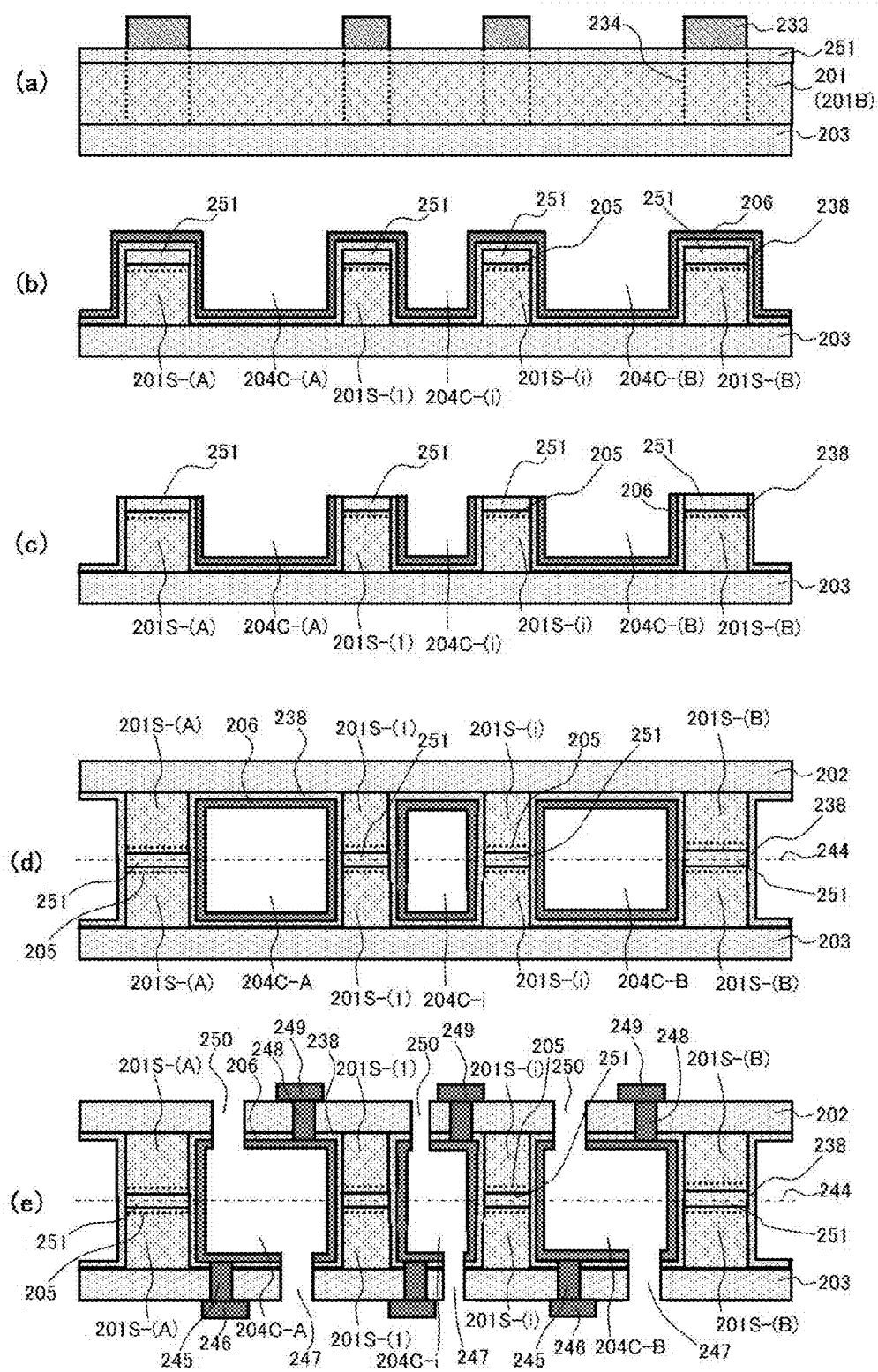

FIG. 8 shows the method to make the charged particle accelerator in the case to make the glass substrate 251 tucked between the upper side substrate (the main substrate 201U, the upper substrate 202) and the lower side substrate (the main substrate 201B, the lower substrate 203) adhere with the upper side substrate and the lower side substrate by the electrostatic binding.

Figure 9:
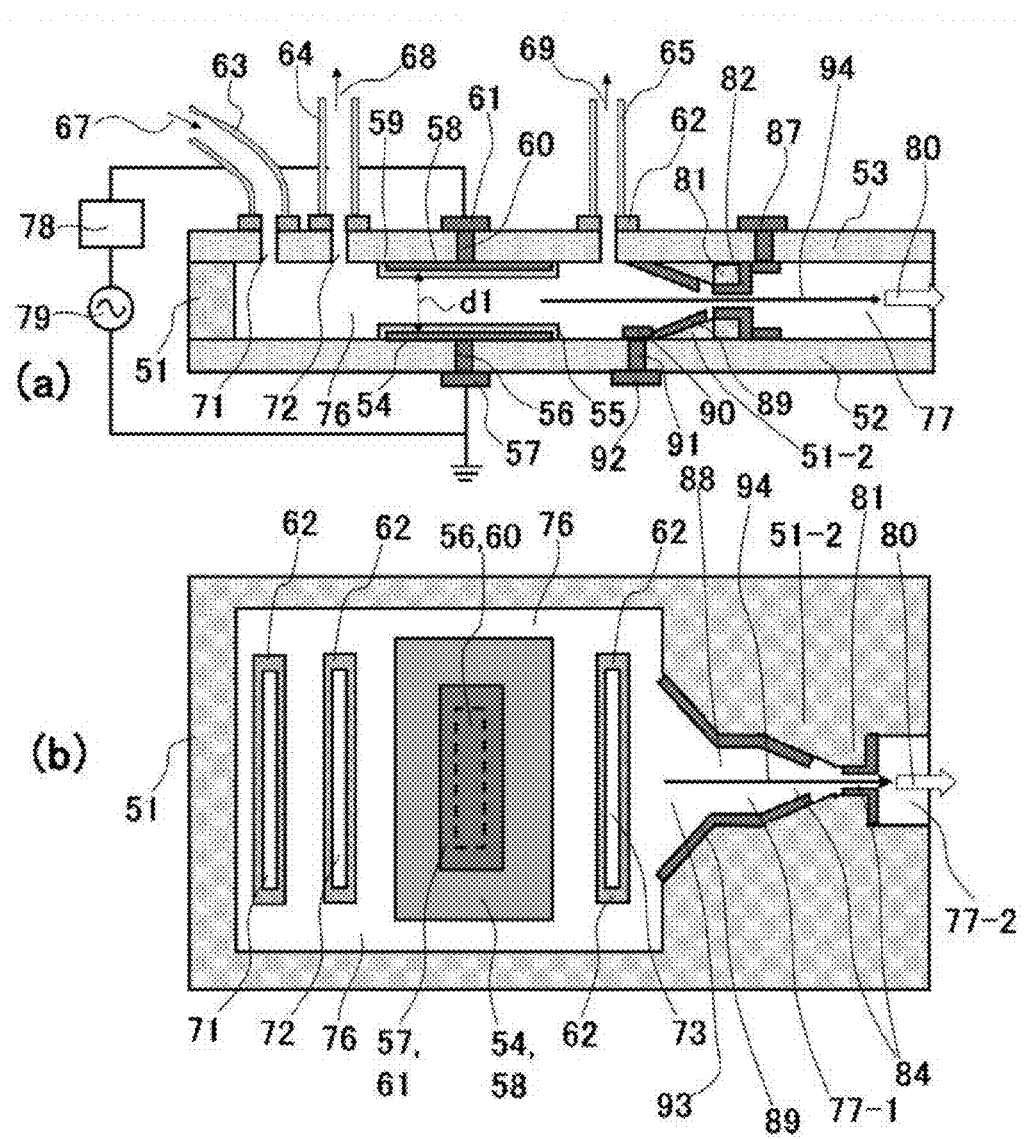

FIG. 9 shows other embodiment to indicate a structure of another drawing electrode.

Figure 10:
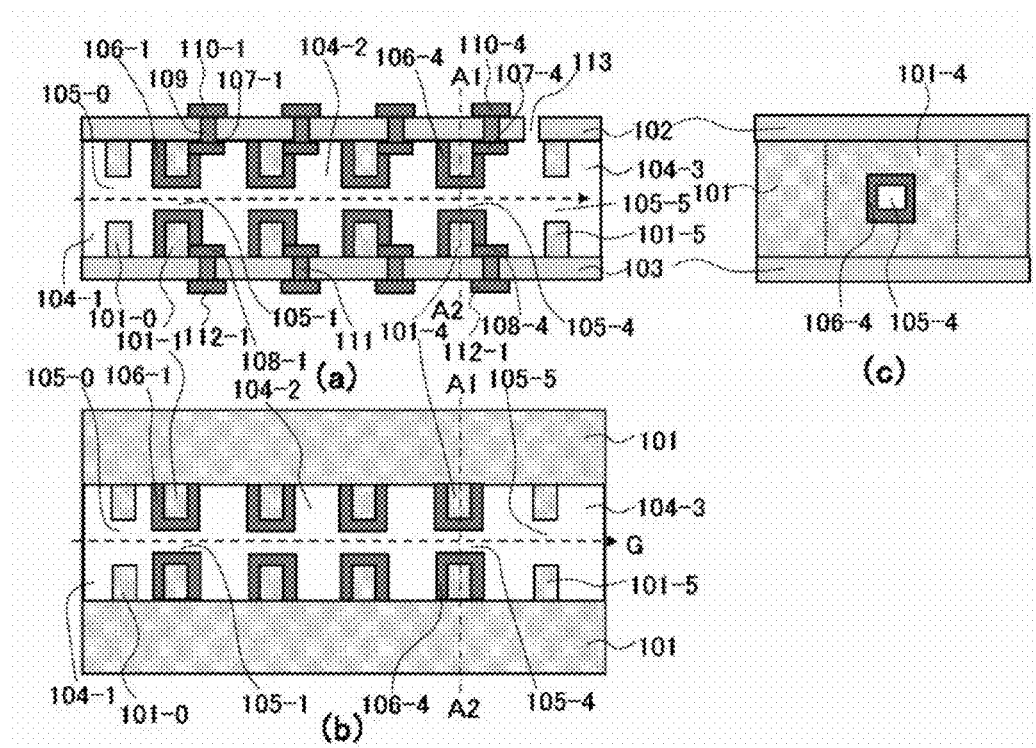

FIG. 10 shows the acceleration cavity room in which plural substrate side walls having the central hole are disposed.

Figure 11:
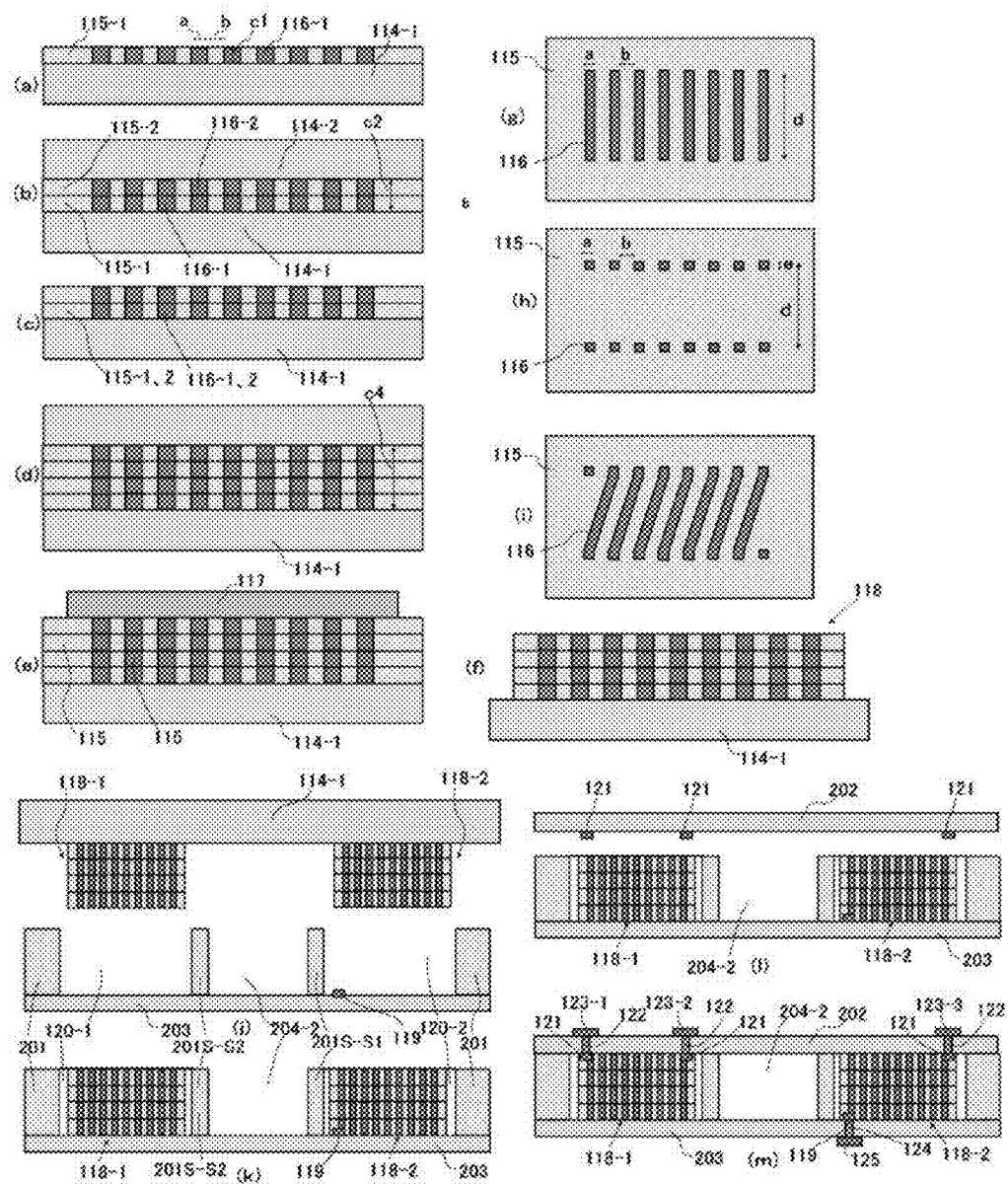

FIG. 11 is one embodiment that shows the method how to make the electric magnet (coil).

Figure 12:
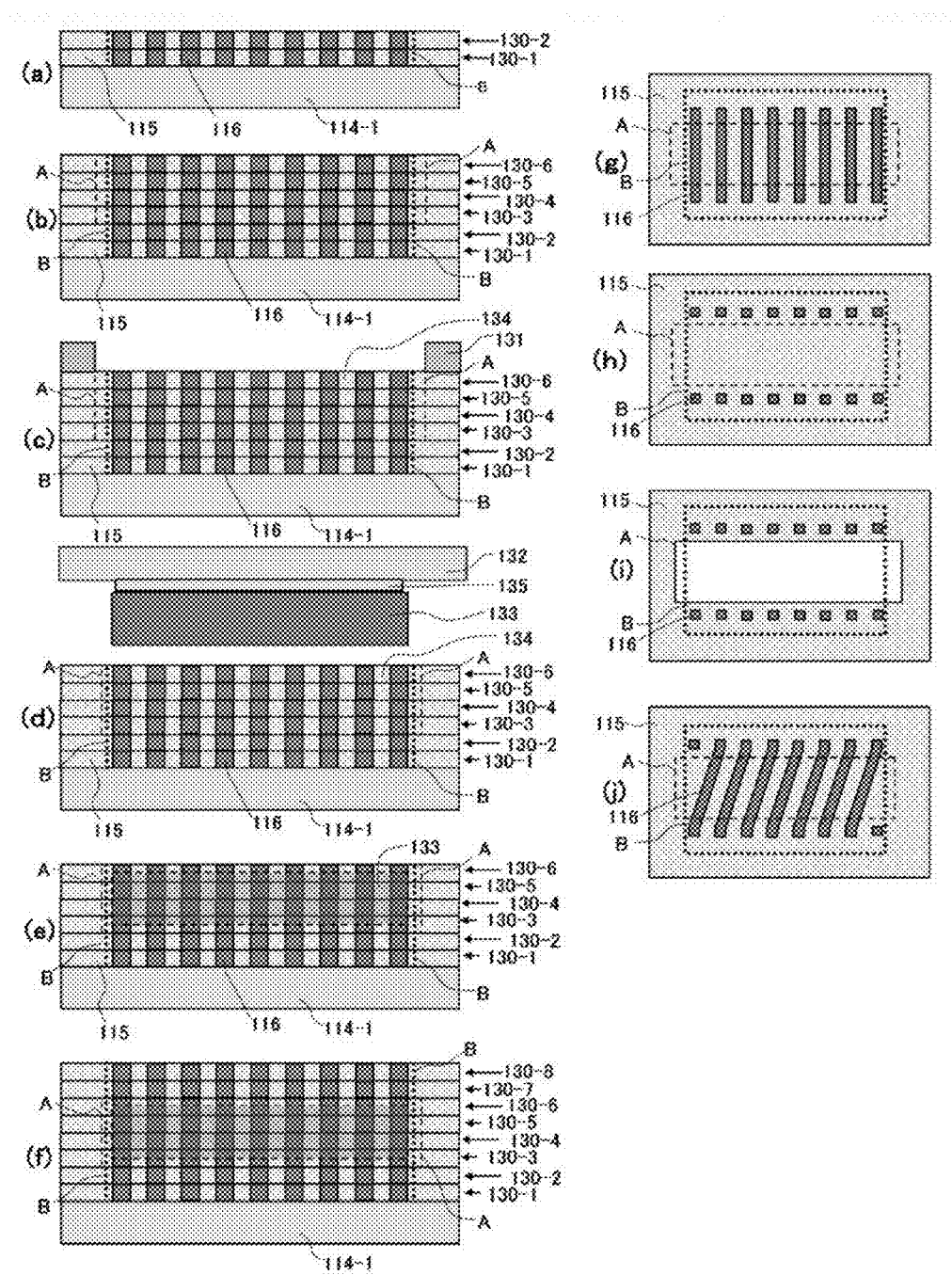

FIG. 12 is the diagram showing the method to make the high-performance coil in which the core having high Relative Permeability μ is inserted.

Figure 13:
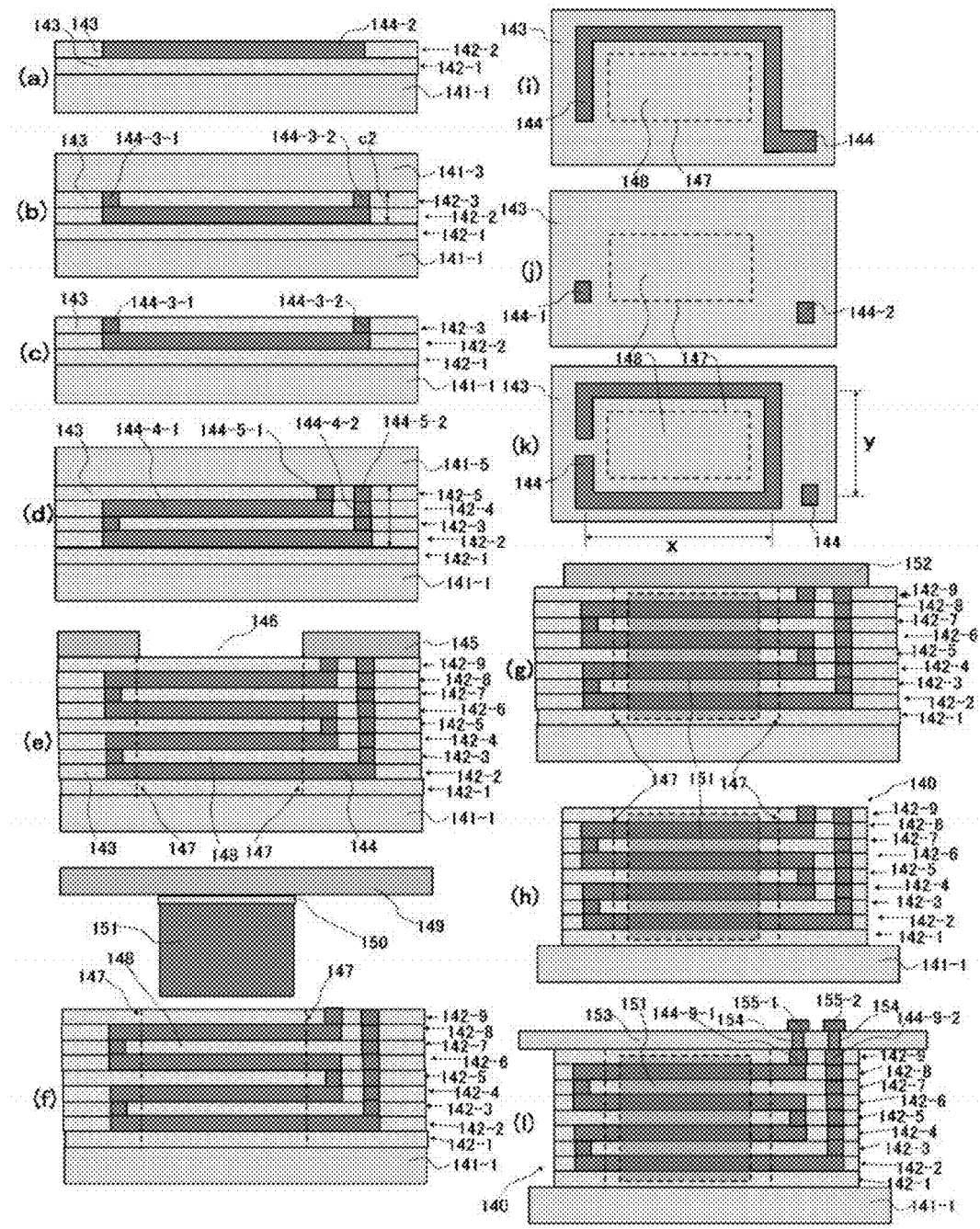

FIG. 13 shows the method to make the coil disposed in the upper and lower substrate.

Figure 14:
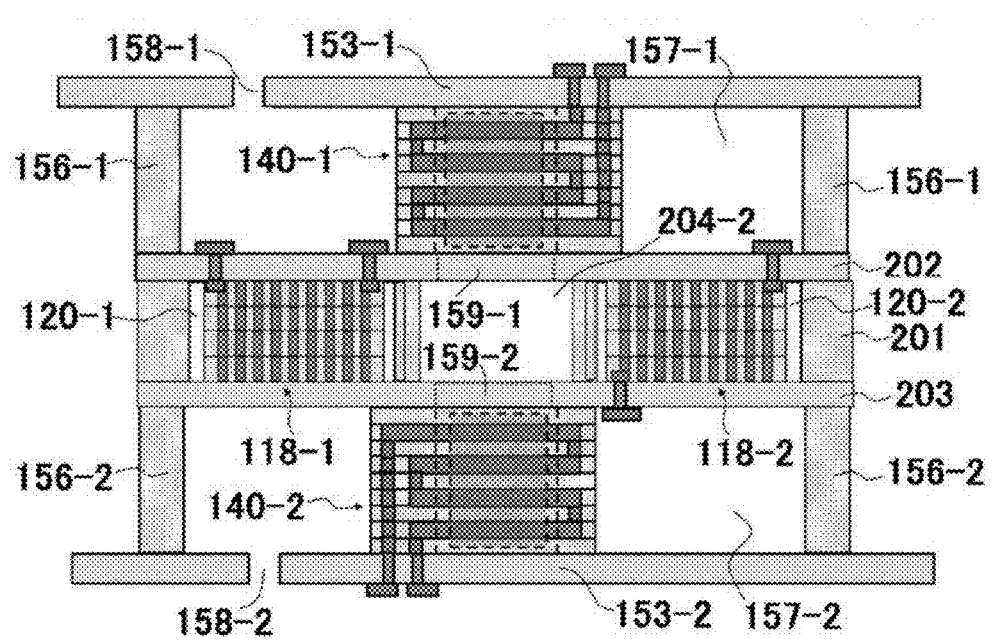

FIG. 14 shows structure quadrupole electromagnets made by the coil (electromagnet) of the present invention.

Figure 1:
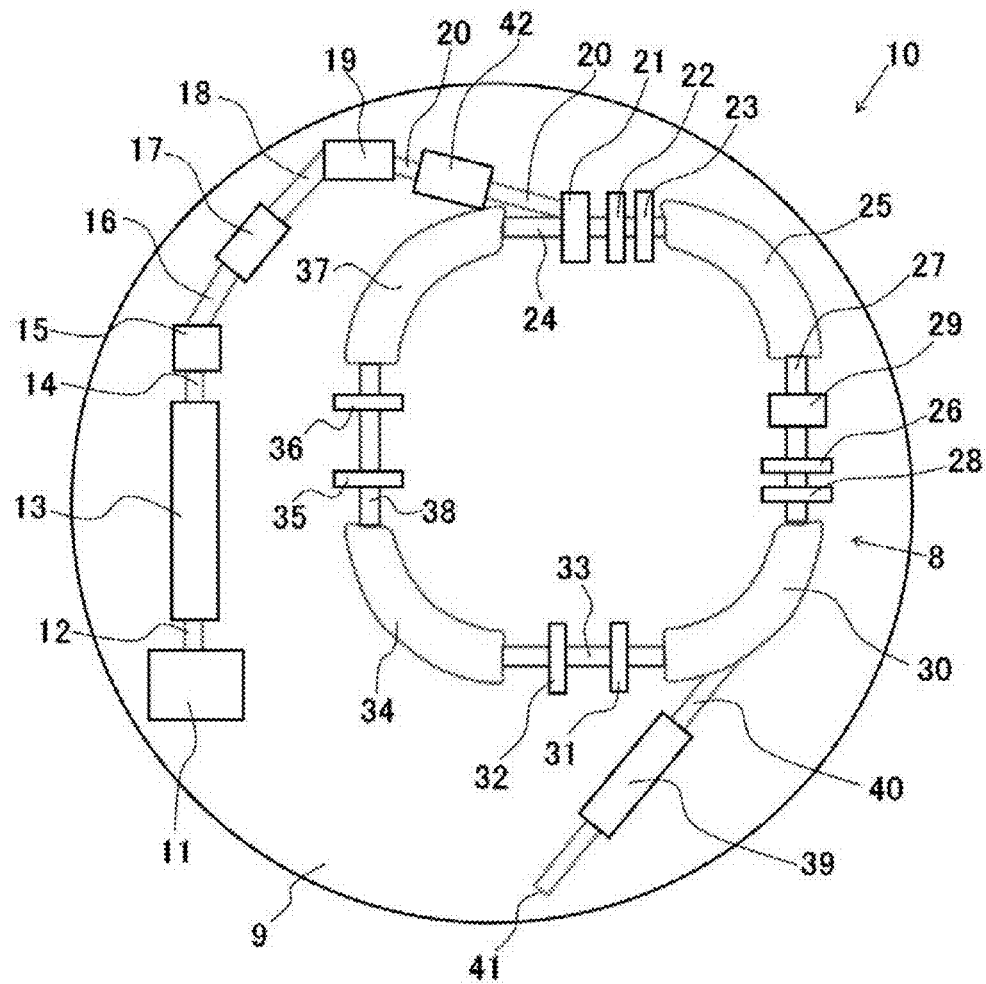
FIG. 1 shows an example of the embodiments of the ultra small particle accelerator of the present inventions.
Figure 15:
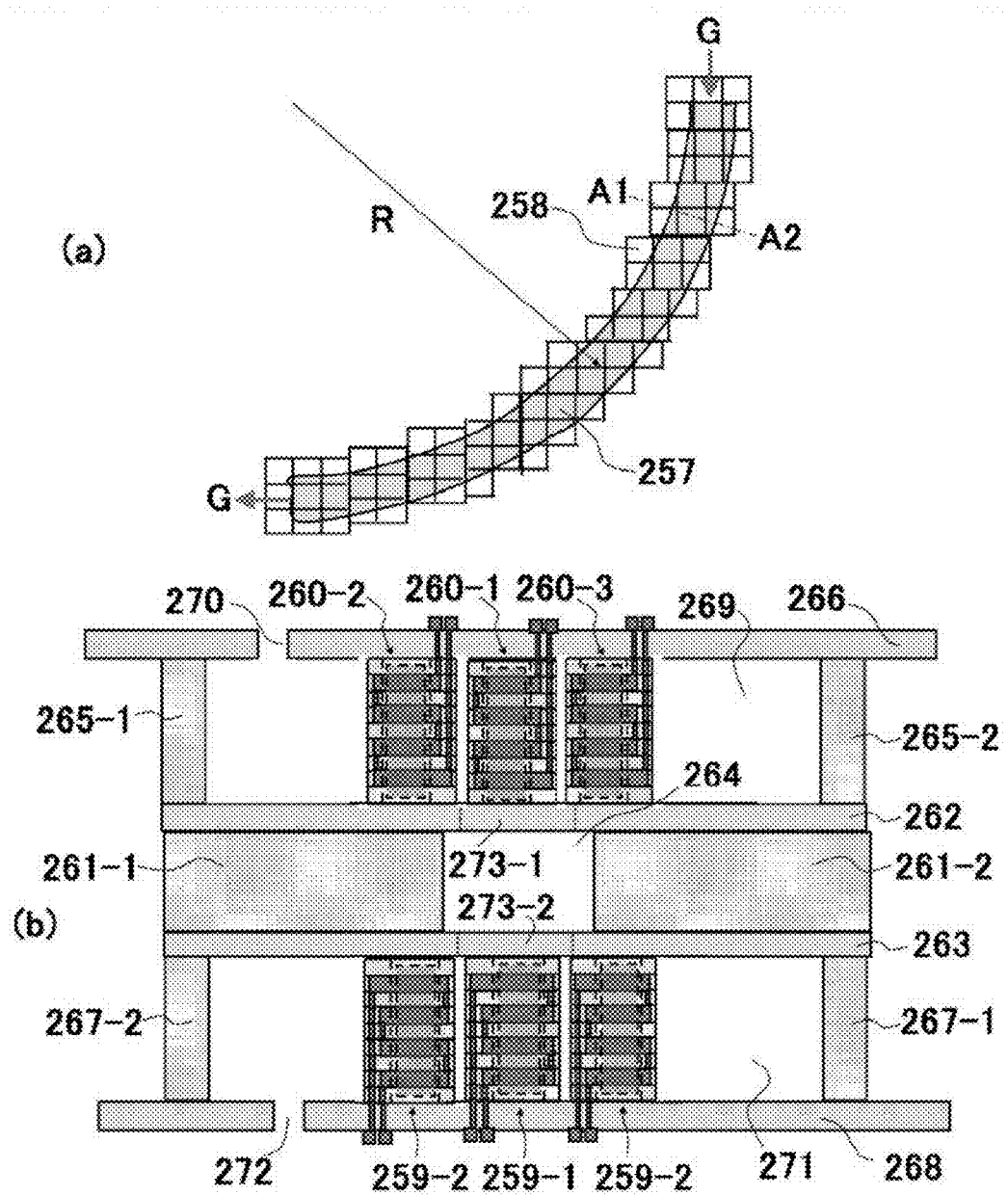

FIG. 15 is the diagram showing the charged particles passing cavity such as the deflecting electromagnets 25, 30, 34, 37, 3tc, in FIG. 1 and the electromagnets arranged there.

Figure 16:
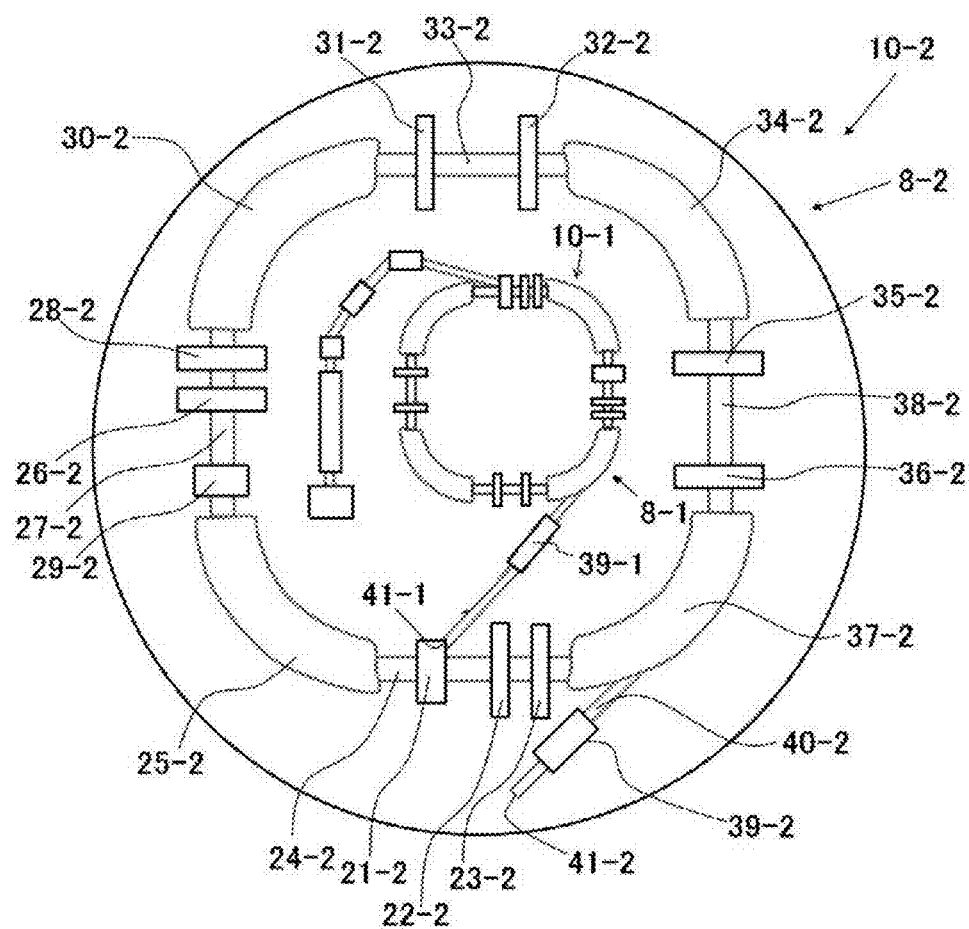

FIG. 16 is the diagram connecting the very small circular accelerator (synchrotron) 8-1 shown in FIG. 1 to slightly larger circular accelerator 8-2, and the diagram showing double synchrotrons (or 2 cycle synchrotrons).

Figure 17:
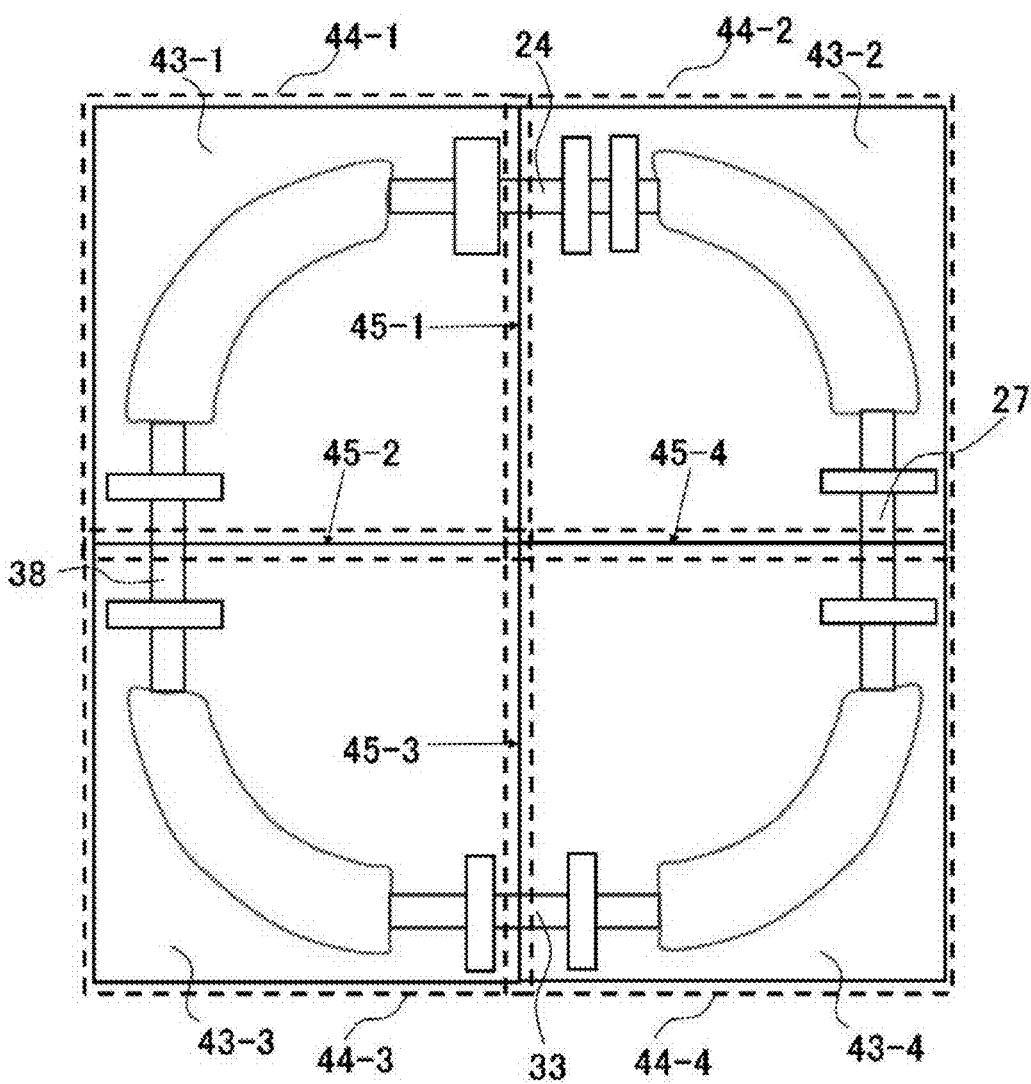

FIG. 17 is the diagram showing the case where the circular accelerator 8 is made by dividing the substrate.

Figure 18:
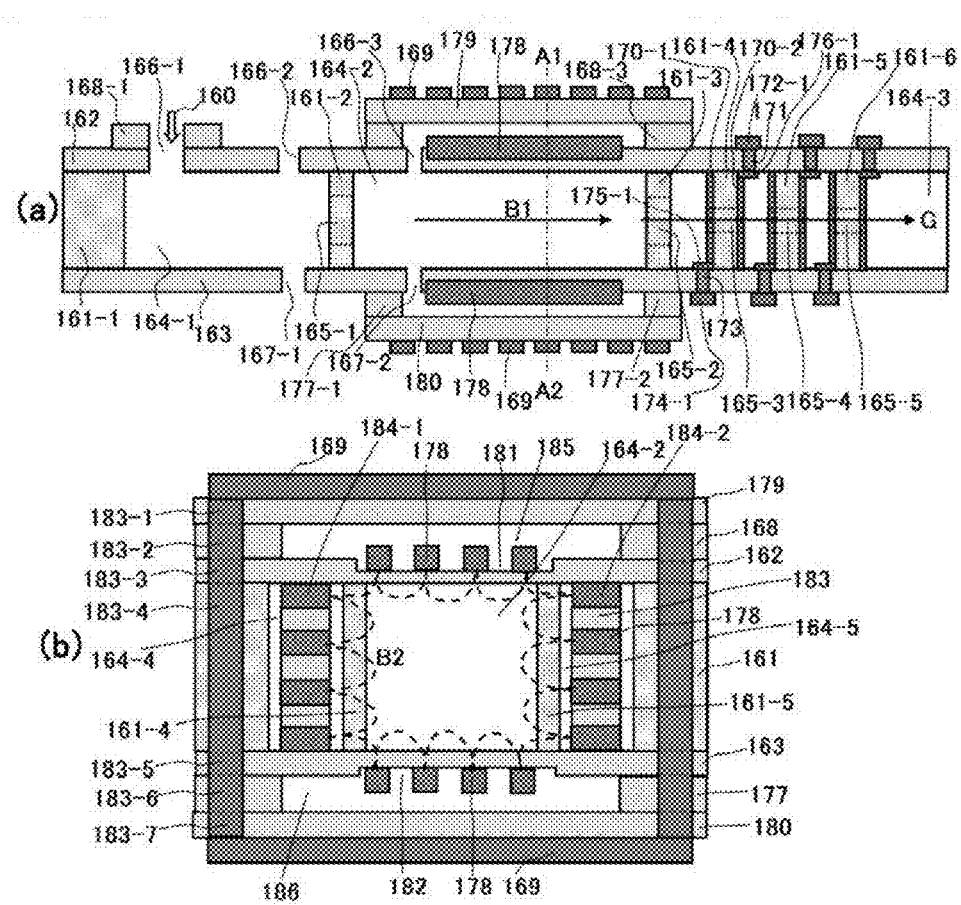

FIG. 18 shows the microwave ion source of the present invention.

Figure 19:
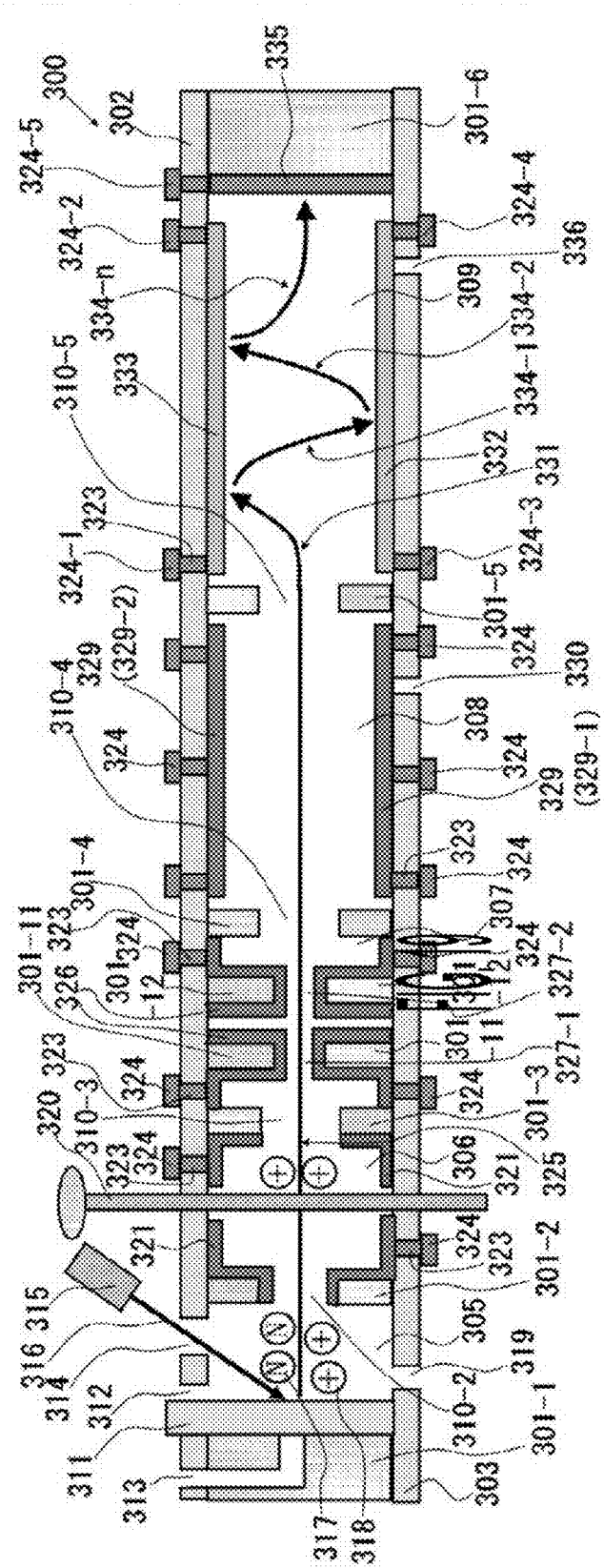

FIG. 19 is the diagram showing one embodiment of the mass analyzer of the present invention.

Figure 20:
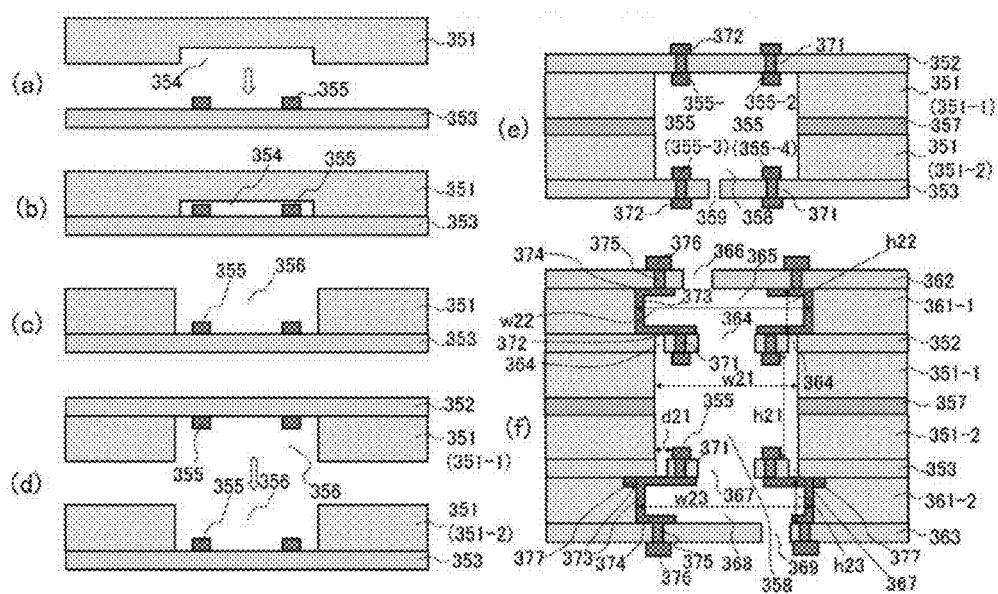

FIG. 20 is the diagram showing one sample of methods to make the quadrupole type mass analysis room.

Figure 21:
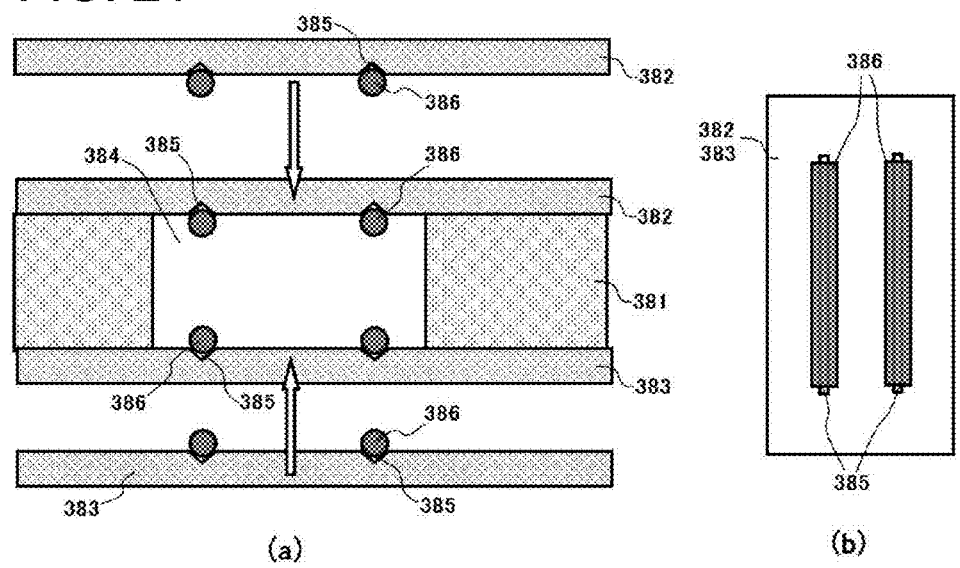

FIG. 21 is the diagram explaining one sample about the structure and the method to adhere the quadrupole electrode to the substrate.

Figure 22:
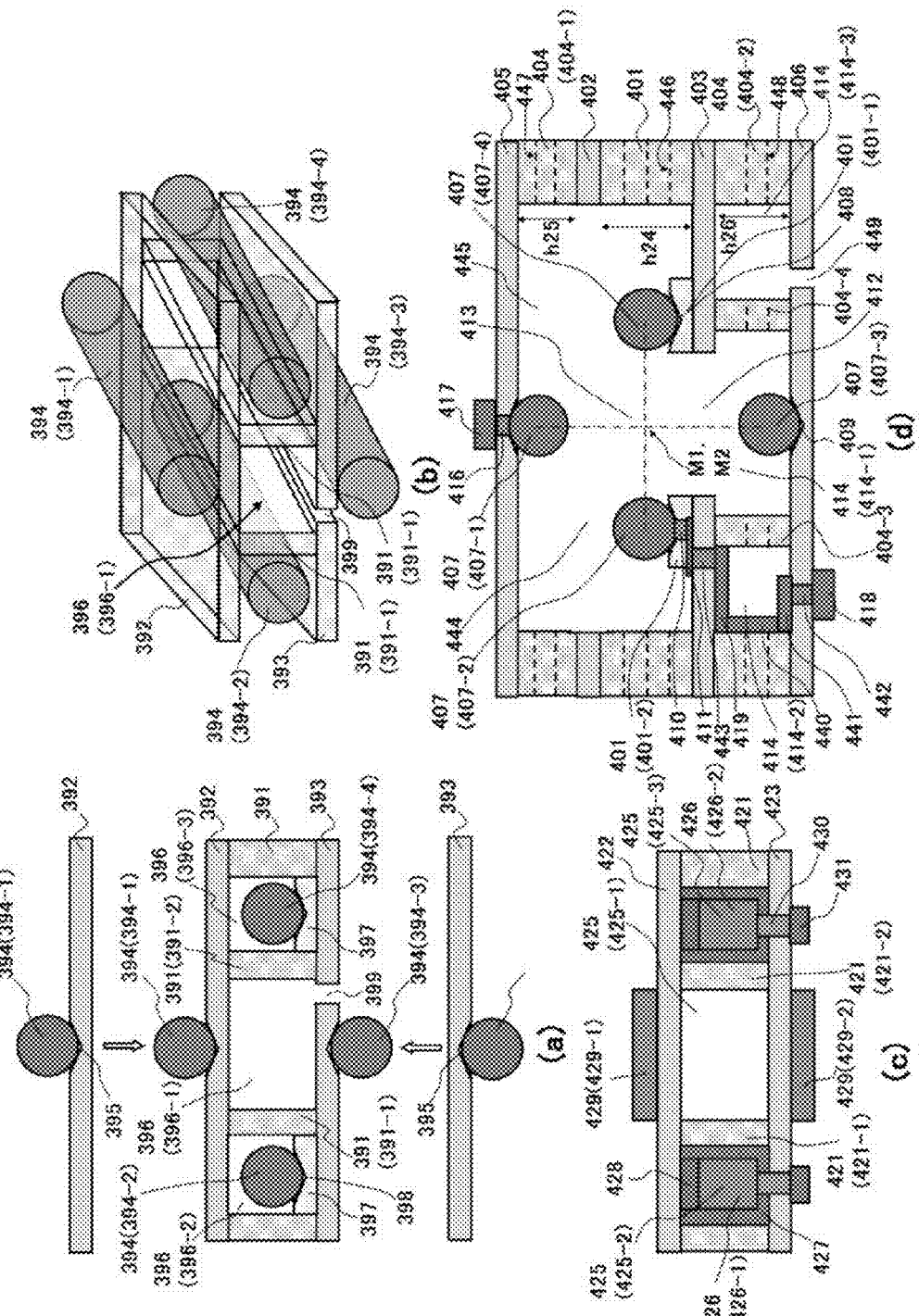

FIG. 22 is another sample about the structure and the method to adhere the quadrupole electrode rods to the substrate.

Figure 23:
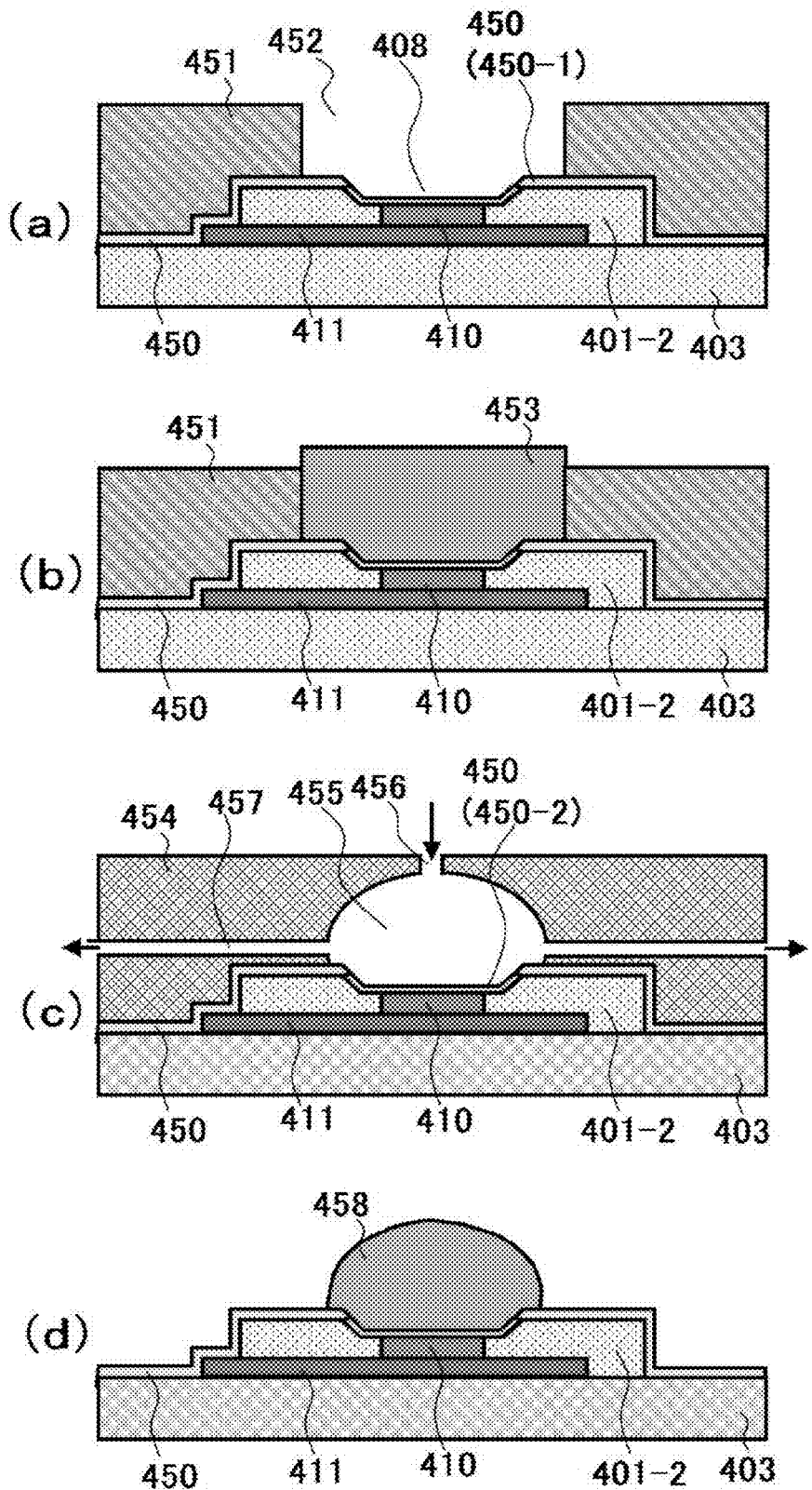

FIG. 23 is the diagram showing the method to make the quadrupole electrodes.

Figure 24:
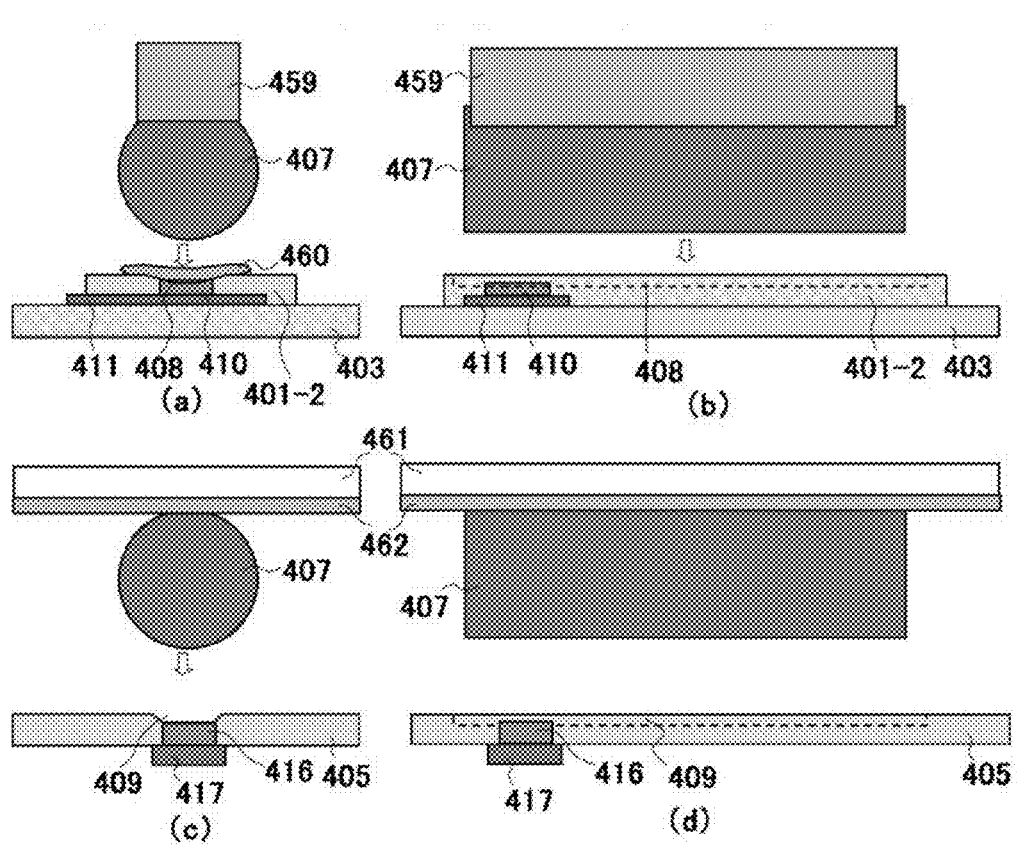

FIG. 24 is the diagram showing the method to adhere the quadrupole electrode to the substrate.

Figure 25:
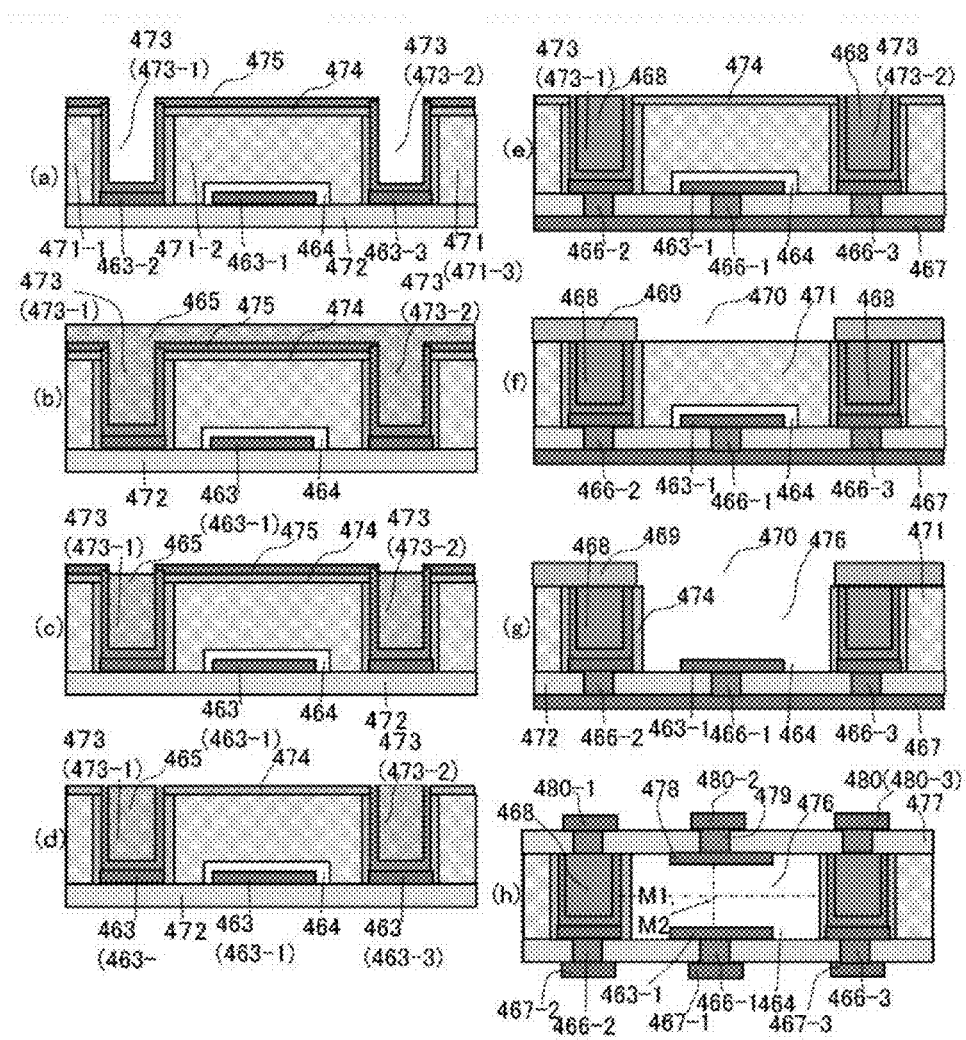

FIG. 25 is the diagram showing the method to arrange the quadrupole electrodes in the mass analysis room using the thin film formation method.

Figure 26:
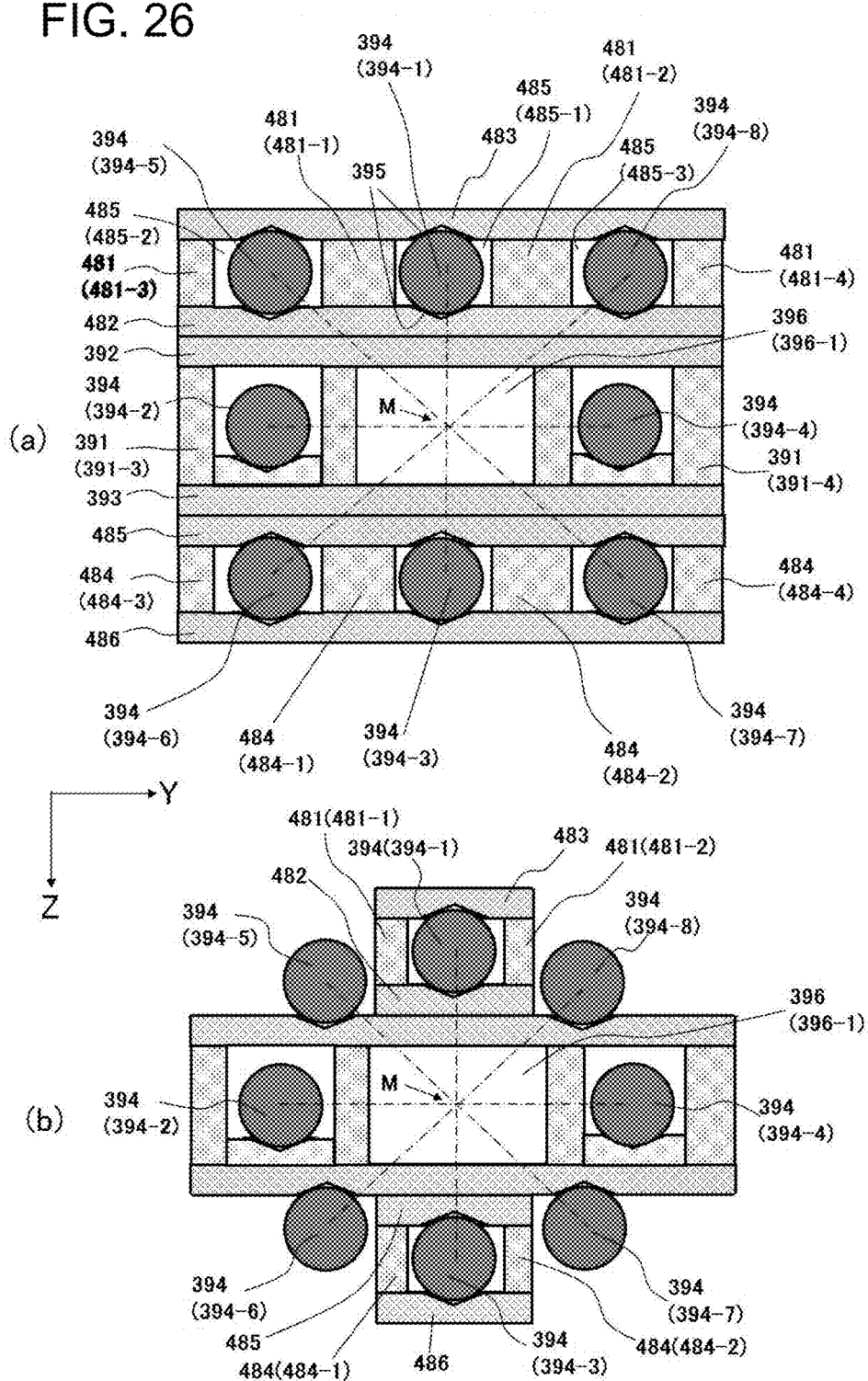

FIG. 26 is the diagram showing the structure of the octopole electrodes ion.

Figure 27:
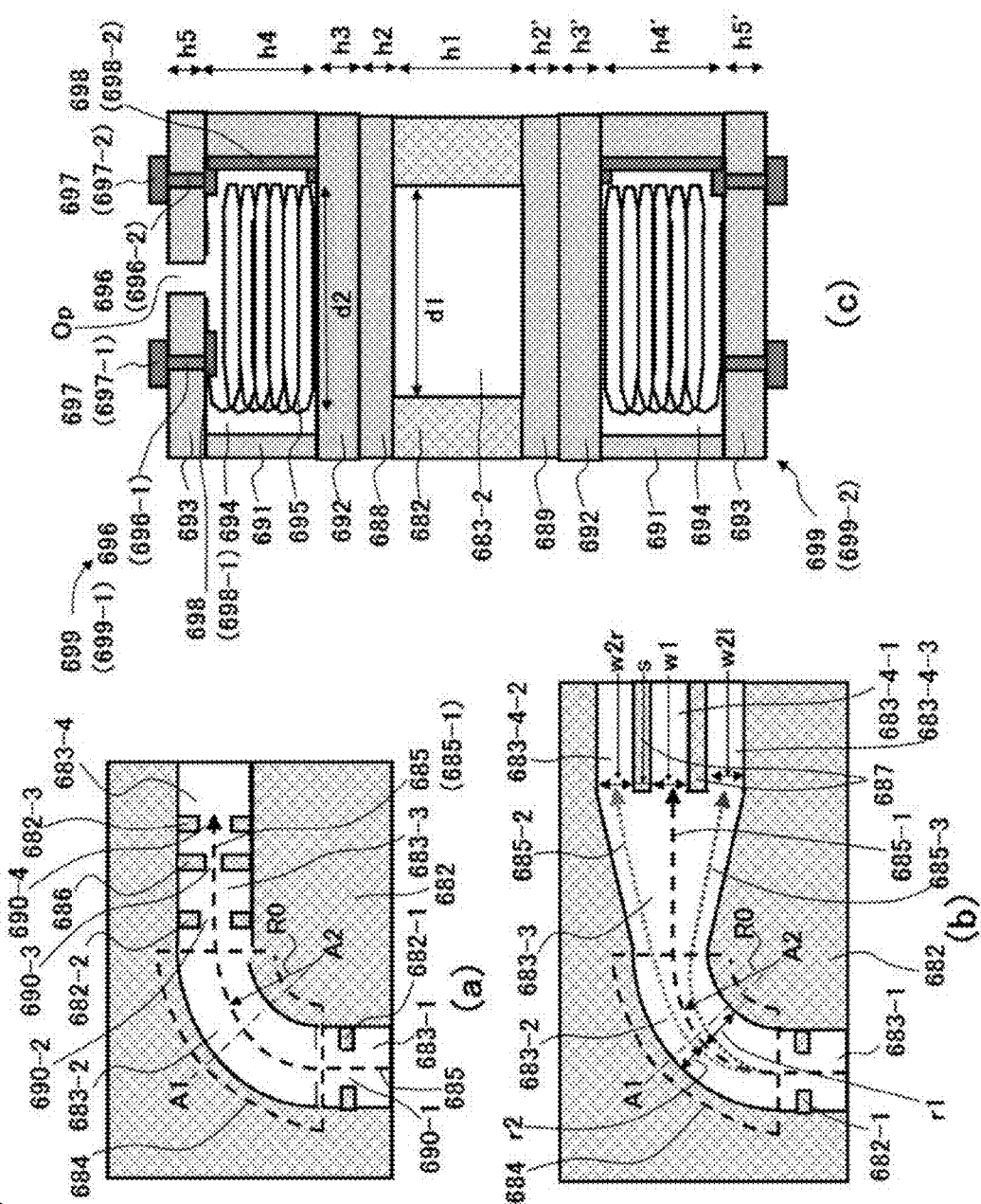

FIG. 27 is a schematic diagram showing a fan-type magnetic field type mass analysis chamber having a penetrating chamber serving as a mass analysis chamber in which a fan-shaped magnetic field acts on the main substrate of the present invention.

Figure 28:
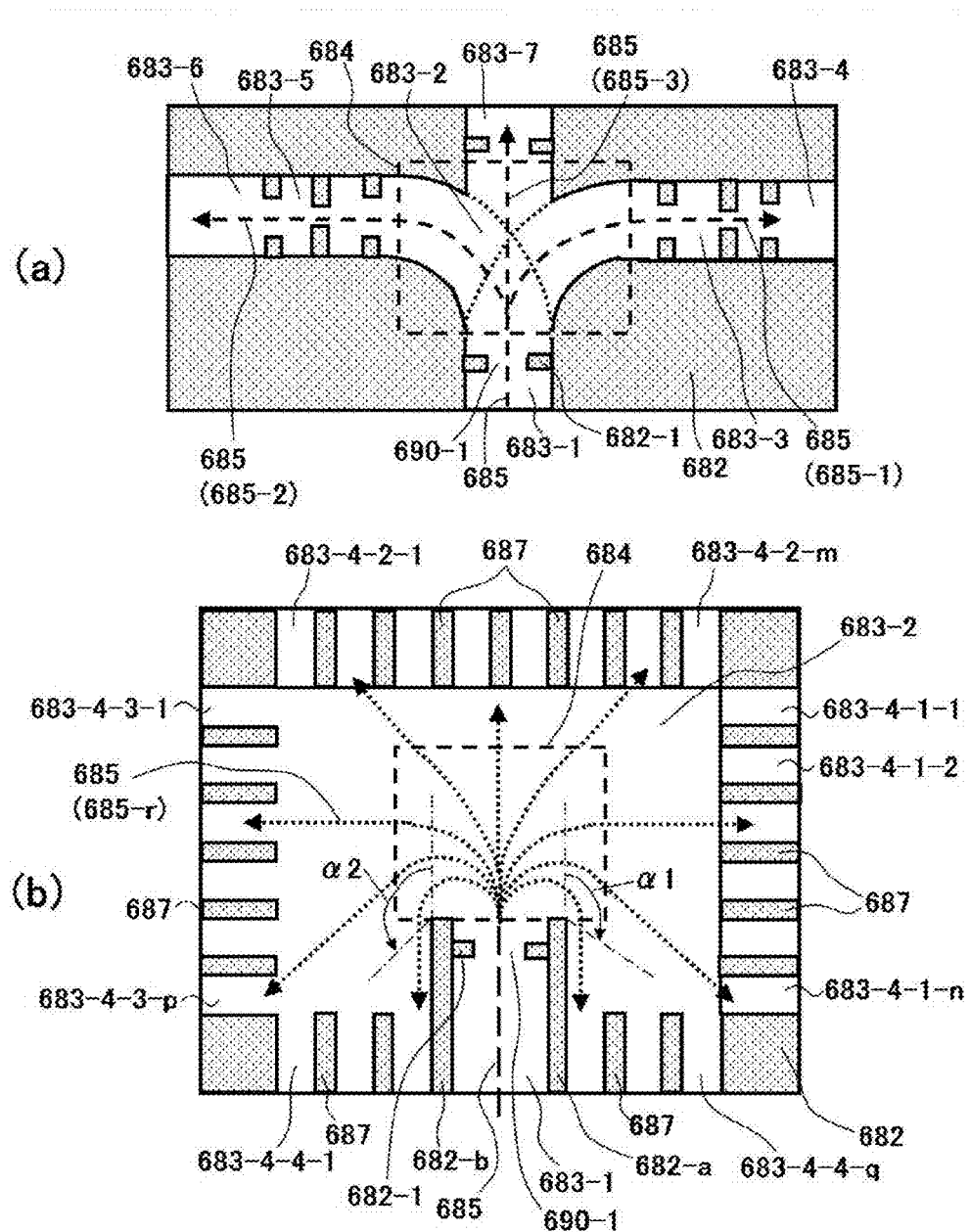
Figure 29:
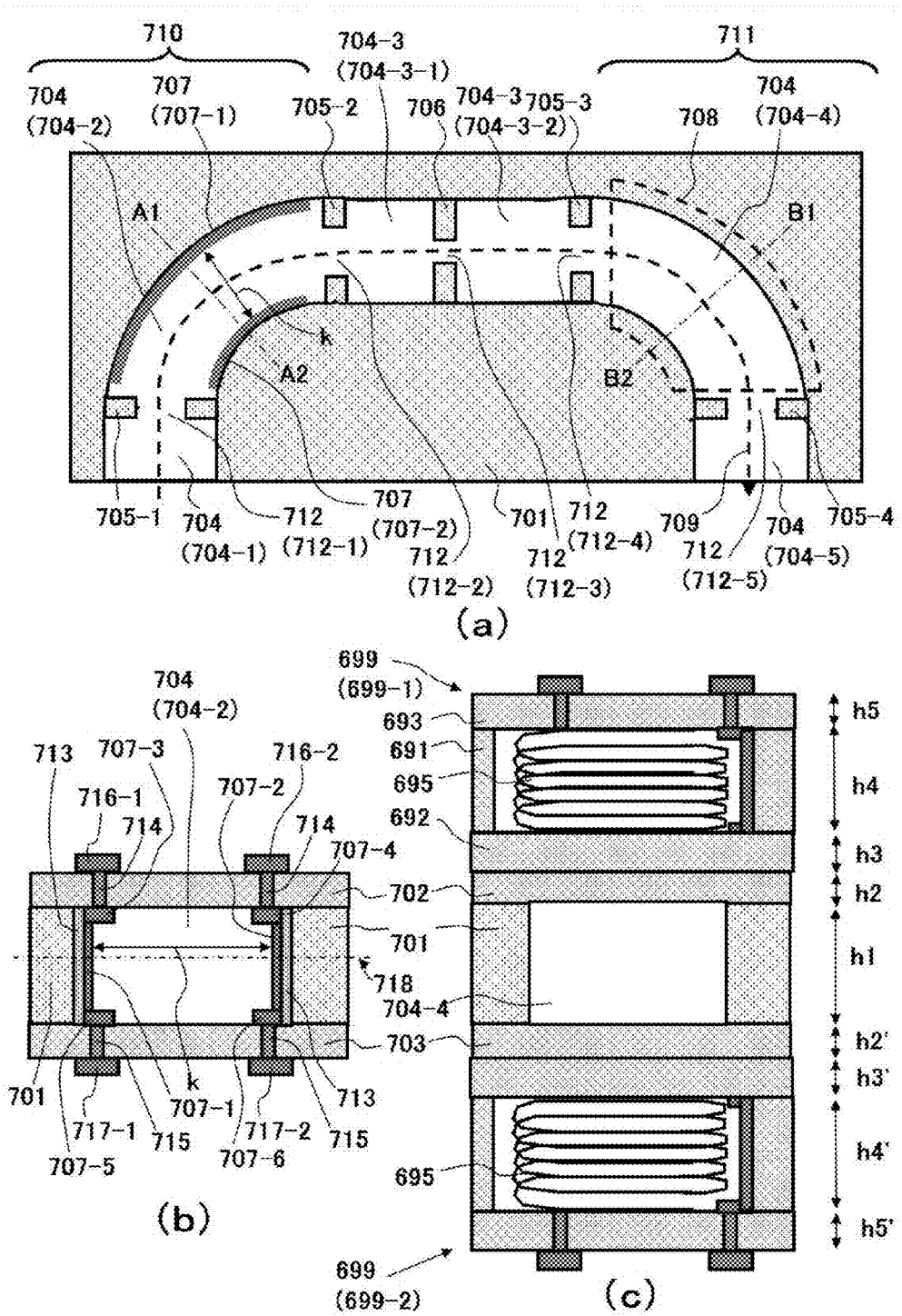

FIG. 28 is a diagram showing a mass analysis device that detects ions with ion detection devices that are arranged in multiple directions, FIG. 29 is another embodiment of the mass analysis device.

Figure 30:
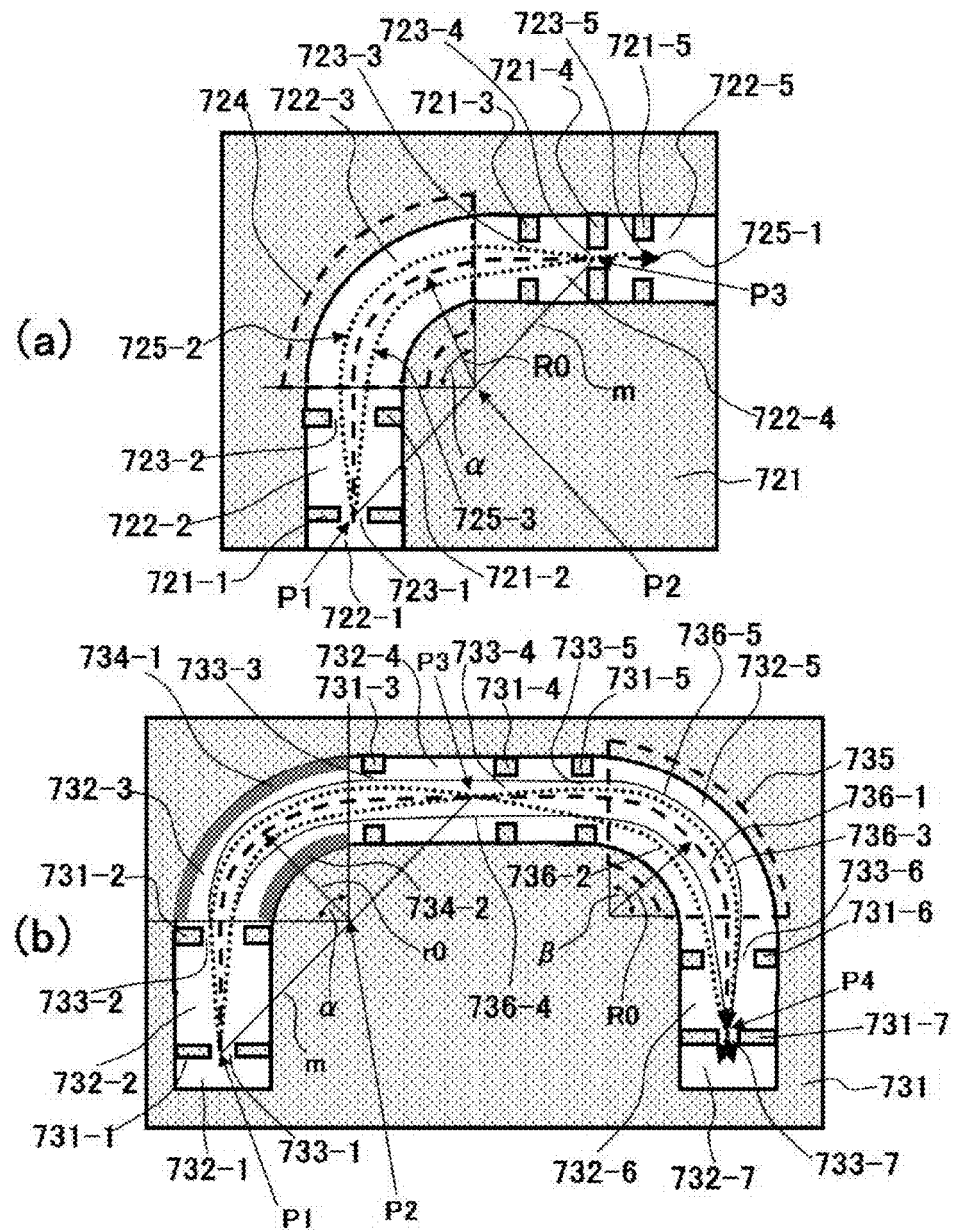

FIG. 30 is a view showing a design guideline of a magnetic field analyzer of single converging fan-type and a magnetic field analyzer of double converging fan-type.

Figure 31:
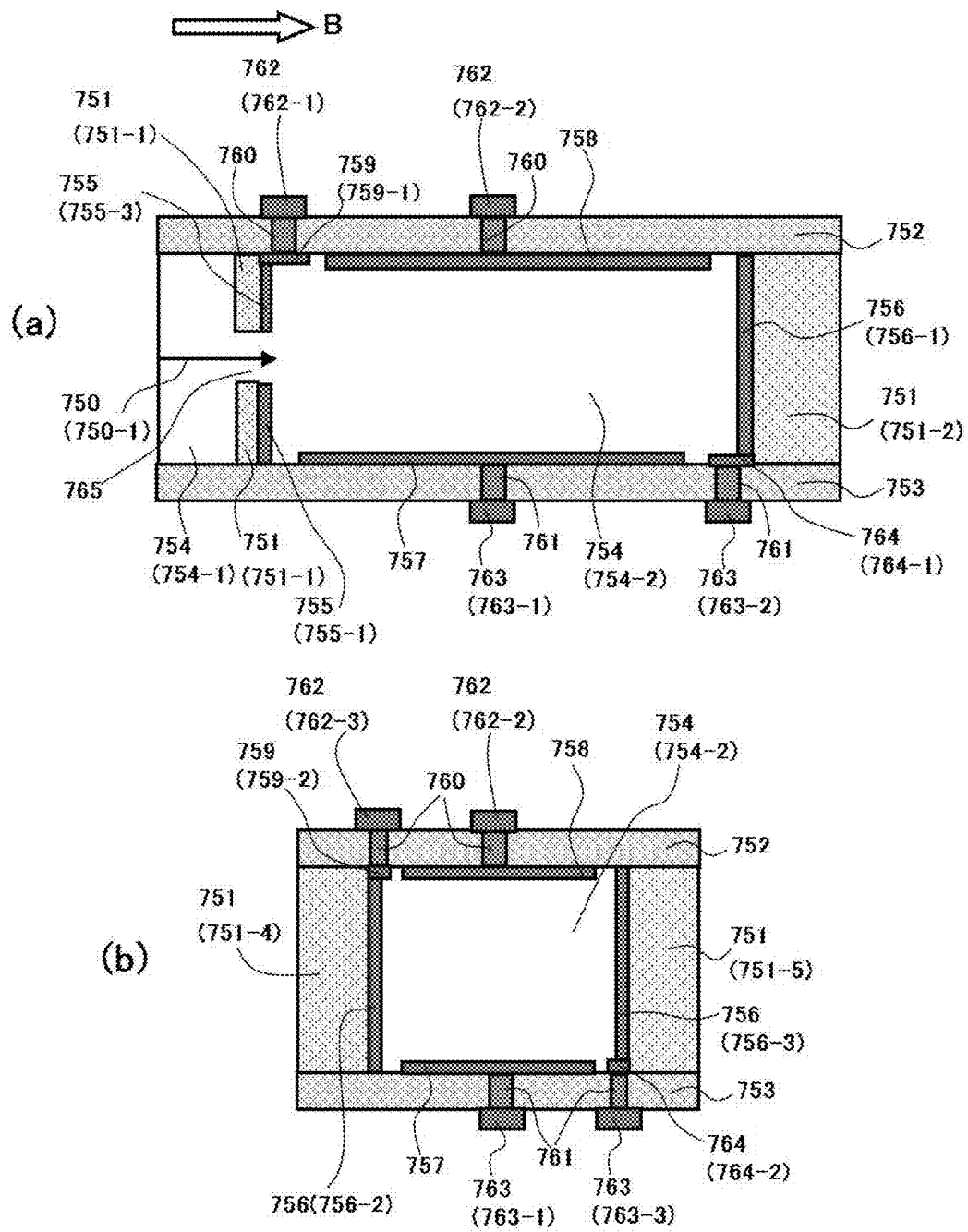

FIG. 31 is a diagram showing FTICR of the present invention.

Figure 32:
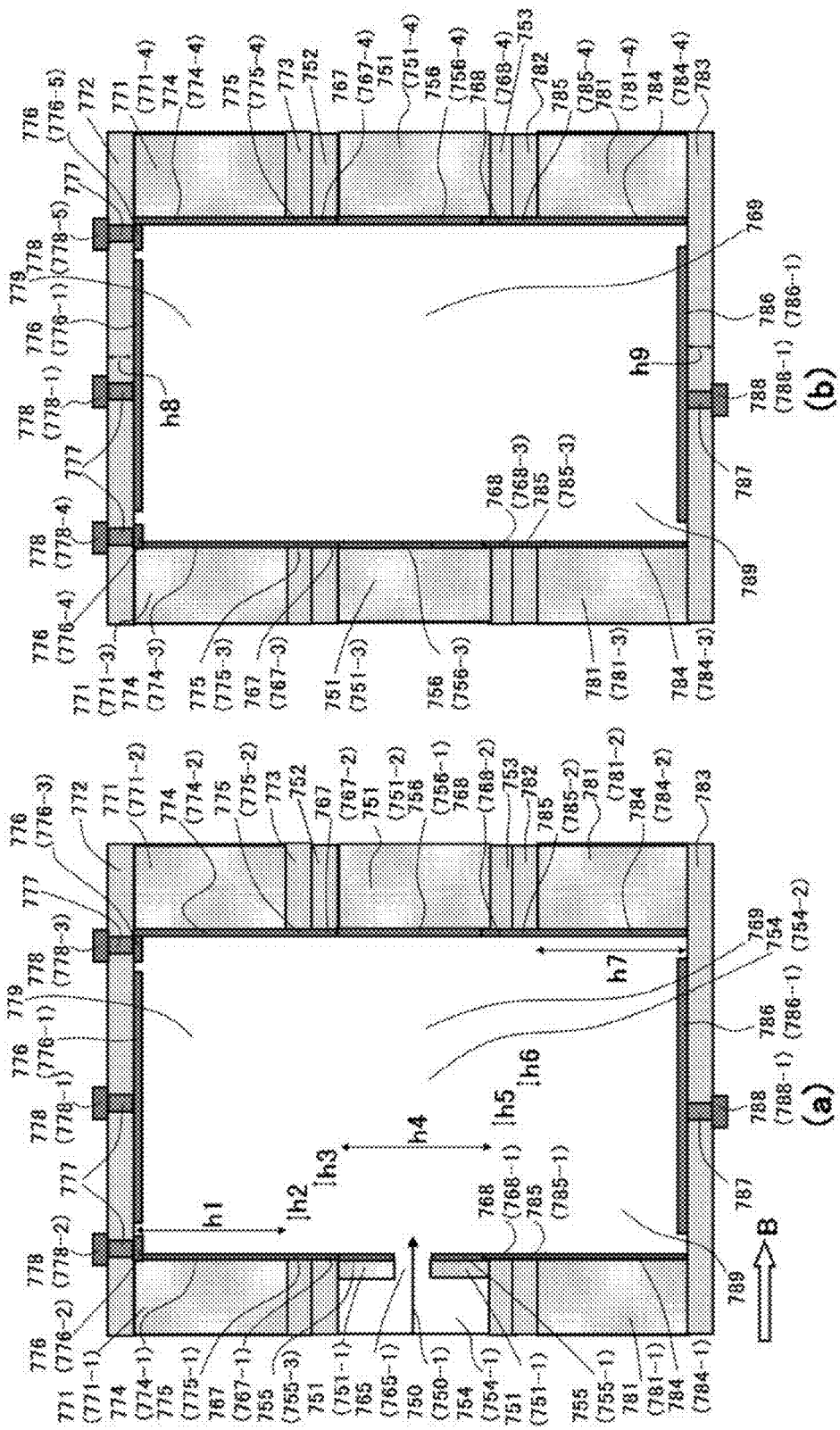

FIG. 32 is a diagram showing a structure where the ICR chamber is enlarged.

Figure 33:
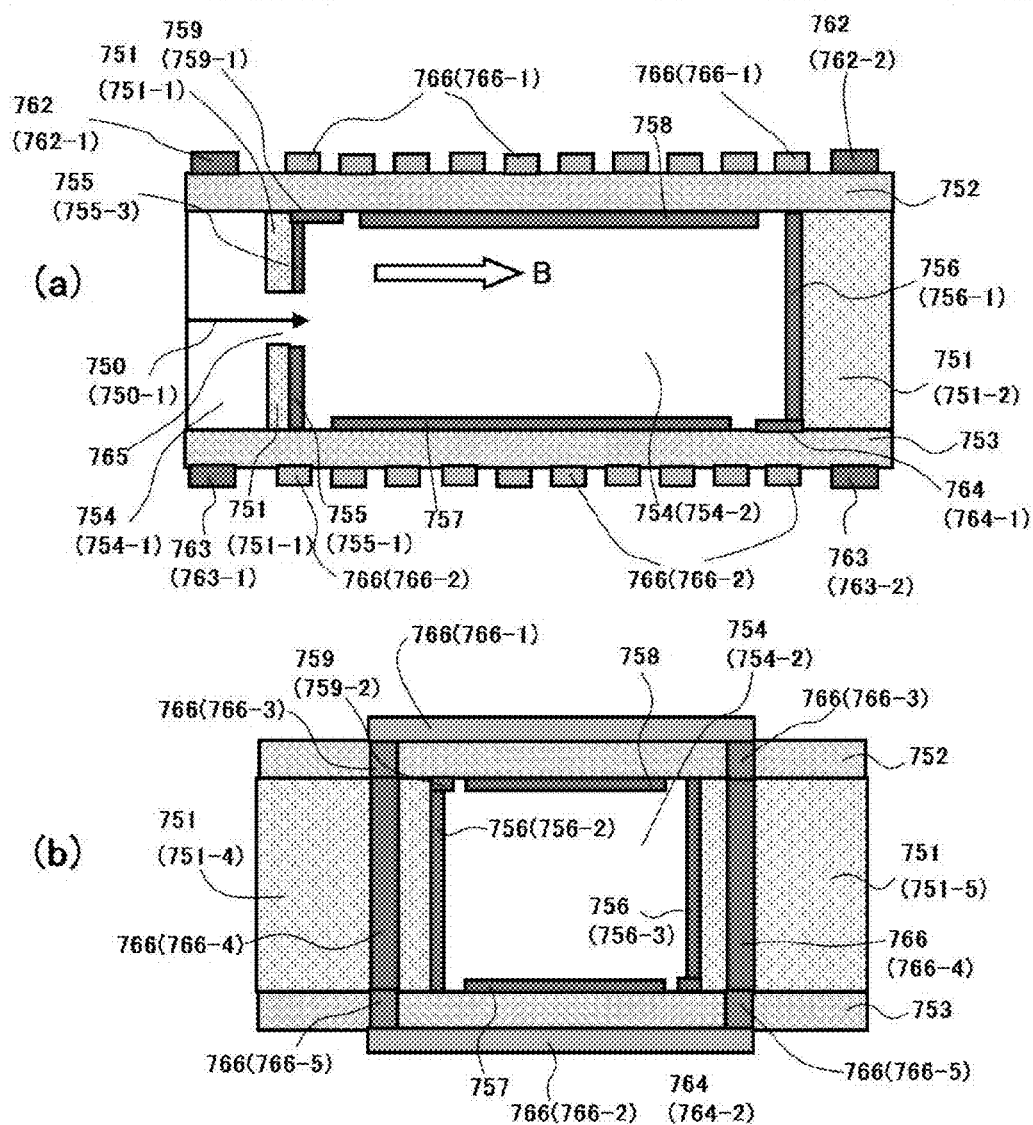

FIG. 33 shows FTICR in which the coil of the present invention is arranged.

Figure 34:
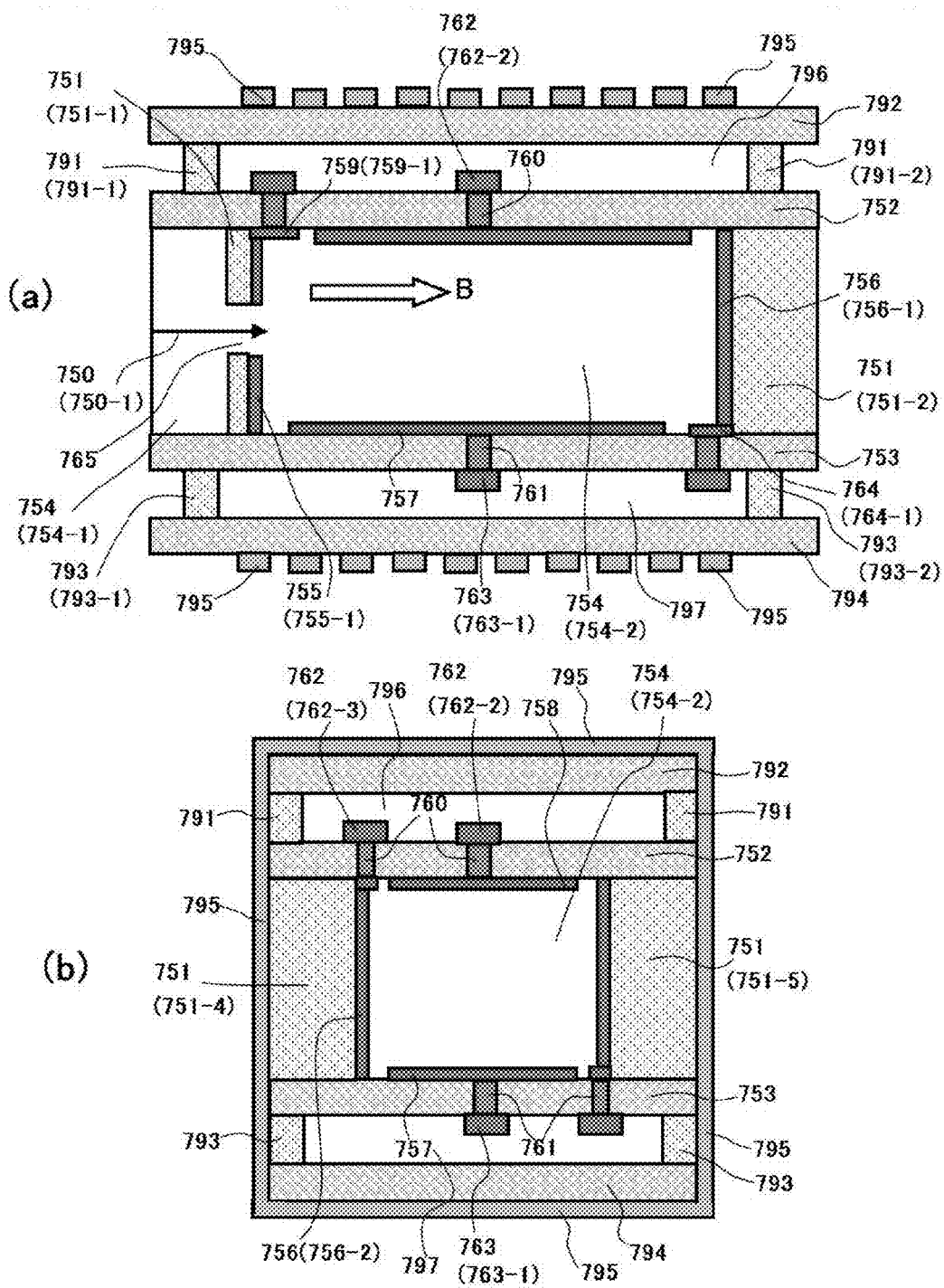

FIG. 34 shows an FTICR in which the coil of the present invention is arranged differently from that of FIG. 33.

Figures 35, 36:
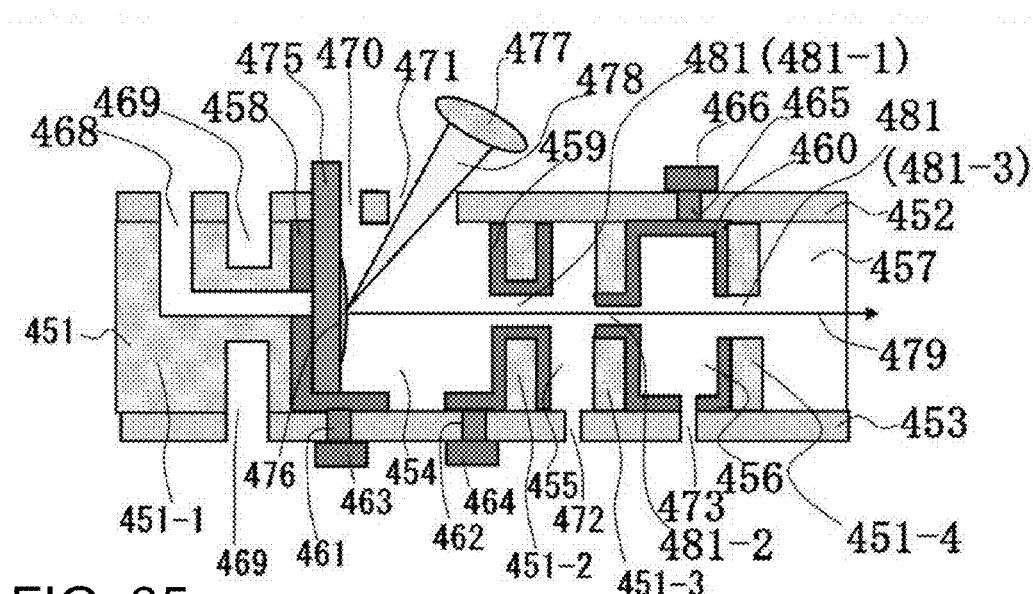

FIG. 35 is a diagram showing an ionization method different from that described in FIG. 19.

FIG. 36 is a diagram showing an embodiment of another ionization method.

Figure 37:
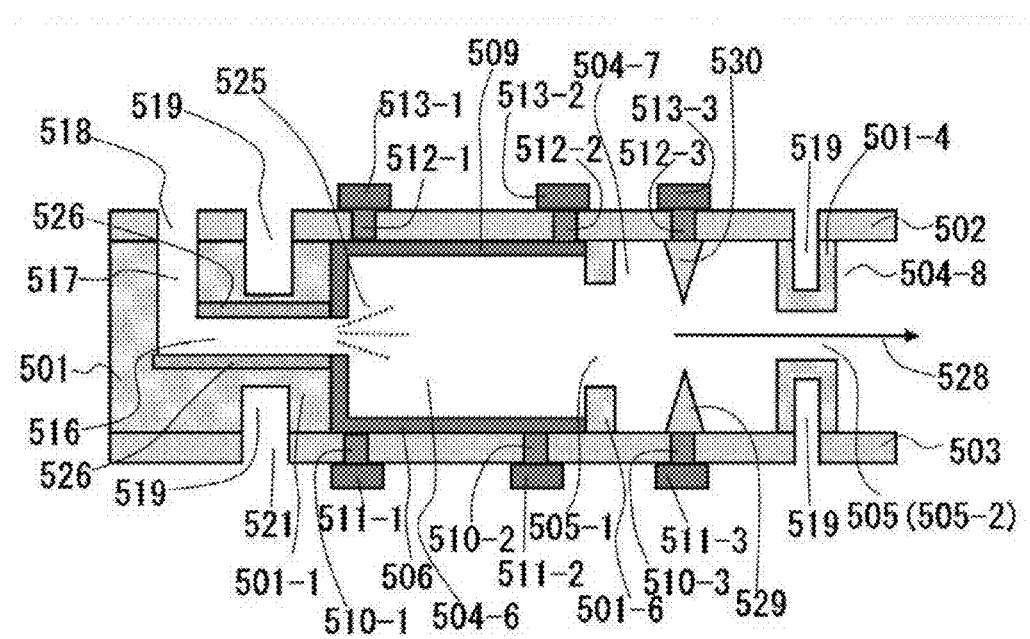

FIG. 37 is a diagram for explaining the atmospheric pressure chemical ionization method.

Figure 38:
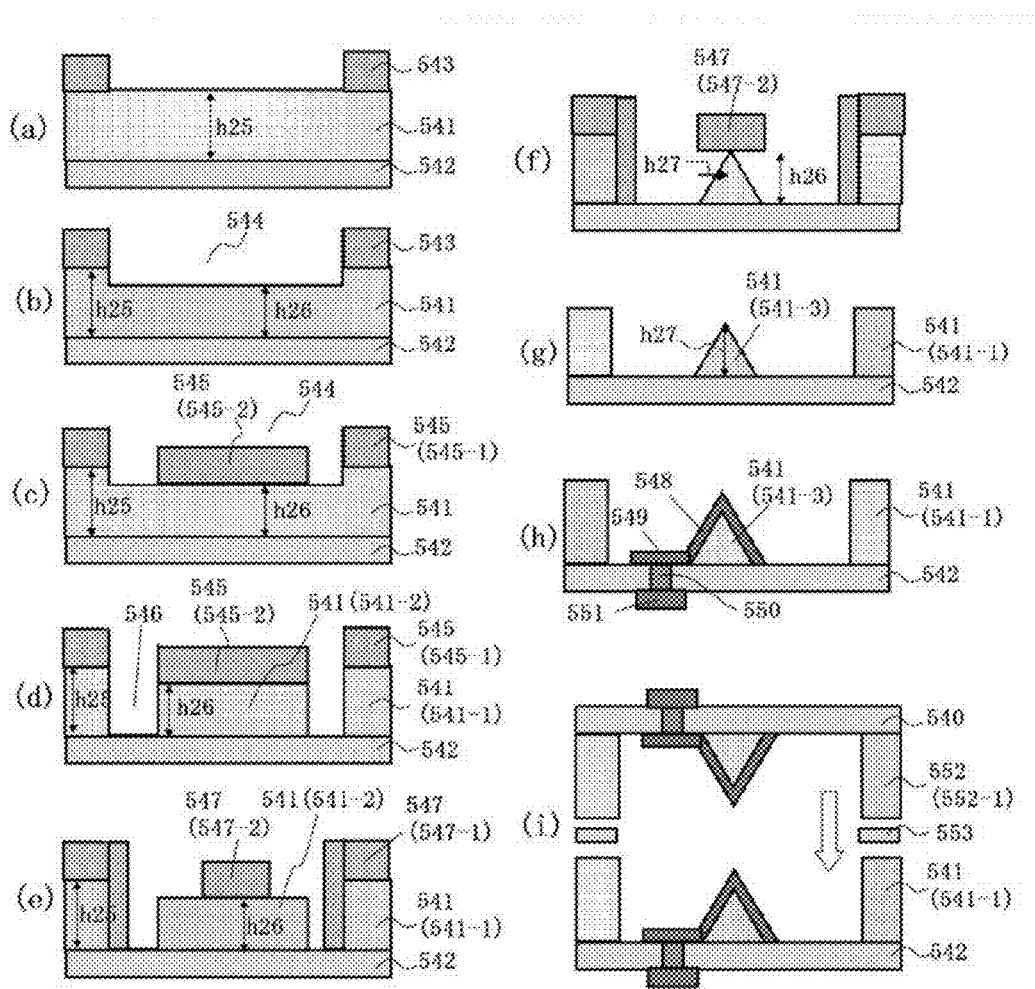

FIG. 38 is a view showing a method for manufacturing an ionization chamber having pointed electrodes.

Figure 39:
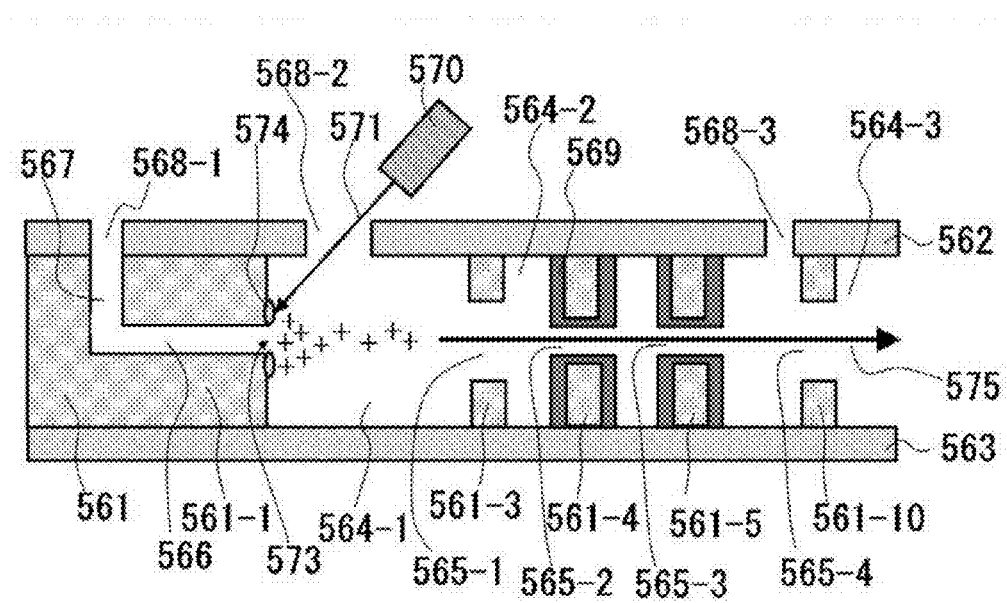

FIG. 39 shows an embodiment in which continuous flow (CF)-FAB ionization, which is one type of fast atom bombardment method (FAB), is applied to the present invention.

Figure 40:
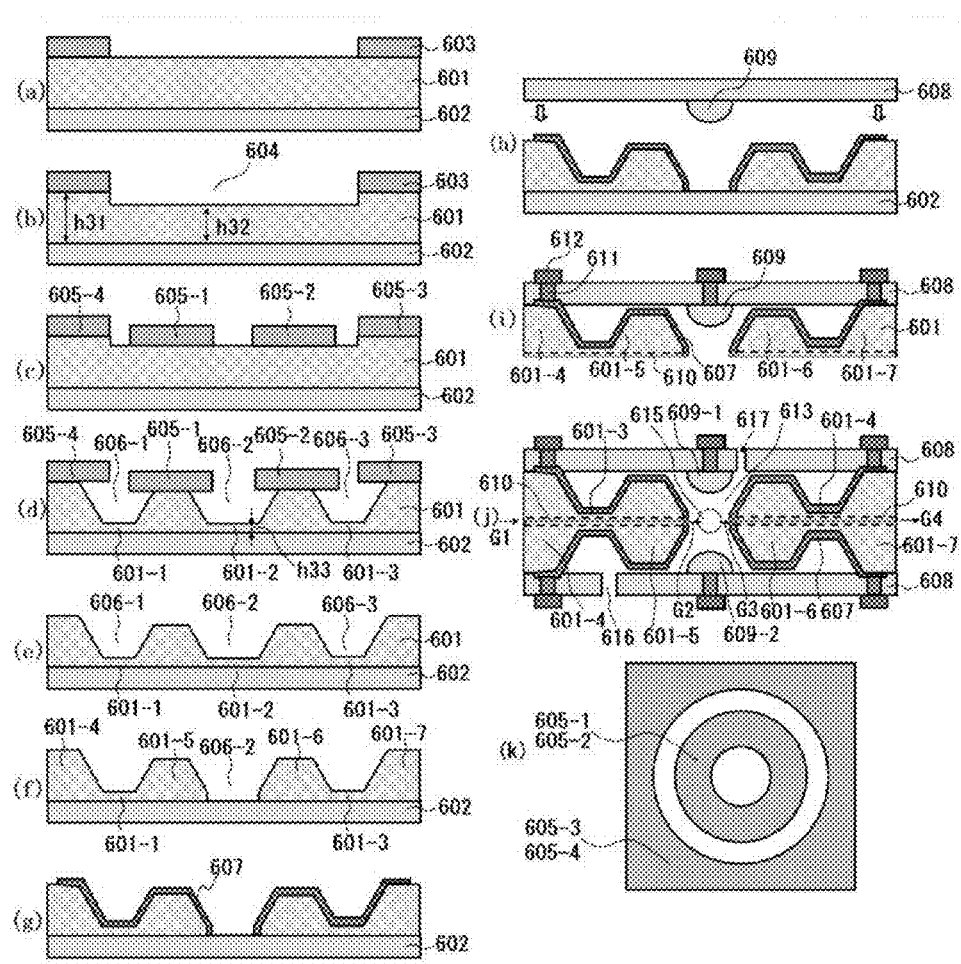

FIG. 40 is a diagram showing a method for manufacturing an ion trap-type mass analysis device.

Figure 41:
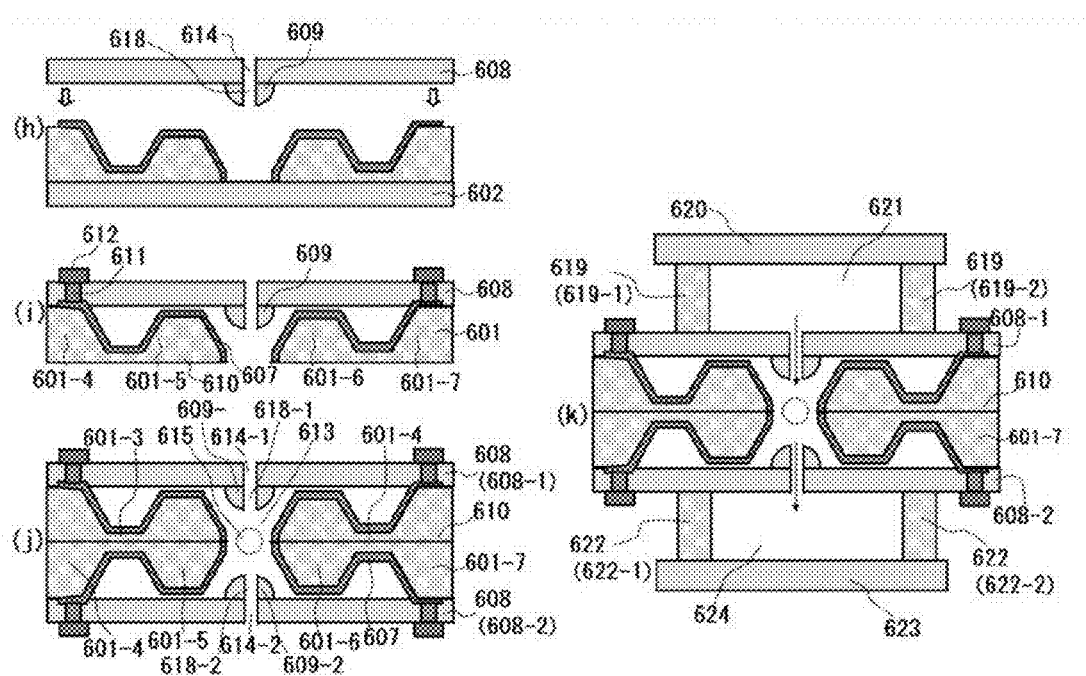

FIG. 41 is a view showing an ion trap-type mass analysis device in which the charged particles pass through an end cap electrodes 609.

Figure 42:
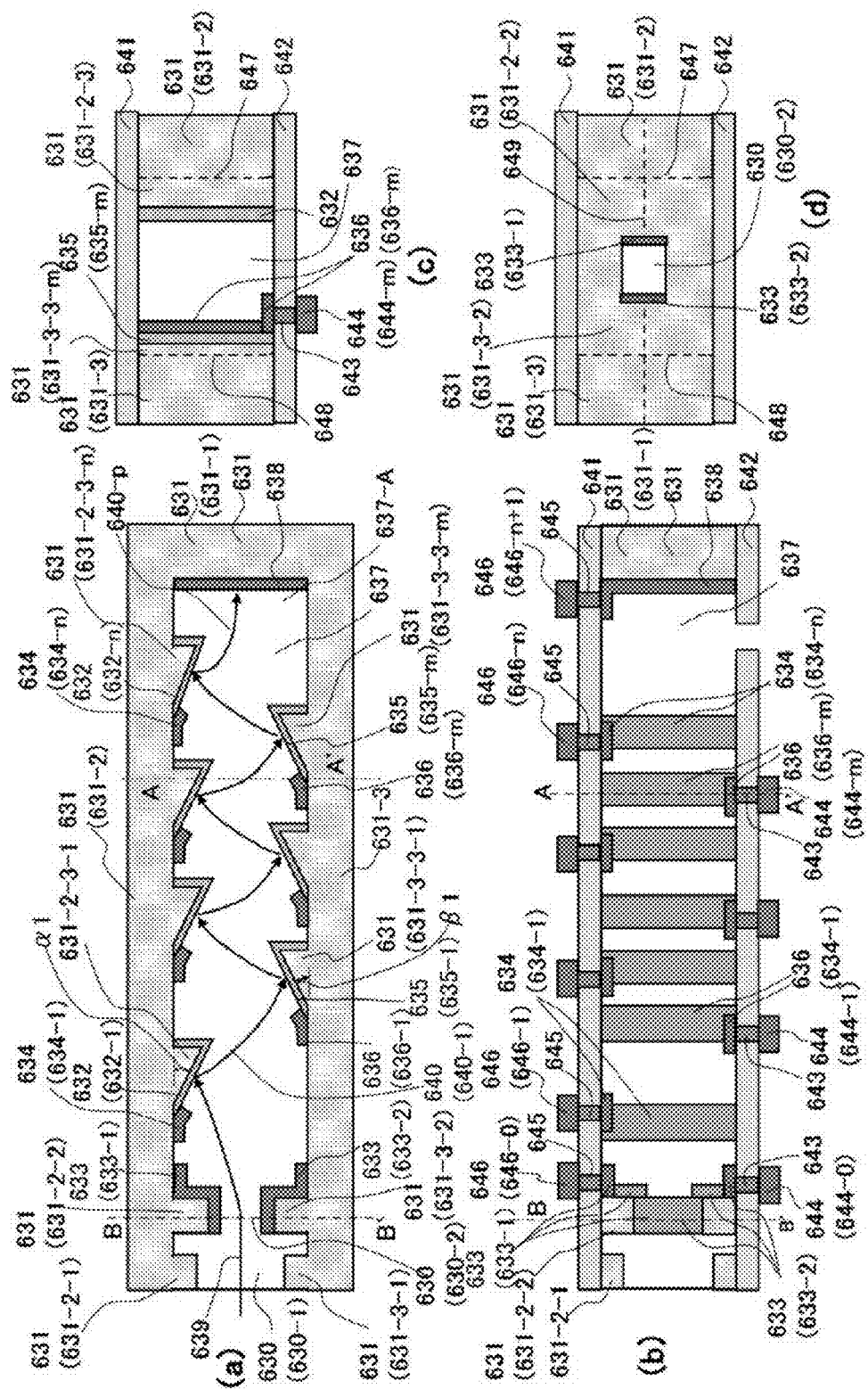

FIG. 42 is the diagram showing the ion detection room where many dynodes using the present invention are arranged.

Figure 43:
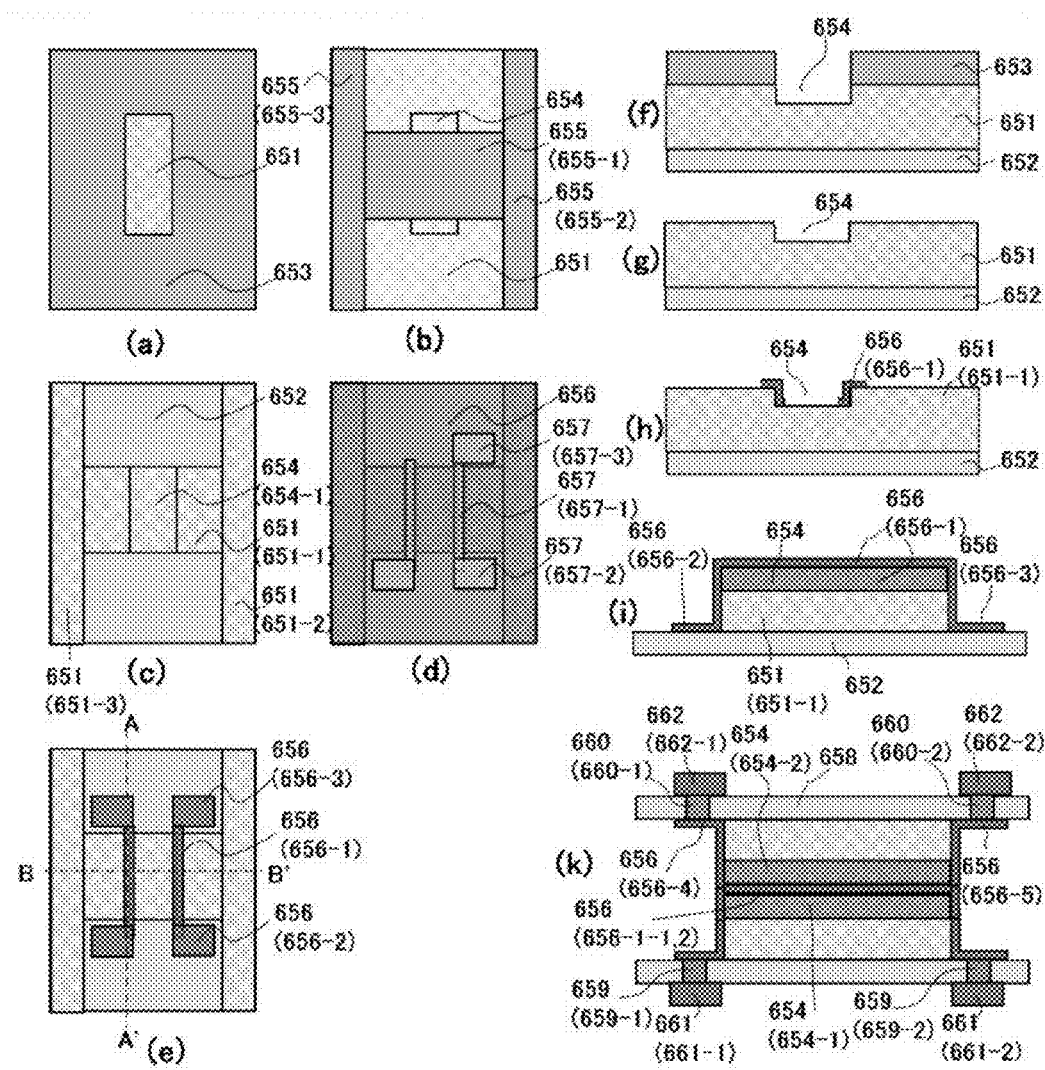

FIG. 43 shows one embodiment of the method to make the parallel plate electrodes shown in FIG. 42.

Figure 44:
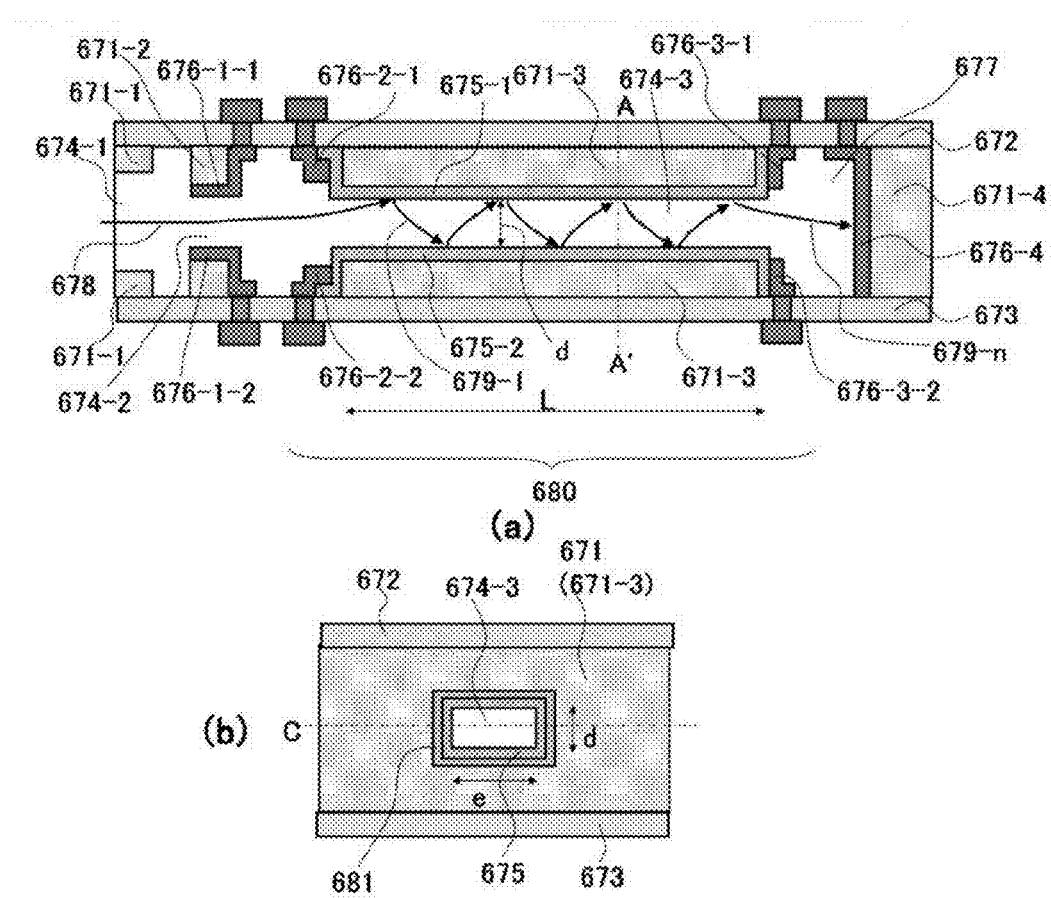

FIG. 44 is the diagram showing the embodiments applying the central hole of the invention to channel type secondary electron multiplier.

Figure 45:
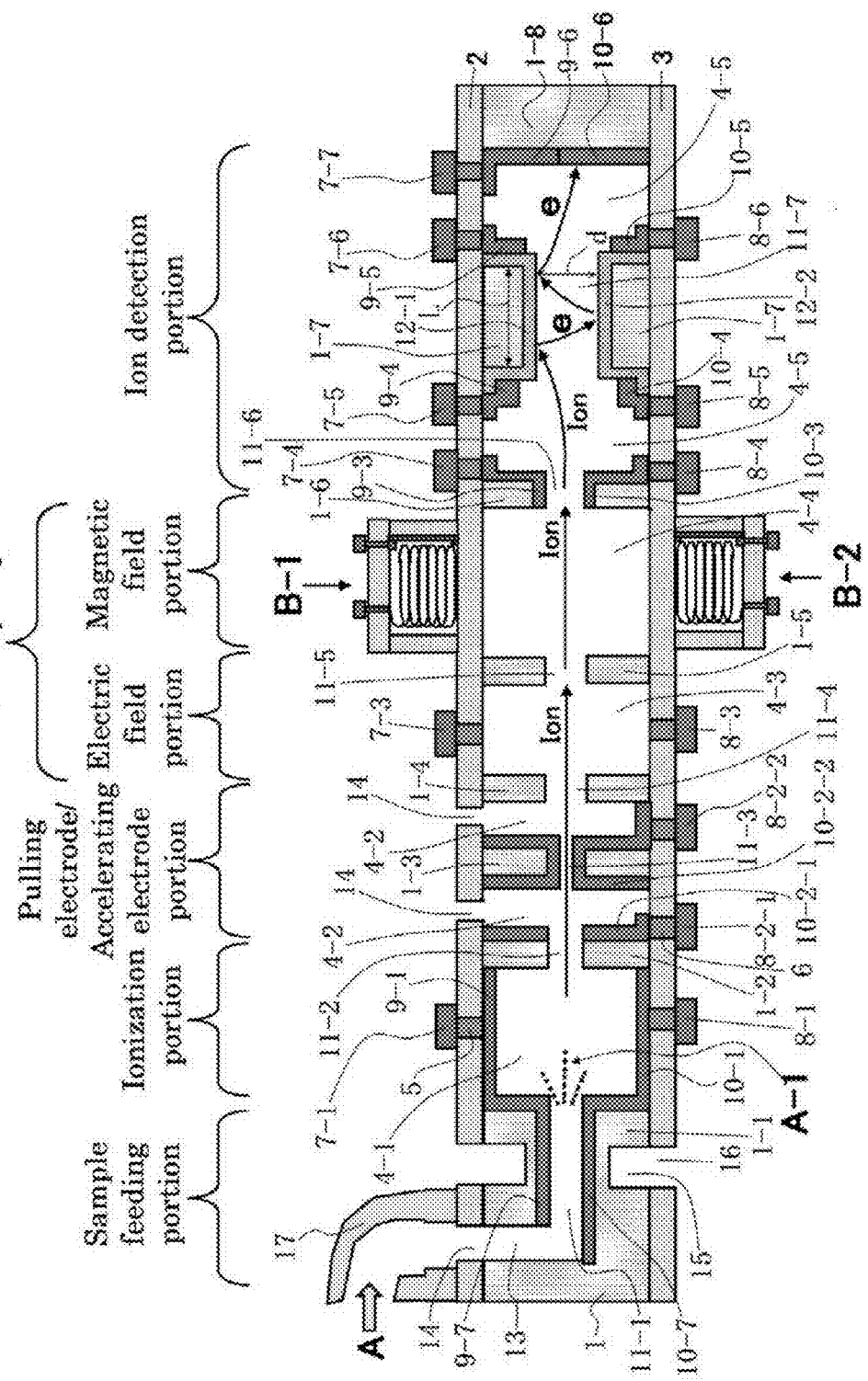
Figure 46:
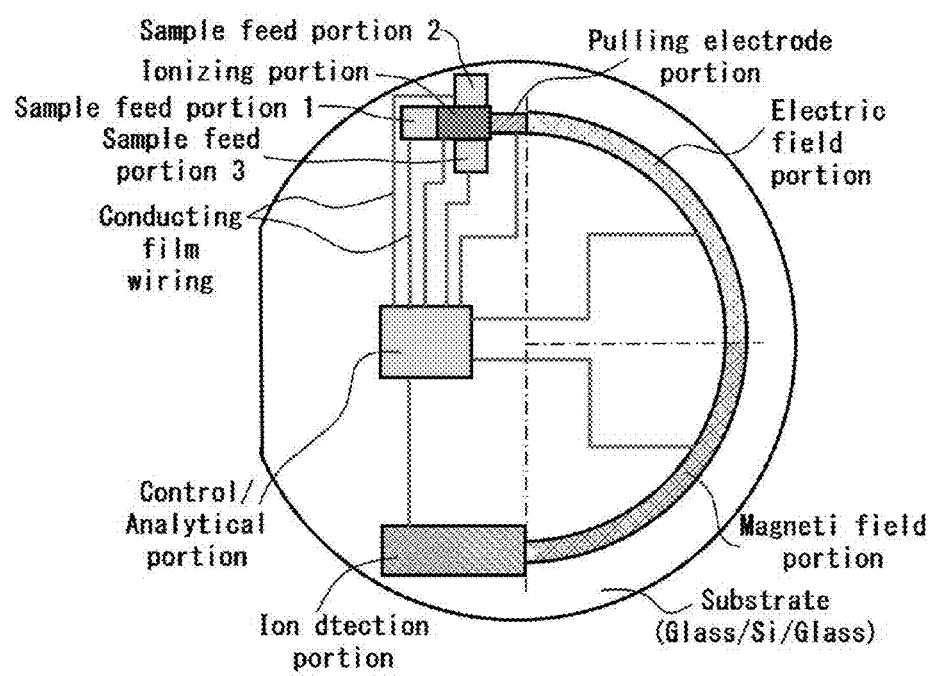

FIG. 45 shows one embodiment of the cross section (vertical direction to substrate surface) of the mass analyzer of the present invention, FIG. 46 is one sample of completed drawing of the final product (only main body) of the present invention.

Figure 47:
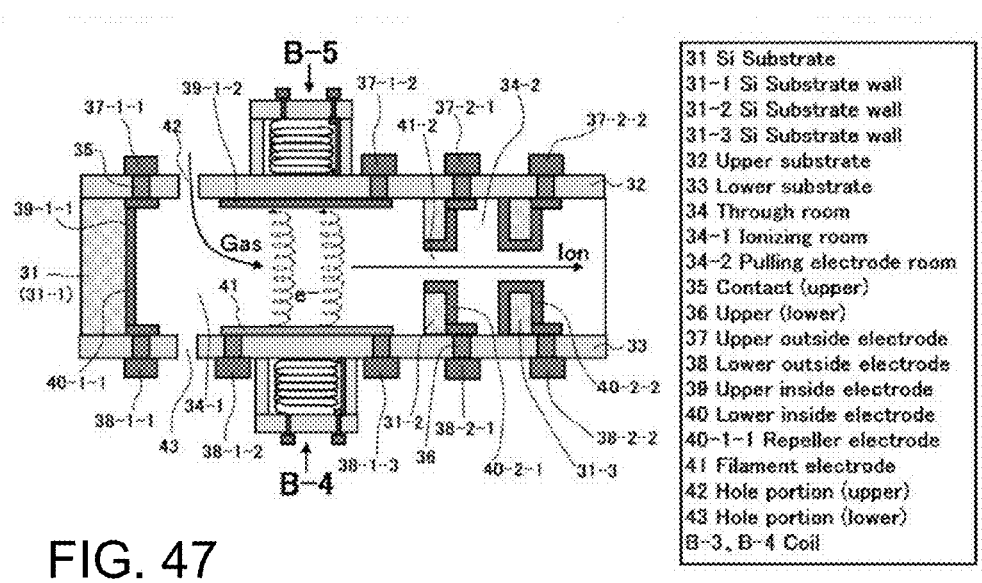

FIG. 47 I the diagram showing Electron ionization (EI) portion (cross section).

Figure 48:
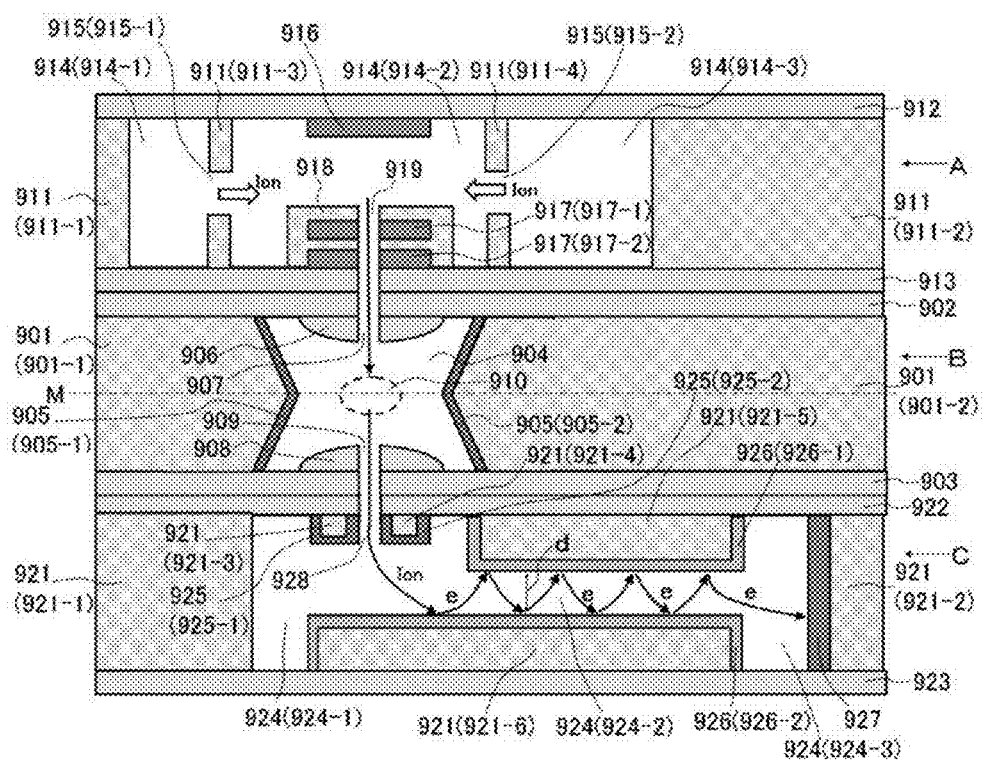

FIG. 48 is a view showing ion trap-type mass analysis device formed in the vertical direction.

EMBODIMENTS FOR CARRYING OUT THE INVENTION

In the present invention, a penetrated channel or a penetrated hole, which is written as "a penetrated cavity," is formed in a thickness direction of a substrate or a thin plate, which is a main substrate or a first substrate, the present invention is an accelerator in which charged particles such as electrons or ions, etc. move in the cavity at very high speed. A substrate or a thin plate, which is a second substrate, on the cavity is attached on the top surface of the both side wall of the first substrate, and a substrate or a thin plate, which is a third substrate, under the cavity is attached underneath the bottom surface of the both side wall of the first substrate. Accordingly, since the top and bottom of the cavity are surrounded by the second and third substrates, and the both sides of the cavity are sandwiched between the side walls of the first substrate, the cavity is a airtight space. A part of or all of the second substrate, and/or a part of or all of the third substrate and/or a part of or all of the both side walls of the first substrate are bored (or the hole is formed). Since gas, for example, air, oxygen, nitrogen, etc., in the cavity is exhausted from the portion bored or the hole, which is written as a vacuum transmission path, the cavity is in a low pressure state, for example, in a low pressure state near a vacuum state.

Since coils, electric magnets, and permanent magnets are disposed upper and/or under the cavity in a part of the cavity, electrons and ions, which is also called charged particles, passing the cavity accelerate and/or deflect by receiving force power by magnetic field that the coils, etc. generate. And/or since coils are disposed in the one side and/or other side of the cavity in a part of the cavity, the charged particle passing the cavity accelerate and/or deflect by receiving force power by magnetic field that the coils, etc. generate. And/or since electrodes are disposed upper and/or under the cavity in a part of the cavity, the charged particles passing the cavity accelerate and/or deflect by receiving force power by electric field that the electrodes generate. And/or since electrodes are disposed in the one side and/or other side of the cavity in a part of the cavity, the charged particle passing the cavity accelerate and/or deflect by receiving force power by electric field that the electrodes generate.

A cavity portion (or room) that generates the charged particle is formed in the first substrate, and after charged particles that are generated in the cavity portion pass a cavity path made in the first substrate, which is also called (a charged particle) cavity path, they can be also led to a cavity room in which the charged particles can be accelerated, which is called also (a charged particle) acceleration cavity room. Or, an external charged particle generator is connected to an inlet portion connecting to the outside of the mass spectroscope, which is called (a charged particles) (outside) inlet portion, in the cavity room made in the first substrate, which is also called (a charged particle) (external) cavity path, and the charged particles can be led to the acceleration cavity room or the cavity room in the main substrate. The charged particles moving in the acceleration cavity room go out of an outlet to discharge the charged particles, which is called (charged particles) discharged outlet, connecting the first substrate and the outside. The outlet to discharge the charged particles and the acceleration cavity room couple through a cavity formed in the first substrate, which is called (charged particles) discharge cavity. The charged particles accelerated can be applied in various purposes of medical application, analysis application, and product reforming application, etc., after discharging from Since the accelerator of the present invention, which is also called a substrate accelerator, can be made using a photolithographic technique, a laser patterning method, a mold forming method, a punching forming method, an imprint method, etc., the width and depth of the cavity in the accelerator, for example, 0.1-0.5 mm, 0.5-1.00 mm, 1.0-10 mm, 1-2 cm, 2-10 cm, or more than and equal to 10 cm, can be made very accurately, and the accelerator having various shapes such as a linear shape, a circle shape, an elliptical shape, a hyperbolic shape, or other curve shape can be made in desired dimensions. For example, in the case of the linear shape, many linear cavities are made in one substrate, and they are cut out in a longer direction of the cavity, for example, with a dicing method, and a linear accelerator of arbitrary length can be made by connecting the substrate cut out between the cavities. For example, the linear accelerator of various lengths such as more than 1 m, 10 m, 100 m, 1 km, or 100 km can be made.

For example, in the case that the first substrate is Si substrate, a width (side) of the acceleration cavity is 5 mm, a depth (vertical length) of the acceleration cavity is 5 mm, plural coils (length 10 mm) is disposed in the both sides of the acceleration cavity in the first substrate, and grass substrates with 0.5 mm thickness as the second and third substrates are attached to the first substrate above and under the acceleration cavity, and plural coils (length 20 mm) is disposed on the second substrate and underneath the third substrate, when the size of the first substrate is 500 mm×500 mm, or the first substrate is a circle wafer (the diameter is 500√12=707 mm) which can get the accelerator of same size, one linear accelerator is 500 mm in length, 10 mm (30 mm in the case of the accelerator containing the coils), and 6 mm in height (46 mm in the case of the accelerator containing the coils), and about 17 accelerators, of which each one is called unit accelerator, can be made from one substrate, which is the first substrate attaching the second substrate and the third substrate. For example, if 10 unit accelerators are coupled, since 5 m length accelerator can be made, 8.5 m length accelerator can be made form one substrate. Accordingly, one km length accelerator can be made using 118 substrates.

In the case of a circular accelerator such as ultra small accelerator made in one substrate, many circular orbits that are different in size (diameter) are made in one substrate, a cavity connecting between their circular orbits, which is also called a connection cavity, is made, and the charged particles increase speed in stages, they transfer the orbit corresponding to the speed, and after they are accelerated to final speed in the last orbit, which is usually the outermost orbit, they go outside the accelerator. In the present invention, since all of the cavities, coils, electrodes, etc. can be formed simultaneously in the same process, a number of the manufacturing process steps do not change regardless a number of circular orbits and the process cost is almost same. For example, when first circular orbit is 10 mm in radius and the width of the cavity is 5 mm, second circular orbit is 25 mm in radius, and third circular orbit is 40 mm in radius. And the orbit increases serially 25 mm in radius. When the circular acceleration is a concentric ring structure and the orbit of it increases serially 25 mm in radius, wherein all of the width of the cavities are 5 mm and the distance between the cavities is 10 mm, 16 circular orbits can be made in 500 mm circular wafer. These circular orbits are connected serially, and the charged particles are serially accelerated in each circular orbit. The charged particles circulate at a speed of 10 m/sec in the first small circular orbit, and they circulate at a speed of 4 times, namely 40 m/sec, in the next circular orbit. When the charged particles circulate at a speed of $10 \times 4^{n-1}$ m/sec in the nth circular orbit, they circulate at a speed of 100,000 km/sec in the final 16th circular orbit, that is, the speed of them can be ⅓ of a speed of a light. Accordingly, the super high speed charged particles can be generated in one wafer.

If the circular accelerator becomes large in size, it can be made by jointing the substrates like the linear accelerator. For example, if the circular accelerator is 1,000 mm in diameter and one substrate is 500 mm×500 mm in size, each of quarter circles are respectively made in 4 substrates, and each substrate of quarter circle can be jointed. When larger circular accelerate is made, for example, if the substrate of 1,000 mm×1,000 mm in size is used, about 100 substrates may be jointed.

In the present invention, the accelerator made in the substrate has the cavity such acceleration cavity in which the charged particles pass, the electrodes that generate electric field that accelerates, decelerates or deflects the charged particles, the coils or the electric magnets that generate magnetic field that accelerates, decelerates or deflects the charged particles. FIG. 1 shows an example of the embodiments of the ultra small particle accelerator of the present inventions. In FIG. 1, the ultra small particle accelerator is made in one substrate 9 and has a generator of the charged particles 11, a linear accelerator 13, various electric magnets 15, 17, 19, 21, 22, 23, 26, 28, 29, 31, 32, 35, 36, deflection electric magnets 25, 30, 34, 37, cavities passing the charged particles 12, 14, 16, 18, 20, 24, 27, 33, 38, 40, which are linear cavities, a linear accelerator 39. Since these are the examples, these can be omitted or added, or parts having other functions can be added.

The charged particles generating in the generator of the charged particles 11 pass the cavity 12 and accelerate in the linear accelerator 13, and pass the cavity 14 and deflect the trajectory with deflection electric magnet 15, and pass the cavity 16, and deflect and/or unspread the trajectory with deflection electric magnet 17, pass the cavity 18 and deflect the trajectory with deflection electric magnet 19, and pass the next cavity 20, and enter an accumulation ring 24 that is a cavity in which the charged particles pass in a circular accelerator 8 through an inflector 21. The speed of the charged particles entering the inflector 21 can be modulated by equipping a linear accelerator on the cavity 20. Also, other deflection electric magnets, acceleration electrodes, deflection electrodes, linear acceleration, etc. may be equipped on the way to enter from the generator of the charged particles 11 to the inflector 21. Also, the cavities themselves may be a linear accelerator.

The charged particles entering from the inflector 21 to the accumulation ring 24 of the circular accelerator 8 converge with a convergence electric magnet 22 (for horizontal direction) and a convergence electric magnet 23 (for vertical direction), and deflect and accelerate with a deflection electric magnet 25. And the charged particles enter to the next accumulation ring 27, and here furthermore accelerate with a high-frequency acceleration cavity 28, and converge with a convergence electric magnet 26 (for vertical direction) and a convergence electric magnet 28 (for horizontal direction), and deflect and accelerate with a deflection electric magnet 30. And next, the charged particles enter to the next accumulation ring 33, and here furthermore converge with a convergence electric magnet 31 (for vertical direction) and a convergence electric magnet 32 (for horizontal direction), and deflect and accelerate with a deflection electric magnet 34. And next, the charged particles enter to the next accumulation ring 38, and here furthermore converge with a convergence electric magnet 35 (for vertical direction) and a convergence electric magnet 36 (for horizontal direction), and deflect and accelerate with a deflection electric magnet 37, and enter to the accumulation ring 24. In this manner, after the charged particles keep rotating in the accumulation rings 24, 27, 33 and 38 with accelerating, and they becomes at a given speed, they enter a cavity 40 that lead outside charged particles, which is also called a charged particle ejection cavity, and they go out of a exit 41 of the charged particle ejection cavity. The charged particle ejection cavity may be additionally accelerated by a linear accelerator 39 equipped on the charged particle ejection cavity. Also, the other deflection electric magnets, acceleration electrodes, deceleration electrodes, linear accelerations, and convergence electric magnets are equipped on the charged particle ejection cavity.

As above explained, the accumulation rings 24, 27, 33 and 38 are a series of annular passages. Also, the holes, which are written above, are formed in the various cavities, and they connect to a vacuuming line, and the vacuuming line connects to a vacuum pump put outside, and a pressure of the cavities is reduced till the near vacuum pressure by the vacuum pump. In addition, since the various cavities has other holes, and inert gases such as nitrogen, He, Ar, etc. can enter to the cavities from the holes, the inside of the cavities can be cleaned and purged by their gases.

Figure 2:
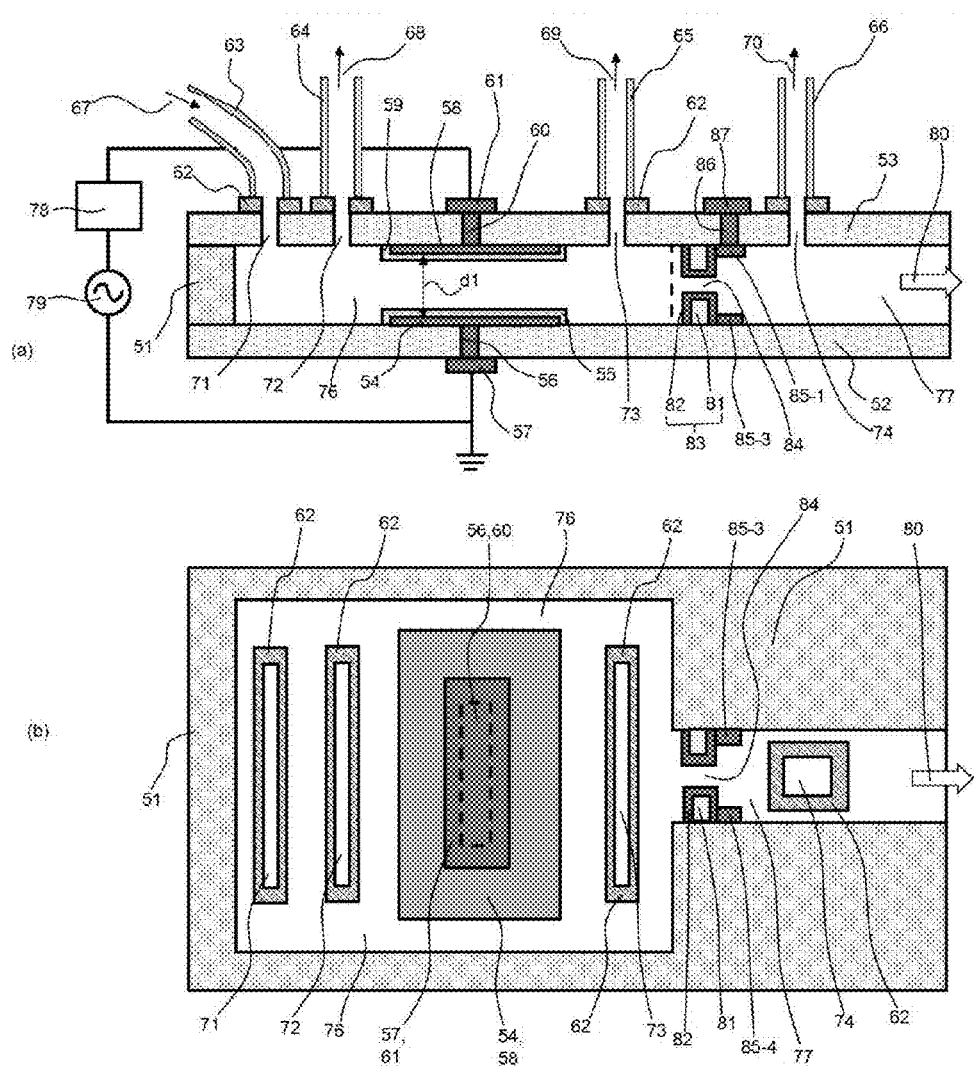
FIG. 2 shows one example of the generator of the charged particles.

As shown in FIG. 1, in the present invention, the generator of the charged particles 11 of electrons or ions is arranged in the main substrate (first substrate). One example of the generator of the charged particles 11 is shown in FIG. 2. The generator of the charged particles (ions) 11 shown in FIG. 2 is the generator of the ions that has parallel flat type of electrodes. FIG. 2(a) shows a cross sectional diagram in the vertical direction to the surface of the substrate, which is the direction of the thickness of the substrate. FIG. 2(b) shows a plan view. A cavity 76 that is a room to generate plasma, and a cavity 77 that is a room to lead charged particles such as electrons, protons, various kinds of ions, etc. to an accelerator, which is 13 shown in FIG. 1, to draw them are formed in the main substrate 51. The second substrate (upper substrate) 53 is attached on the top surface of the main substrate, and the third substrate (lower substrate) 52 is attached underneath the bottom surface of the main substrate.

The (lower) electrode 54 is formed on the top surface of the lower substrate 52, and au insulating film 55 such as silicon oxide film, silicon nitride film, silicon oxynitride film, etc. deposits and covers around the bottom electrode 54 as passivation film of the bottom electrode. The (upper) electrode 58 is formed on the bottom surface of the upper substrate 53, and au insulating film 59 such as silicon oxide film, silicon nitride film, silicon oxynitride film, etc. deposits and covers around the upper electrode 58 as passivation film of the upper electrode. These insulating films may not cover if the electrodes do not degrade even if they do not deposit. These electrodes 54 and 58 are patterned and disposed so as to oppose, and the second substrate 53 is attached on the top surface of the main substrate 51, and the third substrate 52 is attached underneath the bottom surface of the main substrate 51. A contact hole is opened in the lower substrate 52, and a contact electrode (conductive film) 56 is formed in the contact hole, in addition, an outside electrode 57 is formed underneath the other (bottom) surface of the lower substrate. A contact hole is opened in the upper substrate 53, and a contact electrode (conductive film) 60 is formed in the contact hole, in addition, an outside electrode 61 is formed on the other (top) surface of the upper substrate. These electrodes 57 and 61 are disposed outside when the upper and lower substrates 52 and 53 are attached on the main substrate 51, a matching circuit 78, and an alternate current or a high-frequency power source 79 are connected between these electrodes 57 and 61, and the one electrode is grounded.

A hole 71 to inlet gas (inlet gas hole), holes to exhaust gas 72, 73 and lower pressure (gas exhaust hole) in a room 76 to generate plasma (plasma generation room) are opened in the upper substrate 53, in addition, a gas exhaust hole 74 to exhaust gas and lower pressure in a cavity room 77 in the side of an accelerator is opened in the upper substrate 53. Sealing portions are formed on the top surface of the upper substrate 53 in the inlet gas hole 71 and the gas exhaust hole 72, 73, 74. Since these sealing portions connect to a line 63 to introduce gas (introducing gas line), a line 64, 65, 66 to exhaust gas (gas exhaust lines), these sealing portions are airproofed so that external gases such air, etc. do not enter into the plasma generation room 76 and the cavity room 77 from the outside (surrounding environment). Since the gas exhaust lines connect to vacuum pumps 68, 69, 70, the pressure in the plasma generation room 76 and the cavity room 77 are reduced till a given pressure (for example, 0.1 atm to 0.001 atm), and when a high-frequency voltage is applied to the upper and lower electrodes 54, 58 through the outside electrodes 57, 61, gas is plasma-ionized, or electrons generate, or ions generate in the plasma generation room 76, namely the charged particles generate For example, if argon (Ar) gas is introduced, argon ion (Ar+) and electrons generate. If methane (CH4) gas is introduced, various kinds of ions such as C−, CH+, CH2+, CH3+, CH+, etc., generate. If arsenic (As) gas is introduced, As+ and electrons, etc. generate. If the lower substrate 52 or the upper substrate 53 is not an insulating substrate, after an insulating film (for example, silicon oxide film, etc) is deposited on these substrates, electrode (conductive) films 54, 58 are deposited, and the electrodes 54, 58 are formed.

Since a distance d1 between the electrodes 54 and the electrode 58 is almost same as a thickness of the main substrate 51, which is precisely the thickness of the main substrate—the thickness of the upper and lower electrodes, if the thickness of the main substrate is 1 mm, since a high electric field of 1 kV/cm is applied between the upper and lower electrodes by applying 100V, a plasma can be generated at a low voltage. To apply higher electric field between the upper and lower electrodes, the thickness of the main substrate may be smaller. Or, if the (total) thickness of the main substrate cannot be smaller, to reduce d1 in only the place where the electrodes are disposed, the main substrate except the place is etched, and the electrodes are formed on the place, or the convex portion is made on the upper and lower substrates, the electrodes may be made on the electrodes.

The gas exhaust line 66 is connected to the cavity 77 of the side of the accelerator, and the line 66 is connect to the vacuum pump 70. The pressure of the cavity 77 is considerably low compared to that of the plasma generator room 76, for example, $10^{-9}$ atm-$10^{-12}$ atm. Accordingly a part of the plasma generating in the plasma generator room 76 are introduced into the cavity 77 of the side of the accelerator. Also, since the acceleration cavity is connected to the cavity 77 of the side of the accelerator, the charged particles are drawn to the cavity 77 of the side of the accelerator by the difference of the pressures between the plasma generator room 76 and the cavity 77 of the side of the accelerator. Though the plasma generator room 76 is written larger than the cavity 77 of the side of the accelerator in FIG. 2, since the plasma generator room 76 may has only the area to generate plasma, the cavity 77 of the side of the accelerator may be larger than the plasma generator room 76. In that case, since the pressure of the cavity 77 of the side of the accelerator is smaller than that of the plasma generator room 76, an opening and closing valve may be equipped between them, or a part of the pass between the cavity 77 of the side of the accelerator and the plasma generator room 76 may be narrow. Plasma flow 80 runs in the direction of an arrow 80, and it enters to the side of the accelerator.

A drawing electrode 83 may be disposed between the plasma generator room 76 and the cavity 77 of the side of the accelerator, and the ions generating in the plasma generator room 76 are drawn by the drawing electrode 83. The drawing electrode 83 has the structure where a compass of the side wall 81 of the substrate, which is also called a substrate side wall, in the main substrate 51, is covered with conductive film 82, and the substrate side wall has a central hole 84. Shown in FIG. 2(a) of the cross sectional diagram (elevation view) and FIG. 2(b) of the flat view, the substrate side wall 81 of the main substrate 51 is formed with overhanging inside the cavity 77 of the side of the accelerator, and has the central hole 84 in the center. Here, the central hole is formed near the center of the substrate side wall, and the shape of the central hole may be approximately circular shape, approximately elliptical shape, approximately square shape, approximately polygonal shape, their combination shape, or the other shape. Though their shapes had better be same, since they are formed by etch, etc., they are not necessarily the same shapes. (Here, a term "approximately" contains the meaning of "nearly" or "similarly.") Or, their shape may be changed optionally by characteristics of the ions. Also, though a center of the central hole is formed near the center of the substrate side wall. However, the center of the central hole may not be formed near the center of the substrate side wall by an ion orbit. Accordingly the center of the central hole can be formed in the optional position of the substrate side wall corresponding to the ion characteristics. (These can be adopted in the central holes of the substrate side wall in the whole of the specification of the present inventions.) Also, a conductive film wiring 85-1 is formed underneath the bottom surface of the upper substrate 53 (and on the top surface of the inner side in the cavity 77 of the side of the accelerator), and the conductive film wiring 85-1 connects to a conductive film 82. A conductive film 86 in a contact hole formed in the upper substrate 53 connects to the conductive film wiring 85-1, the conductive film 86 in the contact hole connects to the an outside electrodes and wiring 87 formed on the top surface of the upper substrate 53. As a result, a electric voltage to draw ions can be applied to the drawing electrodes 83 from the outside electrodes and wiring 87.

Though the electric voltage having a reverse electric charge opposite to the electric charge of ions is applied to the drawing electrode 83 in FIG. 2 to lead into side of the accelerator, since the drawing electrode 82 in FIG. 2 directly faces the ions, some ions accelerate thorough the central hole 84, but some ions impact the side surface of the drawing electrode 82. Accordingly an efficiency to draw ions may be poor. To resolve the poor efficiency, it can make ions easy to pass through the central hole by adjusting a hole size of the central hole 84. For example, the hole size is same as the size of the cavity 77 of the side of the accelerator, namely there is a case of only a surrounding electrode 85, which is the electrode and wiring 85-1 attached underneath the bottom surface of the upper substrate 53, a side surface electrode 85-2 of the main substrate 51, the electrode and wiring 85-3 on the top surface of the lower substrate, and an annular (rectangular and belt-like) electrode whose side electrode 85-1 of the main substrate 51 connects continuously, in the cavity 77 of the side of the accelerator without the substrate side wall 82. Or, the central hole is formed in the substrate side wall 81, and there is a case of forming the conductive film 82 on the central hole 84 that is optimized in size. Or, if a substrate side wall without a conductive film is made in the front of the drawing electrode 83, since a vertical electrode in the front surface of the drawing electrode 83 is shaded, ions can go in the direction of the central hole.

Or, there is a method shown in FIG. 9. FIG. 9 shows other embodiment to indicate a structure of another drawing electrode. FIG. 9(a) is a vertical cross sectional view, and FIG. 9(b) is a flat cross sectional view. In FIG. 9, there is a convergence electrode 89 between the electrodes 54, 56 to generate ions (ion generation electrode) in the front of the drawing electrode 89. The substrate side wall 81 of the drawing electrode 83 is almost vertical to the (substrate) surface of the upper and lower substrates 53, 52 and the main substrate 51, but the substrate side wall bevels in this embodiment. Namely the substrate side wall narrows gradually as it goes toward the cavity 77-2 of the side of the accelerator (right side of a cavity of the side of the accelerator across the substrate side wall 81), and it connects to the central hole 84 It can be said that the central hole 84 becomes gradually reduced in size as it goes toward the cavity 77-2 of the side of the accelerator. Also, when this portion is an entrance portion 88 of the cavity 77-2 of the side of the accelerator, the entrance portion 88 becomes gradually reduced as it goes toward the cavity 77-2 of the side of the accelerator. Inversely, it can be said that the central hole 84 becomes gradually increased in size as it goes toward the left side of the cavity 77-1 of the side of the accelerator (a cavity of the left side (the side of ion generation electrode) of the substrate side wall 81. In addition, when the exit of the plasma (ion) generation room 76 is larger in size than the entrance of the cavity 77 of the side of the accelerator, the shape of the exit portion 84 is formed so as to reduce gradually in size when viewed in a plane. (In FIG. 2, as shown in FIG. 2(b), the exit size of the plasma (ion) generation room 76 and the entrance size of the cavity 77 of the side of the accelerator change suddenly.) A conductive film electrode 89 is formed on the sloping surface of the main substrate in an entrance portion 88 of the cavity 77 of the side of the accelerator, the conductive film electrode 89 connects to a conductive film wiring 90 formed on the upper substrate or the lower substrate, and the conductive 90 film wiring 90 connects to the outside electrode 92 thorough a contact hole and a conductive film wiring 91 in the contact hole formed in the upper substrate 53 or the lower substrate 52.

The conductive film electrode 89 is formed with extending to the sloping surface of the main substrate (tilted as seen in plane) when in the exit portion of the plasma (ion) generation room 76. Also, the conductive film electrode 82 is formed on a part of the central hole and the side surface of the substrate side wall 81 of the cavity 77-2 of the side of the accelerator, and connects to the outside electrode 87. Since the conductive film 89 does not connect to the conductive film 82, different electric voltages can be applied from the outside electrodes 92 and 87. Namely, if a voltage of the same charge as the ions is applied to the conductive film 89, the ions can be converged to the middle of the cavity. Also, since a voltage of the reverse charge of the ions is applied to the drawing electrode 82, the ions is drawn to the drawing electrode 82 and accelerates, and enters to the neighbor the acceleration cavity 77-2 thorough the central hole 84 of the cavity 77-1. If the acceleration of the ions is small, other substrate side walls having a central hole can be formed in the acceleration cavity 77-2, an acceleration electrode is made by depositing on the substrate side walls, ions can be accelerated by the acceleration electrode, which may be called an electrostatic lens. If the acceleration of the ions is large, the electrostatic lens can change to the deceleration electrode by applying same voltage as the charge of the ions. Since many acceleration electrodes can be made in a short distance in the cavity and outside electrodes connecting to the acceleration electrodes can be made easily, the ions can go at the desired speed in the cavities of the side of the accelerator 77-1 and 77-2. In the structure shown in FIG. 9, ions are drawn to the cavities of the side of the accelerator 77 by the drawing cavity, ions are converged (focused to the middle side of the cavity) by the same charge as the ions applied in the exit portion and the entrance portion. Also, when the exit portion and the entrance portion are applied by the same charge as the ions and the ions rebel at the exit portion and the entrance portion, the number of ions that is pushed back from the exit portion and the entrance portion is small because the exit portion and the entrance portion narrow gradually. Accordingly many ions generated in the ion generation room 76 enter to the cavities of the side of the accelerator 77-2, and they go to the inner side of the accelerator in order to be accelerated.

Or, many ions can be introduced into the cavities of the side of the accelerator 77-2 by applying the larger reverse voltage to the drawing electrode 83 than the reverse voltage of the ions applied to the sloping electrode 89. Namely since the electric field becomes larger as ions 94 go, the ions 94 go with focusing in the middle of the cavity.

I explain about some processes to fabricate the plasma (ion) generator, the cavities of the side of the accelerator, the drawing electrode, and the acceleration (the deceleration) electrode shown in FIG. 2 and FIG. 9. Firstly, I explain about the process to fabricate the plasma (ion) generator, etc. that do not have a central holes. Conductive substrates (metal such as Cu, Al, Ti, Zn, etc., alloy of these metals, conductive C, conductive plastic, conductive ceramics, etc.), semiconductor substrates (Si, SiC, C, compound semiconductor such as GaN, GaAs, etc.), or insulators (plastics, glass, quarts, alumina (Al2O3), AlN, polymer, ceramics, etc.), these complex can be used as the main substrate (first substrate) 51. Though the optimal substrate is plastic, glass, quarts, alumina (Al2O3), AlN, polymer, ceramics, etc. as the upper substrate (second substrate) or the lower substrate (third substrate) because the contact hole is made inside, the same materials as the materials written in the main substrate 51 can be used.

A photosensitive film is adhered on the main substrate 51 by a coating method, a pasting method, etc., and the photosensitive film is patterned. The photosensitive film may be adhered after an insulating film or a material for an etching stopper or a film to improve an adhesion between the main substrate 51 and the photosensitive film is adhered. The main substrate 51 is etched and removed by masked with the photosensitive film patterned, and the penetrated room that is penetrated from the top surface to the bottom surface of the main substrate 51 is formed. The side surface of the penetrated room is preferably a nearly vertical shape that is small in a side etching to be made according to the dimensions. If the side etching can be controlled, it may not be a nearly vertical shape. If the main substrate 51 is Si substrate, appropriate heat treatment are performed and the given locations are opened with light exposure method after the surface of Si substrate is oxidized or nitrided, or insulating films such as SiO2 film, SiN film, etc. are deposited, or a photosensitive film sheet is adhered, the photoresist film is coated. The insulating film is vertically etched using the opened pattern, which is called anisotropic etching, and the substrate is vertically etched using the opened portion with various kinds of etching methods such as the anisotropic etching, DRIE (deep reactive etching), Bosh method, etc., as a result the penetrated room is formed in the main substrate 51. If conductive film pattern is formed inside the penetrated room, the process can be practiced here. If the main substrate is a semiconductor substrate or a conductive substrate, the conductive film is formed after an insulating film is formed on the surface of the substrate and the inside surface of the penetrated room. A photosensitive film is formed on the top surface and side surface of the main substrate 51 using a method to adhere a photosensitive film sheet, a method to coat a photoresist, an electrodeposition method of a photosensitive film, etc. Next, the photosensitive film in the top and side surface of the substrate is patterned by the light exposure method, in which an oblique exposure method, a light exposure equipment whose focus depth is deep, etc. are used. The desired conductive film pattern is formed using this photosensitive film pattern as a mask by etching the conductive film using a wet etching method or an isotropic dry etching method. After that, if necessary, an insulating film as a passivation film is formed on the conductive film pattern. Regarding a portion later connecting between the above conductive film pattern and the conductive films of the upper and lower substrates, the window of the conductive film in the connection portion is opened using the photolithographic process and etching process like the above. Next, to improve the connection between the above conductive film pattern and the conductive films of the upper and lower substrates, the window opening portion may be hilled convexly by a conductive film. As one method of the above, a conductive film is deposited once again, the conductive film is formed only the connection portion using the photolithographic process and etching process like the above, or a conductive film such as a metal, etc. may be selectively deposited on only the connection portion using a selective CVD method or a plating method.

A conductive film pattern, which becomes an electrode, is formed on the upper and lower substrates in advance. If the upper and lower substrates are insulating substrates such as glass substrates, quarts substrates, plastic substrates, etc., a conductive film can be deposited directly on the substrates, or after an insulating film is deposited in order to improve an adhesion, the conductive film may be deposited on the insulating film. A conductive film is, for example, Cu, Al, Ti, W, Mo, Au, Cr, Ni, conductive C, conductive Poly-Si, conductive plastic, conductive ceramics, etc., alloy, composite films, laminated film of these materials, etc. And we use CVD method, PVD method, plating method, coating method, screen printing method, combination of these method, etc. A photosensitive film pattern is made by the light exposure method, etc. using the photosensitive film after the conductive film are deposited, and a conductive film electrode and necessary wirings are formed by using the photosensitive film pattern as a mask. A dry etching and a wet etching can be used in the etching of the conductive film. After the conductive film pattern is formed, the passivation film, etc. may be formed by covering the conductive film pattern with the insulating film If the insulating film, etc. covers the conductive film pattern, regarding a portion later connecting between the above conductive film pattern and the conductive films of the upper and lower substrates, the window of the conductive film in the connection portion is opened using the photolithographic process and etching process like the above. Next, to improve the connection between the above conductive film pattern and the conductive films of the upper and lower substrates, the window opening portion may be hilled convexly by a conductive film. As one method of the above, a conductive film is deposited once again, the conductive film is formed only the connection portion using the photolithographic process and etching process like the above, or a conductive film such as a metal, etc. may be selectively deposited on only the connection portion using a selective CVD method or a plating method. After that, a contact hole and a conductive film in the contact hole may be formed, and a conductive film and electrode can be formed on the contact hole and other portion. Also, a gas inlet and a opening portion may be formed on the upper and lower substrates. These opening portions are formed using the dray etching or the wet etching.

Next, the upper and lower substrates are attached to the main substrate in which the penetrated room and the conductive film wiring pattern are formed while pattern aligning. A conductive adhesive agent, containing a low-temperature solder alloy, is adhered on the connection portion between conductive films, and their substrates can be adhered mutually. The given heat treatment makes the connection between substrates strong after the adhesion. In case of no adhesive agent, heat treatment at a temperature near melting point of the conductive film or a fusion bonding method can makes the connection between substrates strong. In the other location, the bond between the main substrate and the upper or lower substrates is performed using the adhesive adhesion, a room temperature bonding method, a diffusion bonding method, high temperature bonding method, etc. If the main substrate is a semiconductor substrate such as Si substrate, etc. and the upper and lower substrates are glass substrates or quarts substrates or alumina substrates, etc., they can bond mutually using an anodic bonding method. In case of using or not using the adhesive agent, after bonding their substrates mutually, a conductive film can be deposited in the connection portion by utilizing opening portions formed in the upper and lower substrates. In addition, since the conductive film is deposited in the conductive film portions that are not covered by the passivation film, etc., the connection can be absolutely practiced. For example, a quarts tube, a glass tube, a thermally resistant plastic tube, or a metal tube such as SUS, etc. is connected to the opening portions that are opened in the upper and lower substrates, and then a thermally resistant plastic packing may be used in the connection portion. Reactive gas (for example, WF6 gas) is introduced into the penetrated room of the main substrate from some opening portion, and the reactive gas is flowed in the penetrated room of the main substrate by drawing the gas from the other opening portions using a vacuum pump, and a conductive film (for example, W film) can be selectively deposited in the portions where the conductive film is exposed, for example, the connection portion between the conductive films. Also, a plating solution (Cu plating solution, various kinds of solder plating solution) is introduced through the tube, and a plating film can be deposited in the portions where the conductive film (Cu plating film, various kinds of solder plating film) is exposed, by conducting electricity from outside. After that, a bond of the connection portion becomes stronger by a given heat treatment.

In the above explanation, though a support substrate is not used in the formation of the penetrated room of the main substrate 51 in the above explanation, the penetrated room can be form using the support substrate. Particularly when the substrate deforms by a thermal stress, etc. after the penetrated room of the main substrate 51 is formed, the support substrate should be used. If the support substrate is removed later, a thermosoftening adhesive agent or a low-melting-point metal (or alloy), which is called an adhesive agent A, should be used regarding an adhesion of the support substrate and the main substrate. The penetrated room is formed in the main substrate by the above method after the main substrate and the support substrate are bonded. And then the support substrate is etched, but the amount of etching of the support substrate is small if a etching method that has a high etching selectivity is used. After that the deposition process of the insulating film, the conductive film and the passivation film, and their patterning process are same as the above process, but since the support substrate is removed, the formed film formed in the connection portion between the support substrate and the main substrate should be desirably removed by etching. Next, the upper and lower substrates are adhered using an adhesive agent, etc., to the main substrate that the penetrated rooms are formed while aligning patterns. If the adhesive agent, etc., which is called an adhesive agent B, are used, the adhesive, etc. agent need be selected so that the upper and lower substrates and the main substrate can not be removed at the temperature the support substrate is removed. For example, the adhesive agent B may be a thermosetting adhesive agent of which a curing temperature TB is lower than the softening temperature TA of the adhesive agent A or the melting point of the metal A. Or, if the adhesive agent A is the adhesive that is peeled off by light and the adhesive agent B is the thermosetting adhesive, after the upper or lower substrate is adhered to the main substrate, the support substrate can be removed from the main substrate by light illumination. After that, the other substrate (the lower substrate or the upper substrate) is adhered to the main substrate.

Instead of the support substrate, the upper substrate or the lower substrate can be firstly adhered to the main substrate. After the upper substrate is adhered to the main substrate, the patterns and the penetrated rooms in the main substrate are formed. And then, the etching conditions having a high selectivity should be preferably selected so that the upper substrate is not etched so much. After the penetrated rooms are formed, the insulating film, the conductive film and the passivation film are deposited, and these films are patterned. And then, for example, since the electrode and wiring need to be also formed in the upper substrate, photosensitive patterns are formed using a photosensitive sheet technology, electrodeposition resist technology, a rotation exposure technology, a slanted exposure technology, etc., and the patterns of the conductive film, etc. are formed with the wet etching or the dry etching. After that, the upper substrate or the lower substrate on the patterns in which the electrode and wiring are formed is adhered to the main substrate.

In the above process, the electrodes and wirings are preliminarily made in the upper substrate, and a concave portion, which doe not accord with the patterns of the upper substrate when the main substrate is adhered to the upper substrate, is preliminarily formed in the main substrate. The upper substrate is adhered to the main substrate by aligning the concave portion of main substrate with the pattern of the upper substrate. After that, the penetrated rooms are formed in main substrate. And then since the patterns of the electrodes and wirings are already formed in the upper substrate, the penetrated rooms are formed by the etching conditions in the patterns of the electrodes and wirings are not (or not so much) etched. For example, if the main substrate is Si substrate, Si can be etched at high speed with CF-based gases, and then if the electrodes and wirings of Al or Cu, etc. are formed in the upper substrate, we can select the etching conditions in which these materials are not almost etched. After that, after the insulating film is formed and the conductive film is formed, the patterns of the conductive film on the side surface of the main substrate can be formed. The conductive film is formed in the upper substrate, but since the photosensitive film is not covered on the upper substrate, the conductive film on the upper substrate can be etched, and since the patterns f the electrode and wiring on the upper substrate that are already patterned are covered by the insulating film, their patterns are not etched. If the electrode and wiring on the upper substrate connect to the conductive film on the main substrate, after the insulating film is deposited, the insulating film in the connection portion may be removed by patterning. After that since the conductive film is deposited, it is possible to connect enough in the connection portion. Or, all or almost of the insulating film on the electrode and wiring of the upper substrate may be removed. When the conductive film is patterned, the pattern of the conductive film may be patterned repeatedly on the electrode and wiring of the upper substrate.

Next, we explain about how the central holes should be formed in the substrate side wall of the main substrate. The main substrate is divided in the direction of a thickness of the substrate. For example, the main substrate having a half thickness of the main substrate can be used, which the substrate is called a half main substrate. Firstly a pattern to form the central hole is formed. And then the insulating film, etc. is formed on the half main substrate, the film to improve the adhesion between the half substrate and the photosensitive film, and a film as the mask for the etching stopper (so that the half main substrate is not etched when the photoresist is etched and dispersed) may be formed. The central holes are formed using their patterns. If the central holes are formed with a curve, we use the side etching by the wet etching or the (isotropic) dry etching. If the central holes are vertical formed, we use the anisotropic etching. Next the patterns of the penetrated substrates and the substrate side walls (containing the central holes) are formed. If the vertical patterns and the sloped patterns as shown in FIG. 9(a) are mixed in the side surface of the (half) main substrate, their patterns are formed by the different processes. Furthermore in case of patterns having multiple angles of gradient, their patterns are formed differently, the vertical etching, the skewed etching 1, the skewed etching 2, . . . , are performed separately. If a part of the (half) main substrate is left, their processes are performed in the same way. Basically the penetrated rooms are formed in the (half) main substrate. At a result, the (half) central holes, the (half) substrate side walls having the (half) central holes, and the (half) penetrated rooms are formed in the half main substrate. The size of the (half) central holes can be changed optionally by the etching conditions. Also the skewed angle can be selected optionally by the etching conditions. A skewed pattern of the exit portion in the plain direction shown in FIG. 9(b) can be changed optionally. Accordingly, the optional desired shapes can be made. After that, the insulating film is formed, and the conductive film is formed, and the conductive film patterns can be formed. In case of the half main substrate, since the height is half of that of the main substrate, the formations of the various films and their patterning are easy. The insulating film and the conductive films can be formed in the central holes, and they can be etched and removed. Since LSI processes are used in the present invention, the size of the substrate side walls and the penetrated rooms can be formed very accurately. The conductive film patterning is difficult in the deep place in the penetrated rooms, but since it is possible to manufacture the penetrated room to an accuracy of 1 μm-10 μm, there are no problems in the accuracy of the present accelerator.

Two same half main substrates are made, (in the case that their shapes are symmetry in the upper and lower structures, but of course it is easy to make non-symmetrical structures), and they can be adhered so that their central holes are fit each other. The adhesion methods like the above can be used in this process. Furthermore if the electrostatic anode bonding technique is used, the thin glass substrate or the thin quarts substrate, etc, can be used by sandwiched between the two half main substrates. The penetrated rooms, the substrate side walls, the central holes, and the conductive film in the needed portions are formed in same size in the glass, etc, substrates, and the glass, etc. substrate may be adhered to the two half main substrates sequentially or at the same time. The support substrate can be used and adhered to the half main substrate. For example, after the (upper) half main substrate attached to the support substrate is adhered to the upper substrate, the another (lower) half main substrate is adhered to the upper half main substrate, and the support substrate attached to the upper half main substrate is removed, finally the lower substrate is adhered to the lower half main substrate. Or, after the upper half main substrate is adhered to the upper substrate, the support substrate is removed, and after the lower half substrate is adhered to the lower substrate, the support substrate is removed, and the upper main substrate and the lower main substrate can be adhered each other with intermediating them. Finally the contact holes, the conductive film inside the contact holes, and the outside electrodes can be formed. Or these contact holes and outside electrodes are formed preliminarily can be formed in the upper and lower substrates.

Furthermore if the penetrated rooms become deeper in depth, the above processes may be performed repeatedly. If many substrates having the same structures are made at the same time, and they are stacked and adhered, the deep penetrated rooms in depth can be easily made without prolonging the process. For example, if the main substrates having a thickness of 0.5 mm-1 mm are adhered serially, the accelerator having the penetrated rooms having a thickness of 8 mm-16 mm can be made by 4 times adhesions.

Figure 3:
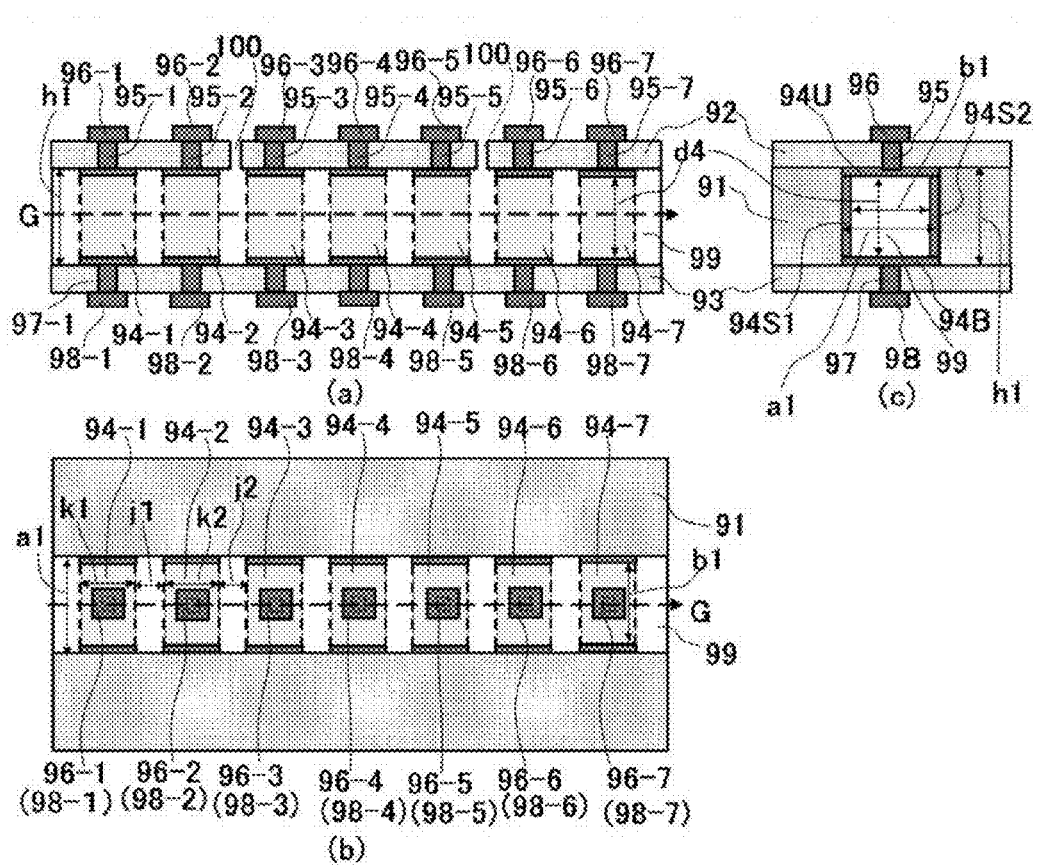
FIG. 3 shows a structure of the linear accelerator of the charged particles.

<Other plasma generation technologies> FIG. 3 shows a structure of the linear accelerator of the charged particles. The structure can be used in 13 or 39 in FIG. 1. Also, the structure can be used as a single linear accelerator. FIG. 3(a) shows a cross sectional structure diagram in the direction of thickness of the substrate, which direction is a traveling direction of the acceleration cavity 99, namely a traveling direction of the charged particles G, wherein the second substrate (upper substrate) 92 is attached to the top surface of the main substrate 91, and the third substrate (lower substrate) 93 is attached to the bottom surface of the main substrate 91. FIG. 3(b) shows a plan view that is parallel to the substrate surface. FIG. 3(c) shows a cross sectional structure diagram in the direction of thickness of the substrate, which direction is a vertical direction to the traveling direction of the acceleration cavity 99, namely the traveling direction of the charged particles G.

Since the upper portion of the penetrated room 99 (width a1) formed in the main substrate (first substrate) 91 (thickness h1) is covered by the second substrate (the upper substrate) 92, and the bottom portion the penetrated room 99 is covered by the third substrate (the lower substrate) 93, the acceleration cavity 99 that the charged particles G pass in the accelerator becomes an airtight space. Many annular electrodes 94 (94-1, 2, . . . ), which are the electrodes that connect continuously (electrically) electrode formed on the side wall and the bottom surface of the upper substrate and the top surface of the lower substrate in the penetrated room 99, are formed apart in a longer direction, which is a traveling direction of the charged particles G, in the acceleration cavity 99. For example, conductive electrodes 94S1 and 94S2 are formed on the side wall of the penetrated hole (room or cavity) 99 in the penetrated room 99 of depth h1 and width a1, furthermore a conductive electrode 94U is formed on the bottom surface of the upper substrate 92, and a conductive electrode 94B is formed on the top surface of the lower substrate 93, these conductive electrodes 94S1, 94S2, 94U and 94B are connected electrically and continuously. The length of the conductive electrode 94-1 (in the long direction of the acceleration cavity 99) is k1, the accurate shape of the conductive electrode 94-1 is rectangular. If the thickness of the conductive electrode is t1, the distance b1 between the conductive electrodes 94S1 and 94S2 is a1-2t1, the distance d4 between the conductive electrodes 94U and 94B is h1-2t1. For example, if ai=1 mm, h1=1 mm, and the thickness of the conductive film is 10 μm, bi=0.96 mm, di=0.98 mm.

Since the annular electrode 94-2 having a length of k2 is formed apart with a distance of j1 in the neighbor of the annular electrode 94-1, and the annular electrode 94-3 having a length of k3 is formed apart with a distance of j2 in the neighbor of the annular electrode 94-2, many annular electrodes 94 are formed in the acceleration cavity 99. In the traveling direction of the charged particles G, a length of ith annular electrode 94-$i$ is ki, and a distance between the ith annular electrode and the (i+1)th annular electrode 94-$i$+1 next to the ith annular electrode 94-$i$ is j1. The contact holes are formed in the upper substrate 92 above the annular electrodes 94 (94-$i$: i=1, 2, ... ), and the contact electrodes 95 (95-$i$: i=1, 2, ... ) are formed in the contact holes, and the upper electrodes 96(96-$i$: i=1, 2, ... ) are formed, as a result the upper electrodes 96 connect electrically to the conductive electrodes 94U formed on the bottom surface of the upper substrate 92. Also, the contact holes are formed in the lower substrate 93 corresponding to the annular electrodes 94 (94-$i$: i=1, 2, ... ), and the contact electrodes 97 (97-I: i=1, 2, ... ) are formed in the contact holes, and the lower electrodes 98(98-$i$: i=1, 2, ... ) are formed, as a result the lower electrodes 98 connect electrically to the conductive electrodes 94B formed on the top surface of the lower substrate 93.

A electric voltage can be applied to the respective electrode of the annular electrodes 94 (94-$i$) formed on the inner surface of the main substrate 91 in the penetrated cavity 99 from the outside electrodes 96 (96-$i$) and 98 (98-$i$) formed on the upper and lower electrodes, but their outside electrodes 96 (96-$i$) and 98 (98-$i$) may be either. Accordingly the electric potentials of the annular electrodes 94 (94-$i$) become same effectively and rapidly by being applied to their electrodes at the same time. If the voltage having a reverse potential of the ions G is applied to the respective electrode of the annular electrodes 94 (94-$i$), the ions G can travel with accelerating by the voltage Vi of the respective electrode of the annular electrodes 94 (94-$i$). For example, if m=10-25 kg, z=1. and V=10V, $\Delta$ui=5.6 km/sec, which is a velocity per one electrode. Accordingly if ten thousand electrodes are disposed linearly, the final velocity of the ions G is 56,000 km/sec. Namely if ki=10 μm, ji=5 μm, the acceleration cavity having a length of 15 cm may be made. Like this, super high speedy ions can be made in the very short distance. But since the ions may be spread by be also drawn by the annular electrodes, the ions need be also converged. The electrodes of which voltage having the same potential as the ions is applied must be disposed so that the ions are converged, or a quadruple magnetic field may be applied. Ions having the desired velocity can be obtained by combining them. Also, the acceleration cavity room shown in FIG. 3, since one of plural of opening portions are opened in the upper substrate 92 and/or the upper substrate, the acceleration room 99 is vacuumed through the opening portion 100, or the inert gases, etc. are introduced in the inside of the acceleration room 99 and the inside can be cleaned and purged.

Plural substrate side walls having the central hole may be disposed in the acceleration cavity room. FIG. 10 shows the acceleration cavity room in which plural substrate side walls having the central hole are disposed. FIG. 10($a$) is a cross sectional diagram that is vertical to the substrate surface, and FIG. 10($b$) is a plan view that is parallel to the substrate surface, and FIG. 10($c$) is a cross sectional diagram of A1-A2, and the diagram that is seen from a right and left direction in FIG. 10($a$) and FIG. 10($b$). As shown in FIG. 10, the penetrated room 104, which is penetrated from the top surface to the bottom surface in the main substrate 101, is formed, the upper substrate 102 is adhered over the penetrated room 104, the lower substrate 103 is adhered under the penetrated room 104, the lateral side surface of the penetrated room 104 is the side surface of the main substrate 101. The charged particles G, such as ions, etc., which is indicated by the dashed arrow, that generates in the penetrated room 104-1 such as a plasma generation room or ions generation room pass through the central hole 105-0 made in the center portion of the side wall 101-0, and enter to the acceleration cavity room 104-2 that is the penetrated room. Plural substrate side walls 101-1 (101-1, ... , 4, ... ) having the central holes 105 (105-1, ... , 4, ... ) are disposed in the acceleration cavity room 104-2. The conductive film electrodes 106 (106-1, ... , 4, ... ) are formed around the substrate side walls 101-1 (101-1, ... , 4, ... ). The conductive film electrodes 106 (106-1, ... , 4, ... ) are also deposited on the inner surface of the central holes 105 (105-1, ... , 4, ... ) in the substrate side walls 101-1 (101-1, ... , 4, ... ). The conductive film electrodes 106 (106-1, ... , 4, ... ) connect to the conductive film wirings 107 (107-1, ... , 4, ... ) formed on the bottom surface of the upper substrate 102, and/or connect to the conductive film wirings 108 (108-1, ... , 4, ... ) formed on the top surface of the lower substrate 103. The conductive film wirings 107 (107-1, ... , 4, ... ) connect to the outside electrodes and wirings 110 (110-1, ... , 4, ... ) formed on the upper substrate 102 through the contact holes and the contact wirings 109 in the upper substrate 102. Also, the conductive film wirings 108 (108-1, ... , 4, ... ) connect to the outside electrodes and wirings 112 (112-1, ... , 4, ... ) formed on the lower substrate 103 through the contact holes and the contact wirings 111 in the upper substrate 103.

A voltage can be applied to the substrate side wall electrodes and wiring 106 from the outside electrodes and wiring 112. Since the voltage is usually the reverse voltage to the electric charge of the charged particles, the charged particles G entering to the acceleration cavity room are drawn and accelerated by the first substrate side wall electrode and wiring 106-1, and pass through the central hole 105-1 of the substrate side wall, and next the charged particles G are drawn and accelerated by the second substrate side wall electrode and wiring 106-2, and pass through the central hole 105-2 of the substrate side wall, and they are accelerated repeatedly, they are drawn and accelerated by the final substrate side wall electrode and wiring 106-$n$, (namely when the number of substrate side wall electrodes is n), they pass through the central hole 105-2 of the substrate side wall, and they go out to the neighbor penetrated room 104-3. The neighbor penetrated room 104-3 is, for example, the cavity room 14 or the deflection electric magnet room 15, etc. in FIG. 1. The substrate side wall 101-5 having the central hole 105-5 is disposed between the acceleration cavity room 104-2 and the neighbor penetrated room 104-3, and the charged particles pass through the central hole 105-5, and enter to the neighbor penetrated room 104-3. Since the area that the charged particles pass is narrow in the substrate side wall electrode having the central hole, the charged particles G pass near the center without spreading so much. But since a part of the charged particles draw to the side of the electrode, the charged particles may be preferably converged by applying the voltage of the same potential (plus or minus) as the charged particles in some places. The charged particles are decelerated if the potential there is same as the potential of the charged particles, but they are accelerated in the next acceleration electrode. While the convergence and the spread, acceleration and the deceleration, are repeated, the charged particles can be much accelerated as a whole by disposing many substrate side wall electrodes having the central hole. Since LSI process is used in the present invention, the very small central holes and the very short substrate side wall, which can not be made by the conventional techniques, can be used. Accordingly many substrate side wall electrodes can be disposed in the short distance, and the charged particles can be accelerated till very high speed in the short distance. Furthermore since the applied voltage can be small, a large electric source need not be used. But since the high voltage can be also applied using the large electric source, the charged particles can be much accelerated in such case.

Also, since the voltage can be applied gradually to the respective substrate side wall electrode in the travelling direction of the charged particles G, a large acceleration can be obtained in the short distance and at the short time. Or if a high-frequency voltage is applied to the respective substrate side wall electrode and the respective substrate side wall electrode is synchronized, a large acceleration can be obtained. If the opening portion 113 is opened in the upper substrate or in the lower substrate in the acceleration cavity room 104-2, a vacuuming and a cleaning and a purging can be performed. Also, since the opening portions 113 can be respectively opened between the respective substrate side walls, the respective rooms can be vacuumed.

If the substrate side wall 101-0 or 101-5 between the neighbor rooms is not needed, it may not be disposed. For example, there is a case where any problems do not occur when the charged particles impact the front side surface of the first substrate side wall electrode 106-1, there is a case where the pressure of the penetrated room 104-2 may be same as that of the neighbor room 104-1, there is a case where the charged particles can pass through the central hole 105-1 of the first substrate side wall electrode 106-1 since they are enough accelerated and converged. Also, if the size of the central hole 105-0 of the first substrate side wall 101-0 is smaller than the size of the central hole 105-1 of the first substrate side wall electrode 106-1, the charged particles can be easier drawn by the first substrate side wall electrode 106-1. But if the central hole 105 (105-1, . . . ) of the first substrate side wall electrode 106 (106-1, . . . ) are same, the acceleration of the charged particles can be preferably uniformed. If the size of the central hole 105-5 of the substrate side wall 101-5, which is a partition between the penetrated room 104-2 and the neighbor room 104-3, is smaller than the size of the central hole 105 (105-4 in FIG. 10) of the final substrate side wall electrode 106 (106-4 in FIG. 10), the charged particles can preferably try not to impact the substrate side wall 101-5.

Figure 4:
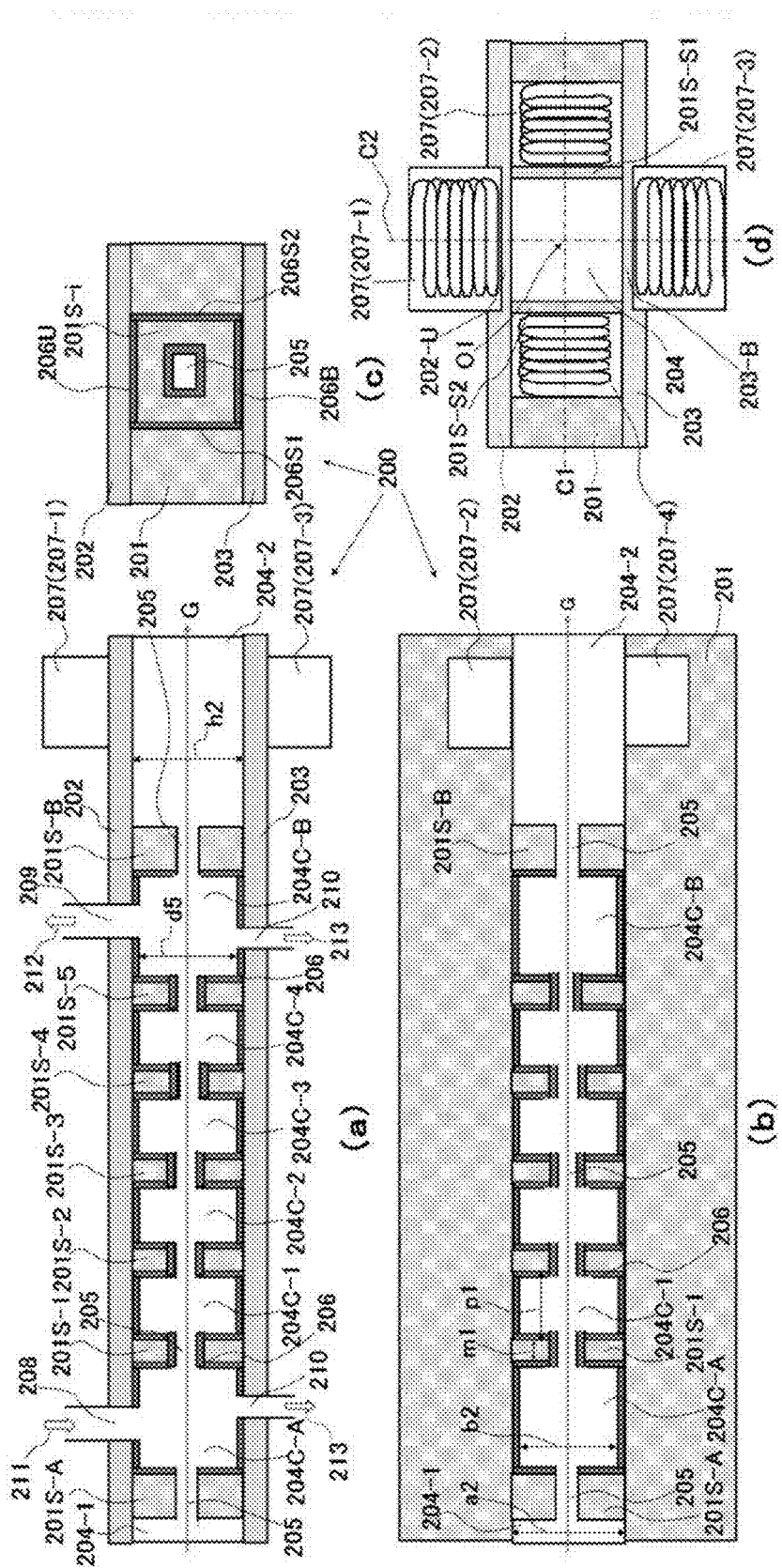
FIG. 4 is a diagram showing an example of an acceleration tube of the charged particles using a high frequency waveguide.

FIG. 4 is a diagram showing an example of an acceleration tube of the charged particles using a high frequency waveguide. FIG. 4(a) is a cross sectional diagram vertical to the substrate surface and the diagram parallel to the travelling direction of the charged particles beam G, and FIG. 4(b) is a cross sectional diagram parallel to the substrate surface, and FIG. 4(c) is a cross sectional diagram vertical to the substrate surface and the diagram seen from a right and left direction of FIG. 4(a) and FIG. 4(b) and a cross sectional diagram of the central hole. The acceleration tube of the charged particles shown in FIG. 4 is formed in a main substrate 201. It is constructed mainly from a penetrated cavity room 204 that is formed in the main substrate 201, which is a path of the charged particles, and an upper substrate 202 and an lower substrate 203 that are adhered to the main substrate 201, which make the penetrated cavity room 204 an airtight space. In the travelling direction of the charged particles G, which is the longer direction in the penetrated room, the both sides of the acceleration tube 200 of the charged particles are partitioned by a substrate side walls 201S-A and 201S-B of which a hole is opened in the center portion, which is a central hole. There are plural spaces partitioned by substrate side walls 201S-i (i=1, 2, 3, . . . ) of which a hole is opened in the center portion, which is a central hole, between the side walls 201S-A and 201S-B. In the both sides of the spaces, there is a space 204C-A in which an inlet 208 to introduce a high-frequency wave such as a microwave, etc. is opened in the upper substrate 202, which may be opened in the lower substrate, which is also called a high-frequency wave introducing room, and there is a space 204C-B in which an outlet 209 to discharge the high-frequency wave such as a microwave, etc. is opened in the upper substrate 202, which may be opened in the lower substrate, which is also called a high-frequency wave discharging room, and there are plural spaces 204C-i (i=1, 2, 3, . . . ), which is also called acceleration cavity, to accelerate the charged particles between the high-frequency wave introducing room and the high-frequency wave discharging room. Also, vacuum exhaust openings 210 are opened in some locations in the supper substrate 202 and the lower substrate 203, and connect to the vacuum pump 213, at a result, the pressure of the space in which the charged particles pass becomes a state near vacuum. The vacuum exhaust openings are opened in the high-frequency wave introducing room or the high-frequency wave discharging room in FIG. 4, but not limited to these, they may be opened in other space room or cavity.

If a semiconductor substrate such as a silicon substrate, etc. is used as the main substrate used in the present invention, since the electric resistance of the main substrate is high, the conductive film 206 is formed inside many penetrated cavity 204 in the acceleration tube 200 of the charged particles. Namely, in the cavity 204 formed in the main substrate 201, the conductive films 206S1 and 206S2 are formed on the side surface of the cavity of the main substrate 201, the conductive film 206U is formed on the bottom surface of upper substrate 201, the conductive film 206B is formed on the top surface of lower substrate 203. Since FIG. 4(c) is the cross sectional diagram in the central hole 205, the conductive films 205S1, S2, U, and B can not be seen, but the diagram is drawn transparently. The central hole 205 is disposed in the center of the substrate side wall 201S-i (i=1, 2, . . . ), and the conductive film is formed annularly on the inside surface of the central hole 205. A cross sectional shape of the central hole 205 is written rectangularly or squarely, but since the central hole 205 is formed using an etching technique (wet or dry) in the state where the main substrate 201 is divided, the shape is formed in the shape which the trapezoids are fitted with the upper and lower, and in the circle shape, various shapes.

Since a high-frequency current is flowed in the inside wall of the acceleration cavity 204C-i (i=1, 2, 3, . . . ), the conductive property of the conductive film 206 had better be lower, for example, the conductive film may be preferably Cu, Au, Ag, Al, W, Co, etc. If the temperature used may increases, the conductive film may be preferably a refractory metal. Since the acceleration tube of the charged particles of the present invention can be smaller in size, the whole equipment can be cooled at low temperature by using a superconducting material as the conductive film. For example, Nb, Nb—Ti, Nb—Sb, magnesium diboride, and superconducting oxide (for example, Y series, Bi series, etc.)

are used. These can be formed as a sputter film or a coating film. If the main substrate 201 is h2 in thickness and a2 in lateral width (plane surface width) and the conductive film 206 is t2 in thickness, the depth d5 of the penetrated cavity 204 is h2-2t2, and the lateral width b2 is a2-2t1. If the insulating film (for example, silicon oxide film, silicon nitride film, or silicon oxynitride film) or the film to improve the adhesion (for example, Ti, TiN film) is formed between the main substrate 201 and the conductive film 206 and the insulating film (as a passivation film) is formed on the conductive film 206, the film thickness of them must be considered.

If a cavity is formed in the substrate so that the cavity surrounds the acceleration cavity, the cooling liquid can be flowed in the cavity. The charged particles G are discharged from the charged particles generation cavity, etc. and pass the inside of the cavity 204-1, and they enter to the charged particles acceleration tube 200 through the central hole 205 of the substrate partition (side) wall 201S-A that is an entrance of the charged particles acceleration tube 200. After the charged particles G enter to the high-frequency introducing cavity 204C-A, they enter to the acceleration cavity 204-1 through the central hole 205 of the substrate partition (side) wall 201S-1, and they enter to the acceleration cavity 204C-i (i=1, 2, 3, . . . ) through the central hole 205 of the substrate partition (side) wall 201S-i (i=1, 2, 3, . . . ). And after the charged particles G finally enter to the high-frequency discharging cavity 204C-B, they pass the central hole 205 of the substrate partition wall 201S-B that is an exit (outlet) of the acceleration tube 200 the charged particles, and they go out to the cavity 204-2 outside the acceleration tube 200 the charged particles. A high-frequency wave 211 enter to the high-frequency introducing cavity 204C-A from the high-frequency introducing inlet 208, and they pass the central hole 205 of the respective substrate partition wall, and it forms a high-frequency electric field that accelerates the charged particles in the respective acceleration space (cavity) 204C-i (i=1, 2, 3, . . . ), and it enters to the high-frequency discharging space (cavity) 204C-B, and it goes out of the high-frequency discharging outlet 209, as the high-frequency wave 212. Accordingly the charged particles are accelerated in succession by the acceleration electric field that is generated in the respective acceleration space (cavity) 204 C-i (i=1, 2, 3, . . . ), and they go out of the acceleration tube 200 of the charged particles through the central hole 205 of the substrate partition (side) wall 201S-B.

A convergence electric magnet 207 to converge the charged particles accelerated and expanded can be disposed in the acceleration tube 200. The convergence electric magnet 207 is put in the portion of the cavity 204 after the charged particles go out of the central hole 205 of the substrate partition wall 201S-B. For example, quadrupole electric magnets 207 (207-1, 2, 3, 4) are disposed around the cavity 204 as shown in FIG. 4. FIG. 4(d) shows the cross sectional structure vertical to the longer direction of the cavity 204 in the place where the quadrupole electric magnets are disposed. A coil 207-2 and a coil 207-4 are disposed so that they sandwich the substrate side walls 201S-S1 and 201S-S2 in the both lateral side surfaces of the cavity 204. As the coil 207 becomes nearer the center portion of the cavity 204, a magnetic flux density (or a magnetic field) becomes stronger. Accordingly since it is possible to control easily the charged particles (the charged particles pass the center portion of the cavity), the substrate side walls 201S-S1 and 201S-S2 may be smaller in thickness. Since LSI process can be used, for example, a very thin substrate side wall of 10 µm-1000 µm can be formed.

The upper substrate 202 exists in the above portion of the cavity 204. The coil 207-1 is disposed above the upper substrate, with be buried inside in the upper substrate 202, or inside the upper substrate 202. As the coil 207 becomes nearer the center portion of the cavity 204, the magnetic flux density (or a magnetic field) becomes stronger, and the control of the charged particles becomes easier. Accordingly if the coil is disposed above the upper substrate 202, the coil 207-1 approximates the top surface of the upper substrate 202 as possible. The coil 207-1 may be disposed so that it optimally contacts the top surface of the upper substrate 202. If the coil 207-1 is buried in the upper substrate 202 or the coil 207-1 is formed inside the upper substrate 202, the upper substrate 202 existing between the cavity 204 and the bottom surface of the coil 207-1 is the upper substrate 202-U, the upper substrate 202-U may be thinner in thickness than the upper substrate 202. The thickness of the upper substrate 202-U had better smaller. For example, it can makes the thickness of the upper substrate 202-U very thinner of 10 µm-1000 µm.

The lower substrate 203 exists in the below portion of the cavity 204. The coil 207-3 is disposed above the upper substrate, with be buried inside in the lower substrate 203, or inside the lower substrate 203. As the coil 207 becomes nearer the center portion of the cavity 204, the magnetic flux density (or a magnetic field) becomes stronger, and the control of the charged particles becomes easier. Accordingly if the coil is disposed below the lower substrate 203, the coil 207-3 approximates the bottom surface of the lower substrate 203 as possible. The coil 207-3 may be disposed so that it optimally contacts the bottom surface of the lower substrate 203. If the coil 207-3 is buried in the lower substrate 203 or the coil 207-3 is formed inside the upper substrate 203, the lower substrate 203 existing between the cavity 204 and the top surface of the coil 207-3 is the lower substrate 203-B, the upper substrate 203-B may be thinner in thickness than the lower substrate 203. The thickness of the upper substrate 203-B had better smaller. For example, it can makes the thickness of the lower substrate 203-B very thinner of 10 µm-1000 µm.

When a central line in the lateral direction of the main substrate 201 is C1 as shown in FIG. 4(d), a center O1 of the cavity 204 is on the lateral direction central line C1, and the coils 207-2 and 207-4 are disposed in the main substrate 201 so that an axis of the coils 207-2 and 207-4 fit the lateral direction central line C1. Also, the coils 207-1 and 207-3 are disposed in the main substrate 201 so that an axis of the coils 207-1 and 207-3 passes the center O1 of the cavity 204 and fit the longitudinal direction central line C2 perpendicular to the lateral direction central line C1. Since a distribution of the magnetic field in the cavity 204 can be near to symmetrical shape, the charged particles can be converged near to the center O1 of the cavity 204. Particularly if the substrate side walls 201S-S1 and 201S-S2 are almost same in thickness, and the characteristics of the coils 207-2 and 207-4 are almost same, and the coils 207-2 and 207-4 are disposed symmetrically to the center O1 of the cavity 204, furthermore the substrate side walls 202U and 202B are almost same in thickness, and the characteristics of the coils 207-1 and 207-3 are almost same, and the coils 207-1 and 207-3 are disposed symmetrically to the center O1 of the cavity 204, and the coils 207-1, 207-2, 207-3, and 207-4 are almost same in characteristics, a distribution of the magnetic field in the cavity 204 can be near to symmetrical shape. But even if the characteristics of the coils constructed, the disposition of the coils, the thickness of the substrates side walls and substrate are a little different for the quadrupole electrodes of the present invention, since voltages applied to the respective coils can be selected optionally and the inside magnetic field of the cavity 204 can be changed optionally, it is very easy to converge the charged particles beam near to the center O1 of the cavity. The center O1 of the cavity 204 fit is preferably on the travelling direction G of the charged particles, and the center of the central hole 205 preferably makes the center O1 of the cavity 204 fit If the width of the substrate side wall 201S-i, namely the length of the central hole 205 is ma1, the length of the acceleration cavity 204C-I (the size in the longer direction of the charged particles accelerator 200) is p1, the distance between the high-frequency introducing room 204C-A and the high-frequency discharging room 204C-B is (n+1)×m1+n×p1. When the charged particles accelerator 200 has n of acceleration cavities, the distribution of the acceleration electric field may be changed by changing the length p1 of the respective acceleration cavities and the length m1 of the respective central holes 205. Also, the distribution of the acceleration electric field may be changed by changing the size (a2, h2) of the cavity 204 and the size of the central hole 205 (for example, if the shape of the central hole is rectangular, the length of the longitudinal and the side, if the shape of the central hole is circular, the diameter). Since the charged particles accelerator can be made using LSI process, these sizes can be changed easily and in expensively. The size and number of the quadrupole electric magnet can be optionally changed corresponding to the size of the cavity 204. The size of the quadrupole electric magnet, especially the length of the coil can be adjusted optionally and the number of turns of the coil can be increased and decreased optionally corresponding to them. Also, the number of the quadrupole electric magnets can be increased by lengthening the length of the cavity 204-2.

Next we explain a method how to make the electric magnet (coil). FIG. 11 is one embodiment that shows the method how to make the electric magnet (coil). A substrate 115-1 to make the coil is adhered to a support substrate 114-1. Since the support substrate 114-1 is separated later from the substrate 115-1 to make the coil, a thermosoftening adhesive agent (thermosoftening temperature T1) is better as the adhesion. The support substrate 114-1 is an insulating substrate such as glass substrate, quarts substrate, Alumina substrate, plastic substrate, epoxy substrate, polymer substrate, etc., or a semiconductor substrate such as Si substrate, etc., and a conductive substrate such as Cu, Al, etc. The substrate 115-1 to make the coil is a non-magnetic substrate and an insulating substrate such as glass substrate, quarts substrate, Alumina substrate, plastic substrate, epoxy substrate, polymer substrate, etc., or a semiconductor substrate such as Si substrate. As shown in FIG. 11(a), patterns of photosensitive films to make coil patterns are formed in the substrate 115-1 to make the coil, and the substrate 115-1 to make the coil is etched with the patterns. The vertical etching, which makes the close patterns to the photosensitive patterns, is desirable in the etching. Or, the substrate 115-1 to make the coil, on which the patterns of the conductive wiring for the coil are formed by punching with a steel stamp, may be adhered on the support substrate 114-1. Or, plastic films or polymer resin films, on which the patterns of the conductive wiring for the coil are formed, may be adhered on the support substrate 114-1. When the substrate 115-1 to make the coil is a semiconductor substrate such as Si, etc., conductive films should be deposited on the side surface of the concave portion so that the coil wirings may not short out.

Next, the patterns of photosensitive films to make coil patterns in the concave portion are filled up by the conductive film. The conductive film is, or example, Cu, Ni, Cr, Au, Al, W, Mo, Ti, Zr, various solder metals, these alloys, these compound metals, various silicide films, or super conductive films. There are some methods as the filling methods. For example, after the conductive film is deposited using CVD method, PVD method, etc. the conductive film is filled up in only the concave portions by grinding or polishing using the method such as CMP. Or, there is a method to fill up in the concave portion using selective CVD method, a method to fill up in only the concave portion using plating method, or a method to fill up in the concave portion using a coating method of conductive paste. Also, the surface of the conductive film can be also planarized. The first layer of the coil wiring patterns 116-1 (width a, depth c1) is formed by these methods. Planer patterns of the first layer are the wiring patterns (length d (width a), distance b) as shown in FIG. 11(g), for example.

Next, patterns of second layer are similarly made. A substrate 115-2 to make the coil is also adhered to a support substrate 114-1 in the second layer, the second layer of the coil wiring patterns 116-2 is formed with the photosensitive film, etc. Cross sectional configurations of the second layer are similar to those in FIG. 11(a), and a planer pattern is a rectangular pattern that is a in (lateral) width, b in distance and e in (longitudinal) width as shown in FIG. 11(h), and the pattern is fitted to the pattern of the first layer when they are overlapped. Since the width of the coil wiring is (lateral) width a×(longitudinal) width e, e should almost equal to a. Next, the coil wiring patterns of the second layer are adhered to the coil wiring patterns of the first layer while their patterns are fitted, as shown in FIG. 11(b). That is, the substrate 115-2 to make the coil, on which the coil conductive wiring patterns of the second layer are formed, adhered to the support substrate 114-2 is adhered to the substrate 115-1 to make the coil, on which the coil conductive wiring patterns of the first layer are formed, adhered to the support substrate 114-1. A room temperature bonding method, a diffusion bonding method, or a high temperature bonding method, etc. is used as the method to adhere these substrates. When the substrate 115-1 or 115-2 to make the coil is an insulating substrate such as a glass substrate or a quarts substrate and the substrate 115-2 or 115-1 to make the coil is a semiconductor substrate such as Si substrate, etc., an electrostatic anode bonding method can be also used. Also, these substrates can be adhered using an adhesive agency. In that case, a conductive adhesive agency should be used in the bonding portion between the conductive films, and an insulating adhesive agency should be used between the other portions. The conductive adhesive agency can be also used in the bonding portion between the conductive films in the other bonding methods. When the distance b between the wiring is more than 10 μm (at the present time), the conductive adhesive agency can be used with a metal mask in the patterns in the bonding portions. If a photosensitive film of the adhesive agency or a method of a photosensitive film pattern+etching is used, the adhesive agency can be coated in the patterns in the bonding portions even if the distance b between the wiring is 1 μm. In addition, these substrates can be adhered by coating or plating solder in the bonding portions. If the depth of the concave portions in the second layer is c1, c2 is 2c1. A thermosetting adhesive agency is desirable for the adhesive agency used in the bonding portion between the substrates 115 to make the coil is desirable so that they do not separate in the later thermal treatments. When the solder metal or the thermoplastic adhesive agency is used, the positions of the substrates 115 to make the coil need not move each other and their patterns need not be misaligned and separated in the later thermal treatments.

Next, the support substrate 114-2 is removed. The adhesive agency that adheres the support substrate 114-2 and the substrate 115-2 to make the coil is the thermoplastic adhesive agency and the softening temperature of the adhesive agency is T2, the adhesive agency should be selected so that T1>T2. Thus, only the support substrate 114-2 can be separated at the temperature between T1 and T2. FIG. 11(c) is the diagram that shows the state where the support substrate 114-2 is separated. Since the patterns in n layer (n≥3) are same as the patterns in the second layer, the coil wiring can be made in the height direction of the coil by piling up these layers in succession. However, since it takes much time to pile up these layers one by one, as shown in FIG. 11(d), when two piled layers, in which one layer is piled up on one layer, are piled up on the another two piled layers, they become four piled layers (the state of FIG. 11(d)). Next, when four piled layers are piled up on another four piled layers, they become eight piled layers. If c1=0.1 mm, the thickness of the coil becomes 0.8 mm by five times adhesions.

Since the last coil wiring pattern needs connect spirally as a coil, it is a wiring pattern like FIG. 11(i). The first wiring pattern is a wiring pattern like FIG. 11(g), and the top wiring pattern is a wiring pattern like FIG. 11(i). (These may be reversed.) The wiring patterns between these patterns are wiring patterns like FIG. 11(h). When the given height becomes c4, after the support substrate in the top layer is removed, a photosensitive film 117 is adhered (coated) and the pattern of the photosensitive film 117 is formed. The substrate 115 to make the coil is etched and removed by the mask of these patterns. Since the support substrate 114-1 is not separated at this point of time, the etching having the high selective ratio (the high selective ratio etching) between the substrate 115 and the support substrate 114-1 is desirable. If the material of the substrate 115 is different from the material of the substrate 114-1, the selective ratio of etching can become large easily. For example, it is a case that the support substrate 114-1 is Si or glass and the substrate 115 is glass or Si. Or, unnecessary portions can be separated by cutting them with a dicing method. For example, when the support substrate 114-1 and the substrate 115-1 to make the coil are adhered, a adhesive agency that can be separated by optical irradiation is used in the portions that are separated as the unnecessary portions, and the ordinary thermoplastic adhesive agency is used in the other portions. And then the substrate 115-1 and a part of the support substrate 114-1 are cut. After that, the unnecessary portions can be separated by the optical irradiation. As a method to adhere the adhesive agencies separately, for example, we can coat them using a mask. Thus the coil 118 that has the configuration shown in FIG. 11(f) can be adhered to the support substrate 114-1.

Next, the electric magnets (coils) 118-1 and 118-2 formed on the support substrate 114-1 are inserted into the main substrate 201 in which the cavity to insert the coils and the cavity 204-2 (see FIG. 4) in which the charged particle beam G passes are formed. For example, since the conductive electrodes and wirings 119 to which the terminals of the coil are connected are formed, the coils are inserted so as to align with the patterns of the conductive electrodes and wirings 119, etc. Also, the size of the coil 118 is adjusted so that the center axis of the coil 118 almost comes to the center of the main substrate 201. The conductive adhesive agency or the solder metal may be preliminarily and preferably adhered in the connected portions. If these are softened with heating, etc., the height in the vertical direction can be adjusted. If an insulating film is deposited and an insulating sheet film is adhered on the wiring pattern of the coil 118 and the window is opened in only the connection portions, since the conductive adhered agency, etc. can be coated widely, the connection is secured and the height and the levelness can be adjusted easily.

If all the terminals of the coils are made on the opposite side like the coil 118-1 shown in FIGS. 11(j) to 11(m), since the patterns 109 of the conductive film electrodes and wirings need not be made in the bottom substrate 203, and since the insulating adhesive agency can be coated on the bottom substrate 203 and or on the bottom side of the coil 118, the adhesion of the coil 118 can be secured and the height and the levelness can be adjusted easily. For example, the levelness and pressure of the lift and press of the support substrate can be easily adjusted. Since the size of the cavity 120 (120-1, 2) to insert the coil is not limited very much and the cavity can be opened largely, it is no problem to insert the coil into the cavity. Also, if the conductive film electrodes and wirings are formed largely, it is no problem to connect them with the coil. Though the distance between the edge surface of the coil 118 and the center of the cavity 204-2 affects the magnetic field that affects the charged particles, since an alignment error in the insertion at the present time is between 1 μm and 10 μm, the alignment error does not affect the magnetic field.

In addition, since the distance between two coils 118-1 and 118-2 does not shift at all, the magnetic field that generates from the two coils does not almost change. Though it is desirable that the size of the edge surface of the coil is larger than the size (in the depth direction) of the cavity 204-2 in order to uniform the magnetic field in the whole portions of the cavity 204-2, the depth of the cavity 120 (120-1, 2) to insert the coil may be larger than that of the cavity 204-2 by reducing the thickness of the bottom substrate 203 in the portion of the cavity 120 (120-1, 2) to insert the coil. In that case, the size of the coil 118 may be larger corresponding to it After the coil 118 is fixed on the bottom substrate 203 in the cavity 120 (120-1, 2) to insert the coil, the support substrate 114-1 is separated. For example, after the coil 118 is fixed on the bottom substrate 203 using the thermosetting adhesive agency, etc. of which the curing temperature T3 of the adhesive agency, etc. used to adhere the coil 118 and the bottom substrate 203 is lower than T1, the support substrate 114-1 is separated by increasing the thermal treatment temperature to the higher temperature than T1. (FIG. 11(k)) Next, as shown in FIG. 11(i), the upper substrate 121 in which the conductive film electrodes and wirings 121 to connect with the coil terminal are formed is adhered to the main substrate 201 by fitting to the terminals of the coil 118. If the wiring patterns are formed on the upper portions of the coil 118, an insulating film is deposited or an insulating film is adhered over the wiring patterns, the connection portions are opened, after the conductive adhesive agency or the solder metal is coated and formed, the coil may be adhered.

Next, the conductive film wirings 122 in the contact hole to connect with the conductive film electrodes and wirings 121 are formed, and the outer electrodes and wirings 123 (123-1, 2, 3) are formed, in the upper substrate 202. Also, the conductive film wirings 124 in the contact hole to connect with the conductive film electrodes and wirings 119 are formed, and the outer electrodes and wirings 125 are formed, in the upper substrate 203. Thus, the coils 118 (118-1 2) are disposed in the cavities 120 (120-1, 2) on the opposite sides of the main substrate side walls 201S-S2 and 201S-S1 to the cavity 204-2. Furthermore, since they are disposed very accurately, (which the alignment error is less than 5 µm in the present time) the magnetic field in the cavity becomes uniform. The electric current to the coil 118-1 can be flowed from the outer electrodes 123-1 and 123-2, and the electric current to the coil 118-2 can be flowed from the outer electrodes 123-3 and 125. (FIG. 11(*m*))

Though the method to adhere the coil to the support substrate from the first layer pattern is adopted in the process shown in FIG. 11, the coil pattern of the first layer is preliminarily formed on the lower (bottom) substrate and the coil patterns of more layer than or equal to second layer can be formed on the support substrate. The first layer process can be omitted by this method. Likely, the patterns of the last and top layer can be formed on (the under surface of) the upper substrate. Thus the last layer process can be also omitted by this method. In addition, in that case, since the coil wiring patterns from second layer to (n−1)th layer (n layer is the top layer) are same, these layers can be piled up simply, or the piled layers can be piled up repeatedly so as to realize the given size. Lastly, they may be adhered to the first layer pattern of the lower substrate, and the (n−1) layer pattern may be adhered and aligned to the top layer pattern of the upper substrate.

Though there are the substrate side wall 201S-S1 and the substrate side wall 201S-S2 as the partitions between the cavity 204-2 that the charged particle beam G passes and the cavity 120 (120-1, 2) to insert the coil, since they act to weaken and disturb the magnetic field and, they can be removed. However, since the cavity 204-2 is the cavity that the charged particles pass, the pressure of the cavity 120 (120-1, 2) must be the pressure of the cavity 204-2. The opening windows to draw a vacuum can be equipped in the cavities 120 (120-1, 2) and in the upper or lower substrate. If the substrate side wall 201S-S1 and the substrate side wall 201S-S2 are not equipped, since the cavity 204-2 and the cavity 120 (120-1, 2) are the same cavity, it is simple to insert the coils 118-1 and 118-2 because they do not encounter the substrate side wall 201S-S1 and the substrate side wall 201S-S2.

In addition, for the distance between the substrate side walls 201S-S1, S2, and the coils 118-1, 2, the extra margin (distance) of safety need not be considered. Accordingly, since the distance becomes short, the electric current to make the magnetic field of the cavity can become small, or the magnetic field can become stronger. Or, If the central holes are opened in the substrate side walls 201S-S1 and S2, the magnetic field in the portions is not affected by (the materials of) the substrate side walls 201S-S1 and S2, and the pressure of the cavity 204-2 is not much affected by the cavities 120 (120-1, 2).

In addition, though the support substrate 114-1 is used in the above, if the upper substrate 202 or the lower substrate 203 is used instead, the support substrate may be not removed and can be used in the process shown in FIG. 11(*j*). Also, like FIG. 12(*d*), if the coil 118 is made by making the convex portions in the support substrate 114-1, since the support substrate 114-1 can be removed without contacting the support substrate 114-1 with the main substrate 201 when the coils are inserted, which is the process shown in FIG. 11(*j*), the main substrate 201 is not damaged. As shown in FIG. 11(*m*), the electrodes connecting the edge of the coil wiring can be freely formed in the upper substrate 202 or the lower substrate 203. Though the edge of the coil 118 need be aligned to the electrode and wiring patterns since the electrode and wiring patterns are formed in the lower substrate 203 in FIG. 11(*j*), since the electrode and wiring patterns may not be formed in the lower substrate 203, the process can be shorten because the fitting is not needed when the coils are inserted. In addition, the conductive adhesive agencies need not be used, and the coils can be adhered to the lower substrate 203 using the ordinary one kind of adhesive agency (for example, the insulating adhesive agency). And then, if the upper substrate 202 or the lower substrate 203 is used instead of the support substrate 114-1, the coil 118 need not be adhered to the lower substrate 203, and the accurate alignment is not needed because the upper substrate 204 that the coil 118 is adhered to may be only adhered to the main substrate 201.

In the process of FIG. 11, when a=e=30 µm, d=1 mm (coil radius: d/2=500 µm), height=1 mm, and length=5 mm for the coil size, the coil of 100 turns can be made. If the coil conductive wiring is made of Cu and can pass an electric current of $10^6$ A/cm$^2$, which is enable from the tolerant electromigration, the coil can pass the current of I=9 A. Accordingly, the magnetic field Hc=$8\times10^5$ A/m in the center of the edge surface of the coil.

In addition, the magnetic field generating can be larger by inserting the core having high Relative Permeability µ into the coil. So, I explain the method how to insert the core having high Relative Permeability µ into the coil that is used in the accelerator of the present invention. Since the similar method is disclosed in JP 2012-134329, they can be available in the present invention. FIG. 12 is the diagram showing the method to make the high-performance coil in which the core having high Relative Permeability µ is inserted. 4 kinds of patterns to make the coil are used in the embodiment of FIG. 12. FIGS. 12(*g*)-(*j*) are plan views. FIG. 12(*g*) is same as FIG. 11(*g*) and shows the area of the hole to insert the core (core insertion hole) by the broken line A. The outline of the coil is shown by the broken line B. There are the same substrates (layers) in each layer outside the coil in FIG. 11 and FIG. 12. Though the external substrate layers 115 are etched and removed at once using the mask of the photosensitive patterns 117 in the process of FIG. 11(*e*), after they are adhered to the support substrate 114, the photosensitive film patterns, etc. are formed in the portion showed by the broken line B, and the substrate layers 115 outside the area shown by the broken line B are etched and removed using the mask of the photosensitive film patterns, and only the area to make the coil can be adhered and piled up. Or, only the portions of the coil are adhered and piled up without adhering to the support substrate, and finally the coil is adhered to the given portions of the support substrate 114, and the state showed in FIG. 11(*f*) can be made.

FIG. 12(*a*) is the same diagram as FIG. 11(*c*). Namely, the substrate 130-1 to make the coil (coil making substrate) is the coil making substrate 115 having the coil wiring pattern 116 shown in FIG. 12(*g*). The area to insert the coil (coil insertion area) is rectangular shown by the broken line A and in the longitudinal side (the width direction of the coil) the area is inside the coil wiring pattern 116 shown in FIG. 12(*g*) and in the horizontal side (the axis direction of the coil) the area is protruded out of the coil wiring in both sides. The broken line B is the portion of the coil outline. The coil making substrate 130-2 is the coil making substrate 115 having the coil wiring pattern 116 shown in FIG. 12(*h*). The coil wiring pattern 116 is the coil wiring pattern piled up in the hight direction of the coil. In the patterns of FIGS. 12(*g*) and (*h*), the coil insertion area A is same as the coil making substrate 115, and is the flat pattern adhered on this is the coil making substrate 115 having the pattern shown FIG. 12(i). Namely, the coil making substrate 130-3 is the coil making substrate 115 having the pattern shown FIG. 12(i). The coil insertion area A is the cavity opened in FIG. 12(i). This cavity can be made by etching the coil making substrate 115 after the coil making substrate 115 is adhered to the support substrate and opened, or by punching with steel stamp. Furthermore the coil making substrate 115 shown in FIG. 12(h), which is preliminarily made in the size of the coil area B, can be made by being etched and punched. The coil making substrate 115 having the cavity of which the coil insertion area A shown in FIG. 12(i) is bored is adhered on the coil making substrate 130-3, and these adhered at the given numbers. (FIG. 12(b)) Here, the coil making substrates 130-4, 5, 6 are the coil making substrates 115 having the patterns shown in FIG. 12(i). The substrate adhering many of the coil making substrates 115 having the patterns shown in FIG. 12(i) is shown in FIG. 12. This can be adhered on the coil making substrate 130-2, which is the coil making substrate 115 of which the coil insertion area A is not bored In that case, the inside is the cavity in the portion shown by the broken line A in FIG. 12(b). the cavity has the vertical lateral side surface shape when piled up if the substrate has the vertical side surface. However, the lateral side surface of the area A may not be always vertical shape since it is larger than the coil area B in the axis direction.

Or, the coil making substrate 115 shown in FIG. 12(h) of which the coil insertion area A is not bored may be piled up and adhered on the substrate shown in FIG. 12(a). Namely, all the coil making substrates 130-2-130-8 are flat since the coil insertion area A is not bored. In that case, as shown in FIG. 127(c), the photosensitive film 131 is patterned, the portion of the coil insertion area A is opened, the coil making substrate 115 in the area A is etched, and the concave portion (opening portion) 134 that is the coil insertion area A is formed. Though the concave portion (opening portion) 134, which is the coil insertion area A and etched, reaches to the portion of the coil making substrate 130-3, the portion of the coil making substrate 130-2 may be etched. If the concave reaches to the area of the coil making substrate 130-1, since it is not desirable since the coil wiring 116 is exposed (because the coil wiring 116 is etched and damaged), the etching is stopped at the extent that the coil wiring 116 is not exposed. After that, the photosensitive film pattern 131 is removed.

Next, the adhesive agency (the coating liquid) is put in the concave portion 134, or the adhesive agency is adhered to the core material 133 shown in FIG. 12(d), and the core material 133 is inserted into the concave portion 134. The core material 133 is preliminarily adhered to support substrate 132. For example, after the sheet or film or thin plate of the core material is adhered to the support substrate 133, the desirable patterns may be formed using the photolithography method+etching, and may be made by punching using the steal stamp. Or, the sheet of the core material, etc. are diced, the unnecessary portions may be removed by picking up. In that case, if the adhesive agencies are divided in the removed portions and the remained adhesive portions, only the unnecessary portions can be removed easily using the different peeling methods. For example, the adhesive agency having the different thermosoftening temperature can be used. Though the non-magnetic insulating adhesive agency can be used as an adhesive agency, a paste or liquid adhesive agency including ferromagnetic particles such as ferrite, etc. may be used. Since these ferromagnetic particles become a kind of core, they can increase the effect of the core.

The core material 133 adhered to the support substrate 132 is inserted into the concave portion (opening portion) of the coil insertion area A. And then, if the concave portion 135 is equipped in the support substrate, the whole core material 133 can be put into the concave portions (opening portion) 134 so that the upper portion of the core material 133 is not outside of the upper surface of the top portion of the coil making substrate 130-6. (The sum of the height h1 of the core material 133 and the thickness h2 of the adhesive agency makes smaller than the depth h3 of the concave 134, namely h1+h2<h3, when the height of the concave portion 135 is h4, if they are designed so that h1+h2+h4>h3, since the support substrate 132 does not touch the upper surface of the coil making substrate 130-6, the core material 133 can be put in the concave portion (the opening portion) 134.) The adhesive agency put into the concave portion is, for example, the thermosetting adhesive agency (curing temperature T1), when the adhesive agency between the core material 133 and the support substrate is the thermosoftening adhesive agency (thermosoftening temperature T2), after the core material 133 is fixed in the concave portion 134 at the temperature between T1 and T2, the core material 133 may be separated from the support substrate 132 at the higher temperature than T2, here the adhesive agencies that are T1<T2 may be used.

After the core material 133 is inserted into the concave portion 134, if the foreign materials such as the adhesive agencies, etc. are not adhered on the surface of the coil making substrate 130-6, the next coil making substrate 130-7 can be adhered to the coil making substrate 130-6. If the foreign materials such as the adhesive agencies, etc. are not adhered on the top surface of the coil making substrate 130-6, or the core material 133 is buried perfectly inside the concave portion, after the core material 133 is inserted and fixed in the concave portion, the same adhesive agency is put into the concave portion 134 from the upper of the core material 133, the gap space of the concave portion 134 is filled with the adhesive agency. Or the insulating film may be deposited or coated. And then, since the adhesive agency or the insulating film is adhered or deposited on the surface of the top coil making substrate 130-6, the adhered or deposited adhesive agency or insulating film is removed and planarized by CMP, BG (Back Grinding), or etching back, and the coil wiring patterns 116 are exposed. This planarization is, for example, after planarized with coating the organic film such as the resist liquid, etc., polished or grinded using CMP or BG, etc. or etched using etching back method, to exposed the surface of the coil making substrate during planarizing. (FIG. 12(e))

After that, the coil making substrate 130-7, which is the coil making substrate 115 of which the coil insertion area A is not bored as shown in FIG. 12(h), is adhered to the coil making substrate, which is etched or grinded. After that, the coil making substrate 130-8, which is the coil making substrate 130-5 having the coil wiring patterns shown in FIG. 12(j) that is the top coil making substrate, is adhered to the coil making substrate 130-7. Thus the coil incorporating the core material 133 can be made. The necessary number of the coils having the core materials 133 is made preliminarily in the necessary places on the support substrate 114-1. After that, the coil incorporating the core material 133 is inserted into the coil insertion cavity 120 in the process after FIG. 11(j). The coils incorporating the core material 133 can be disposed simultaneously and at once in the portions needing many accelerators and electric magnets. If the insulating film lies since the insulating film is coated or deposited on the coil making substrate 130-1, which is the coil making substrate 115 having the coil wiring patterns shown in FIG. 12(*g*), the coil making substrate 130-3, which is the coil making substrate 115 of which the coil insertion area A is not bored as shown in FIG. 12(*h*), can be adhered without adhering the coil making substrate 130-2 of which he coil insertion area A is not bored as shown in FIG. 12(*h*). (Because the coil wiring patterns and the core materials 133 do not pass electrically.) Also likely, if the insulating film lies on the upper surface of the core material 133, the coil making substrate 130-8, which is the coil making substrate 115 of which the coil insertion area A is not bored as shown in FIG. 12(*h*), can be adhered without adhering the coil making substrate 130-7 of which he coil insertion area A is not bored as shown in FIG. 12(*h*) to the coil making 130-6. The intervening and insulating film can be realized with the insulating adhesive agency, the insulating sheet, the deposition of the insulating film (CVD, PVD, coating method, etc.) Thus the layer shown in FIG. 12(*h*) is not needed. As the core materials, there are soft magnetic materials such as Fe ($\mu$=about 5000), pure iron ($\mu$=about 10000), ferrosilicon ($\mu$=about 7000), permalloy ($\mu$=about 100000), superalloy ($\mu$=about 100000), amorphous Fe ($\mu$=about 3000), ferrite ($\mu$=about 200), sendust ($\mu$=about 30000), or permendur ($\mu$=about 5000).

Next I explain about the method to make the coil disposed in the upper and lower substrate. FIG. 13 shows the method to make the coil disposed in the upper and lower substrate. The coil wiring substrate 142-1 of the first layer is adhered to the support substrate. The support substrate 142-1 is the substrate that does not have the coil wiring, for example, the substrate that does not have the conductive wiring patterns 144 as shown in FIG. 13(*i*). If the coil wiring substrate 142-1 is the semiconductor substrate such as Si, etc. or the conductive substrate, the wiring and the coil wiring substrate 142-1 should be made not to connect each other by forming the insulating film on the surface of the substrate. When the coil wiring substrate 142-1 is a glass, a sapphire, an alumina, plastics, polymer, etc., though the insulating need not be formed ordinarily, the insulating film may be needed to improve the adhesion with the conductive film. Though the coil wiring substrate 142-1 of the first layer protects the wiring pattern of the wiring substrate adhered on it, since the insulating film formed on the lower surface of the coil wiring of the second layer can protect the wiring pattern, the coil wiring substrate 142-1 of the first layer may not be equipped. However, the coil wiring substrate 142-1 of the first layer should be equipped to strengthen the coil.

Next the coil wiring substrate 142-2 of the second layer is adhered. Here since the patterns of the first layer do not exist, the pattern fitting is not needed. The coil wiring substrate 142-2 of the second layer is the wiring substrate having the wiring patterns shown in FIG. 13(*i*). For the adhesive method, the coil wiring substrate 142-2 of the second layer is adhered to another support substrate 141-1 (not shown) as already written, after the coil wiring substrate 142-1 adhered to the support substrate 141-1 is faced and adhered to the coil wiring substrate 142-2 adhered to the support substrate 141-2, the support substrate 141-2 may be separated from the coil wiring substrate 142-2. Or, if the coil wiring substrate 142 can be supported by itself, the coil wiring substrate 142-1 and the support substrate 141-2 can be directly aligned and adhered. Or, the coil wiring substrate 143 that does not have the wiring patterns is adhered to the support substrate 141-2, the coil wiring substrate 143 that does not have the wiring patterns is patterned, the photosensitive film patterns of which the wiring patterns are the opening portions are formed using the photolithography method, the coil wiring substrate 143 is etched, and the penetrated room patterns are formed. For the penetrated room patterns, the vertical shapes are desirable. Or, the coil wiring substrate 143 that does not have the wiring patterns is punched by the steal stamp, etc. having the wiring patterns, and the penetrated room patterns can be formed. Or, the penetrated room patterns are formed by coating the photosensitive resin on the support substrate 141 and opening the penetrated room patterns and curing the resin except the opened portions. Or, the penetrated room patterns are formed by coating the insulating paste and opening the penetrated room patterns by the steal stamp, etc. and curing the paste. Or, the penetrated room patterns are formed by coating paste using the screen printing method and opening the penetrated room patterns and curing the paste.

The insulating film is formed, if necessary, on the coil wiring substrate 143 in which the penetrated channels are formed as shown in the above, and next the conductive film is formed and the patterns of the penetrated channels are filled with the conductive film. After the conductive film are formed thickly using CVD method, PVD method and Plating method and the penetrated channels are buried, the surface of the conductive film is etched (ex. Etch Back method) or grinded (mechanical and chemical etched) (BG method or CMP method), and the conductive film of the surface is removed and only the penetrated channels are filled. Or, after the conductive film (called seed layer) is deposited thinly on the inside walls of the penetrated channel and on the surface of the coil wiring substrate 143 using CVD method or PVD method, the photosensitive film is coated or the photosensitive sheet is attached, and the area except the penetrated channel patterns is covered by the photosensitive film using the photolithography method, after that, the penetrated channel patterns are filled with the plating film using the plating method, and the conductive film, which is deposited on the surface of the coil wiring substrate 143, is removed, the patterns in which the conductive film is filled in only the penetrated channel patterns, for example, shown in FIGS. 13(*i*) to 13(*k*), are formed in the coil wiring substrate 143. Or, the conductive paste is coated, and the penetrated channel patterns are filled with the conductive paste, and the paste in the area except the penetrated channel patterns is removed, after that the conductive paste in the penetrated channels is cured with the thermal treatment, etc. Or, after the melted metal is poured in the penetrated channel patterns, it is cooled and solidified, and the metal (conductive material) is filled in the penetrated channels. The coil wiring pattern 144-2 of the coil wiring substrate 142-2 in the second layer is the first layer of the spiral pattern shown in FIG. 13(*i*). The patterns are written by the rectangle, but they may be circular or ellipsoidal. Next, if the coil wiring substrate 142-2 is adhered to the support substrate 141-2, the support substrate 141-2 should be removed from the coil wiring substrate 142-2. (FIG. 13(*a*)) Though the wiring pattern 144 deriving to the right side in FIG. 13(*i*) is the pattern to make the coil terminal in the upper portion, since it is only written as known well in the figure, the wiring of the pattern may be spread in the left side of the figure.

Next the coil wiring substrate 142-3 of the third layer is adhered to the coil wiring substrate 142-2 of the second layer. The wiring pattern (144-1) of the coil wiring substrate 142-3 of the third layer is used to contact with the upper and lower circle wiring patterns as shown in FIG. 13(*j*). The right wiring pattern 144-2 is the contact wiring to make the coil terminal electrode in the upper portion. After the coil wiring substrate 142-3 is adhered to the support substrate 141-3, the coil wiring substrate 142-3 of the third layer is adhered on the coil wiring substrate 142-3 of the second layer. (FIG. 13(*b*)) The figure in which the support substrate 141-3 is separated is FIG. 13(*c*). Since the electric current does not flow in the lateral direction in the upper and lower contact wiring like this but flow in the vertical direction, the thickness of the coil wiring substrate 143 may be thin. After the insulating film is directly formed on the coil wiring substrate 142-2 of the second layer using CVD method and PVD method, or coating method (SOG, paste), etc., or if necessary, and treated thermally, etc., the contact holes are opened using the photolithographic method, and the conducting film is deposited using CVD method, PVD method, plating method, or coating method (paste), etc., and the contact holes are filled with the conductive film, (however, they do not need to be always filled by the electric current to flow the coil), the conducting film patterns surrounding the contact and the contact conducting film pattern to contact with the wiring of the upper layer are formed using the photolithographic method and the etching method, etc. The thickness between the coil wirings, namely the depth of the contact hole can be made in 1 μm to 10 μm by using these methods. (FIG. 13(*c*))

The contact size (if the contact is the rectangular, height a μm, and width bμm) is selected by the electric current flowing the coil. (Of course, the width d and thickness h of the upper and lower coil wiring are selected.) The electric current flowing the coil determines the magnetic field that the coil makes. For example, if the contact holes (144-1 and 144-2 in FIG. 13(*j*)) and the coil wiring 144 are formed with the plating method, since the current having the current density of about $10^6$ A/cm$^2$ can be flowed, the current of about 10 A can be flowed at a-=b=30 μm, or d=30 μm and h=30 μm. When the coil size is the rectangle of x=1 mm and y=1 mm and 100 turns, the center magnetic field in the coil edge surface generating then is very large. If the depth of the contact is 2 μm, a pitch per one turn of the coil becomes 32 μm. And then, if the coil is 100 turns, the coil length becomes 3200 μm=3.2 mm. If the depth of the contact is 20 μm, a pitch per one turn of the coil becomes 50 μm, if the coil is 100 turns, the coil length becomes 5000 μm=5.0 mm. The coil wiring substrate having the coil wiring patterns winded circularly can be made by the piling method except the adhesion method, The method is the same method as the method to form the contact wiring patterns as the above mentioned.

Next the coil wiring substrate 142-4 that is the coil wiring substrate 143 having the ring-shaped coil wiring pattern 144 is adhered on the coil wiring substrate having the contact hole patterns, or the insulating layer 142-3 having the contact hole patterns, as shown in FIG. 13(*k*). After the coil wiring substrate 142-4 is adhered to the support substrate 141-4, it is adhered on the coil wiring substrate 142-3, after that the support substrate 141-4 is separated. When the coil wiring substrate 142-4 can be treated alone, the coil wiring substrate 142-4 can be adhered directly on the coil wiring substrate 142-3. After the coil wiring substrate 142-5 that is the coil wiring substrate 143 having the contact patterns as shown in FIG. 13(*j*) is adhered to the support substrate 141-5, it is adhered to the coil wiring substrate 142-4. As the above mentioned, the contact 144-5-1 can be formed without using the coil wiring substrate 142-5. Also, the contacts 144-3-2, 144-4-2 and 144-5-2 connecting the lower coil terminals to the upper electrode serially are piled up and connected. (FIG. 13(*d*))

While these are repeated, the coil having the desirable turns are formed by adhering or piling up alternately the annular coil wiring patterns as shown in FIG. 13(*k*) and the contact patterns as shown in FIG. 13(*i*). In FIG. 13(*e*), the coil wiring substrates having the annular coil wiring patterns are 4 layers of 142-2, 4, 6, 8, and the coil wiring substrates having the contact wiring patterns are 4 layers of 142-3, 5, 7, 9. Though the turns of the coil wiring are low, they can be piled up numerously. Or, what is piled up can be stacked each other. When the core inserted in the coil, the photosensitive film pattern 145 to hollow the portion to insert the coil, namely the inside portion of the coil wiring 144 formed circularly and the inside portion of the part shown by the dash line 147 in FIG. 13(*e*), which is inside of the part the dash line 147 in FIG. 13(*i*) to (*k*), are formed. Since the considerably thick portions are etched, the film or the thin plate for the etching stopper may be intervened. The coil wiring substrates inside the coil wiring are removed by etching from the opening portions 146 by using the photosensitive pattern 134 as mask All of the coil wiring substrate inside in the coil wiring substrate 142-2 having the wiring pattern of the lowest layer is removed, and further the coil wiring substrate 142-1, which is under the coil wiring substrate 142-2 and does not have the wiring pattern, is etched and removed on the way, or wholly. Thus the coil insertion hole 148 (the side surface is 147) is formed. Since significant amount of the coil substrates are etched, the etching selective ratio between the photosensitive film pattern, and the etching stopper if the etching stopper is used, and the coil substrate needs to be selected much larger. Or the photosensitive film 145 needs to be formed much thicker. So, the portion 148 of the coil insertion hole may be hollowed preliminarily at the stage where each coil wiring substrate is made. For example, show in FIG. 13(*i*) to (*k*), the portion 148 inside the area shown by the dash line 147 may be removed. Since the removal can be practiced simultaneously when the wiring channel (the penetrated hole) is formed at the formation of the wiring pattern 144, the process steps do not increase and the process cost does not increase. When the wiring pattern 144 is formed, the conductive film formed in the hollowed portion 148 may be removed simultaneously or the conductive film may not be formed by masking. These do not lead to the increase of the process steps. Thus if the desirable number of the coil wiring substrate is piled up, the coil insertion hole 148 is formed simultaneously, and the process such as the photosensitive film pattern or the adhesion of the etching stopper, etc. is not needed.

Next as shown in FIG. 13(*f*), the core 151 adhered to the support substrate 149 is inserted in the coil insertion hole 148. The core 151 may be adhered to the convex portion 150 and inserted in the coil insertion hole 148 so that the support substrate 149 does not impact the coil wiring substrate 142-9 in the top portion. Thus the core 151 can be wholly put in the coil insertion hole 148. The core 151 may be inserted within the coil insertion hole 148 after the adhesion agency is poured within the coil insertion hole 148 using a dispenser or coating, etc., or the core 151 may be inserted after the adhesion agency is adhered on the lower surface or the side surface. If the adhesion agency is paste form, liquid form, or gel form, since it also becomes buffering agent, the damage given to the coil wiring substrate 142 can be reduced. Or a adhesive sheet may be adhered to the core 151. The adhesive sheet can play the role of the buffering material by having cushioning characteristics. As stated already, the effects as the core can be increased in addition by using the materials of the liquid form or the gel form as the adhesive agency. The density of magnetic flux in the coil can be increased to some extent by filling the paste, liquid form or gel form materials containing the powder form of the soft magnetic materials in the coil insertion hole even if the core 151 is not used. Or if the paste, liquid form or gel form materials containing the powder form of the soft magnetic materials are poured to the extent that they are filled in the coil insertion hole 148, or the above materials are poured to the extent that they are filled in the coil insertion hole 148 when the core 151 is put in the coil insertion hole 148, since the core 151 is covered by these materials, the materials such as the adhesive agency, etc, to fill the coil insertion hole 148 do not need to be used. When the core 151 is put and covered by the adhesive agency, etc. in the coil insertion hole 148, since the wiring layer exposing on the upper surface of the coil wiring substrate 142-9 in the top portion may be covered by the adhesive agency, etc., the adhesive agency, etc. adhering on the upper surface of the coil wiring substrate 142-9 in the top portion can be removed using the grinding method (BG method, CMP method, etc.) or the etching method. Also, the upper surface of the coil wiring substrate of the top portion may be desirably planarized.

Next as shown in FIG. 13(*g*), the pattern 152 of the photosensitive film is formed to determine the outline of the coil. The coil wiring substrate 142 is etched by using the photosensitive film pattern 152 as the mask, and the unnecessary portions are removed to the coil wiring substrate 142-1 in the lowest layer. Since the coil wiring substrates 142 is thick, they can be piled up in the state where the coil outline is determined. The patterns that are formed as the penetrated hole patterns for wiring and the patterns to fill with the conductive film in the penetrated holes may be used as the outlines of each coil wiring substrate 142 (142-1, 2, . . . ) in the substrate in which the outlines are determined from the beginning (for example, the substrate 142 having only the outlines shown in FIG. 13(*i*) to (*k*)). Or the coil wiring substrate 142 (142-1, 2, . . . ) having the large area in which many of the outline portion, the penetrated hole for the wiring and the patterns to fill with the conductive film in the penetrated holes are formed can be piled up. Thus as shown in FIG. 13(*h*), the coil 140 adhered to the support substrate 141-1 is formed.

Next forth substrate 153 is adhered on the upper surface of the coil 140 (the coil wiring substrate 142-9 in FIG. 13(*g*)). (FIG. 13(*l*)) The forth substrate 153 is an insulating substrate such as glass, quarts, sapphire, alumina, ALN, various polymer such as ceramics or epoxy, etc., plastics, etc. In the case of metal substrate or semiconductor substrate such as Si, etc., the surface or the portion of the contact hole need be covered by the insulating film. After the forth substrate is adhered, to the conductive wiring patterns 144-9-1 and 144-9-2 in the coil wiring substrate 142-9 of the top portion, the contact hole and the conductive wiring 154 inside the contact hole in the forth substrate 153 is formed, additionally the electrode and wiring patterns 155-1 and 155-2, which are connected the contact 154, are formed. The conductive wiring pattern 144-9-2 is the wiring connecting to the coil wiring terminal of the coil wiring substrate of the lowest portion, the portion connecting to it is the electrode and wiring pattern 155-2. The other terminal of the coil wiring is the coil wiring terminal 144-9-1 of the coil wiring substrate of the top portion, the portion connecting to it is the electrode and wiring pattern 155-1. Thus current can flow in the coil 140 between the conductive wiring patterns 144-9-1 and 144-9-2 and the magnetic field can generate. When the forth substrate 153 is the insulating substrate, or the conductive substrate and semiconductor substrate of which the surface is covered by the insulating film, since the coil wiring substrate 142-9, which has only the coil wiring pattern, can be omitted, the coil wiring substrate 142-8 having the annular coil wiring pattern can be directly adhered. The insulating adhesive agency is used as the adhesive agency. Though the forth substrate 153 having preliminarily the contact 154 and the conductive wiring electrode 155 can be adhered to the coil 140, the conductive adhesive agency can be used in the connection between the contact 154 and the conductive wiring patterns 144-9-1 and 144-9-2, and the insulating adhesive agency can be used in the other portion. Also the contact 154 and the conductive wiring patterns 144-9-1 and 144-9-2, or the other portions can be grafted by the direct grafting such as the room temperature grafting, high temperature grafting, fusion splicing, etc., After that, the support substrate 141-1 is separated. Thus the coil 140 adhered to the forth substrate 153 can be made. The coil 140 has the core 151 inside the coil wiring. If the core is not used, the process becomes simple since the coil insertion hole 148 need not be formed. If the support substrate 141-1 is used as the forth substrate, since the similar coil 140 can be made, there are some merits, namely the last support substrate 141-1 need not be separated and the coil wiring substrate 142-1 that does not have the first wiring pattern need not be used. Since the forth substrate 153 is used as a product, the materials and process need be designed and selected by considering the reliability such as the endurance, etc. Then the contact hole and the electrode and wiring are formed in the forth substrate 153, which is the support substrate.

The coils 140 adhered to the forth substrate 153 are adhered to the second (upper) substrate 202 and the third (lower) substrate 203 adhered to the upper and lower portions of the cavity 204-2 in which the charged particles run as shown in FIG. 11. The status is shown in FIG. 14. Namely quadrupole electromagnets made by the coil (electromagnet) of the present invention are shown in FIG. 14. The coils 118-1 and 118-2 are respectively disposed in the cavities (coil insertion cavities) 120-1 and 120-2 equipped in the right and left side (Y direction) of the cavity 204-2 in which the charged particles pass (the charged particle passing cavity), and the second substrate (upper substrate) 202 is adhered to the upper portion and the third substrate (lower substrate) 203 is adhered to the lower portion. The bottom surface of the coil 140(140-1) adhered to the forth substrate 153(153-1) is adhered on the second substrate (upper substrate) 202 on the charged particle passing cavity 204-2 in such acceleration device. The adhesive agency is coated or the adhesive sheet is overlaid on the adhesive face of the second (upper) substrate 202 and the coil 140(140-1) is adhered. Or the adhesive agency is coated or the adhesive sheet is overlaid on the lower face of the coil 140(140-1) and the coil 140(140-1) is adhered. The concave portion is made in the given part of the second (upper) substrate 202 and the part of the second (upper) substrate 202 is made thinner and then the coil 140(140-1) may be inserted into the concave portion. Since the thickness of the second substrate (upper substrate) on the charged particle passing cavity 204-2 is smaller, thus since the edge face of the coil 140(140-1) comes closer to the charged particle passing cavity 204-2, the strength of the magnetic field in the charged particle passing cavity 204-2 can be larger. Since the second (upper) substrate 202 weakens or disturbs the magnetic field, a part of the second (upper) substrate 202 (for example, the opening portion 159-1 shown in dot-line) on the charged particle passing cavity 204-2 may be removed. In that case, the opening portion 159-1 is sealed using the adhesive agency etc. so that the coil 140-1 can occlude perfectly the opening portion 159-1 to protect the increase of the pressure in the charged particle passing cavity. If the conductive film (or the thin conductive plate) or the semiconductor such as Si film (or Si substrate) etc. is adhered and the second (upper) substrate is glass substrate etc., these can be adhered strongly by anodic electrostatic binding. Or if these film, thin plate, layer or substrate is used in the coil wiring substrate 142-1, they can be adhered strongly by anodic electrostatic binding.

Or as shown in FIG. 14, if a supporting pole 156-1 is adhered to the second (upper) substrate and the forth substrate 153-1 is adhered to the supporting pole 156-1, and the cavity 157-1 is formed, and the coil 140-1 is disposed in the cavity 157-1, and the cavity 157-1 is vacuumized through the opening portion 158-1 equipped in the forth substrate 153-1, the increase of the pressure of the charged particle passing cavity 204-2 can be prevented. In that case, when the forth substrate 153-1 is adhered to the supporting pole 156-1, if the distance between the second (upper) substrate 202 and the edge face of the coil 140-1 is almost zero, the supporting pole 156-1 and the edge face of the coil 140-1 can be adhered simultaneously to the second substrate, and the distance between the charged particle passing cavity 204-2 and the edge face of the coil 140-1 can be fixed even if the second (upper) substrate 202 and the edge face of the coil 140-1 are not adhered. If the supporting poles 156-1 are formed using the coil wiring substrate 142, there is not the increase of the process. Or the cavity 157-1 is made in the substrate having the thickness that is the same as the length or of the coil 140-1 or is a small longer than the length or of the coil 140-1, and the supporting poles 156-1 are adhered to the second (upper) substrate 202 or the forth substrate 153-1, and when the coil 140-1 is disposed, the supporting poles 156-1 are adhered to the second (upper) substrate 202 or the forth substrate 153-1. If the second (upper) substrate 202 and the forth substrate 153-1 is the glass substrates, etc. and the supporting ports 156-1 are the conductive substrates or the semiconductor substrate such as Si substrates, etc., they can be adhered strongly with the anodic electrostatic binding. Though the vertical direction to the paper face, (namely the travelling direction of the charged particles) is not written, since the cavity 157-1 surrounds by the supporting poles 156-1 more widely than the charged particle passing cavity 204-2, the upper portion of the charged particle passing cavity 204-2 includes perfectly the charged particle passing cavity 204-2 within the cavity 157-1. Accordingly, since the outside of the charged particle passing cavity 204-2 is surrounded by the cavity 157-1 of which the pressure is controlled, the pressure of the charged particle passing cavity 204-2 can be controlled at the lower pressure. Though the electrodes of the coil 118(118-1,2) are put in the cavity 157-1, since the electrodes can be lengthened as wiring, they can be disposed outside the cavity.

The coil 140-2 can be also extremely similarly disposed in the lower portion of the charged particle passing cavity 204-2. The formation of the supporting poles 156-2, the opening portion 159-2 of the third (lower) substrate, the concave, the cavity 157-2, and the opening portion 158-2 for vacuumizing is similarly. The plural coils 118(118-1, 2) and the plural coils 140(140-1, 2) can be disposed in the vertical direction to the paper face, namely along the charged particle passing cavity 204-2, and the space of the plural four-pole electromagnets can be made simultaneously and simply. Thus the convergence or focusing and the spread of the charged particles travelling in the charged particle passing cavity 204-2 can be controlled.

Though the substrate coils are disposed (arranged) in FIG. 4, the ordinary electromagnets may be arranged. For example, the quadrupole electromagnet can be arranged in the portions that focus the charged particles by arranging various kinds of electromagnet. (For example, the portions of 15, 17, 19, 21, 22, 23, 26, 28, 29, 31, 32, 35, 36 etc. in FIG. 1) One magnetic pole of the electromagnet can be easily arranged in the upper and lower direction, namely the magnetic pole may be made contact or close to the upper or lower substrate. As the magnetic pole comes close to the upper and lower, since it approaches the orbital of the charged particles (the charged particle orbital), which is near or equal to the center of the penetrated room, the charged particles can be focused even small magnetic field. Since the electromagnets can not be arranged at this structure in the lateral side, the area of the opening portion is equipped in the both side by cutting the area (both side) outside the portion, where the charged particles are focused, almost parallel to the charged particle orbital, and the electromagnets are arranged in the opening portion area so that the magnetic field is vertically applied to the charged particle orbital. Since the space is limited as the area where the electromagnets are arranged, the electromagnet may be desirably the electromagnet that is small and generates the strong magnetic field. If the strength of the magnetic field of the superconducting electromagnet can be as large as desired by considering the holder space, the superconducting electromagnet can be arranged. Since the accelerator of the present invention is small in size, even if the whole of the portion where the superconducting electromagnets are arranged is housed in the box of the temperature at which the superconductivity is kept, the size of the box does not much large. Laser dicing method or high pressure water dicing method, etc. can be used as the methods how to make the opening portions in the substrate. Also, the desirable portions in the substrate can be opened accurately. Since the electric magnets arranged in the lateral side are made contact to the substrate or as they come close to the substrate by closing, they approach the charged particle orbital (near the center of the penetrated room), the charged particles can be focused even small magnetic field.

In the synchrotron, the higher speed charged particles can be generated by accelerating them in the cavity between the deflected (or bending) magnets 25, 30, 34, and 37. For example, the electrode for acceleration (acceleration electrode) explained later can be used. Namely many acceleration electrodes, of which the conductive film is deposited on the substrate side wall (plate) having the central hole, (and which can be used as the focusing and the deceleration) are made parallel in the penetrated room. If the voltage applied to many acceleration electrodes arranged in the travelling direction of the charged particles becomes larger gradually, the charged particles passing the central hole of the acceleration electrodes accelerate larger. For example, when 100 of the substrate side wall (plate) are arranged at 1 mm intervals, the total length is 100 mm, and if the applied voltage is divided between them and 100V is applied in total, since $\frac{1}{2}mv^2=qV$ (m: mass of the charged particle, q: electric charge, V: applied voltage), v=14 km/sec as m=$10^{-25}$ kg, q=e. If the charged particles are accelerated at four places, v=56 km/sec. If the charged particles turn 1000 laps, v=56000 km/sec, which is $\frac{1}{5}$ of the light speed. Or if high-frequency voltage is applied to the acceleration electrodes arranged numerously, the charged particles are accelerated, accordingly as the frequency becomes larger, the velocity of them can increase larger. Since many of the circular orbital of the synchrotron can be arranged (show FIG. 16), if the frequency of the high-frequency voltage increases gradually in the respective orbital, the velocity of the charged particles can increase easily. In the case of the linear accelerator, since the substrate of the both sides of the penetrated rooms may be cut, the electromagnets can be simply arranged in the both sides.

Figure 5:
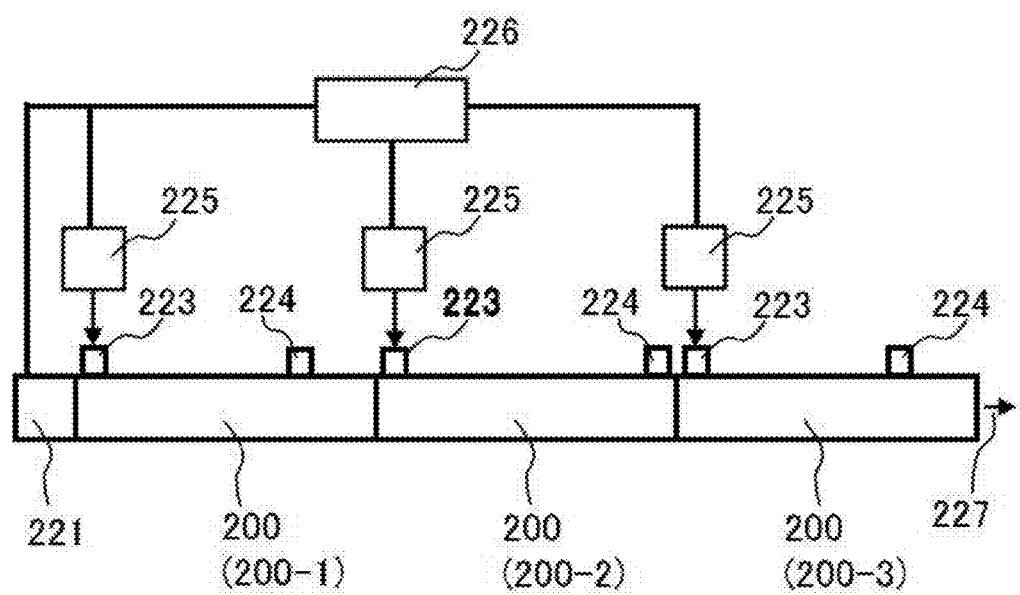
FIG. 5 shows the accelerators in which plural of charged particle accelerators of the present inventions are interlinked.

FIG. 5 shows the accelerators in which plural of charged particle accelerators of the present inventions are interlinked. Many of the accelerators 200(200-1, 2, 3, . . . ) shown in FIG. 4 are connected, the high-frequency is input into the accelerators from the high-frequency generators 225 through the high-frequency guiding tubes (waveguides) 223 that input the high-frequency into the respective accelerators, and the acceleration electric field is made, thus the velocity of the charged particles input into the accelerator 200(200-1) from the high-frequency generator 225 is accelerated, thus the charged particles 227 come out at high speed from the last stage of the accelerator 200(200-3). The high-frequency passing the accelerators 200 comes out of the high-frequency guiding output tube 224. The control device 226 controls the frequency, electric power, timing (of the pulse, etc.), etc. in the respective high-frequency generators and the charged particle generator 221. Since the accelerator of the present invention can be made by changing the size freely, it can be selected as usage. For example, if the depth of the cavity (h1, namely the thickness of the main substrate) is 1 mm, since the width of the accelerator can be about 3 mm, in the wafer (here rectangle) of the size 300×300 mm, 100 accelerators having 300 mm in length can be made. Accordingly the accelerator of 30 m in length can be made using one wafer. Since whole of the accelerator having a small width like this can be covered by the box vacuumized (the very low pressure box), the cavity of super very low pressure can be actualized if the inside of the accelerator is vacuumed. Since the whole can be immersed in liquid He or liquid nitrogen, etc., the heat generated by applying the high-frequency can be protected, also since the electromagnets for focusing can use the superconductor, the magnetic field of the electromagnet can be larger.

Figure 6:
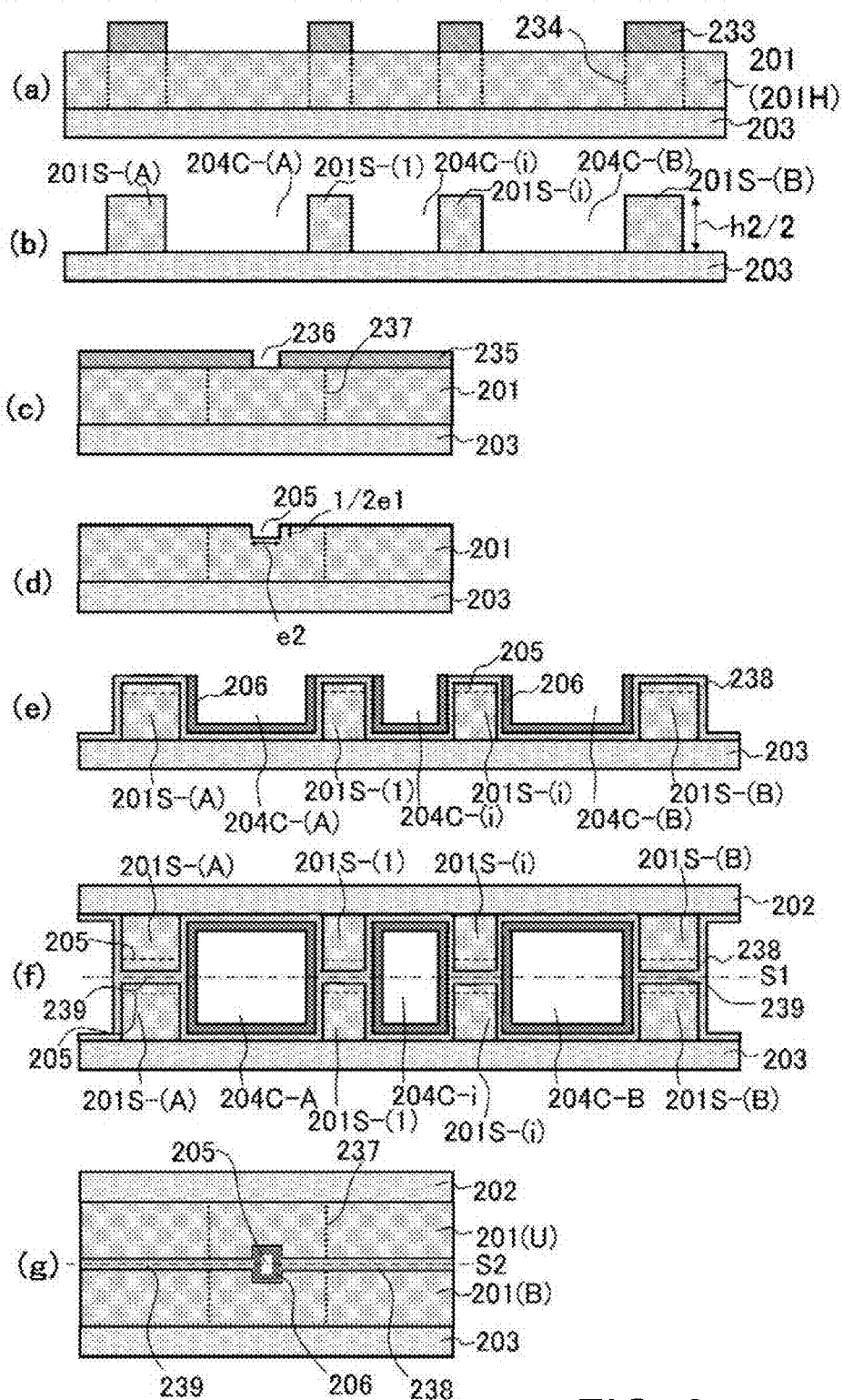
FIG. 6 shows one example of the manufacturing method of the charged particle accelerator of the present invention.

FIG. 6 shows one example of the manufacturing method of the charged particle accelerator of the present invention. The penetrated cavity formed in the main substrate 201 is used as the acceleration cavity of the charged particle. The main substrate 201 is adhered to the lower substrate 203. The material of the main substrate 201 is conductive substrate, insulating substrate, or semiconductor substrate, etc. The material of the conductive substrate is a metal substrate such as Cu, Al, etc., a semiconductor substrate in which high concentration of carrier is doped (for example, semiconductor substrate having low resistivity), conductive plastics, conductive ceramics, or conductive carbon substrate, etc. Ferromagnetic and paramagnetic materials may not be desirably used. Accordingly we can use a stainless steel that is not non-magnetic material such as austenitic stainless steel, etc. We can use glass substrate, quarts substrate, sapphire substrate, alumina substrate, AlN substrate, plastic substrate, ceramic substrate, etc. as the insulating substrate. We can use Si substrate, Ge substrate, SiC substrate, carbon substrate, compound semiconductor substrate, etc. as the semiconductor substrate. If not written particularly in the specification, we explain in the present specification by considering that the main substrate is the silicon substrate of the semiconductor substrate The conductive substrate, the insulating substrate, the semiconductor substrate, etc. can be used as the lower substrate 203. Their materials are the same as those of the main substrate 201. If not written particularly in the specification, we explain in the present specification by considering that the lower substrate is the glass substrate of the insulating substrate. There are a method to adhere using the adhesive agency, a fusion method to adhere by fusing bonding surfaces, a room, a high temperature adhesive method, a diffusion adhesive method, etc. as the method how to adhere the main substrate 201 and the lower substrate 203. The electrostatic (anodic) adhesive method can be used in the case of the glass substrate and the semiconductor substrate such as Si substrate, etc. or the conductive substrate. After insulating film or metal film, etc. is formed on the lower surface of the main substrate 201 using CVD (Chemical Vapor Deposition) method or PVD (Physical Vapor Deposition) method, the main substrate 201 can be adhered with the lower substrate 203. Next as shown in FIG. 6(*a*), the photosensitive film 233 such as photoresist, etc. is formed on the upper surface of the main substrate 201 using the coating method or the sheet adhesive method, and the opening portions are formed using the photolithography method, and the photosensitive pattern 233 is formed. The photosensitive pattern 233 is the pattern to form the penetrated holes in the main substrate 201. The insulating film or the metal film may be formed between the main substrate 201 and the photosensitive film. The role of these insulating film and metal film is to protect the device or to stop etching when the photosensitive film is etched wholly since the photosensitive film is etched during etching the main substrate 201.

Next the main substrate 201 in the portions of which the photosensitive film 233 is opened is etched. If the main substrate 201 is Si, the etching gases are CF series, SF series, CCl series, SiCl series, Cl series, Br series, etc. The pattern of the penetrated (through) hole (room) is desirably the vertical pattern to the surface of the main substrate as possible. It may be desirably etched in the close shape (which shown in the dotted line 234 of FIG. 6(*a*)) to the photosensitive film pattern 233. For example, there is RIE (Reactive Ion Etching) method, Bosch method, cryoetching method as such vertical etching methods.

If the lower substrate 203 is the glass substrate, since the etching selectivity ratio can be selected in the above etching gas or etching method, even if the surface of the main substrate 201 is etched uniformly by overetching silicon in the thickness direction of the main substrate 201, the etching amount of the lower substrate 203 is small. For example, when the thickness of main substrate 201 is 500 μm and the etching selectivity ratio is 50, the etching amount of the lower substrate 203 is at most 5 μm by 25% overetching (by which the penetrated room of the main substrate 201 can be formed wholly). Accordingly though 10 μm thickness of the lower substrate is enough, the thickness is desirably more than about 100 μm to keep the constant strength. Another substrate may be adhered to the lower substrate 203 to reinforce. After the thick lower substrate 203 (for example, more than 300 μm) are adhered, they can be made thinner less than 100 μm using polishing method (CMP method or BG method) or etching back method.

FIG. 6(*b*) is the cross sectional diagram after the main substrate 201 is etched and the penetrated room is formed and the photosensitive film 233 is removed. The cross sectional face is the diagram seeing the right and left in the longitudinal direction. The substrate side walls 201S-(A), 201S-(1), 201S-(i) {i=1, 2, . . . }, 201S-(B), etc. and cavity (which is called the penetrated hole or room or groove) 204C-(A), 204C-(i), 204C-(B), etc. are formed corresponding to FIG. 5(*a*). To write the parenthesis here means that a half of the cavity or the substrate side wall is formed, as mentioned later. Accordingly the substrate thickness of the main substrate 201 (201H) is about h2/2, here. Word "H" of the main substrate 201(201H) means a half in FIG. 6(*a*). The substrate side wall 201S is formed as almost the vertical main substrate side wall to the surface or the reverse face of the main substrate 291. However even if it can not be formed vertically, the given characteristics as accelerator can be obtained by keeping within 90±10 degrees. Or even if the degrees exceed these, the velocity and the direction of the charged particles can be controlled by adjusting the conditions of the high-frequency input voltage or the charged particle generator, or the electromagnet for focusing.

FIGS. 6(*c*) and (*d*) is the diagrams seeing from the rectangular direction to the longitudinal direction (the travelling direction of the charged particles, the right and left direction in FIG. 6(*a*) and FIG. 6(*b*)). Namely they are the diagrams showing the method to form the central hole 205. After the substrate side wall 201S shown in FIG. 6(*b*) is formed, the photosensitive film 235 is formed (for example, using photolithography method in the photosensitive sheet adhesive method or the photosensitive film coating method), the window 236 to form the central hole 205 is opened. the photosensitive film 235 may be formed after the insulating film is formed on the surface of the main substrate 201. The main substrate 201 is etched through the window opening portion 236 using the central hole 205 patterned as a mask, and the central hole 205 is formed. When the shape of the central hole is rectangular, if the longitudinal length is e1 and the lateral length is e2, the depth of the central hole (the longitudinal length) in this step is about ½×e1 as shown in FIG. 6(*d*) that shows the status after the photosensitive 235 is removed. Though the cavity is not seen in FIGS. 6(*c*) and (*d*), the cavity exists un the front or the back of the substrate side wall 201 (for example, 201S-(i)) (i=1, 2, 3, . . . ), and the boundary is shown by the dotted line 237. The central hole 205 in FIG. 6© and (*d*) can be also formed before the substrate side wall 201S and the cavity 204 are formed, namely before FIG. 6(*a*), as known simply. This process has a merit that the photosensitive film pattern can be easily formed since there are no concaves and convexes such as the cavity, etc.

Next as shown in FIG. 6(*e*), the insulating film 238 is formed on the main substrate and in the penetrated room. This insulating film 238 is formed so that the main substrate 201 does not connect electrically to the conductive film 206 formed later, or as the film to improve the adhesion with the conductive film. However since the conductive film does not conduct electrically with the substrate when the substrate is the insulating substrate, though the insulating film is not needed, the insulating film may be deposited as the film to improve the adhesion with the conductive film. The insulating film 238 is formed with CVD method, PVD method, etc. For example, they are silicon oxide film (SiOx), silicon nitride film (SiNx), or silicon oxynitride film (SiNxOy). If the main substrate 201 is silicon, the insulating film can be formed by oxidizing or nitirizing. After that, the conductive film 206 is formed. Since the conductive film 206 is used to form an acceleration electric field by the high-frequency, the higher electroconductivity is better. Also non magnetic materials (containing diamagnetic materials) that do not affect the magnetic generation are better. For example, they are Cu, Au, Ag, Ti, Zr, Ta, W, Al, C (for example, conductive nanotube, grapheme), various silicide, these alloy, conductive polySi, these compounds. These conductive film can be formed by CVD method, PVD method, or plating method. The conductive film 206 may be formed after the film (adhesion improvement film) to improve the adhesion between these conductive films 206 and the insulating film 238, the main substrate 201, the lower (upper) substrate 202, 203 is formed. The adhesion improvement film, for example, Ti, TiN.

Since the conductive film in the cavity except the portions of the charged particle accelerator need be removed or patterned, the photosensitive film is formed and patterned, and the conductive film 206 in the unnecessary portions is etched. The conductive film 206 is formed in the cavity in the charged particle accelerator (acceleration cavity) 204C-(i), the high-frequency input room 204C-(A) and the high-frequency output room 204C-(B). Though the insulating film for the passivation film can be formed after the conductive film 206 is patterned, the passivation film may not be formed if not necessary.

Figure 7:
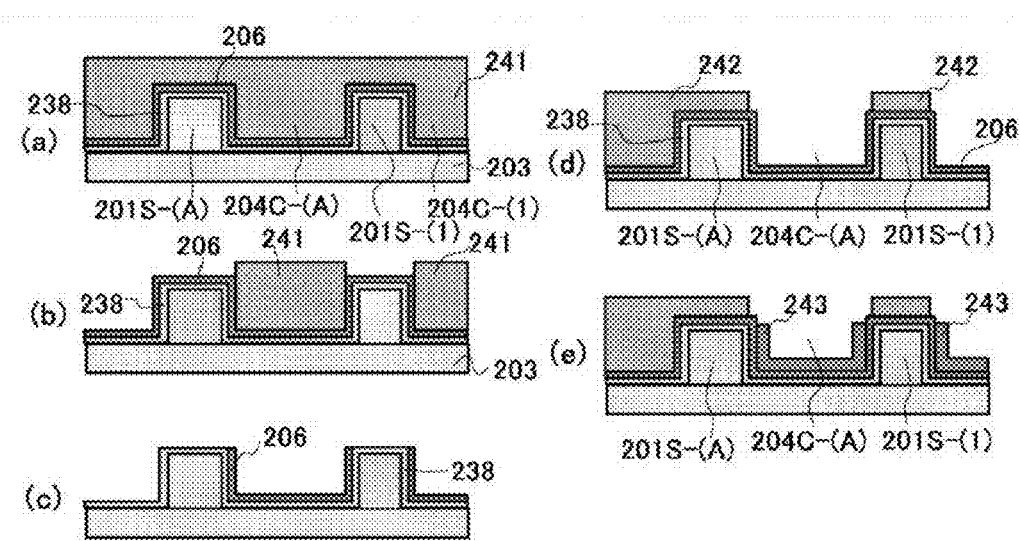
FIG. 7 shows one example of the manufacturing method of the charged particle accelerator of the present invention, and the diagram showing the process from the formation of the substrate side wall till the patterning of the conductive film.

The detail of the process is shown in FIG. 7. FIG. 7 is the diagram showing the process from the formation of the substrate side wall till the patterning of the conductive film and only one part of the structure shown in FIG. 6 is shown simply. After the substrate side wall 201S (201S-(A), 201S-(1), etc.) and the cavity 204 (204C-(A), 204C-(1), etc.) are formed, the insulating film 238 is formed, next the conductive film 206 is formed, and the photosensitive film 241 is formed. The photosensitive film 241 is formed by coating method or adhering the photosensitive sheet and softening the sheet. Next as shown in FIG. 7(*b*), the desirable pattern 241 is formed by the exposing method (containing development and baking), and the photosensitive film in the portion to remove the conductive film 206 is removed and thus the portion is opened. The conductive film 206 exposing in the opened portion is etched and removed by dry-etching or wetetching. If the passivation film, etc. exists on the conductive film 206, the conductive film 206 is etched after etching and removing the passivation film. After the conductive film is etched, if the insulating film 238 exists under the pattern of the conductive film 206 and the insulating film 238 need be removed, the insulating film 238 is etched and removed by dryetching or wetetching. After that, as shown in FIG. 7(*c*), the conductive film 206 is formed in the desirable portions by removing the photosensitive film 241. If the conductive film 206 in the accelerator is connected, the conductive film 206 in the concave portions of the substrate side wall 201S can be left. If the conductive film is formed in the central hole, the photosensitive film may be formed (left) in the portion of the central hole.

We explain about the method to deposit thickly the conductive film by plating method in the portion to leave the conductive film 206. Since the conductive film 206 may be the seeds of plating, it may be deposited only thinly. For example, if the conductive film 206 is Cu, the thickness of Cu film may be about 100 nm. After FIG. 7(*a*), the portion to deposit the conductive film 206 is opened. Namely as shown in FIG. 7(*d*), the photosensitive film 242 is patterned, and the acceleration cavity portion, etc., which is the portion to deposit the conductive film 206, is opened. Accordingly it is the reverse patterning to FIG. 7(*d*). It is soaked in the plating liquid (for example, if Cu plating, for example, copper sulfate solution), and the plating film 243 such as Cu, etc. is plated in the given thickness in the exposed part of the conductive film 206 by applying the electric field. If non electric field plating method is used, the conductive film 206 deposited firstly may not be needed. After the photosensitive film 242 is removed, though the thin conductive film 206 is etched, since the conductive film 206 is thinner than the plating film 243 (+206), it is etched wholly using the etching solution or etching gas of the conductive film 206. Thus the new mask (the photosensitive film, etc.) is not needed, and the conductive film 206 and 243 can be formed in only the desirable area.

The same structure is formed on the upper substrate 202 using the process showing in FIG. 6(a) to (e). The upper and lower portions and the lateral (right and left) portions are almost symmetric to the center of the cavity 204 in the charged particle accelerator of the present invention. Accordingly as shown in FIG. 6(f), the respective upper surfaces are adhered each other in the structure shown in FIG. 6(e) formed in the lower substrate 203 and the structure shown in FIG. 6(e) formed in the upper substrate 202. Since the upper substrate 202 or the lower substrate 203 is glass, and the visible light passes through the cavity portion 204 that does not have the conductive film 206, and the upper side substrate (namely the upper substrate 202 and the main substrate 201) and the lower side substrate (namely the lower substrate 203 and the main substrate 201) can be directly aligned, the alignment is very accurate. Since the accelerator of the present invention can be made using LSI process and the patterning accuracy is less than 1 μm, if the alignment accuracy is 3 μm, the upper side substrate and the lower side substrate can be adhered at the accuracy less than 5 μm. The accuracy is enough for the accelerator.

The adhesion between the main substrates can be performed strongly using the room temperature bonding, the diffusion bonding, the high temperature bonding, or the adhesion agency. If the insulating film exists in the adhesion portion 239 and the adhesion is not sufficient, after the insulating film in the portion is removed, their substrates (for example, Si) can be adhered using the room temperature bonding, the diffusion bonding, the high temperature bonding, or the surface activation bonding, etc.

Or the metal film or the adhesion agency is adhered in the portion, the upper side substrate and the lower side substrate can be adhered strongly by applying heat or pressure, or the room temperature bonding. Furthermore after the thin glass substrate is put between the upper and lower main substrates (for example, Si) in the portion, they can be adhered strongly by the electrostatic binding (anodic bonding). Also, if the conductive adhesive agency is used, the conductive film 206 formed in the upper side substrate and the conductive film 206 formed in the lower side substrate can be connected electrically. Even if the conductive adhesive agency is not used, their conductive films 206 can be connected electrically by applying the adequate temperature or pressure, or using the room temperature bonding. Here S1 is the bonding face, and the center of the acceleration cavity is almost the position of S1. Also, the center of the central hole is almost the position of S1.

FIG. 6(g) is the diagram seeing the cross sectional face of the substrate side wall 201S in FIG. 6)f) from the vertical direction to the longitudinal direction of the cavity. It is the diagram the upper side substrate (the upper substrate 202 and the main substrate 201) and the lower side substrate (the lower substrate 203 and the main substrate 201) are adhered at the bonding face S2, the boundary of the cavity is shown in the dashed line. If the upper substrate 202 and the lower substrate 203 are almost the same substrates, the upper side substrate and the lower side substrate are almost symmetric to the bonding face S2. And the central hole 205 is formed in almost the center. If the central hole is rectangular, as known from FIG. 6(d), the height is e1 and the width is e2. The insulating film 239 may be deposited and furthermore the conductive film 205 may be formed on the surface of the substrate side wall 201 in the central hole 205. Though the conductive film 206 between the upper side substrate and the lower side substrate is removed in FIG. 6(g), the conductive film 206 in the portion to be left is masked by the photosensitive film and the photosensitive film in the portion to be removed is opened, and the conductive film 206 is etched and removed by the etching solution and etching gas. The insulating film 239 may be removed in the bonding face (adhesive face) S2. In that case, S2 becomes the bonding between the main substrate 201 and the main substrate 201. Also, they can be adhered strongly by the electrostatic (anodic) bonding with putting the thin glass between the main substrate 201 (which is 201(U) since it is the upper side) and the main substrate 201 (which is 201(B) since it is the lower side).

As explained in the above, the charged particle accelerator can be made using the flat plate shaped substrate (containing the main substrate, the lower substrate, and the upper substrate). In the conventional accelerator, after disks arranged in the acceleration tube are made one by one, and the acceleration cavities are made one by one, since they are built up, the size of the accelerator becomes larger and the assemble time and the assemble cost are very large, and it is very difficult to increase the accuracy. The present invention use or adopt LSI process, the accelerator of the present invention can be made in large quantity, and very cheaply, very accurately (the fitting accuracy is less than 1 to 5 μm).

FIG. 8 shows the method to make the charged particle accelerator in the case to make the glass substrate 251 tucked between the upper side substrate (the main substrate 201 U, the upper substrate 202) and the lower side substrate (the main substrate 201B, the lower substrate 203) adhere with the upper side substrate and the lower side substrate by the electrostatic binding. The overlapped portions may be omitted in FIG. 6 and FIG. 7. The silicon substrate 201 (which is called 201B because it is the lower side substrate) and the glass or quarts substrate of the lower substrate 203 are bound by the electrostatic binding. Next the glass or quarts substrate 251 is bound on the other surface of the silicon substrate 201 by the electrostatic binding. Then since plus (+) voltage is applied to the silicon substrate 201, the plus (+) voltage is applied from the side face of the silicon substrate 201, or the silicon substrate 201 of the surround of the lower substrate 203 is exposed by etching and removing using the photolithography method, the plus (+) voltage is applied from the exposed portion. (The anodic binding is available in the conductive substrate such as metal plate, etc. instead of the silicon substrate 201. Also, if the silicon substrate 201 binds with the glass substrate after depositing thin metal film such as aluminum on the silicon substrate 201, it is possible to bind at lower temperature than the anodic binding in the case of no metal film.) Since the thinner glass substrate, etc. is better, for example, the thickness of the glass substrate is less than 100 μm, desirably less than 50 μm, more desirably less than 20 μm, or less than 10 μm. After firstly thick glass substrate, etc. is adhered, it can be thinner using the polishing method (CMP, BG, etc.) or etching method (wet, dry, etc.)

Next the pattern 233 of the photosensitive film is forme by the photolithography method to form the substrate side wall 201S. Next the glass substrate 251 in the area opened is etched and removed using the photosensitive film pattern 233. To etch as faithfully as possible to the photosensitive pattern 233, anisotropic dry etching (namely vertical etching) is desirable, if the amount of the side etching is considered, wet etching or isotropic etching may be adopted. After the glass substrate 251 is etched and removed, the silicon substrate 201 is etched and removed. To etch as faithfully as possible to the photosensitive pattern 233, anisotropic dry etching (namely vertical etching) is desirable, if the amount of the side etching is considered, wet etching or isotropic etching may be adopted. In FIG. 8(*a*), the line of the vertical etching is shown in the dashed line.

For the formation of the central hole 205, the photosensitive film is patterned from the upside of the glass substrate 251, and a part of the glass substrate 251 and the main substrate 201 are etched. If the size of the central hole is smaller than the thickness of the glass substrate 251, only the glass substrate 251 may be etched. The thickness of the glass substrate 251 can be equaled to the size of the central hole. In that case, By increasing the etching selectivity ration between the glass substrate 251 and the main substrate 201, since the size of the central hole becomes equal to the thickness of the glass substrate, the size of the central hole can be controlled much accurately. The central hole can be formed before the substrate side walls 201S-(A), 201S-(i) {i=1, 2, . . . }, 201S-(B) and the penetrated rooms 204C-(A), 204C-(i), 204C-(B) are formed. Next insulating film 238 is formed and the conductive film 206 is formed. (FIG. 8(*b*)) Next the necessary pattern of the conductive film is formed by the photolithography method and etching method. (FIG. 8(*c*)) The conductive film 206 is formed in the inside face of the penetrated rooms 204C-(A), 204C-(i) {i=1, 2, . . . }, 204C-(B), which become the acceleration cavity. Also, the conductive film 206 is left in the necessary portions of the inner face of the central holes 205 connecting them. The other side (the side of the upper substrate 202 in the upper side in FIG. 8) is formed alike, they are adhered. (FIG. 8(*d*)) Since the conductive film 206 is deposited on the side face of the glass substrate 251, they are adhered and pressured and treated thermally and can be connected. Furthermore if necessary, they can be sufficiently connected by adhering the conductive adhesive agency or solder metal, and adhering them by fitting them. The conductive adhesive agency or solder metal can be coated with tracing using dispenser, etc. Or the dispenser, etc. having the same inlet as the connecting portion are made, the conductive adhesive agency or the solder metal (melting material or paste) can be adhered into the connecting portion from the inlet. Or the necessary portion of the conductive film is exposed by patterning the photosensitive film, and the solder metal is plated in the exposed portion. These may be adhered and treated thermally. Furthermore after that, though the opening portion for vacuumizing or purging and cleaning is opened in the upper substrate 202 or the lower substrate 203, the connecting portions, etc. can be plated by pouring the plating solution using the opening portion. Or the gas for selective CVD (for example, WF6) are introduced from the opening portion, the metal film (for example, W) can be selectively deposited in the portions where the conductive film 206 is exposed in the connecting portions, etc. Or even if the connection is not sufficient, since the electrodes can be formed in the upper and lower substrates, the same high-frequency voltage may be applied from the both electrodes. The bonding face in the case where the same substrates as FIG. 8(*c*) are adhered each other is the chain line 244. the upper and lower portions are almost symmetric. Since the adhesion is the adhesion between the glass faces, the electrostatic anodic binding can not be used. So if the glass substrate 261 is used in one side, since the electrostatic anodic binding can be used when the upper and lower substrates are adhered, the strong binding is available.

Next as shown in FIG. 8(*e*), the contact hole is formed in the lower substrate 203 and the insulating film 238, and the conductive film is formed in the contact hole, and the contact 245 connecting to the conductive film 206 is formed. Furthermore the conductive film and electrodes and wiring 246 connecting to the contact 245 are formed.

Equally, the contact hole is formed in the upper substrate 202 and the insulating film 238, and the conductive film is formed in the contact hole, and the contact 248 connecting to the conductive film 206 is formed. Furthermore the conductive film and electrodes and wiring 249 connecting to the contact 248 are formed. As shown in FIG. 8(*e*), since these contacts 245, 248 and electrodes and wirings 245, 249 can be respectively made so that they can connect to the conductive film 206 formed on the inner (inside) face of each cavity rooms (which is also written chambers in all the present patent application) 204C-A, B, 204C-I, the process does not increase. Thus the voltage can be individually applied from outside to the conductive film 206 formed on the inner (inside) face of each cavity rooms. Furthermore though the upper and lower conductive films 206 are fitted and bonded in the binding face 244, even if the bond is not sufficient, since the (high-frequency) voltage can be applied from the upper and lower electrodes 246 and 249, they can become the same voltage. Also, the opening portion 247 for vaccumizing in the lower substrate 203 and the opening portion 250 for vaccumizing in the lower substrate 202 are formed. These opening portions 247 and 250 can be made simultaneously in each cavity room, and the pressure in each cavity room can be controlled individually, and since the very small space (cavity) can be vacuumized individually, the very low pressure cavity (space) can be made. We can plate on the connecting portion of the conductive film in the inside by putting the plating solution into the cavity room using the opening portions, and we can deposit the selective conductive film on the connecting portion of the conductive film in the inside by putting the gas for the selective CVD into the cavity room using the opening portions. As above, the very small acceleration cavity rooms can be made very simply. Next we explain about the deflecting electromagnet The deflecting electromagnet can be made using the coils arranged in the upper and lower portions of the four-pole electromagnet shown in FIG. 4, and FIG. 11 to FIG. 14. FIG. 15 is the diagram showing the charged particles passing cavity such as the deflecting electromagnets in FIG. 1 and the electromagnets arranged there. FIG. 15(*a*) is the diagram showing the charged particles passing cavity 257 in the portion of the deflecting electromagnets and the configuration state of the coils. The charged particles passing cavity 257 is the cavity having the curvature of which the central orbital is R and along the curvature. Many very small coils 258 of the electromagnets arrange in the upper and lower portions of the cavity. The very small coils 258 are arranged closely over the whole of the charged particles passing cavity 257. The charged particles G enter from the entrance of the charged particles passing cavity 257, receive Lorentz force by the vertical magnetic field in the charged particles passing cavity 257, circulate in the orbital radius R, and come out of the exit of the charged particles passing cavity 257.

FIG. 15(*b*) shows the cross sectional diagram along the vertical cross sectional face A1-A2 to the center of curvature in the charged particles passing cavity 257. the upper and lower portions of the penetrated (or penetrating) room (or cavity or chamber) 264 formed in the main substrate 261 are closed by the upper substrate 262 and the lower substrate 263. This penetrated room 264 is the charged particles passing cavity 257, and the cavity having the circle orbit of the radius R that is the central orbital. The plural coils 260 (260-1, 2, 3) are arranged on the upper surface of the upper substrate 262. The coils 260 (260-1, 2, 3) are adhered to the forth substrate 266, the forth substrate 266 is adhered to the support poles 265 (265-1, 2), and the support poles 265 are adhered to the upper substrate 262. Since the magnetic field of the edge face of the coil is larger, the smaller the coil size is, the more the coil turns is, the larger the electric current flowing the coil is, the magnetic field giving to the charged particles passing cavity 257 becomes larger by arranging and setting many small coils in line. Though it is easy to make the coil size small as shown in FIG. 13, the current flowing the coil becomes small if the wiring size becomes small. Accordingly, though the coil size cannot be necessarily determined, if the size of the coil 260 is small compared to the charged particles passing cavity 257, the plural coils 260 are arranged so that they may cover perfectly the whole of the charged particles passing cavity 257. For example, when the coil size is 0.5 mm×0.5 mm and the width of the charged particles passing cavity 257 is 1 mm, at least 3 coils are arranged in the width direction of the charged particles passing cavity 257. Then since the central orbital of the charged particles G is almost the center in the width direction of the charged particles passing cavity 257, one coil should be desirably arranged so that the axis of the coil may nearly fit in the center. The reason is because the magnetic field is largest in the center of the coil edge face. (The difference is small.) Coils are arranged closely in the width direction among the central coil. Since the distance between the coils (for example, the distance between coils 260-1 and 260-2) is determined when the coils are made (namely when the coil wiring substrates are piled up and adhered) and their coils need not be separated each other, the coils size can become much small. For example, it is possible to make the distance between wirings the size near the width of the coil wiring. If the coil size is larger than the width of the charged particles passing cavity 257, one coil may be arranged in the width direction. Then the coil should be desirably arranged so that the axis of the coil may nearly fit in the center of the charged particles passing cavity 257.

For the travelling direction of the charged particles in the charged particles passing cavity 257, the coils may be tightly arranged using the coil patterns of the coil wiring substrate fitting the orbit. For example, the coils 258 are arranged as shown in FIG. 15(a). And the groups of the coil array are separated in groups (or they may not be separated), and they are adhered to the forth substrate, and they are adhered to the upper substrate 262 based on (or with) the supporting poles 265 (265-1, 2). This is similar to the explanation in FIG. 14. The axis of the coil 260 may become vertical to the surface of the main substrate. Also, since the edge face of the coil 260 may be closer to the charged particles passing cavity 257 as possible, it is made contact and adhere to the upper substrate 262, or it is made closer to the upper substrate 262 as possible. Reducing the thickness of the portion 273-1 of the upper substrate 262 in the portion where the coils 260 are arranged, (Really, since the coils 260 (260-1, 2, 3) is wider than the width of the charged particles passing cavity 257, we make the concave portion where all the wider coils 260 than the width of the charged particles passing cavity 257 can be put.) the coils 260 (260-1, 2, 3) may be desirably inserted in the concave portion. Furthermore opening the portion 273-1 of the upper substrate 262 in the portion where the coils 260 are arranged in the charged particles passing cavity 257, the magnetic field of the coil 260 may not be desirably weakened and disturbed. In that case, since the airtight space of the charged particles passing cavity 257 is broken, the outer circumferential portion of the lower edge face of the coils 260 (in the case, the outer circumferential portion of the lower edge face of the plural coils) and the upper substrate should be desirably adhered perfectly. For example, the adhesive agency (solder metal) is adhered in the outer circumferential portion, the room temperature binding, the high temperature binding, the diffusion binding, or the electrostatic anodic binding is performed perfectly. Furthermore, the space (cavity) 269 arranging the coil is made as an airtight space, the opening portion 270 for vacuumizing is equipped in the forth substrate 266, the airtight space 269 becomes very low pressure through the opening portion 270 for vacuumizing. Of course, the opening portion for vacuumizing is equipped in the upper substrate 262 and the lower substrate 263 in the charged particles passing cavity 257, the charged particles passing cavity can be vacuumized through the opening portion. Thus the charged particles passing cavity 257 can become the very low pressure space.

The coils 259 (259-1, 2, 3) are arranged in the lower substrate 263. The concave portion 273-2 and the opening portion 273-2 can be equipped to make the edge face of the coil 259 (259-1, 2, 3) close to the charged particles passing cavity 257. The coil 259 is adhered to the forth substrate 268, the supporting pole 267 (267-1, 2) is adhered to the lower substrate 263, and the forth substrate 268 is adhered to the supporting pole 267. The space 271 arranging the coils 259 become the airtight space and the opening portion 272 for vacuumizing can be equipped in the forth substrate 268. In the coil 259 in the side of the lower substrate 263, the same coil and the same number of the coils as them in the coil 260 in the side of the upper substrate 262 are desirably arranged symmetrically to the charged particles passing cavity 257. If the characteristics of the coils are same, it is easy to control the magnetic field in the charged particles passing cavity 257. However even if the size of the coils is different, the magnetic field in the charged particles passing cavity 257 can be controlled by adjusting the electric current. In the present invention, even if the shape of the cavity arranging the coil is any shape, the shape of the coil can be changed so that it may fit the shape of the cavity. For example, the coil wiring can be changed to any curve profile. Also, the coil size can be changed freely, the number of the coils arranged and the arrangement configuration can be changed freely. Though the deflection magnet portions 25, 30, 34, 37, etc. in the synchrotron type accelerator shown in FIG. 1 are the sectoral shape cavities having the curvature of radius R, the coils corresponding to the shape can be arranged freely. Of course, the quadrupole electromagnet in the linear shape cavity, or the arrangement shape and the arrangement number of the electromagnet for focusing can be made freely.

As mentioned previously, in the accelerator of the present invention, since the devices having various functions can be made simultaneously, more devices can be connected using larger substrate. Since the very small accelerator, which is the synchrotron type accelerator shown in FIG. 1, can be connected to slightly larger synchrotron type accelerator than that in FIG. 1, they can be made simultaneously at a dash. FIG. 16 is the diagram connecting the very small circular accelerator (synchrotron) 8-1 shown in FIG. 1 to slightly larger circular accelerator 8-2, and the diagram showing double synchrotrons (or 2 cycle synchrotrons). The second synchrotron 8-2 surrounds the first small "very small accelerator" 10-1. We call these the very (ultra) small accelerator 10-2 as a whole. The exit 41-1 of the first small "very small accelerator" 10-1 connects to the inflector 21-2 of the second larger synchrotron 8-2. Namely the charged particles coming out of the exit 41-1 of the first smaller synchrotron 8-1 enter the accumulation ring 24-2 that is the cavity of which the charged particles pass in the circular accelerator 8-2 by way of the inflector 21-2. Equipping the linear accelerator 39-1 on the way of the cavity out of the circular accelerator 8-1, the velocity of the charged particles entering the inflector 21-2 can be adjusted. Also, other deflection electromagnets, acceleration electrodes, deceleration electrodes, linear accelerators, or focusing electromagnets, etc. may be equipped on the way.

The charged particles entering from the inflector 21-1 to the accumulation ring 24-2 of the circular accelerator 8-2 may be focused by the focusing electromagnets (in the horizontal direction and in the vertical direction), and are deflected and accelerated by the deflection electromagnet 25-2, and enter to the next accumulation ring 27-2, here are more accelerated in the high-frequency acceleration cavity 29-2, and are focused by the focusing electromagnets 26-2 (in the horizontal direction) and by the focusing electromagnets 28-2 (in the vertical direction), and are deflected and accelerated by the deflection electromagnet 30-2, and enter to the next accumulation ring 33-2, here are focused by the focusing electromagnets 36-2 (in the horizontal direction) and by the focusing electromagnets 35-2 (in the vertical direction), and are deflected and accelerated by the deflection electromagnet 37-2, and enter to he next accumulation ring 24-2. Thus the charged particles continue to rotate around the accumulation ring 24-2, 27-2, 33-3, and 38-2 with accelerating, and if their velocity and their number reach to the given values, they enter to the cavity 40-2 leading them outside (which is also called the charged particle exhaust cavity), they are took out outside from the exit 41-2 of the charged particle exhaust cavity 40-2. The linear accelerator 39-2 is equipped on the way of the charged particle exhaust cavity 40-2, and the charged particles may be more accelerated there. Also, other deflection electromagnets, acceleration electrodes, deflection electrodes, linear accelerator, or focusing electromagnets may be equipped on the way.

Thus many circular accelerators can be connected. The charged particles can increase the speed using these. Also, since the charged particles can be stored in the respective accumulation rings, the necessary amount of the charged particles can be prepared in a short time. For example, when the diameter of the cavity of the accumulation ring in the charged particles travel is 1 mm and the radius of the small accelerator is 50 mm and the distance between the rings is 3 mm and the radius of the substrate is 270 mm, 70 circular accelerators can be made.

FIG. 17 is the diagram showing the case where the circular accelerator 8 is made by dividing the substrate. Namely when one substrate cannot be sized up and the circular accelerator, etc. is larger than the substrate, the method to make the accelerator is shown. The circular accelerator 8 shown in FIG. 1 is large, for example, though the substrate of 2 m×2 m in size is needed, when only the substrate of 1 m×1 m in size can be prepared, 4 substrates of m×1 m in size 44-1 to 44-4 (which is shown in the dashed line) are prepared ¼ of patterns 43-1 to 43-4 of the circular accelerator 8 are made. Since the connected portions 45-1, 2, 3, 4 are the accumulation rings 24, 27, 33, 38, the substrates 44-1 to 44-4 are connected so that the central axis of the accumulation rings can be fitted. The connected faces are smoothened by polishing and etching the connected portions to make sure the connections. The adhesion of the connected portions can be performed using various kinds of bindings. The other material can be put between the connection portions. For example, the glass substrate, the plastic substrate, the metal substrate, etc. are used, the fusion binding and the electrostatic anodic binding, etc. between these materials and the connected portions can be performed. If the inner portions of the accumulation rings 24, 27, 33, 38 can be very low pressure, the connected portions need not be adhered perfectly. For example, preparing the materials or boxes, they may be adhered with the substrates 44-1 to 44-4. Their materials, etc. are desirably soft or flexible materials, etc. so that the axis fitting of the accumulation rings 24, 27, 33, 38 can be adjusted. The vacuumizing lines are equipped in the materials, etc. their inner portions may be better to enable vacuumizing. A very large circular accelerator can be made by repeating the above process. Also, the method, as mentioned previously, can be adopted in making the source of ionization and the long linear accelerator.

FIG. 18 shows the microwave ion source of the present invention. The microwave ion source of the present invention includes the upper substrate 162 on upper surface of the main substrate 161, the penetrating (penetrated) room (chamber, cavity) 164-1, 164-2, 164-3, the penetrated room 164-1 is the waveguide which the high-frequency 160 is input from the high-frequency or microwave (hereinafter called high-frequency) oscillator through the opening portion 166-1 opened in the upper substrate 162 or the lower substrate 163. The penetrated room 164-2 is the neighbor room (chamber) of the waveguide 164-1 and is a discharge room separated by the substrate side wall 161-2 having the central hole 165-1 and the high-frequency is input through the central hole 165-1 of the substrate side wall 161-2 from the wave guide room 164-1. The coil 169 in which the coil wirings are wound is arranged around the discharge room 164-2, the magnetic field B1 generates in the direction of the coil axis in the discharge room 164-2 by the coil 169. Electrons in the discharge room 164-2 are accelerated by the high-frequency, the discharge generates by ionizing collision of gas, and plasma generates. Though the high-frequency oscillator connects to the opening portion 166-1, the high-frequency and the vacuum should desirably be not to be escaped from the connecting portion between the input of the high-frequency oscillator and the waveguide room 164-1 by equipping the sealing portion 168-1 in the connecting portion. The insulating substrate such as the glass or the plastic, etc. can be adhered by the adhesive agency, etc. in the sealing portion 168-1. Well, the waveguide room 164-1 can be equipped outside of the main substrate 161. In that case, the high-frequency 160 is directly input to the discharge room 154-2. The opening portion 166-2 for introducing gas in the upper substrate 162 and/or the lower substrate 163 of the waveguide room 164-1, various kinds of gases that are the ion sources are introduced from the opening portion 166-2, they are sent with the high-frequency to the discharge room 164-2. Also, the opening portion 167-1 for vacuumizing is equipped in the upper substrate 162 and/or the lower substrate 163 of the waveguide room 164-1, the pressure of the waveguide room can be set in the given value, Furthermore, the opening portion for vacuumizing is equipped in the upper substrate 162 and/or the lower substrate 163 of each penetrated room, the pressure and the temperature can be measured. The temperature in each penetrated room can be controlled by irradiating infrared rays from outside. Or each penetrated room can be warmed using heater, thermal water or thermal wind from outside, and can be cooled using peltier device, etc., cooling water, cooling wind, cooling gas, cooling liquid, liquid He, liquid nitrogen, etc. Since the volume is very small, they can be controlled.

The penetrated room 164-3 next to discharge room 164-2 is an electrode room to extract ions (extraction electrode) and is separated from the discharge room 164-2 by the substrate side wall 161-3 having the central hole 165-2. There are the substrate side wall 161-4 having the central hole 165-3, which is the extraction electrode, the substrate side wall 161-5 having the central hole 165-4, which is the deceleration and focusing electrode, the substrate side wall 161-6 having the central hole 165-5, which is the acceleration electrode. Ions (charged particles) generating in the discharge room 164-2 are drawn by the electric field of the extraction electrode, pass the central hole 165-2 of the substrate side wall 161-3 for separating, and are accelerated through the central hole 165-3 of the extraction electrode 161-4, are focused through the central hole 165-4 of the next deceleration and focusing electrode 161-5, and are accelerated through the central hole 165-5 of the next acceleration electrode 161-6. By repeating these, the charged particles are accelerated and decelerated and focused, or enter to the deflection magnetic room, or are focused in the quadrupole magnetic room, and go out to the various penetrated rooms having the other uses. In the ion extraction electrode room, we can obtain the ion beam having the desired velocity and the electric current density while combining the acceleration electrodes and the deceleration electrodes and the focusing electrodes.

Since the conductive film is not usually deposited in the substrate side wall having the central hole for separating each penetrated room, the charged particles are accelerated and decelerated. In the substrate side wall 161-4 having the central hole 165-3 that is the extraction electrode, the conductive film 170-1 is deposited on the front side face and the conductive film 170-2 is deposited on the back side face. If the main substrate 161 is insulating material, the conductive film 170 can be directly formed. If the main substrate 161 is not insulating material, the insulating film may be formed between the main substrate 161 and the conductive film 170. The conductive film 170 connects to the conductive film 176 formed on the lower surface of the upper substrate 162 and/or connects to the conductive film 175 formed on the upper surface of the lower substrate 163, furthermore connects to the contact 173 formed in the upper substrate 162 and the lower substrate 163, and connects to the conductive film electrode wiring 172 formed the upper surface of the upper substrate 162 and/or the conductive film electrode wiring 174 formed the lower surface of the lower substrate 163. Accordingly the voltage can be applied to the conductive film 170 from the conductive film electrode wiring 172 and/or 174. If the ions are minus charges, the plus voltage is applied to the extraction electrode 161-4, the extraction electrode 161-4 draws and accelerates the ions. If the ions are plus charges, the minus voltage is applied to the extraction electrode 161-4, the extraction electrode 161-4 draws and accelerates the ions. The deceleration and focusing electrode 161-5 is equipped to prevent the spread of the ions and not to accelerate too much. The structure is the same as the extraction electrode 161-4. If the ions are minus charges, the minus voltage is applied to the deceleration and focused electrode 161-5, the ions are focused and decelerated. If the ions are plus charges, the plus voltage is applied to the deceleration and focused electrode 161-5, the ions are focused and decelerated. The structure and the method applying the voltage of the acceleration electrode 161-6 are same as those of the extraction electrode 161-4. In the present invention, since these substrate side wall electrodes can be arranged freely and numerously, the ion beam G can be controlled by setting freely the plus value and minus value of the voltage applied to each substrate side wall electrode.

The opening portion 166-3 for introducing gas into the upper substrate 162 and/or the lower substrate 163 of the discharge room 164-2 is equipped, the gas may be introduced into the discharge room 164-2 from the opening portion 166-3 and may be ionized. The opening portion 167-2 for vacuumizing in the upper substrate 162 and/or the lower substrate 163 of the discharge room 164-2 can be equipped. The wirings of the coil 169 wind spirally the outside of the discharge room 164-2 and the magnetic field generates in the discharge room 164-2 by the coil 169 (the first magnetic field generation means). And the plural magnets 178, which is the second magnetic field generation means, are arranged outside of the discharge room 164-2. These magnets may be permanent magnets, the polar character is the same in the longitudinal direction (the travelling direction of ions) of the discharge room 164-2, as shown in FIG. 18(*b*), (FIG. 18(*b*) is the diagram along A1-A2 in FIG. 18(*a*)), they are arranged numerously around the charge room 164-2 at regular intervals. (16 poles magnet in FIG. 18) The polar characters of each magnet 178 in the surface facing the discharge room 164-2 are the same, and the magnets are arranged so that the polar character of adjacent magnet is reverse. Thus the magnetic fields generating between each magnets become multipolar magnetic fields (shown in the dashed line) B2, which are localized in the inner surface around the inner face of the discharge room 164-2. The multipolar magnetic fields become smaller as approaching the inside from the inner surface of the discharge room 164-2. Thus the magnetic field B2 is very small near the center of the discharge room 164-2, and the uniform plasma generates near the center of the discharge room 164-2. The ingress of the plasma is simultaneously prevented by the magnetic field B2 in the inner surface of the discharge room 164-2, and the loss of the plasma is reduced. Furthermore, by these magnets, the generation of the plasma is more stabilized by the high-frequency, and the deviation of the ion current can be reduced by the main magnetic field B1. Though the stabilization of the plasma in the discharge room 164-2 can be performed and the amount of the ion beam G can be generated stably by controlling the main magnetic field B1 precisely, they can be controlled more precisely by arranging the magnets 178.

If the magnets 178 are the permanent magnets, for example, ferrite magnets, neodymium magnets, samarium-cobalt magnets, Fe—Cr—Co magnets, Fe—Pt magnets, Fe—Al—Ni—Co magnets, Co—Pt magnets can be used. The magnets 178 may be the small coils of the invention arranged numerously besides the permanent magnets. Namely in the case of 16 polar magnet, the plural small coils are arranged so that they become the same polar characters in the same side of each pole. Or each pole may be one coil. In that case, it is the coil wound spindly in the travelling direction of the ions. If the small coils are used, since the magnetic field that each coil makes can be controlled by the applied current, more precise magnetic field B2 can be generated and controlled. When the magnets 178 are arranged, the concave portions 181 and 182 are formed in the arrangement area of the magnets 178 in the discharge room 164-2 in the upper substrate 162 and the lower substrate 163, the thickness of the substrate in the portions may be reduced, thus the magnetic field generated in the discharge room 164-2 can be increased. Also, when the magnets 178 are arranged, the forth substrate 168 and the fifth substrate 177 adhered to the upper substrate 162 and the lower substrate 163 in the outside of the discharge room 164-2, as shown in FIG. 18, the upper portion of the magnets 178 can be opened. Particularly when the small coils are arranged, if the portions are opened, it is easy to flow the electric current to the terminal of the small coil. For example, the wire can be bonded to the small coil terminal. The forth substrate 168 (168-2, 3) can double as the sealing substrate 168-1. Namely the same substrate can be adhered to the upper substrate 162.

The space is made in the upper portion of the magnets 178, as shown in FIG. 18, the sixth substrate 179 is adhered to the forth substrate 168, and the seventh substrate 180 is adhered to the substrate 177. Then, the coil wiring 169 is formed in the sixth substrate 179 and seven substrate 180, and the contact 183-1 connecting to the coil wiring 169 is formed in the sixth substrate 179 and seven substrate 180, it connects to the contact 183-2 formed in the forth substrate 168. The contact 183-2 formed in the forth substrate 168 connects to the contact 183-3 formed in the upper substrate 168. The contact 183-3 formed in the upper substrate 168 connects to the contact 183-4 formed in the main substrate 161. The contact 183-4 formed in the main substrate 161 connects to the contact 183-5 formed in the lower substrate 163. The contact 183-5 formed in the lower substrate 163 connects to the contact 183-6 formed in the fifth substrate 177. And the contact 183-7 formed in the seventh substrate, which connects to the coil wiring 169 made in the seventh substrate 180, connects to the contact 183-6 formed in the fifth substrate 177. Thus the coil wiring 169 connects spirally, it surrounds the discharge room 164-2, and the coil 169 is made. When the magnets 178 are not arranged, the forth substrate to the seven substrate are not needed, the coil wiring patterns may be formed in the upper substrate 162 and the lower substrate 163.

For the contacts 183 (183-1-7) of the coil wiring 169, the contact holes are formed in each substrate, if the substrate is not insulating substrate, the insulating film is formed on the inner surface of the contact hole. Next, if necessary, after the conductive film for adhesion or seeds is deposited on the inner surface of the contact hole, the contact hole is filled or semi-filled with the conductive film using plating method, squeezing method, melting metal pouring method, dispensing method, electrocasting method, CVD method, selective CVD method, bias PVD method, etc. These may be adhered step by step. As shown in FIG. 18(b), The group of the magnets 184 (184-1, 2) arranged in the side of the side surface of the discharge room 164-2 are inserted in the penetrated rooms 184-4 and 164-5 for insertion of the magnet group, which are the penetrated rooms formed so that they sandwich the discharge room 164-2 and the substrate side walls 161-4 and 161-5. The insertion method is the same as the coil insertion method mentioned previously. Also, for the method to make the magnet groups 184 (184-1, 2), the magnets 178 may be piled up with sandwiching the non-magnetic material 183. The method is the same as the method to make the coil.

Or the magnet groups 184 (184-1, 2) can be arranged in the side of the side surface of the charge room 164-2 by dividing the main substrate 161 to some parts and putting the magnet groups 184 (184-1, 2) and the non-magnetic material in the divided main substrate and adhering them in order of precedence. In that case, it is desirable to make the magnet thickness in the magnet groups 184 (184-1, 2) and the thickness of the non-magnetic material between their magnets almost equal to the thickness of the divided main substrate. And in FIG. 18, the magnets 178 can be arranged in the upper portion of the discharge room 164-2 by adhering the upper side magnets 178 to the sixth substrate 179. Then it is desirable to approach the magnets, etc. to the discharge room 164-2 as possible by make the thickness of the forth substrate 168, the depth of the concave portion 181 and the thickness ob the magnets 178 almost same. Similarly the magnets 178 can be arranged in the lower portion of the discharge room 164-2 by adhering the lower side magnets 178 to the seventh substrate 180. Then it is desirable to approach the magnets, etc. to the discharge room 164-2 as possible by make the thickness of the fifth substrate 177, the depth of the concave portion 182 and the thickness ob the magnets 178 almost same.

The space 185 formed by the upper substrate 162, the forth substrate 168 and the sixth substrate 179 can be made airtight, and the space 186 formed by the lower substrate 163, the fifth substrate 177 and the seventh substrate 180 can be made airtight. In that case, if a part of the upper substrate 162 and a part of the lower substrate 163 in the discharge room 164, particularly in the area where the magnets 178 are arranged, are removed, the efficient magnetic field can be generated. In that case, when the magnets 178 are adhered to the upper substrate 162 and a minimum thickness of the lower substrate 163, the upper substrate 162 and the lower substrate 163 that can support the magnets 178 may be left. If the magnets are adhered to the sixth substrate 179 and the seventh substrate 180, the substrate 162 or 163 located direct above or below can be removed. Similarly the substrate side wall 161-4 and or 161-5 in the side of the side surface of the discharge room 164-2 can be removed. Or a part of them may be left. In that case, the opening portion to vacuumize the space 185 or 186 and to introduce gases can be equipped in the sixth substrate 179 or the seventh substrate 180. Similarly the opening portion to vacuumize the penetrated room 164-4 or 164-5 for the insertion of the magnet group to introduce gases can be equipped in the upper substrate 162 or the lower substrate 163.

The size of the high-frequency ion source using the substrate of the present invention is estimated. The penetrated room of the present invention is 0.1 mm to 100 mm in height and width, and we can make the larger size than these using the adhesion method. The length can be determined by the substrate size, for example, 10 mm to 1000 mm, and we can make the larger size than these using the adhesion method. As one example, if the thickness of the main substrate is 1 mm, the thickness of the upper and lower substrates and the forth substrate to seventh substrate is 9.2 mm, the substrate size is 600 mm×600 mm, the height of the discharge room is 1 mm in one main substrate, and is 10 mm in 10 piled substrates, and is 50 mm in 50 piled substrates, and is 100 mm in 100 piled substrates, and the width is, for example, 1 to 100 mm and can be equal to the height, and the length can be made to about 500 mm. Also, if the length of the discharge room 164-2 is 200 mm, the width and the thickness of the coil 169 is 1.5 mm×1.5 mm and the coil pitch is 2 mm, the coil of 100 turns can be made. Though the coil 169 is made by implanting the conductive film in the substrate in FIG. 18, after the substrate is cut and the accelerator, etc. including the discharge room 164-2 are cut out individually, the coil 169 can be made by winding the coil wiring around the discharge room 164-2 manually or automatically. Thus the ion generation source of the present invention can be made in the various sizes.

FIG. 19 is the diagram showing one embodiment of the mass analyzer of the present invention. The penetrated (penetrating) grooves (channels or chambers or rooms are also written here) 305, 306, 307, and 308, which penetrate the upper surface to the lower surface in the main substrate 301, are formed, the upper substrate 302 is adhered to the upper surface of the main substrate 301, the lower substrate 303 is adhered to the lower surface of the main substrate 301. The method to make them is the same as the above method. The penetrated room 305 is a sample room, and it is the space sandwiched between the main substrate side wall 301-1 and the substrate side wall (partition (wall) is also written here) 301-2, which partitions the sample room 305 and the next ionization room 306. (The side surface of the penetrated room is the side wall of the main substrate 301.) The sample 311 is put in the sample room 305. The sample is inserted from the sample opening portion 312 opened in a part of the upper substrate 302. For example, the sample 311 is adhered and fixed to the substrate wall 301-1 by vacuumizing from the vacuum line 313 equipped in the back surface side of the sample 311.

The opening portion to introduce ion beam (ion beam introducing opening portion) is opened in the upper substrate 302 in the sample room 305. Component materials of the sample 311 are sputtered by emitting the ion beam 316, which is projected from the ion gun 315 arranged in the outside of the mass analyzer 300, to the sample 311 through the ion beam introducing opening portion. Well, the ion gun 316 can be arranged in the main substrate 301, in that case, the ion beam is emitted to the sample 311 thorough the penetrated room of the main substrate 301 from the ion gun 315 formed in the side of the side surface (the vertical direction to the paper face in FIG. 19) of the sample room 305. The ion beam is, for example, nitrogen (N) ions, argon (Ar) ions, xenon (Xe) ions, etc. The sample component materials sputtered are neutral particles 317 or ions (second ions) 318. These particles move to the central hole 310 of the partition wall (plate) 301-2 and enter to the ionization room 306. Though the pressure in the sample room 305 may be the pressure near to the atmospheric pressure, the opening portion 319 to vacuumize (vacuumizing line is also written here) is opened in the lower substrate 303, etc., and the pressure of the sample room 306 may be reduced by connecting the vacuum pump to the vacuumizing line.

In the sample room 305, the insylating film such as silicon oxide film, silicon nitride film or silicon oxynitride film, etc. may be deposited on the inner side surface of the main substrate 301, and these film can be deposited using CVD method, PVD method, or oxidation method, or nitridation method. As explained in the above, after (the half of) the penetrated rooms and the partition walls such as the partition wall (plate) 301-2, etc. formed in the state where the main substrate 301 is divided in the upper and lower portions, a part of the central portion of the partition wall (side wall) (plate) 301-2, etc, are removed, (these may be reverse, namely the side wall is formed after the central hole is formed), and after that, the upper and lower substrates divided are adhered, thus the central hole 310-2 can be formed. The insulating film is formed before the main substrate is adhered, or after the main substrate is adhered.

The ionization room 306 formed adjacent to the sample room 305 is the space to ionize the neutral particles entering from the sample room 305 and to focus the ion ionized there and the ion entering from the sample room 305 near the center. The charged particle acceleration room 307 is next to the ionization room 306 and draws out and furthermore accelerates the ions existing in the ionization room 306, and the ionization room 306 and the charged particle acceleration room 307 are partitioned with the partition wall plates 301-2 and 301-3. Namely the ionization room 306 is the space sandwiched between the partition wall plates 301-2 and 301-3. (The side of the side surface (the vertical direction to the paper face in FIG. 19) is the side wall of the main substrate 301.)

In the ionization 306, the ionized beam 320 is emitted to the neutral particles 317 existing in the ionization room 306 through the upper substrate 302 or the lower substrate 303, the neutral particles are ionized. Various kinds of beams introduced in the previous literatures can be used as the ionized beam 320, they are, for example, laser beam, electron beam, synchrotron radiation beam, X-ray, etc. Also, beside laser beam, the neutral particles may be ionized using X-ray generated by emitting the laser beam to the solid target. The portion of the upper substrate 302 or the lower substrate that the ionized beam 320 passes may be removed (or the opening portion is equipped) to pass easily the ionized beam 320 to the ionization room.

Also, the conductive film 321 is deposited in the inner surface of the ionization room 306, and the contact hole 323 is formed in the upper substrate 302 or the lower substrate 303, and the conductive film is deposited in the contact hole 323, and the conductive film electrode wiring 324 is formed, thus the electric voltage can be applied to the conductive film 321 from the electrode wiring 324. If the conductive film 321 covers the inner surface of the ionization room except the portion where the ionized beam 320 passes, the inner surface of the ionization room can be in the same potential state. Thus the ions are focused near the center by applying the voltage having the same charge as the ions to the conductive film 321. If the conductive film in the upper and lower and right and left is divided and the contact hole and the electrode and wiring are connected to the divided conductive film, since the voltage in the respective conductive film area can be controlled individually, the position of the charged particle beam 325 can be adjusted in the ionization room 306. If the main substrate is the semiconductor substrate such as Si, etc., or the conductive substrate such as Cu, Al, etc., after the insulating film is deposited, the conductive film 321 is deposited. Well, if the ions 318 generated in the sample room 305 enter the ionization room 306, they are focused by the voltage applied to the inner face of the ionization room 306 and becomes a part of the ionized beam 325.

The charged particle beam 325 focused in the ionization room 306 enter the charged particle acceleration room (chamber) 307. The partition wall plate 301-11 having the central hole 327-1 is arranged at the nearest place to the entrance side of the acceleration room 307, and the conductive film 326 are deposited around the partition wall (plate) (or side wall plate) 301-11 and patterned. The conductive film 326 connects to the conductive film deposited in the contact hole 323 and conductive film electrode wiring 324, the opposite voltage to the ion charge of the charged particle beam 325 is applied to the conductive film 326, thus the charged particle beam 325 is extracted from the ionization room 306 and accelerated. Accordingly, the partition wall (side wall) 301-11 may be called extracting (extraction or extracted) electrode. If the conductive of the left, right, top and bottom is divided and the contact hole and electrode wiring are formed in the respective conductive film, since the voltage in the respective conductive film area can be individually controlled, the position of the charged particle beam 325 can be adjusted in the central hole 327-1.

The partition wall plate 301-12 (having the central hole 327-2) is arranged next to the partition wall plate 301-11 in the charged particle beam 325, the conductive film 326 is deposited and patterned around the partition wall plate 301-12. The conductive film 326 connects to the conductive film deposited in the contact hole 323 and the conductive film electrode wiring 324, and the voltage having the same charge or the reverse charge as the ions of the charged particle beam 325 is applied. If the voltage having the same charge as the ions of the charged particle beam 325 is applied, the charged particle beam 325 is focused, and if the voltage having the reverse charge to the ions of the charged particle beam 325 is applied, the charged particle beam 325 is accelerated. The necessary number the partition wall plates (having the central hole) in which the same conductive film as the conductive film deposited in the partition wall plate 301-12 is deposited are formed after the partition wall plate 301-12 in the travelling direction of the charged particle beam 325, and the voltage having the same charge or the reverse charge as the ions of the charged particle beam 325 is applied, and the necessary number of the charged particle beam 325 is accelerated, also the necessary number of the charged particle beam 325 is focused, thus the charged particle beam 325 is leaded to the adjacent mass analysis room 308 partitioned by the partition wall plate 301-4 having the central hole 310-4. Since the different voltages can be applied respectively and individually to the divided conductive films by dividing the conductive film of the respective partition wall plate after the partition wall plate 301-12 in the left, right, top and bottom and forming the contact holes and the conductive film in them and the electrode wiring, the travelling direction and the focused position of the charged particle beam 325 can be controlled. Thus the radius, the position or the travelling direction of the charged particle beam can be freely controlled.

We can make the hole size of the central hole 310-2, 3, 4, 5 and the central hole 301-1, 12, . . . , etc. that the partition wall plates 327-1, 2, . . . in the acceleration room 307 have change freely. For example, the central hole 310-2 can be made larger to lead almost of the neutral particles 317 and the ions 318 sputtered to the ionization room. The central hole 327-11 in the acceleration room 307 can be made smaller than the central hole 310-3 arranged in the border of the ionization room 306 to extract easily the ions. The central holes 327-2, . . . in the acceleration room 307, etc. can be made smaller than the central hole 310-3 and the central hole 327-11 to accelerate. We may divide the main substrate into two of the upper and the lower portions, and form patterns (for example, photo resist pattern) fitting to the size of central hole formed in each partition wall plate after the partition wall plates are formed, and may etch and remove the portion of the partition wall plate so as to fit to the size of each central hole. Or we may divide the main substrate into two of the upper and the lower portions, and form patterns (for example, photo resist pattern) fitting to the size of central hole in the place where each partition wall plate should be formed later, after the main substrate is etched and removed fitting to he size of each central hole, the each partition wall plate is formed. After that, the insulating film and the conductive film and the passivation film are formed, and their patterning is performed. The charged particle beam 325 accelerated and focused in the acceleration room 307 enters the mass analysis room 308, and since the orbital of the charged particle is sorted by the ratio m/q (called mass charge ratio) between the charge q and the mass m that the charged particle has by the electric field and the magnetic field in the mass analysis room 308, only the specific charge particle travels to the ion detection room 309. The ion detection room 309 is separated by the partition wall plate 301-5 having the central hole 310-5 from the acceleration 307.

The mass analysis room (or cavity or chamber) 308 is, for example, a quadrupole type. FIG. 19 shows the quadrupole type mass analysis. There are not the partition wall plate except the partition wall plates 301-4 and 301-5 that are the separating walls in the mass analysis room 308, which is the penetrated room penetrating the main substrate from the upper substrate 302 to the lower substrate 303. (Here, the side surfaces are the main substrate 301.) The four long quadrupole electrodes 329 are arranged in the travelling direction of the charged particle beam 325 in the mass analysis room. (329-1 and 2 are shown in FIG. 19.) One of the plural conductive film electrode wirings 324 connect to the respective quadrupole electrodes 329 through the conductive film in the contact holes 323, and the voltage can be applied. Also, the other opening portions are formed, and gases for purging or cleaning can be flowed from them. Furthermore to connect the conductive films in the mass analysis, the opening portions to introduce or eject gases for selective CVD (for example, WF6) or solutions for plating (for example, copper sulfate solution in Cu plating) can be equipped.

FIG. 20 is the diagram showing one sample of methods to make the quadrupole type mass analysis room. The conductive film 355 of the quadrupole electrode is deposited on the third substrate 353. The conductive film 355 is, for example, metal such as Mo, W, Cr, Ti, Cu, Fe Ni, Al, etc., or these alloy, or silicide that is a compound between Si and these metal, etc., and is deposited using CVD method or PVD method, and is patterned by photolithography and etching method. Or the quadrupole electrode poles of the same size are adhered using adhesion method. When the third substrate 353 is the insulator such as glass, quarts, ceramic, plastic, etc., the conductive film 355 can be deposited. When the third substrate 353 is the semiconductor or the conductive materials, after the insulating film is deposited, the conductive film 355 can be deposited. Or the conductive film 355 can be formed using the coating method. For example, the conductive paste is coated using metal masks on the third substrate 353, the desirable the quadrupole type electrode 355 can be formed by thermal treatment. The conductive paste includes the above metal, etc. Or foil of the above metal, etc. is adhered on the third substrate 353, and the conductive film can be formed by patterning it. Also, the concave portion 354 hollowing the portion 354 arranging the quadrupole type electrode 355 is formed in the main substrate 351. (FIG. 20(a))

Next as shown in FIG. 20(b), the main substrate 352 and the third substrate 353 are adhered. These adhesions can be performed using the method written in the present specification. Then the depth of the concave portion 354 makes larger than the height of the quadrupole electrode 355, thus the main substrate 351 and the quadrupole electrode 355 do not contact. Next the upper surface of the main substrate 351 is patterned by the photo resist, etc., and the penetrated room that becomes the mass analysis room is formed. Then since the fitting between the patterns is needed, they are fitted precisely. If the penetrated room 356 is formed by etching the main substrate 351, the conductive film 355 and the third substrate 353 doe not be make etched as possible by etching using the dray etching gas or wet etching solution having the high etching selectivity ration between the conductive film 355 and the third substrate. (FIG. 20(c)) We can deposit the passivation film as an insulating film (for example, SiO2 film, SiN film, etc.) on the conductive film 355. In that case, the etching selectivity ration is for the main substrate 351 and the passivation film.

The similar process is performed in the side of the second substrate 352, the main substrate 351 (351-1) is adhered to the second substrate 352, the penetrated room 356 and the conductive film as the quadrupole electrode in it are formed. Thus the main substrate 351 (351-1) adhered to the second substrate 352 and the main substrate 351 (351-2) adhered to the third substrate 353 are superimposed and adhered by aligning them so as their penetrated rooms 356 are fitted each other. There are the adhesion binding methods, the diffusion binding method, the room temperature binding method, the high temperature binding method, etc. as their adhesion methods. If the main substrate 351 is the semiconductor substrate such as Si, etc. or the conductive substrate such as metal, etc., the strong adhesion can be performed by the electrostatic (anodic) binding using the glass substrate or the quarts substrate 357. In that case, the portion that becomes the mass analysis 356 in the substrate 357 sandwiched between them is removed is removed, the second substrate 352 and/or the third substrate 353 adhere with the substrate 357 by aligning them. (They may be either one.) Thus the mass analysis 358(is made by combining 356) sealed can be formed. (FIG. 29(d), (e)) In the process shown in FIG. 20(a), we can adhere the main substrate 351 in which the concave portion is not formed but the penetrated room is formed. Then we need to make the penetrated room and the conductive pattern fit precisely. If the depth of the penetrated room may be one penetration, The one substrate that does not have the main substrate (for example, the second substrate 352 that has the conductive film but does not have 351 (351-1)) can be adhered to the main substrate 351(351-2).

Next the contact hole 371 is formed in the second substrate 352 third substrate 353, the conductive film is deposited in the contact hole 371, and the electrode airing 372 is formed. The conductive film in the contact hole 371 can be deposited using CVD, PVD, plating, coating, etc. The electrode wiring 372 can be formed using CVD, PVD, plating, coating, etc. The conductive film in the contact 371 and the electrode wiring 372 can be formed together. The electrode wiring can extend on the second substrate 352 and the third substrate 353, and the pad electrode (which becomes the connection portion with the outside portion) can be formed in the adequate place. If necessary, the passivation can be formed. FIG. 20 is the diagram seen from the travelling direction of the ion beam 352 in FIG. 19, namely the cross sectional diagram in the vertical direction to the paper face in FIG. 19.

Thus the alternate current (high-frequency voltage) and the direct voltage can be applied to the four quadrupole electrodes 355 (355-1, 2, 3, 4) from the outside electrode 372. Since the mass analysis room can be formed using the semiconductor process as mentioned above, the mass analysis room having very accurate size can be made and the high accurate mass analysis can be performed. The depth of the mass analysis room can become larger by piling up the main substrates and making them adhere (the glass substrate may be sandwiched between their main substrates), as known clearly from the present process. For example, though the thickness of the ordinary Si substrate is at most about 1 mm, it becomes 10 mm by piling up 10 main substrates. Since thicker Si substrate can be made, the given thickness can be available by stacking fewer main substrates. Also, if the opening portion 359 of the vacuum line is formed and the vacuum pump is connected, the mass analysis room 358 can be vacuumized and the pressure can be reduced. Since the present invention is the mass analysis room having the desirable size (even if it is very small, for example, the mass analysis room is less than 1 mm, or less than 100 μm) and the number of the bond portions is small and the binding is strong, the very low pressure and the desirable pressure can be available. Since the process is simple and the vacuum pumps are very small, the low cost of the mass analysis device can be available.

In the case of the quadrupole type mass analysis, though only the ion having the given m/q can pass the quadrupole electrodes 355 (329 in FIG. 19) and reach the detection room (309 in FIG. 19), since the ions having other m/q than it impact the quadrupole electrodes 355, the main substrate 351 outside of them, the second substrate 352, the third substrate 353, they may be damaged. So if the mass analysis room 358 becomes larger, since the kinetic energy becomes smaller, the damage can become smaller. FIG. 20(f) shows the structure and the method to make the mass analysis larger. Namely the second main substrates 361 (361-1, 2), the forth substrate 362 and the fifth substrate 363 are adhered to the upper and lower of the second substrate 352 and the third substrate 353, the mass analysis upper room 365 and lower room 368 are equipped in the upper portion and the lower portion of the mass analysis room 358, and the width of the left and right (w21) of the mass analysis 358 is broaden, and the left and right wall of the main substrate 351 is left from the quadrupole electrodes 355 (namely d21 becomes larger). The planar area of the mass analysis upper room 365 and lower room 368 is made larger than the area of the mass analysis upper room 358, (namely when the left and right width of the mass analysis upper room 365 is w22, the left and right width of the mass analysis lower room 368 is w23, w22 and w23>w21) the area of the second substrate 352 and the third substrate 353 is made to the extent that the quadrupole electrodes 355 can be supported in strength, and the partitions (the second substrate 352 and the third substrate 353) between the mass analysis room 367 and the mass analysis upper room 365 and lower room 368 are removed, thus the opening portions 364 and 367 are extended. (The plural opening portions may be divided.) Also, the opening portions 366 and 369 for vacuum line are opened in the both of the forth substrate 362 and the fifth substrate 363. Furthermore the opening portions 366 and 369 for vacuum line should be opened larger to the extent of no matter. (The plural opening portions may be divided.) The height (h22, h23) of the mass analysis upper room 365 and lower room 368 should be made larger.

Thus even if the ions passing through the clearance among the quadrupole electrodes 355 without reaching the ion detection room 309 travel toward the wall (side surface) of the main substrate 351, the speed of the ions become smaller and the damage to the wall (side) of the main substrate 351 is small. Particularly by equipping numerously the opening portions 364 and 367 for vacuumizing with the wide area around the wall (side surface) of the main substrate 351, the ions missed from the inside of the quadrupole electrodes go out of their opening portions 364 and 367 to the mass analysis upper room 365 and the mass analysis lower room 368. Furthermore the damages become smaller by covering the inner surface of the mass analysis room 358 with the film difficult to be attacked by the ions. For example, silicon oxide film, silicon nitride film and alumina, etc. are large in ion resistance properties. Also, the ions travelling toward the upper mass analysis upper portion room 365 and the lower mass analysis lower portion room 368 become smaller in speed, and the damages giving to the wall (side surface) of the forth substrate 362, the fifth substrate 363 and the second substrate 361 become smaller. Also, since the ions are ejected from the opening portions 366 and 369 for vacuumizing to the vacuum pump, the influence giving to the mass analyzer is small. Furthermore the opening portions for purging or cleaning are equipped in the forth substrate 362 and the fifth substrate 363, for example, it is effective to keep the mass analysis room clean and to give it a longer life by purging and cleaning sometimes using nitrogen, Ar, He, etc.

Or if the conductive film is formed on the inner side surface of the ion detection room 309, and the small voltage of the same charge as the ions is applied to the conductive film from outside, the impact of the ions can be reduced. The quadrupole electrodes 355 connect to the conductive film 372 formed on the second substrate 352 and the third substrate 353 through the conductive film deposited in the contact hole 371 formed in the second substrate 352 and the third substrate 353, and connect to the conductive film 373 formed on the inner side surface of the second substrate 352 and the third substrate 353, furthermore connect to the conductive film 374 formed on the upper and lower faces of the forth substrate 362 or the fifth substrate 363. The conductive film 374 connects to the conductive film electrode wiring 376 formed on the top surface of the forth substrate 362 or the fifth substrate 363 through the conductive film deposited in the contact hole 375 formed in the forth substrate 362 or the fifth substrate 363. Thus the direct voltage and the alternating (high-frequency) voltage can be applied to the four quadrupole electrodes 355 from the outside electrode wiring 376. Also, if the plural outside electrode wirings are equipped in one of quadrupoles as shown in FIG. 19, since the direct voltage and the alternating (high-frequency) voltage can be applied from these plural electrodes, the orbital of the ion 325 can be controlled accurately.

We explain one sample about the method to make FIG. 20(*f*) from FIG. 20(*e*). We make the penetrated substrate 368 penetrating to the fifth substrate 363 in the second main substrate 361 (361-2) adhering to the fifth substrate 363. The concave portion 377 is formed to broaden the overlapped area between the conductive film 373 formed in the side of the second main substrate 361 (361-2) and the conductive film 372 formed in the bottom surface of the third substrate (the lower substrate). The depth of the concave portion 377 makes the extent of the thickness adding the thickness of the conductive film 372 to the thickness of the conductive film 373 (in that case where the insulating film is formed, the thickness should be considered. In that case where the conductive adhesive agency containing the low-melting point solder alloy is used, the thickness should be considered.) the connection between the conductive film 372 and the conductive film 373 should be performed sufficiently. After the penetrated hole 368 and the concave portion 377 are formed, the conductive film 373 and the conductive film 374 are deposited, and the conductive film 373 and the conductive film 374 are formed on the necessary portion of the side surface of the concave portion 377 and the penetrated portion 377 and on the necessary portion of the upper surface of the fifth substrate 363. The conductive films 373 and 374 are, for example, the above conductive materials. If the electric connection between the conductive films 373 and 374 is not sufficient, the conductive adhesive agency or the solder alloy (for example, Ag—Cu—Sn series) is adhered on the conductive films 372, 373 and 374.

The conductive film 372 formed on the lower surface of the third substrate 353 is extended as wirings as shown in FIG. 20(*f*) and is formed in the side to connect with the concave portion 377 and can be connected with the conductive film 373. Also, the opening portions 364 and 367 for vacuumizing are formed in the second substrate (the upper substrate) and the third substrate (the lower substrate). These opening portions 364 and 367 may be formed before forming the conductive film 372, or they can be formed by etching and removing the second substrate (the upper substrate) and the third substrate (the lower substrate) after the conductive film 372 is patterned. Or they can be formed similarly in the case of the quadrupole electrodes 355 before the main substrate 351, the second substrate (the upper substrate) and the third substrate (the lower substrate) are adhered. Next the second main substrate 361 to which the fifth substrate 363 is adhered is adhered to the third substrate 353 with aligning so that the mass analysis lower portion room 368 fits to the mass analysis room. After that the contact hole 375 and the opening portion 369 for vacuumizing in the fifth substrate 363, and the conductive film is deposited in the contact hole 375, furthermore the conductive film electrode wiring 376 to the contact hole 375 is formed. In the case where the conductive film intrudes into the mass analysis lower portion room 368 from the opening portion 369 for vacuumizing, the opening portion 369 for vacuumizing may be formed after the conductive film electrode wiring 376 is formed.

The same can be mentioned in the forth substrate 362, the second main substrate 361 (361-1) and the second substrate (the upper substrate). Also, as written in the other portions in the specification, if the lower surface is not the insulating material, the insulating film such as silicon oxide film, etc. is deposited before the conductive film is deposited, and the insulating film such as silicon oxide film, etc. is deposited on the conductive film to protect the conductive film. Also after the main substrate 361 is adhered to the upper substrate 362 and the lower substrate 363 and the opening portion 369 and 366 are formed, the conductive film can be selectively deposited in the connection portion by flowing the selective CVD gas or introducing the plating solution through the opening portion 369 and 366 to connect the conductive film 372 and 373 perfectly FIG. 21 is the diagram explaining one sample about the structure and the method to adhere the quadrupole electrode to the substrate. FIG. 21(*a*) is the cross sectional diagram, and FIG. 21(*b*) is the plan view. The quadrupole electrodes 386 are adhered on the second substrate 382 and the third substrate 383. Though the cross sectional face of the quadrupole electrodes 386 is shown in the circular form, it may be rectangular hyperbola used usually, or it may be the other any shape, also the optimize shape can be selected as the quadrupole electrode. Also, as shown in FIG. 21(*b*), the shape in the longitudinal direction of the quadrupole electrodes is a linear form, and the whole becomes rod-shaped. the shape in the longitudinal direction of the quadrupole electrodes can be wave form, namely the optimized shape can be selected for the mass analysis so that the electric field of the quadrupole electrode is optimized. Various kinds of materials such as Mo series alloy, SUS, Cu series alloy, etc. can be used as the material of the quadrupole electrodes. The quadrupole electrode 386 can be made using the mold or can be made as wire rod or can be made using plating method or electrocasting method by making the pattern.

The pattern of the adhesion agency is made on the second substrate 282 and the third substrate 383, and the quadrupole electrode rods can be arranged accurately on the second substrate 282 and the third substrate 383 by making the quadrupole electrode rods adhere to the pattern. The groove pattern 385 is formed by the photolithography method and the etching method on the second substrate 282 and the third substrate 383, if necessary, the quadrupole electrode rods can be arranged more accurately on the second substrate 282 and the third substrate 383 by forming the adhesion agency in the groove pattern 385 and putting the quadrupole electrode rods in the groove pattern 385 and adhering the quadrupole electrode rods 386. If the length of the quadrupole electrode rods 386 is larger, it can be uniformed accurately by the photolithography method and the etching method. The adhesive agency may be an ordinal adhesion agency, a conductive adhesion agency, or a metal such as solder, etc. The quadrupole electrode rods are desirably arranged by fitting the surface shape of the quadrupole electrode rods so that the electric field of the quadrupole electrode rods can be optimized. After that, the quadrupole electrode rods are fixed on the second substrate 282 and the third substrate 383 using the thermal treatment and ultraviolet radiation.

The main substrate 381 in which the mass analysis room 384 is hollowed are adhered to the second substrate 282 and the third substrate 383. These adhesions may be performed separately or simultaneously. The quadrupole electrode rods 386 are adhered to the main substrate 381 with aligning the second substrate 282 and the third substrate 383 so that the quadrupole electrode rods 386 are arranged in the given position of the mass analysis room 384. If the main substrate is divided in two portions of the lower and upper portions, the upper portion of the main substrate 381 having the (upper) mass analysis room 384 to the second substrate 382 and the lower portion of the main substrate 381 having the (lower) mass analysis room 384 to the third substrate 383 are adhered. Then these can be adhered using the electrostatic binding method by sandwiching the glass substrate or the quarts substrate between the main substrates 381. Furthermore the height of the mass analysis room can be adjusted freely by dividing numerously the main substrate and adhering them with superimposing. The various size (for example, 50 μm to 5 mm in diameter) of the quadrupole electrode rods 386 can be used in the embodiment shown in FIG. 21. The length of the quadrupole electrode rods 386 can be selected corresponding to the size of the substrate, if the substrate size is the wafer of 300 mm diameter, the length can be made in (for example) 1 mm to 200 mm. The contact holes and the extending electrodes can be made simply by the method shown in FIG. 20. It can be made simply by the method shown in FIG. 20 to extend the mass analysis room, to remove a part of the second substrate and the third substrate and to equip the mass analysis upper portion room and the mass analysis lower portion room.

FIG. 22 is another sample about the structure and the method to adhere the quadrupole electrode rods to the substrate. FIG. 22 is the embodiment that the quadrupole electrodes are not arranged in the mass analysis room 396 (396-1) by arranging the quadrupole electrodes 394 (394-1, 2, 3, 4) in the place separated by the boundary wall (for example, the substrate side wall (plate) or the substrate partition wall (plate)) from the mass analysis room 396 (396-1). The substrate 391 has the mass analysis room 396 (396-1, 2), which is partitioned by the substrate partition wall plates 391 (391-1, 2) in the left and right, and the penetrated rooms 396 (396-2, 3) are made. The quadrupole electrodes 394 (394-2, 4) are respectively arranged in these penetrated rooms 396 (396-2, 3). To adjust the height, a part of the main substrate 391(called base board) 397 may be left, or the base board 397 may be adhered to the third substrate 393. Or the portion of the mass analysis room 396 (396-1) is removed by adhering the main substrate 391 having the same height as the base board 397 to the third substrate. If the quadrupole electrodes having the size, in which the height adjustment is not needed, are used, the base board is not needed.

After that, the quadrupole electrodes 394 (394-2, 4) are adhered to the base board 397. If the groove patterns 398 are formed on the base board 397, the quadrupole electrodes can be fixed certainly and the arrangement accuracy can be increased. The main substrate 391 is adhered to the side of the second substrate 392, the portion of the mass analysis room 396 (396-1) on the main substrate 391 and the portion 396 (396-2, 3) arranging the quadrupole electrodes 394 (394-2, 4) are hollowed, thus the penetrated rooms 396 (396-2, 3) reaching the second substrate 392 are formed. Then the main substrate outside of the penetrated room 396 (396-2, 3), the partition wall plate 391 (391-1) between the penetrated room 396-2 and the mass analysis room 396-1, and the partition wall plate 391 (391-2) between the penetrated room 396-2 and the mass analysis room 396-1 are left.

Next the main substrate 391 adhered to the third substrate 393 and the main substrate 391 adhered to the third substrate 392 are adhered by aligning them so that each other of the mass analysis rooms 396-1 are fitted, the quadrupole electrodes 394 (394-2, 4) arranged on the base board 397 are put in the penetrated room 396 (396-2, 3) formed in the main substrate of the side of the second substrate. The bond between the main substrates 391 can be adhered using the adhesive agency, the room temperature binding, the diffusion binding, the high temperature binding. Also, if the glass substrate, etc. intermediate between them, if the main substrate 391 is the semiconductor substrate such as Si substrate, etc. or the conductive substrate, they can be adhered strongly by the electrostatic anodic binding.

The quadrupole electrodes 394 (394-1, 3) are adhered to the given positions of the second substrate 392 and the third substrate 393 after that, or the quadrupole electrodes 394 (394-1, 3) are adhered preliminarily to the given positions of the second substrate 392 and the third substrate 393, and the quadrupole electrodes 394 (394-1, 2, 3, 4) can be arranged in the state where the mass analysis room 396 (396-1) is surrounded and furthermore in the position separated from the second substrate and the third substrate and the partition wall in the mass analysis 396 (396-1).

FIG. 22(*b*) is the oblique perspective view of the mass analysis room having the quadrupole electrodes shown in FIG. 22(*a*). The quadrupole electrodes 394 (394-1, 2, 3, 4) are arranged with the rod shape in the longitudinal direction of the mass analysis room 396-1. Though the cross sectional shapes of the quadrupole electrodes are shown as the cylinder rod shape in FIG. 22(*b*), they may be the other shapes such as rectangular hyperbola, hyperbola, elliptical, etc. Generally it may be the rectangular hyperbola. The direct voltage and the high-frequency voltage, namely $\pm(U+V \cos \omega t)$, are applied to the opposite electrodes each other. Namely $+(U+V \cos \omega t)$ is applied to the quadrupole electrodes 394-1 and 3, and $-(U+V \cos \omega t)$ is applied to the quadrupole electrodes 394-2 and 4 simultaneously. Thus only the ions having the specific m/e can pass the mass analysis room 396-1 of the charged particle beam (ions) entering the mass analysis room 396-1. Since the quadrupole electrodes are separated perfectly from the mass analysis room and from the charged particle (ion) beam passing the mass analysis room by the partition wall plates 391 (391-1, 2), the second substrate 392 and the third substrate 393 in the mass analysis room having the quadrupole electrodes shown in FIGS. 22(*a*) and (*b*), the damages of the quadrupole electrodes are very few. Though instead the charged particles (ions) may impact the partition wall plates 391 (391-1, 2), the second substrate 392 and the third substrate 393, the charged particles (ions) that may impact their walls can be ejected outside by making the vacuumizing opening portion 399 wide. Also, the inner surface of the mass analysis room 396-1 may be protected by depositing the film (for example, silicon nitride film, alumina) having the large resistant properties to the charged particles (ions)

Though the structure shown in FIG. 22(c) is almost the same as that shown in FIG. 22(a), FIG. 22(c) shows in the case where the quadrupole electrodes are the conductive films. The mass analysis room 425 (425-1) in the center is surrounded by the partition wall plate (the substrate side wall (plate)) 421-1 and 421-2 of the main substrate 421 in the sides of the right and left side surfaces and by the second substrate 422 and the third substrate 423 in the side of the upper and lower surfaces. The penetrated room 425-2 is arranged with being separated by the partition wall plate 421-1 in the left side of the mass analysis room 425 (425-1), and the inner surfaces of the penetrated room 425-2 are surrounded by the insulating film 427 and the conductive film 426 (426-1) is formed on the inside surface of the insulating film 427. Here though the insulating film 428 is also formed in the upper portion of the conductive film 426 (426-1), it may not be formed. The conductive film 426 (426-1) becomes one of the quadrupole electrodes. The penetrated room 425 (425-3) in the right side of the mass analysis room 425 (425-1) has the similar structure, and the conductive film 426 (426-2) becomes one of the quadrupole electrodes After the penetrated rooms 425 '425-2, 3) are formed, the insulating film 427 is formed on the inner surface of the penetrated rooms 425 '425-2, 3), the conductive film 426 is formed using CVD method and PVD method on the insulating film 427. The penetrated rooms 425 (425-2, 3) is not filled with the conductive film 426 in this state. Though only the conductive film 426 enable to become the quadrupole electrodes, the space in the penetrated rooms 425 (425-2, 3) should be almost filled with the conductive film using the plating method to make the good quadrupole electrodes. Or the space in the penetrated rooms 425 (425-2, 3) should be almost filled with the conductive film using selective CVD method. Or after the space in the penetrated rooms 425 (425-2, 3) is almost filled with the conductive film using CVD method or PVD method, the conductive film in the portion except the space in the penetrated rooms 425 (425-2, 3) should be removed using the etching back method. The upper space in the penetrated rooms 425 (425-2, 3) is a few left, and the rest space may be covered by the insulating film 428. This insulating film 428 can be formed using CVD method, PVD method, coating method, or screen printing method, or after the insulating film is formed using the combination of these methods, the upper surface of the penetrated rooms 425 (425-2, 3) may be planarized using the etching back method. After that, the upper substrate 422 is adhered.

The conductive film patterns 429 (429-1, 2) are formed in the area of the upper portion and the lower portion of the mass analysis room in the upper surface of the second substrate (the upper substrate) 422 and the lower surface of the third substrate (the lower substrate) 423. The conductive film patterns 429 (429-1, 2) can be formed using CVD method or PVD method, the plating method, the screen printing method, or these combination, etc. These conductive film patterns 429 (429-1, 2) become the rest of the quadrupole electrodes. The contact hole 430 and the conductive film are formed in the quadrupole electrodes of the right and the left sides. The electrode 431 is formed connecting to the conductive film in the contact hole, from the electrode 431 the voltage is applied to the quadrupole electrodes 425 (425-1, 2). Also, the voltage is applied to the quadrupole electrodes 429 (429-1, 2) in the upper and the lower sides. The electric field is formed by applying these voltages in the mass analysis room, the orbital of the charged particles (ions) beam travelling in the mass analysis room 425-1 changes by the value of m/q. In the present embodiment, since the quadrupole electrodes are formed using the conductive film and the ordinal semiconductor process, the mass analysis room can be made very accurately.

FIG. 22(d) shows the embodiment in the case where all the quadrupole electrodes are arranged in the mass analysis room and the mass analysis room is extended. The penetrated room 413 that becomes the mass analysis room is formed in the main substrate 401 adhered to the third substrate 403, two quadrupole electrodes 407 (407-2, 4) are arranged separately in the right and left sides of the penetrated room 413. One electrode 407-1 of the quadrupole electrodes is arranged in the upper side and one electrode 407-3 of the quadrupole electrodes is arranged in the lower side on the line (B) meeting orthogonally with the line (A) in the middle (M1) of the line (A) connecting between these two quadrupole electrodes 407 (407-2, 4), and the middle (M2) of the line (B) connecting between these two quadrupole electrodes 407 (407-1, 3) almost fits M1. Also the distance between two quadrupole electrodes 407 (407-2, 4), namely which is the length of line A, almost equals to the distance between two quadrupole electrodes 407 (407-1, 3), namely which is the length of line B. However even if the difference of A and B is a little large, the ions can be selected by the specific value of m/e by changing the voltage and the frequency applied to the quadrupole electrodes. The two quadrupole electrodes 407 (407-2, 4) are adhered on the third substrate 403, or to a part of the main substrate 401 (the base boards 401 (401-1, 2)) adhered on the third substrate 403. The quadrupole electrodes may be fixed by adhering the adhesive agency in the given position of the third substrate 403 or the base boards 401 (401-1, 2) in which the quadrupole electrodes 407 (407-2, 4) are arranged. Or the quadrupole electrodes 407 (407-2, 4) are arranged and fixed in the given position by equipping the grooves 408, etc. there. If the base boards 401 (401-1, 2) exist, the contact hole 410 is opened and the conductive film is deposited in the contact hole 410. The conductive film is, for example, metal such as Cu, Al, Mo, W, Ti, Ni, Cr, Au, Ag, etc., conductive carbon (for example, carbon nanotube, graphene) these laminates, these alloies, or these silicides, or low resistive (poly) silicon). The conductive film 411 is patterned preliminarily in the portion where the contact hole 410 is formed on the upper surface of the third substrate 403, the base boards 401 (401-1, 2) are arranged on it.

The second main substrate 404 (404-2) are adhered to the lower portion of the third substrate 403, and the penetrated room apace 414 that becomes the mass analysis lower portion room is formed. The mass analysis lower portion room 414 may be formed so that it becomes almost the same size as the mass analysis room 413 or larger than he mass analysis room 413 (in the planar size). The portion of the third substrate 403 included in the area connecting the upper and lower electrodes of the quadrupole electrodes 407-1, 3 should be removed as widely as possible and the opening portion 412 should be opened widely. One of the merits is to make the disturbance of the electric field by the quadrupole electrodes small as possible. Since the third substrate 403 in the portion where the quadrupole electrodes are arranged may change by the load as the result widen the opening portion, the second main substrate 404 (404-3, 4) can be arranged as the support poles in the portion of the third substrate 403 where the quadrupole electrodes 407 (407-2, 4) are arranged. These supporting poles 404 (404-3, 4) need not be continued in the travelling direction (vertical direction to the paper face or the longitudinal direction of the mass analysis room) of the charged particles, and they may be arranged discontinuously.

By these, the pressure of the penetrated room space 414-2, 3 outside of the supporting poles 404 (404-3, 4) becomes the same as the pressure of the central mass analysis lower portion space 414-1. The fifth substrate 406 is adhered to the lower surface of the second main substrate 404. The quadrupole electrode 407-3 adheres to the given position of the fifth substrate 406. The adhesive agency patterns or the solder alloy patterns, etc. is formed in the given position of the fifth substrate 406, the quadrupole electrode 407-3 is fitted to the patterns and arranged and the thermal treatment, etc. is performed, and the quadrupole electrode 407-3 is fixed on the fifth substrate 406. The groove patterns 409 are formed in the given position of the fifth substrate 406, and if the quadrupole electrode 407-3 is fixed by putting a part of the quadrupole electrode 407-3 in the groove patterns 409, it can be fixed more accurately. The quadrupole electrodes 407 (407-1, 2, 3, 4) are, for example, the curve profile such as the cylindrical, the elliptical, the hyperbola, etc., or the triangular, the quadrangular, the polygonal, or these combination shapes in the cross section, and are the rod-shaped electrodes. The rod electrode is adhered on the given portion using mounting equipments, for example, a flip chip bonder. When the adhesive agency, etc. are liquid, the quadrupole electrodes can be arranged. For example, they are easily arranged in self alignment in the given portion by small oscillation of light ultrasonic wave, etc. Or the rod electrodes are mounted in another (support) substrate, and another substrate is aligned with the substrate to be mounted, the rod electrodes are adhered in the given position of the substrate to be mounted, and the another substrate is separated after the rod electrodes are fixed.

The contact hole 416 is formed at the position of the quadrupole electrodes 407-3 in the fifth substrate 406, and the conductive film is deposited there, and the outside portion electrode wiring (the conductive film) 417 is formed. (Though it is not shown in the side of the fifth substrate 406, it is shown in the side of the forth substrate 405.) The conductive film wiring patterns 443, 419, 440, 441, 442 connecting to the outside portion electrode 418 from the conductive film wiring pattern 411 formed on the third substrate 403 connecting to the quadrupole electrode 407-2 are formed. The contact hole 443 is formed in the third substrate 403, and the conductive film is deposited in the contact hole 443, and it connects to the conductive film wiring pattern 411. The contact hole 443 and the conductive film in it are preferably formed before the second main substrate 404-2 is adhered to the third substrate 403. After that, the second main substrate 404-2 is adhered to the third substrate 403, the penetrated hole (the mass analysis lower portion room) 414 is formed, and the conductive film 419 and 440 are deposited, and the conductive film wiring pattern 419 and 440 are formed. After that, the opening portion 412 of the third substrate 403 is opened. Or the contact hole 443 and the conductive film in it are formed before the second main substrate 404-2 is adhered to the third substrate 403, and the conductive film wiring 419 is formed, next the second main substrate 404-2 is adhered to the third substrate 403. Then since the concave and convex of the conductive film wiring 419 are formed in the third substrate 403, if the concave and convex cause trouble, the concave portion may be formed by etching preliminarily such portions of the second main substrate. After that, the penetrated room (the mass analysis lower portion room) 414 is formed, and the conductive film wiring pattern 440 connecting to the conductive film wiring pattern 419 is formed in the inner face of the mass analysis lower portion room 414.

Or the second main substrate 404-2 is adhered to the third substrate 403 after the contact hole 443 and the conductive film in it are formed before the second main substrate 404-2 is adhered to the third substrate 403, next the penetrated room (the mass analysis lower portion room) 414 is formed in the second main substrate 404-2, and the conductive film wiring pattern 419 connecting to the conductive film in the contact hole 443 is formed on the lower surface of the third substrate. Furthermore the conductive film wiring pattern 440 connecting to the conductive film wiring pattern 419 is formed in the inner surface of the mass analysis lower portion room 414.

The conductive film wiring 441 connecting to the conductive film wiring pattern 440 is formed in the fifth substrate 406 adhering the quadrupole electrodes 407. Or the quadrupole electrodes 407 may be adhered after the conductive film wiring 440 is formed in the fifth substrate 406. The fifth substrate 406 is adhered to the lower surface of the second main substrate 404-2 in which the penetrated room (mass analysis lower portion room) 414 and the conductive film wiring 419 and 440 are formed. Then these are adhered with aligning so that the position of the quadrupole electrodes 407-3 come to the given place and the conductive film wiring 441 connects perfectly to the conductive film wiring 440. The connection between the wirings mentioned above may be performed using the method to form the concave portion 377 shown in FIG. 20(f). After that, the contact hole 441 connecting to the conductive film wiring 441, and the conductive film is deposited in it, and the outside electrode wiring 418 is formed. (Simultaneously the contact hole 416 connecting to the quadrupole electrode 407-3, and the conductive film is deposited in it, and the outside electrode wiring 418 can be formed.) Though the connection wiring to the quadrupole electrode 407-4 is not shown, it can be formed similarly to the quadrupole electrode 407-2.

The quadrupole electrode 407-1 is adhered to the forth substrate 405. The adhesive method of the quadrupole electrode 407-1 to the forth substrate 405 is the same as the method of the quadrupole electrode 407-2 to the fifth substrate 406. The conductive film wiring and the outside electrode wiring connecting to the quadrupole electrode 407-2 and 407-4 need not be made. Of course, it is possible to make them in the side of the fifth substrate 406, but the connection distance becomes longer. The second substrate 402 is adhered to the upper portion of the main substrate 401 in which the mass analysis room, in which the quadrupole electrodes 407-2 and 407-4 are arranged, is formed, and the second main substrate 404-1 is adhered on the second substrate 402, and the forth substrate 405 having the quadrupole electrode 407-1 is adhered on the second main substrate 404-1. Since the quadrupole electrodes 407-2 and 407-4 are adhered and fixed to the third substrate 403 (there is the case where the base board is sandwiched), and the third substrate 403 is supported by the support poles 404-3, 4, etc., the upper portion of the quadrupole electrodes 407-2 and 407-4 may be opened. Accordingly, the second substrate 402 of the upper portion of the mass analysis room 413 can be opened in whole. (the opening portion 444) Similarly the space of the mass analysis upper portion room that the second main substrate 404-1 has can become equal to or larger than the mass analysis room 413.

Though the second substrate 402 is adhered on the main substrate 401, the opening portion 444 of the second substrate 402 may be formed before the second substrate 402 is adhered on the main substrate 401, and the opening portion 444 of the second substrate 402 may be formed after the second substrate 402 is adhered on the main substrate 401. Or the mass analysis upper portion room 445 is formed after the second main substrate 404-1 is adhered on the second substrate 402, after that, the opening portion 444 of the second substrate 402 can be formed. It may be adhered to the second substrate 402 after the mass analysis upper portion room 445 is formed in the second main substrate 404-1. The second main substrate 404-1 having the mass analysis upper (portion) room 445 is adhered to the forth substrate having the quadrupole electrodes 407, and it can be adhered to the second substrate 402. Or after the mass analysis upper (portion) room 445 is formed by adhering the second main substrate 404-1 to the forth substrate 405, the quadrupole electrodes 407 are adhered, they may be adhered to the second substrate 402.

If the etching time to form the mass analysis room becomes mush longer because the thickness h24 of the main substrate is large, or if it is difficult to etch it (for example, the etching mask can not be kept by the long time etching) the main substrate may be divided to the plural semi-substrate, after they are etched, they may be adhered each other as shown in the dashed lines. For example, in the case of h24=1 mm, using the main substrate (divided) of 1 mm thickness, the portion that becomes the mass analysis room 413 (the penetrated room) is etched (the thickness is 1 mm), after that, 10 semi-substrates are superimposed, thus h24=10 mm, and they can be made by adhering to the third substrate 403. If the electrostatic binding method is used as the adhesion method, for example, the glass substrate of 0.2 mm thickness, etc. is adhered to the main substrate of 0.8 mm thickness using the electrostatic binding method, the portion that becomes the mass analysis room 413 (the penetrated room) is etched (the thickness is 1 mm), after that, 10 semi-substrates are superimposed, thus h24=10 mm, and they can be made by adhering to the third substrate 403. (If only the main substrate in the lowest layer is adhered to the third substrate 403, since the third substrate 403 need not be adhered to the glass substrate, all can be adhered using the electrostatic binding.)

The main substrate (divided) in the lowest layer of 1 mm thickness is adhered to the third substrate 403, a part of the mass analysis room (in the height direction) is etched (the thickness is 1 mm), after that the main substrate (divided) of 1 mm thickness of which the portion of the mass analysis room 413 is etched is adhered in succession, or the plural (semi) main substrate adhered are adhered in gross, thus the third substrate 403 adhering the main substrate (whole) can be made. Then if the height of the base board is 1 mm (which is the same as the thickness of the main substrate (divided) in the lowest layer), the etching process to form the base board is not needed. Also, the adhesion of the quadrupole electrodes 407 (407-2, 4) to the third substrate 403 or the base board 401-1 can be performed firstly, on the way, or finally in the process to adhere the main substrate (divided).

Similarly in the case of the second main substrate 404 (404-1, 404-2), the second main substrate 404 is divided (for example, as shown in the dashed lines 447 and 448), and the second main substrate 404 (404-1, 404-2) of the given thickness can be made by adhering the mass analysis upper room and lower room. For example, in the case of h25=10 mm, 5 second main substrates of 2 mm thickness may be superimposed. In the case of the glass substrate, the process is the same as the above main substrate. In the case of h26=10 mm, 10 second main substrates of 1 mm thickness may be superimposed. In the case of the glass substrate, the process is the same as the above main substrate. In the case of the second main substrate 404-2, though the conductive film wiring 440 need be made, it can be made after all substrates are imposed, or it can be made and connected in each case.

In that case, in the side surface of the second main substrate 404-2, the insulating film may be formed between the second main substrate and the conductive film to improve the electric insulation and the adhesion. Particular in the case where the second main substrate is the insulating material, the insulating film need be formed. Cutting the conductive film in the uneven portion can be protected by tapering the side surface of the second main substrate 404-2. Since the side surface of the second main substrate 404-2, namely the shape of the side surface of the mass analysis lower room may not be vertical, the step coverage of the conductive film can be improved by tapering. Tapering is effective for the plating method or the electrocasting method besides CVD method, PVD method. Of course, the similar process can be used in the second main substrate 404-1 and the mass analysis upper room, but if the conductive film is not deposited, the shape need not be considered.

As mentioned above, since 4 quadrupole electrodes are arranged in the given position and in the wide space, the ideal electric field of the quadrupole electrodes can be made accurately. Also since the outside spaces of the quadrupole electrodes (particularly the outside spaces of the quadrupole electrodes 407 (407-2, 4) can be widened, the kinetic momentum of the ions passing through the empty space between the quadrupole electrodes can be reduced, and the damage to the substrate surrounding the mass analysis room 413, the mass analysis upper room 445 and the mass analysis lower room 414 can be reduced. Since the ions passing through the empty space between the quadrupole electrodes can be exhausted by making the vacuumizing line portions 449 numerously, the damages to the side substrate can be decreased in additional. Also as shown in FIG. 51(*f*), if the sixth substrate and the seventh substrate adhering the third substrate having additionally the space outside of the forth substrate 405 and the fifth substrate 406, since the opening portion can be widened in the forth substrate 405 and the fifth substrate 406, the damages to the forth substrate 405 and the fifth substrate 406 by the ions can be decreased in additional. The opening portions conducting the mass analysis lower room 414 (414-2, 3) outside of the quadrupole electrodes 407 (407-2, 4) can be partially made in the third substrate 403. Though the opening portion can be made wholly, in that case, the conductive film wiring is formed on the side surface of the supporting poles 404 (404-3, 4). Well, the quadrupole electrodes 407 can be made directly besides the method to adhere the rod to the substrate. One example is explained next.

FIG. 23 is the diagram showing the method to make the quadrupole electrodes. Though the FIG. 23 shows one sample of the method to make the quadrupole electrodes 407-2 and 407-4, the similar process can be used in the other cases. Accordingly the same symbols are used for the same portions as FIG. 22(*d*). FIG. 23(*a*) to (*d*) shows the method to make the quadrupole electrodes using the plating method. The third substrate 403, the conductive film 411, the main substrate 401-2, the contact 410 made in the main substrate 401-2, and the groove 408 in FIG. 23(a) to (d) are the same as the explanation mentioned previously. The groove 408 may not be used in the plating method. If the main substrate 401-2 and the third substrate 403 are not the insulating material, the insulating film is sandwiched between them and the conductive film 411 or the conductive film 410 in the contact hole.

As shown in FIG. 23(a), the film to improve the adhesion characteristics, the conductive film for barrier and the plating seeds film 450 are deposited. For example, if the plating film is Cu, the plating seeds film is Cu film, and it is deposited by CVD method or PVD method, etc. The film to improve the adhesion characteristics and the conductive film for barrier are, for example, Ti/TiN, or Ta/TaN films, and these are deposited by CVD method or PVD method, etc. After the film to improve the adhesion characteristics and the conductive film for barrier are deposited, for example, in about 50 nm to 500 mm, the plating seeds film is deposited in about 500 nm to 5000 nm. Next the photosensitive film 451 is deposited on the substrate 403 using the coating method and the sheet adhesion method, and the opening portion 452 is formed by the photolithography in the place where the quadrupole electrodes should be formed. The depth of the opening portion 452 is made in the same extent as size of the quadrupole electrodes. For example, if the height of the quadrupole electrodes is 0.1 mm, the depth of the opening portion becomes about 0.1 mm, if the height of the quadrupole electrodes is 1.0 mm, the depth of the opening portion becomes about 1.0 mm, if the height of the quadrupole electrodes is 5.0 mm, the depth of the opening portion becomes about 5.0 mm. After that, the substrate 403 is dipped on the plating solution, or it is splayed by the plating solution, the plating film 453 is formed in the opening portion 452 by flowing the current through the plating seeds layer, (Cu plating solution is, for example, a sulfate of copper.) The plating film 453 becomes the quadrupole electrodes. (FIG. 23(b)) If the given thickness of the plating film 453 is formed, the plating is stopped and the photosensitive film 451 is removed. The plating seeds layer and the film to improve the adhesion characteristics and the conductive film for barrier in the portion where the plating film 453 is not formed are removed using the mask of the plating film. Ordinarily though the plating seeds layer and the plating metal are the same materials, since the thickness of the plating seeds layer is much smaller than that of the plating metal, even if they are wholly etched (wet etching or dry etching), the thickness of the plating metal does not almost change. Namely the plating metal becomes thinner in the amount of the thickness of the plating seeds layer and the amount of the over etching.

In the method how o use the photosensitive film pattern shown in the FIGS. 23(a) and (b), though the shape of the side surface of the photosensitive film 451 in the vertical direction to the paper face can be changed freely using the photosensitive mask pattern, the shape in the depth direction cannot be changed. We can only make the shape incline. Accordingly though the shape of the plating film 453 can be changed freely in the vertical direction, the shape cannot be changed in the depth direction and in the upper portion side. Do as shown in FIGS. 23(c) and (b), the mold 454 having the space 455 corresponding to the final plating shape is formed, as explained in FIG. 23(a), after depositing the adhesion improving film and the barrier conductive film and the plating seeds layer 450, the mold 454 is fitted to the forming portion of the contact 410 where the quadrupole electrode is placed, and it is pressed into the substrate. The mold 454 is made of the plastic, the polymer, or brazing materials, etc.

and includes the space 455, the inlet 456 of the plating solution, and the outlet 457 of the plating solution, which is the space. Also since the connecting portion between the mold 454 and the substrate 403 is made of the softening materials, the damage to the substrate 403 is not given even if the mold 454 is pressed to the substrate, so the patterns (411, 401-2, etc.) formed in the substrate 403 are covered certainly, the plating solution is intruded in the connecting portion of the substrate 403 and the mold 454. The plating solution is poured from the plating solution inlet 456 formed in the upper portion of the space 455 of the mold 454, and the plating solution is ejected from the plating solution outlet 457 formed in the lower portion of the space 455 of the mold 454. The plating film grows from the plating seed by conducting electricity to the plating seed, and the plating film having the corresponding shape to the space 455 can be formed. If the plating film 458 having the given size and shape is formed, the power distribution and the plating solution injection are stopped, and the mold 454 is removed, thus the quadrupole electrode having the given shape is formed. (FIG. 23(d)) After that the plating film 458 becomes the mask, the plating seeds layer and the adhesion improving conductive film and barrier conductive film are removed in the portion where the plating film 453 is formed. Well, in FIG. 23(a) to (d), the plating seeds layer and the adhesion improving conductive film and barrier conductive film are removed in the portion where the plating film 453 may be formed using the photolithography method and etching method prior to the plating process. In the case of FIGS. 23(a) and (b), the plating can be performed even if the photosensitive film patterns are not existed, if a part of the conductive patterns are left, since the plating film grows in the portion, the photosensitive film patterns may be formed.

FIG. 24 is the diagram showing the method to adhere the quadrupole electrode to the substrate. The quadrupole electrode is made preliminarily with the desirable shape.

The merit of this method is that the electric field characteristics of the quadrupole electrode becomes very good since the quadrupole electrode using the optimal material and shape can be used. FIGS. 24(a) and (b) is the diagram showing the state to mount the quadrupole electrode using the flip chip mounting machine (bonder). The longitudinal cross sectional diagram shown in FIG. 24(a) is the cross sectional schematic diagram in the contact portion, FIG. 24(b) is the cross sectional schematic diagram in the vertical direction to the paper face in FIG. 24(a). Namely FIG. 24(b) is seen in the longitudinal direction of the quadrupole electrode and in the travelling direction of the ions, FIG. 24(a) is the vertical cross section to it. The groove (or concave portion) 408 is formed in the portion where the quadrupole electrode rod 407 is adhered to the first main substrate 401-2 adhered to the third substrate 403, the surface of the contact 410 is exposed in the area. Seeing in the longitudinal direction of the quadrupole electrode rod 407, though the area of the contact 410 is drawn as a part, if the electric field characteristics do not become bad, the contact 410 can be formed in the portion where the whole of the quadrupole electrode rod 407 contact, the voltage is applied to the quadrupole electrode 407 from the contact portion.

The conductive adhesive agency, the solder metal or the conductive paste is adhered in the portion where the quadrupole electrode rod 407 is adhered in the first main substrate 401-2 adhered to the third substrate 403. There are various methods as the coating method, for example, dispenser method, screen printing method, photosensitive patterning method. Though the adhesive agency, etc. 450 is not written in FIG. 24(b) to see easily the figure, they are coated in the whole area of the groove portion 408 (shown in the dashed line in FIG. 24(b)) where the quadrupole electrode rod 407 is put. The shape of the groove 408 is desirably formed so that the quadrupole electrode rod 407 fit exactly into the groove portion, and can be formed using wet etching method, dry etching method, laser method, etc. When the first main substrate 401 is the semiconductor substrate such as Si substrate, etc., or the conductive substrate such as Cu substrate, etc., the connection portion with the quadrupole electrode rod 407 should be covered with the insulating film. Accordingly the conductive film in the contact 410 is desirably deposited after the insulating film is formed. Or if the first main substrate 401 is adhered to the third substrate 403 of the insulating substrate as an isolated pattern (namely it does not contact with the other conductive portion or the semiconductor portion) in the portion where the quadrupole electrode rod 407 is mounted, the insulating film may not be formed on the first main substrate 401. Well, the adhesive agency, etc. can be also adhered on the quadrupole electrode rod 407. Namely the adhesive agency, etc. can be adhered in the area where the quadrupole electrode rod 407 is adhered to the contact portion 410 and the first main substrate 401-2.

The quadrupole electrode rod 407 is stuck fast to by the flip chip mounting machine, and is adhered with aligning to the adhesive portion of the third substrate 403 and the first main substrate 401. In the adhesion using the adhesive agency, the quadrupole electrode rod 407 is fixed by treating thermally at higher temperature than the curing temperature of the adhesive agency and solidifying the adhesive agency. Or In the adhesion using the ultraviolet curable adhesive agency, the quadrupole electrode rod 407 is fixed by irradiating ultraviolet ray and solidifying the adhesive agency. In the case of the metal, after the quadrupole electrode rod 407 is adhered at the higher temperature than the melting point, the quadrupole electrode rod 407 is fixed by lowering the temperature and solidifying the adhesive agency. In the case where the quadrupole electrode rod 407 can be aligned automatically by the surface tension of the adhesive agency, etc., even if the quadrupole electrode rod 407 and the third substrate 403 or the first main substrate 401 are not certainly fixed, the sucking portion 459 of the flip chip mounting machine (bonder) can be desirably left from the quadrupole electrode rod 407. In the case where the quadrupole electrode rod 407 cannot be aligned automatically, after the quadrupole electrode rod 407 and the third substrate 403 or the first main substrate 401 are certainly fixed, the sucking portion 459 of the flip chip mounting machine (bonder) can be desirably left from the quadrupole electrode rod 407. After the quadrupole electrode rod 407 is adhered, the contact 410 can be formed at the same time as the contact of the third substrate 403. In FIG. 22(d), though the quadrupole electrode rod 407-1 and 407-3 are adhered directly to the second substrate 405 and 406, we may consider the case where the first main substrate 401 is not adhered in FIGS. 24(a) and (b). If the groove 409 is necessary, it is formed in the second substrate 405 and 406. After the contact hole 416 and the outside electrode wiring 417 are formed preliminarily, the quadrupole electrode rod 407 may be adhered, FIGS. 24(c) and (d) are the diagrams showing the method to adhere the quadrupole electrode rod 407 adhered to the support substrate 461 to the forth substrate 405 or the fifth substrate 406. The adhesive agency, etc. 462 is adhered to the support substrate 461, and the quadrupole electrode rod 407 is adhered to the support substrate 461 by reversing the portion where the quadrupole electrode rod 407 is adhered. The groove 409 is formed in the portion where the quadrupole electrode rod 407 is adhered in the forth substrate 405 that is made the quadrupole electrode rod 407 adhere. The method to make the groove 409 is the same as the method in FIGS. 24(a) and (b), The shape of the groove 409 is desirably the shape in which the quadrupole electrode rod 407 fits certainly. The contact 416 and the electrode wiring 417 can be formed preliminarily in the fifth substrate 405. The conductive adhesive agency, etc. 460 is formed in the contact portion of the quadrupole electrode rod 407 in the groove 409, and the quadrupole electrode rod 407 adhered to the support substrate 461 is adhered to the contact portion of the forth substrate 405 with aligning. The adhesion film 462 bonding the support substrate 461 and the quadrupole electrode rod 407 is, for example, a thermoplastic adhesive agency of softening temperature T1. Also, the adhesive agency 460 between the quadrupole electrode rod 407 and the fifth substrate 405 is the thermosetting adhesive agency of curing temperature T2. The material of T1>T2 is selected. After contacting the quadrupole electrode rod 407 adhering to the support substrate 461 to the given portion of the forth substrate 405, the thermal treatment temperature is kept between T1 and T2, and the quadrupole electrode rod 407 and the forth substrate 405 are fixed by making the adhesive agency 460 cure. Next increasing the temperature more than T1, the support substrate 461 is separated by make the adhesion film 462 softening. Thus the quadrupole electrode rod 407 adheres strongly in the given portion of the fifth substrate 405. After that, the contact 416 and the electrode wiring 417 can be formed. Well, the area of the contact 416 can be widened if it is better for the electric field to widen it. Namely the area of the quadrupole electrodes 410 may be extended in the longitudinal direction in FIG. 24(d). Also the area of the quadrupole electrodes 410 may be extended in the width direction in FIG. 24(c). Well, the above is enabled using the same method in the fifth substrate 406. After the first main substrate 401 is adhered in the second substrate 402 and 403, the quadrupole electrode rod 407 can be adhered using the similar process. Thus the quadrupole electrode rod 407 constructed with the desirable shapes and from the desirable materials can be fixed to the substrate.

FIG. 25 is the diagram showing the method to arrange the quadrupole electrodes in the mass analysis room using the thin film formation method. The method is similar to the method of FIG. 22(c). The electrode pattern 463 is formed on the lower substrate 472, and the main substrate is adhered to the lower substrate. Then the concave portion 464 is formed in the adhered surface of the main substrate 471, thus the main substrate 471 is not made contact to the electrode pattern 463. The electrode pattern 463 (463-1) is one of the quadrupole electrodes, and the concave portion 464 becomes the mass analysis room finally. The electrode pattern 463 (463-2) and the electrode pattern 463 (463-3) become a part of the quadrupole electrodes finally, though it is not shown in FIG. 25(a), the concave portion is formed in the main substrate 471, thus the electrode pattern 463 (463-2) and the electrode pattern 463 (463-3) are not contacted to the main substrate 471. The penetrated rooms 473 (473-1,2) to form two of the quadrupole electrodes in the right and left direction are formed in the main substrate 471 adhered to the lower substrate 472. The concave portion 464 around the electrode pattern 463 (463-2) and the electrode pattern 463 (463-3) is made include in the penetrated room 473 (473-1, 2). Namely the penetrated room 473 (473-1, 2) is larger than the concave portion 464 around the electrode pattern 463 (463-2) and the electrode pattern 463 (463-3). When the anisotropic etching is performed to form the penetrated room 473 (473-1, 2), since the concave portion 464 is penetrated fast, the conductive film 463 (463-2, 3) and the lower substrate 472 exposed between the conductive film 463 (463-2, 3) and the concave portion are exposed by etching of the main substrate 471. Accordingly the etching selectivity between the lower substrate 472 or the conductive film 463 (463-2, 3) and the main substrate 471 should be taken sufficiently larger, and the thickness of the lower substrate 472 and the conductive film 463 (463-2, 3) should be taken more than the etching amount.

Next if the main substrate 471 is not the insulating material, for example, Si substrate, the insulating film 474 is deposited so that the silicon substrate do not conduct with the conductive film 475 deposited later. The insulating film 474 is deposited in the mass analysis room 473. The thickness of the insulating film is, for example, 500 nm to 5000 nm in the side surface of the mass analysis room 473. In the case of 500 nm, the breakdown voltage is more than 200V. In the case of high voltage, the thickness of the insulating film may be thicker. For the etching of the mass analysis room 473 (473-1, 2), the vertical etching is better not to make the size change. Since the insulating film 474 is deposited on the bottom of the penetrated room 473 (473-1, 2) and the conductive film 463 (463-2, 3) is covered by the insulating film 474, the vertical etching (dry etching) to the substrate surface is practiced to etch the insulating film 474 in this portion. Then though the insulating film 474 deposited on the upper surface of the main substrate 471 is etched, since the insulating film 474 is thicker than the insulating film 474 deposited on the conductive film 463 (463-2, 3) in the bottom portion of the penetrated room 473, even if the insulating film 474 deposited on the conductive film 463 (463-2, 3) in the bottom portion of the penetrated room 473 is etched wholly, the insulating film 474 deposited on the upper surface of the main substrate 471 is left a little. However even if the insulating film 474 deposited on the upper surface of the main substrate 471 is etched in all, though the main substrate 471 is expose, the main substrate 471 is not etched so much by taking the etching selectivity sufficiently larger, and since the main substrate 471 is thick in itself, there is no problem even if it is etched. Also the insulating film deposited in the side surface of the penetrated room 373 is very thick in the depth direction, and the insulating film is not almost etched in the horizontal (side) direction.

The conductive film 475 is deposited in the state where the conductive film 463 (463-2, 3) in the bottom portion of the penetrated room 473. The conductive film 474 connects to the conductive film 463 (463-2, 3). The conductive film 475 is the adhesion improving conductive film with the insulating film 474 and the conductive film 463 (463-2, 3) and the plating seeds conductive film, for example, Ti, TiN, Ta, TaN, and the thickness may be about 100 nm. After the adhesion improving conductive film is formed, the plating seeds conductive film is deposited. If the plating film is Cu, it may be Cu film, is deposited using CVD method, OVD method, etc. (FIG. 25(a)) Next mobile resin film 465 such as photo resist film, etc. is coated, and treated thermally and cured, and the surface of the main substrate 471 is planarized. Then it is important to put the resin film 465 into the penetrated room 473 and to make fill with the resin film 465. The width of the penetrated room 473 can be taken comparatively largely, for example, 0.1 mm to 0.5 mm and to 5 mm, and may be set corresponding to the depth of the penetrated room 473. Accordingly since the aspect ratio can be set in about 1 to 5 even if the depth of the penetrated room 473 is 1 mm to 19 mm, there is no problem in the step coverage of the insulating film or the conductive film, and the step coverage can be available within the range of 0.5 to 1.0. Also there is no problem for making the space of the penetrated room 473 fill with the resin film 465

Next the conductive film 475 deposited on the upper surface of the main substrate 471 is exposed by etching and removing the planarized resin film 465 from the upper direction using etching back method. Then the inside portion of the penetrated room 473 is filled with the resin film 465, the conductive film 475 deposited in the inner surface of the penetrated room 473 is covered by the resin film 465. (FIG. 25(c)) Accordingly the exposed conductive film 475 is etched (wet or dry), and the conductive film 475 deposited on the upper surface of the main substrate 471 is removed. However the conductive film 475 deposited on the inner surface of the penetrated room 473 can be left. (FIG. 25(d)) Or in the state of FIG. 25(b), the resin film 465 and the conductive film 475 planarized using the polishing method (CMP method or BG method) is removed in the planarized state, thus the state of FIG. 25(d) can be made. Next after the resin film 465 left in the penetrated room 473 is removed, the contacts 466 (466-1, 2, 3) connecting to the conductive film 463 (463-1, 2, 3) are formed in the lower substrate 472. Furthermore the conductive film 467 connecting to the contacts 463 (463-1, 2, 3) is deposited on the lower surface of the lower substrate 472. The conductive film 467 can be deposited at the same time as the conductive film in the contacts 466. Though the conductive film 467 becomes later the electrode wiring from which the voltage is applied to the quadrupole electrodes, in this moment the conductive film 467 is not patterned and deposited in the whole lower surface of the lower substrate 467, and in the state where the current flows, the plating solution or the plating spray is flowed in to the penetrated rooms 473 (473-1, 2), thus the penetrated rooms 473 (473-1, 2) are filled with the plating film 468 by making the plating film 469 grow. (FIG. 25(e))

Next the surface of the main substrate 471 is planarized by polishing or etching the side of the main substrate 471 using the polishing method (CMP method or BG method) or etching back method. Next the photosensitive film 469 using the coating method or the photosensitive sheet using the adhesion method, etc. are formed on the surface of the main substrate 471, and the portion 470 that becomes the mass analysis room is opened using photolithography. The opening portion 470 is opened till the penetrated room 473 (473-1, 2), and the main substrate 471 between the penetrated room 473 (473-1, 2) is opened wholly. (FIG. 25(f)) After that, the main substrate 471 is etched to the lower substrate 472, and the penetrated room 476 is formed. Since the main substrate 471 between the penetrated room 473 (473-1, 2) is etched wholly, the penetrated room 476 faces directly to the conductive film 475 and the plating filled film 468 made in the penetrated room 473 (473-1, 2). (the insulating film 474 exist between them) In the case where the main substrate 471 is Si substrate, since we can take the etching selectivity of the insulating film 474 (for example, SiO2 film, SiN film) surrounding the side surface of the penetrated room 473 (473-1, 2) and Si substrate largely, the insulating film 474 surrounding the side surface of the penetrated room 473 (473-1, 2) is not so much etched. Since the circumference of the conductive film 463 (463-1) is the concave portion, the lower substrate 472, though the conductive film 463 (463-1) in this portion are exposed to the etching of the main substrate 471 more than the other portion, since we can take the etching selectivity ratio of these the lower substrate or the conductive film 463 (463-1)

and Si substrate largely, these are not etched so much. Also the lower substrate 472 and the conductive film 463 (463-1) may be thicker. (FIG. 25(*g*))

After the penetrated room 476 is formed by etching (vertical etching) the main substrate 471 from the opening portion 470 of the photosensitive film 469 and the photosensitive film 469 is removed, the upper substrate 477 adhering the conductive film wiring 478 to the lower surface is adhered to the upper surface of the main substrate 471 adhered to the lower substrate 472. Since the conductive film wiring 478 becomes on of the quadrupole electrodes, it is arranged in the penetrated room 476 of the mass analysis room. the conductive film wiring 478 formed in the upper substrate 477 is formed using, for example, CVD method, PVD method, the plating method, the screen printing method, etc. Pr the conductive film may be formed using the dispenser. For example, in the case where the upper substrate 477 is the insulating material, the adhesion improving conductive film Ti/TiN film is deposited in 100 nm to 1000 nm, next Cu plating seeds film is form in 500 nm to 10000 nm, and the electrode formation portion is opened using photolithography, and Cu plating (100 μm to 5 mm) is practiced. The Cu plating seeds film and the adhesion improving conductive film Ti/TiN film are etched and removed as masking the thick Cu plating. The upper substrate 477 is adhered by adhering the adhesive agency, etc. in the plating film 468. In the case where the main substrate 471 is Si substrate and the upper substrate 488 is the glass substrate, etc., they can be adhered using the electrostatic binding. After that, the contact 479 connecting to the plating film 468 and the conductive film electrode 478 is formed in the upper substrate 477, Furthermore the conductive film electrodes 480(480-1, 2, 3) connecting contact 479 are formed on the upper surface of the upper substrate 477.

Also the conductive film electrodes 467(467-1, 2, 3) are formed in the side of the lower substrate. Thus the quadrupole electrode 463-1 and the quadrupole electrode 478 facing it in the upper and the lower, and two quadrupole electrodes 468 in the right and the left are formed in the mass analysis room 476. The upper and lower quadrupole electrodes 463-1 and 478 are arranged desirably so that they become symmetrical shapes to the central line in the right and left. Also the right and left quadrupole electrodes 468 are arranged desirably so that they become symmetrical shapes to the central line in the upper and lower. Thus the center M1 in the line connecting the upper and lower quadrupole electrodes 463-1 and 478 is fitted desirably to the center M2 in the line connecting the right and left quadrupole electrodes 468. Thus the stable quadrupole electrodes can be easily formed. Well, the mass analysis room can be made by superimposing two of the structures of FIG. 25(*g*) in the upper and lower, (The photosensitive film 469 is removed.) Thus the mass analysis room can be made heighten. When they are adhered, for example, they can be adhered using the conductive adhesive agency or the solder metal on the surface of the plating film 468 and the insulating adhesive agency or no adhesive agency in the other portion. Since the quadrupole electrodes are arranged in the mass analysis room, the quadrupole electrodes can be formed more stably in the mass analysis room The present invention can be applied to the multipolar electrodes having more electrodes than the quadrupole electrodes. There are, for example, hexapole electrodes ion guide, octopole electrodes ion guide, as the multipolar electrodes ion guide. FIG. 26 is the diagram showing the structure of the octopole electrodes ion. 4 electrodes are added to the quadrupole electrodes shown in FIG. 22(*a*). The same parts as the parts used in FIG. 22(*a*) are shown by the same symbols. As the different parts from FIG. 22(*a*), the upper side of the octopole electrodes is adhered on the third lower substrate 482 but not on the upper substrate 382. The upper side of the octopole electrodes is adhered to the second upper substrate 483. (Here, the term "adhesion" includes both the case adhered externally and the case formed by thin film, in so far as distinguished particularly.). However since it is natural that it can be adhered to the upper substrate 392 (the other electrodes 393-2, 398-8, and the lower side are in the same way), as with FIG. 22(*a*), the details is not explained. Three octopole electrodes 394 (394-5, 1, 8) are adhered on the second lower substrate 482. When three octopole electrodes 394 (394-5, 1, 8) are adhered externally (the octopole electrodes made aside are adhered), they are adhered in the groove or the concave portion using the adhesive agency, etc. after the grooves or the concave portions, which are fitted to the shape of the octopole electrodes (394-5, 1, 8), are formed on the second lower substrate 482 (using the photolithography and etching method, or laser, etc), they are adhered in the groove or the concave portion using the adhesive agency, etc. The second upper substrate 483 is adhered to the upper side of the octopole electrodes 394 (394-5, 1, 8), and the octopole electrodes 394 (394-5, 1, 8) are fixed certainly. Then after the grooves or the concave portions, which are fitted to the shape of the octopole electrodes (394-5, 1, 8), are formed on the lower surface of the second upper substrate 483, they are adhered in the groove or the concave portion using the adhesive agency, etc.

The second main substrate 481 is adhered between the second lower substrate 482 and the second upper substrate 483 (then the upper substrate 392 is the first upper substrate 392, the lower substrate 393 is the first lower substrate 393), and the penetrated rooms 485 (485-1, 2, 3) are formed in the second main substrate 481, and the octopole electrodes 394 (394-5, 1, 8) can be also respectively arranged in the penetrated rooms 485 (485-1, 2, 3). There are various methods as the arranging method. For example, the second main substrate 481 is adhered to the second lower substrate 482, and the penetrated rooms 485 (485-1, 2, 3) are formed, and the grooves 395 are formed in the given portions of the second lower substrate 482. (After the grooves 395 are formed in the given portions of the second lower substrate 482, the second main substrate 481 is adhered, and the penetrated rooms 485 (485-1, 2, 3) can be formed.) Here the substrate side wall plate 481-1 of the second main substrate 481 exists between the penetrated rooms 485-1 and the penetrated rooms 485-2, the substrate side wall plate 481-2 of the second main substrate 481 exists between the penetrated rooms 485-1 and the penetrated rooms 485-3. The oppositional face of the substrate side wall plate 481-1 is the substrate side wall plate 481-3 in the penetrated room 485-2. The oppositional face of the substrate side wall plate 481-2 is the substrate side wall plate 481-3 in the penetrated room 485-3.

Next the octopole electrodes 394 (394-5, 1, 8) are put into respective the penetrated rooms 485 (485-1, 2, 3) using the flip chip mounting machine, and they are adhered to the second lower substrate 482, after that, the second upper substrate 483 is adhered to the second main substrate 481. Then the upper portion of the octopole electrodes 394 (394-5, 1, 8) is adhered to the second upper substrate 483. The grooves or the concave portion 395 are formed in the given portion of the second upper substrate 483, and the adhesive agency, etc, are adhered in the portions, the upper portion of the octopole electrodes 394 (394-5, 1, 8) may be fitted to these grooves, etc. Or The grooves or the concave portion 395 are formed in the given portion of the second upper substrate 483, and the adhesive agency, etc, are adhered in the portions, the upper portion of the octopole electrodes 394 (394-5, 1, 8) adhered so that they are fitted to these grooves, etc. The second upper substrate 483 adhering the octopole electrodes 394 (394-5, 1, 8) is adhered to the second main substrate adhered to the second lower substrate 482 by inserting the octopole electrodes 394 (394-5, 1, 8) into the penetrated rooms 485 (485-1, 2, 3) formed in the second main substrate 481 adhered to the second lower substrate 482. Then the lower portion of the octopole electrodes 394 (394-5, 1, 8) is adhered by fitting the grooves, etc. 395 formed in the second lower substrate 482. Thus the octopole electrodes 394 (394-5, 1, 8) can be adhered to the second upper substrate and the second lower substrate. Here the second upper substrate may be the same material as the first upper substrate. The second lower substrate may be the same material as the first lower substrate. The second main substrate may be the same material as the first main substrate.

In the connection portion of three octopole electrodes 394 (394-5, 1, 8) and the second upper substrate 483, the contacts are made in the second upper substrate 483, and the outside electrode wiring, to which the voltage is applied from the outside, can be made. When the vertical direction to the surface of the main substrate, the upper substrate and the lower substrate is Z direction, the travelling direction of the charged particles is X direction (the vertical direction to the paper face in FIG. 26, however the tangential direction if the charged particles draw the curved line), and the vertical direction to both X and Z directions is Y direction, three octopole electrodes 394 (394-5, 1, 8) are arranged in Y direction. If the substrate side wall plates (substrate partition wall plats) 481-1 and 481-2 between the penetrated rooms 485 (485-1, 2, 3) are not needed, they may be removed or not made. Since the second lower substrate 482 and the second upper substrate 483 are also supported by three octopole electrodes 394 (394-5, 1, 8), all can be removed or not made. In that case, the side walls of the second main substrate are only the second main substrate 481-3 and 481-4 outside of three octopole electrodes 394 (394-5, 1, 8). Furthermore the second main substrate 481 can be removed or not equipped. And the second upper substrate 483 can be removed or not equipped. Then the outside electrode wiring for the voltage supply to three octopole electrodes 394 (394-5, 1, 8) connects directly to three octopole electrodes 394 (394-5, 1, 8), or the outside electrode wiring can be made in the side of the second lower substrate. Though the second lower substrate can be removed or not equipped, in that case, since three octopole electrodes 394 (394-5, 1, 8) are adhered on the upper surface of the first upper substrate 392, the outside electrode wiring can be made on the upper surface of the first upper substrate 392.

Thus the electrodes module substrate consisted of three octopole electrodes 394 (394-5, 1, 8) mounted in the penetrated room formed in the second main substrate 481 adhered to the second lower substrate 482 and the second upper substrate 483 is adhered to the upper surface of the first upper substrate 392. If there are contact wiring in the first upper substrate 392, the contact wiring is made in the second lower substrate 482, and it may connect with the contact wiring of the first upper substrate 392. If the module is adhered to the first lower substrate 393, it becomes the lower side shown in FIG. 26(*a*). Namely the electrodes module substrate consisted of three octopole electrodes 394 (394-6, 3, 7) mounted in the penetrated room formed in the third main substrate 484 adhered to the third lower substrate 486 and the third upper substrate 485 is adhered to the lower surface of the first lower substrate 393. The octopole electrodes 394-6 is arranged in the penetrated room surrounded by the substrate side walls 484-3 and 484-1 of the third main substrate 484, the octopole electrodes 394-3 is arranged in the penetrated room surrounded by the substrate side walls 484-2 and 484-1 of the third main substrate 484, the octopole electrodes 394-7 is arranged in the penetrated room surrounded by the substrate side walls 484-2 and 484-4 of the third main substrate 484.

The main charged particles are made travel near center of the penetrated room 396-1 arranged in the middle. The electrical field that 8 electrodes of the octopole electrodes 394-1 to 8 make becomes desirably symmetric in the penetrated room 396-1. So, 8 electrodes of the octopole electrodes 394-1 to 8 may be arranged so that they become symmetric as possible to the center of the penetrated room 396-1. However in the present invention, since the voltage or the frequency can be individually applied to each electrode with changing them, may be near symmetry. For example, the center of the distance between the faced electrodes (394-1 and 3, 394-5 and 7, 394-2 and 4, 394-6 and 8) becomes near the center of the penetrated room 396-1. Also in the case of FIG. 26(*a*), so that 3 electrodes 394-4, 1, 3 and 2 electrodes 394-2, 4 and 3 electrodes 394-6, 3, 7 are arrayed in Y direction, and so that 3 electrodes 394-5, 2, 6 and 2 electrodes 394-1, 3 and 3 electrodes 394-8, 4, 7 are arrayed in Z direction, they are arranged. Also purging and cleaning opening portions and vacuumizing opening portions connecting to each penetrated rooms are formed in the first and second upper substrate and the first and second lower substrate.

Though the octopole electrodes 394 (394-1 to 8) are formed with rod shape in X direction, since they need not be supported wholly by the upper substrate or the lower substrate, other the upper substrate (the first upper substrate 392, the third upper substrate 485) or the lower substrate (the first lower substrate 393, the second lower substrate 482) or the side wall plate 391-1, 2 of the first main substrate 391, or the side wall plate 481-1, 2 of the second substrate, or the side wall plate 484-1, 2 of the third substrate can be removed or not equipped except only the portions supporting a part of the octopole electrodes 394 (394-1 to 8) in the inside of the second lower substrate 486, the third main substrate 484-3, the first main substrate 391-3, the second main substrate 481-2, the second main substrate 481-4, and the first main substrate 391-4,484-4. In that case, since the main substrate, the upper substrate and the lower substrate, which affect the electric field generating from the octopole electrodes, are removed, the stability of the electric field in the mass analysis room 396-1 can increase. Also in this vase, the pressure of the penetrated rooms around the mass analysis room 396-1 is the same. Furthermore we can extend the space of the penetrated rooms outside the octopole electrodes and can additionally adhere the upper substrate and the lower substrate adhered the main substrate having the penetrated room on the second upper substrate 483, and we can extend the penetrated room. Thus the given space can be made outside of the octopole electrodes. In that case, the pressure of the whole mass analysis room can be reduced by equipping the opening portion for vacuumizing in the upper substrate and the lower substrate arrange in the outermost.

FIG. 26(*b*) is the embodiment changing the structure the octopole electrodes 394 (394-1-8) shown in FIG. 26(*a*). In this embodiment, all the distances between the facing electrodes are almost equal and the centers between the facing electrodes almost meet, and the middle point (M) becomes desirably almost the central portion of the mass analysis room. Accordingly 8 of the octopole electrodes 394 (394-1-8) are arranged on the same circle of R in radius centered at M. Also since it is desirable that the adjacent electrodes have the same relations respectively, the central angle of the adjacent electrodes is desirably about 45 degrees. Also the size and shape of each electrode is desirably almost same, and it is desirable that the shape in the direction facing the middle point M is almost same or similar. Since the shape of the electrodes is the circle in the cross section and the rod (namely cylindrical shape), it has the same shape by rotating. If the shape is hyperbolic, the shape in the direction facing the middle point M is desirably hyperbolic. Accordingly when the electrodes are arranged, they are adhered in the given places so as to become such shapes. If the height of the electrodes 394-2, 4 is smaller than that of the mass analysis room, the base board 397 should be arranged in the same way shown in FIG. 22(*a*) so that the center of the electrodes 394-2 and 4 becomes the center of the height of the mass analysis room. To equal almost the distances between the electrodes 394-5-8 arranged in the inclined direction and the electrodes 394-1,3 arranged in Z direction in FIG. 26(*b*), the electrodes 394-5-8 are adhered to the upper surface of the first upper substrate 392 and/or on the lower surface of the first lower substrate, and/or the electrodes 394-1,3 are adhered to the upper surface of the second lower substrate 482 and/or on the lower surface of the third upper substrate 485, in addition the base board can be used. The electrode 394-2, 4 arranged at the same level can change the distance freely comparably.

We can make the octopole electrodes using the method shown in FIG. 25 or the method to form the electrodes 425-2, 3 in FIG. 22(*c*). Namely in all the electrodes in FIG. 26(*a*), we can make the octopole electrodes using the method shown in FIG. 25 or the method to form the electrodes 425-2, 3 in FIG. 22(*c*). Also we can make similarly the arrangements of the octopole electrodes shown in FIG. 26(*b*). For example, the electrodes 394-5-8 in the inclined direction are formed between the second lower electrode 482 and the second upper electrode 483, or between the third lower electrode 486 and the third upper electrode 485, and the position of the electrode may become higher by putting the base board for the electrodes 394-1 and 394-3 arranged in the central portions. Thus all the middle points of the distances from all the electrodes can fit almost.

The hexapole electrodes type mass analysis room can be made using the present invention. For example, we explain using the octopole electrodes shown in FIG. 26(*a*). The electrodes in Y direction of the mass analysis room 396-1 are arranged similar to these, and the electrodes 394-1 and 394-3 in FIG. 26(*a*) are omitted. For other 4 electrodes, 2 electrodes (394-5, 8) are arranged in the upper side in the direction of the central angle 60 degrees, and 2 electrodes (394-6, 7) are arranged in the lower side in the direction of the central angle 60 degrees, to these electrodes (394-2 and 394-4). These electrodes can be arranged on the same circle. Namely they are arranged in the positions where the distance from M is equal. Also These can be arranged on the upper surface of the first upper substrate and on the lower surface of the first lower substrate as shown in FIG. 26(*b*). Well, for the quadrupole electrodes, the adjacent electrodes are arranged so that they make 90 degrees to the central point M and the four electrodes are arranged on the same circle.

<Fan-shaped magnetic field> In the mass analysis device of the present invention, a fan-shaped magnetic field method can be used for a mass analysis chamber (room). FIG. 27 is a schematic diagram showing a fan-type magnetic field type mass analysis chamber having a penetrating (or penetrated) chamber (or room) serving as a mass analysis chamber in which a fan-shaped magnetic field acts on the main substrate of the present invention. FIG. 27(*a*) shows a type of mass analysis device having one ion detection chamber, and FIG. 27(*b*) shows a type of mass analysis device having a plurality of ion detection chambers. The mass analysis chamber 683-2 of the present invention is a penetrating chamber hollowed out in a fan-shape formed in the main substrate 682, and the upper substrate 688 and the lower substrate 689 are attached to the upper and lower sides thereof. (FIG. 27(*c*)) The penetrating chamber (adjacent room) 683-1 which is on the input side of the ion beam 685 that enters the mass analysis chamber 683-2 is, for example, the extraction electrode/acceleration chamber 307 shown in FIG. 19. And the ion beam having the velocity v, accelerated by the accelerating voltage V, enters the mass analysis chamber 683-2 from the adjacent chamber 683-1 through the central hole 690-1 of the substrate sidewall 682-1. An electromagnet 684 is disposed above and/or below the mass analysis chamber 683-2, and a magnetic field B generated by the electromagnet 684 is applied in the directions above and below the mass analysis chamber 683-2, that is, in the direction perpendicular to the substrate surfaces of the main substrate 682, the upper substrate 688, and the lower substrate 689. Because of this magnetic field B, the ions that enter at velocity v draw a circular orbit of (approximately) radius Rθ and pass through the central hole 690-2 of the substrate sidewall 682-2 which is the exit of the mass analysis chamber 683-2 and advance to the adjacent chamber 683-1. In this way, the mass analysis chamber 683-2 has its penetrating chamber hermetically sealed by the upper and lower substrates 688 and 689 and in its lateral direction (the direction of movement of the ion beam) it is sandwiched between the sidewalls (of the main substrate) having the central hole. And in the direction of the side surface of the main substrate 682 (the direction perpendicular to the movement of the ion beam) it is surrounded by the main substrate. However, the upper and lower substrates 688, 689 of the mass analysis chamber 683-2 are each provided with an opening for vacuating, and the the mass analysis chamber 683-2 is set at a predetermined pressure (for example, $10^{-4}$ to $10^{-8}$ torr). Further, it is possible to provide an opening for introducing gas for cleaning such as an inert gas ($N_2$, He, Ar, etc.) for cleaning the inside of the mass analysis chamber 683-2.

The penetrating chamber 683-2, which is a mass analysis chamber, is a cavity having a width (lateral direction) of approximately r1 from the center line thereof, where normally the orbit 685 of the ion beam is taken as the center line. Therefore, as shown in FIGS. 27(*a*) and 27(*b*), the penetrating chamber 683-2 is a fan-shaped cylindrical cavity (a hollow of a width r1 from the center line along the fan shape of the radius Rθ) when seen in a flat plane view. However, the penetrating chamber 683-2 which is the mass analysis chamber, does not necessarily have to be formed as a fan-shaped cavity, but it may be a cavity that is at least larger than the one that includes the fan-shaped cylindrical hollow as given above. Since a magnetic field is applied in the direction perpendicular to the penetrating chamber 683-2, that is, in the direction perpendicular to the substrate surfaces of the main substrate 682, the upper substrate 688 and the lower substrate 689 within the cavity, the ion beam forms almost a circular orbit with a radius Rθ (fan shape: its angle can be selected, for example, from 30° to 180°). For example, if the velocity of ion at the time of incidence is v (m/sec), the mass of ion is m (kg), the number of electric charges of ion is z, and the magnetic field (magnetic flux density) is B {N/(Am)}, and in view of the fact that the centrifugal force and the Lorentz force are in equilibrium in the mass analysis chamber 683-2, and the ion takes a circular orbit of radius Rθ, then $mv^2/R\theta = B \, zev \ldots$ (1).

Assuming that the ion is accelerated with the voltage V (volt) in the acceleration chamber before entering the mass analysis chamber 683-2, then, $zeV = m \, v^2/2 \ldots$ (2) From above (1) and (2), $m/(ze) = B^2 R\theta^2/2 \, V \ldots$ (3) is obtained. (e is the elementary charge, and is about $1.6 \times 10^{-19}$ C (coulomb)).

The ions 685 entering the mass analysis chamber have various masses (m) and charges (ze). And the ions take various orbits R when subjected to a magnetic field force in the mass analysis chamber. (It can be seen from equation (3).) For example, as can be seen from FIG. 27(*b*), in the same magnetic field B and with an acceleration voltage V, the ions with a smaller (m/z) have orbits smaller than Rθ (for example 685-3) and the ions with a larger (m/z) have orbits larger than Rθ (for example 685-2). An adjacent chamber 690-3 of the mass analysis chamber 683-2 is an ion selection chamber, where a substrate sidewall 686 having a central hole 690-3 is arranged. The central hole 690-3 of the substrate sidewall 686 is arranged so that the ion beam advancing along the orbit with the radius Rθ can pass. That is, the orbit of the ion beam that moves along the center orbit by being affected by the magnetic field B passes just through the central hole 690-3. Namely, the ions 685-1 that satisfy the formula (3) pass through the central hole 690-3. Therefore, the substrate sidewall 686 having the central hole 690-3 may be called an ion-selection slit. If the ions do not satisfy the formula (3), those ions, such as those having the orbits such as shown in 685-2 or 685-3 of FIG. 27(*b*) cannot pass through the central hole 690-3. The ions 685-1 that have passed through the central hole 690-3 enter the adjacent chamber 683-4 through the central hole 690-4 of the substrate sidewall 682-3. The adjacent chamber 683-4 is, for example, an ion detection chamber, where the amount of ions selected by the mass analysis chamber 683-2 and the ion selection chamber 683-3 is detected. In this way, the ion selection chamber 690-3 is surrounded by the substrate sidewalls 682-2 and 682-3. Since the ions that cannot pass through the ion selection chamber 683-3 are left behind, it is desirable to provide an opening for vacuating and/or an opening for cleaning on the upper and lower substrates to sufficiently vacuate or appropriately clean the ion selection chamber. Normally, the size of the central hole 690-3 of the ion selection slit is smaller than the size of the central hole 690-2 of the substrate sidewall 682-2. Since the ion selection chamber 683-3 is likely to get more contaminated than any other chamber, it is preferable to surround it with the substrate sidewalls 682-2 and 682-3. However, since the ion selection chamber 683-3 is apt to have a slightly larger size, and if one does not care about the contamination so much, it can be omitted. However, the ion selection slit 686 must be provided. In this way, the mass analysis method using the mass analysis device of fan-shaped magnetic field type as shown in FIG. 27(*a*) detects ions by changing the magnetic field B and the acceleration voltage V.

The mass analysis method of fan-shaped magnetic field type as shown in FIG. 27(*b*), can also detect not only the ions having an orbit of a radius Rθ, but also the ions having other orbits, by providing a plurality of ion detection chambers {683-1-1, 2, 3, . . . }. For example, if the center (the vicinity of the position where the ion beam passes) of the mass detection chamber 683-2 is at a radius Rθ, the distance from the center to the side surfaces of the main substrate is r1 on one side and r 2 on the other in the mass detection chamber 683-2 of FIG. 27(*a*) and given that r1=R1 (constant) and r2=R2 (constant), then supposing that in the mass detection chamber 683-2 of FIG. 27(*b*) r1>R1 and r2>R2 are to be observed, and even if the directions of the ions are being bent by the magnetic field, it is arranged that the ions do not collide with the side surfaces of the main substrate 682 and advance to the ion selection chamber 683-3, which is the chamber adjacent to the mass detection chamber 683-2. Further, the sidewall of the substrate (682-2 in FIG. 27(*a*)), which is the partition wall between the mass detection chamber 683-2 and the ion selection chamber 683-3, is made smaller (that is, the central hole 690-2 is enlarged) or removed. Further, as in the ion selection chamber 683-3, the orbits (for example, 685-2 and 685-3) other than the center orbit 685-1 are spreading as shown in FIG. 27(*b*), the side surfaces of the main substrate 682 are to be widened from each other along the direction of movement of the ion beam so that as much as possible the ion beam does not collide with the side surfaces of the main substrate 682. Further, the substrate sidewall 686, which is the ion selection slit, is also removed, so that as many ions as possible enter the ion detection chamber 683-4. The ion detection chamber 683-4 has a number of individual ion detection chambers 683-4-1, 2, 3, . . . in the direction of the sides of the main substrate 682 (in the direction parallel to the substrate surface of the main substrate 682 and placed in the direction vertical to the movement of the ions (central orbit)).

Various detection methods can be adopted for the ion detection chamber, and in particular all those described in this specification can be used. There are substrate sidewalls 687, each between the individual ion detection chambers 683-4-1, 2, 3, . . . of the ion detection chamber 683-4 so that the individual ion detection chamber does not interfere with each other. Of course, a collector electrode is also independently arranged for each individual ion detection chamber. The each entrance width of the individual ion detection chamber is w1, w2*r*, w2*l*, w3*r*, w3*l*, . . . . Here, w1 is the entrance width of an individual ion detection chamber (683-4-1 in FIG. 27(*b*)) along the ion center orbit 685-1. The w2*r* is the entrance width of the individual ion detection chamber next to the ion detection chamber (683-4-1 in FIG. 27(*b*)), that is, the individual ion detection chamber (FIG. 27(*b*) 683-4-2) arranged for the orbit that is to the outside of the ion center orbit 685-1. w3*r* is the entrance width of the individual ion detection chamber (not shown in FIG. 27(*b*) that is arranged at the orbit that is further to the outside of the ion detection chamber having the entrance width w2*r*. w2*l* is the entrance width of the individual ion detection chamber (683-4-3 in FIG. 27(*b*)) next to the ion detection chamber (683-4-1 in FIG. 27(*b*)) that is arranged at the orbit that is to the inner side of the ion center orbit 685-1. w3*l* is the entrance width of the individual ion detection chamber (not shown in FIG. 27(*b*)) that is arranged at the orbit that is further to the outside of the ion detection chamber having the entrance width w2*l*. Given that the width of the sidewall of the substrate between the individual ion detection chamber is s and the height of the individual ion detection chamber is equal to the thickness of the main substrate 682, then the total height D of the ion detection chamber 683-4 is w1+(w2*r*+W3*r*+ . . . )+(w2*l*+W3*l*+ . . . )+N×s (n is the number of substrate sidewalls 687). If the heights of the individual ion detection chamber is all equal, the number of individual ion detection chambers is n+1, so that the total height D of the ion detection chamber 683-4 is D=(n+1)×w1+n×s. Ions are always counted when they enter any of the individual ion detection chambers, but those that collide with the partition walls 687 are not counted. Ions that collided with the side faces of the outermost and innermost main substrates 682 (and the side faces of the ion selecting chamber, etc.) of the ion detection chamber are also not counted. However, supposing that there areno such ions, the detection-capture ratio of ions is n+1)×w1/D. For example, if w1=500 µm, s=100 µm, and n=20, then D=10500+2000 (µm)=1.25 cm and the capture ratio is 84%.

In the present invention, it can also be easily carried out by the photolithography method and an etching method, to enlarge the cavity of the mass analysis chamber 683-2, which is a chamber of the fan-shaped magnetic field or to gradually enlarge the curved cavity 683-2 in the direction of the movement of the ion beam 685. So, a desired mass analysis chamber 683-2, an ion selecting chamber 683-2, and an ion detection chamber 683-4 can be manufactured. Also, each ion orbit is inclined with respect to the orbit 685-1 of the ion moving in the center orbit. So, if the entrance area of the individual ion detection chamber is made constant, the area for capture would differ. However, in the present invention, the entrance area of the individual ion detection chamber can easily be changed depending on the gradients of the ion orbits. For example, the entrance area of the individual ion detection chamber can be increased as the relevant ion orbits move outward. In addition, it is easy to align the orientation of the individual ion detection chamber with the ion orbit. So, the ingressive area of the ions can be the same in each individual ion detection chamber by making the entrance area of the individual ion detection chambers same, Even in a mass analysis device having a plurality of ion detection chambers as shown in FIG. 27(*b*), the acceleration voltage V and the magnetic field B can be continuously varied to perform more precise measurement.

The fan-shaped magnetic field 684 is arranged in a way that a permanent magnet or an electromagnet is disposed above and/or under the mass analysis chamber 683-2, and the magnetic field is applied in a direction perpendicular to the mass analysis chamber 683-2 (from the top to the bottom, or vice versa). That is, the S pole or the N pole of the magnet is disposed outside the upper substrate or the lower substrate that covers the mass analysis chamber 683-2, and/or the pole of the magnet and the pole of the magnet opposite to the former pole are to be arranged, on the outer sides of the lower substrate and the upper substrate, respectively. For example, when the mass analysis chamber 683-2 is curved in a clockwise direction as shown in FIGS. 27(*a*) and 27(*b*), it is necessary to bend the ion beam 685 in the same clockwise direction. Therefore, when the ion has a positive charge, the S pole is arranged on the upper side and the N pole is arranged on the lower side, so that the magnetic field is directed from the lower side (lower substrate side 689) to the upper side (upper substrate side 688) of the mass analysis chamber 683-2 (Fleming's rule of left hand). The magnet is placed only in a region where a force is exerted on the ions by applying a magnetic field, for example, only in the region of the fan-shaped magnetic field 684 as shown in FIGS. 27(*a*) and 27(*b*).

The electromagnet may be a coil. Or the coil is manufactured within the substrates and the substrates can be mounted on the upper part and/or the lower part of the main substrate 682 that has the mass analysis chamber 683-2 and a cavity (penetrating chamber) through which the ion beam 685 passes. FIG. 27(*c*) is a view showing a cross section along line A1-A2 of the mass analysis chamber 683-2 of FIG. 27(*a*) or FIG. 27(*b*). FIG. 27(*c*) shows a cross section of the mass analysis device having the main analysis substrate 682 having a mass analysis chamber 683-2, where a substrate module 699 (699-1) having a built-in coil is mounted on the upper surface of the upper substrate 688 and/or where a substrate module 669 (699-2) having a built-in coil is mounted on the lower surface of the lower substrate 689.

A coil module 695 is mounted between the upper substrate 693 and the lower substrate 692 of the substrate module with a built-in coil, and electrodes/wirings 697 (697-1, 2) are formed on the outer surface of the upper substrate 693 or the lower substrate 692. An electric current can flow from the electrode/wiring 697 (697-1, 2) to the conductive wiring of the coil 695. A coil built-in substrate 691 is attached to and between the upper substrate 693 and the lower substrate 692, and the coil 695 is mounted in the substrate 691. The conductive wiring of the coil 695 is wound in parallel to the substrate surface of the substrate 691, and the conductive wirings are stacked in the direction perpendicular to the substrate surface. Therefore, when a current is passed from the electrode/wiring 697 (697-1, 2) to the coil 695, the current I within the coil passes in parallel to the substrate surface, so that a magnetic field penetrating the conductive wiring of the coil in the vertical direction, that is, in the axial direction of the coil (a cylinder that is formed by the winding of the coil) is generated. If the number of the windings of the coil is n and the radius of the coil (cylinder) is a, the magnetic field H at the center of the coil is H=nI/(2a) In order to have the magnetic field generated by the coil transmitted to the outside, the materials surrounding the coils 695 such as the upper substrate 693, the lower substrate 692, the coil built-in substrate 691 and the like are a nonmagnetic material. A conductive film wiring 698-1 connected to the lead wire at the end of the coil 695 is formed on the built-in substrate 691 on which the coil 695 is mounted, and the conductive film wiring 698-1 is connected the contact hole 696 (696-1) formed on the upper substrate or the lower substrate, and to the conductive film formed therein. Further, the contact hole 696 (696-1) and the conductive film formed therein are connected to the electrode/wiring 697-1 formed on the upper substrate or the lower substrate. Further, a conductive film wiring 698-2 connected to the lead wire at the other end of the coil 695 is formed on the built-in substrate 691 on which the coil 695 is mounted, and the conductive film wiring 698-2 is connected to the contact holes 696 (696-2) and a conductive film formed in the contact hole 696 (696-2) formed on the upper substrate or the lower substrate. Further, the contact hole 696 (696-2) and the conductive film formed therein are connected to the electrode/wiring 697-2 formed on the upper substrate or the lower electrode.

A method of forming a coil built-in substrate, for example, is the following: after the substrate 691 is attached to the lower substrate 692, a cavity (penetrating chamber) 694 for mounting a coil at a place where the coil 695 is to be mounted. An insulating film is deposited in the cavity 694, the inner surface of the cavity is covered with an insulating film, a conductive film is formed, and conductive film wirings 698 (698-1, 2) are formed in the cavity 694. When the substrate 691 is an insulator, depositing the insulating film in the cavity 694 is not indispensable. Next, the coil 695 is inserted into the cavity, and the terminal of the conductive wiring of the coil 695 is connected to the conductive film wiring 698 (698-1, 2). On the other hand, conductive film wiring 698 (698-1, 2) is formed on one side of the upper substrate 693. Next, the upper substrate 693 is attached to the coil built-in substrate 691 that is attached to the lower substrate 692 and having the cavity 694 formed therein. At this time, the conductive film wirings 698 (698-1, 2) formed in the cavity and the conductive film wirings 698 (698-1, 2) formed on one surface of the upper substrate 693 are connected. Next, a contact hole/conductive film 696 and an electrode/wiring 697 are formed on the upper substrate 693. These may be formed in advance on the upper substrate 693 and then attached to the coil built-in substrate 691. Here, the upper substrate 692 and the lower substrate 693 are usually insulators. If they are semiconductor substrates or conductor substrates, the insulating films, etc., should be formed in advance, so that no electrical current flows between the electrodes and the wirings before forming the conductive films 697, 698, etc., in the contact holes 696, in the cavities 694, and the substrate surface. In this way, manufacturing of a coil 699 surrounded by the substrates 691, 692, and 693 is completed.

A number of coils can be provided in these module substrates 699-1 and 2. However, there are places where it is unnecessary to dispose coils in the mass analysis device, So, the coil 695 is disposed at an appropriate place of the module substrate 699-1 so that the coil 695 is positioned as a desired place when the module substrate 699-1 is mounted on the module substrates (for example, they are formed by the substrates 301, 302, and 303 in FIG. 19, or formed by the substrates 682, 688, and 689 in FIG. 27) of the mass analysis device. In this case, the areas that are not used are also formed on the module substrate 699-1, but the module substrate 699-1 and the module substrate, on which the mass analysis device is formed, can be attached at the same time. So, there is an advantage in that a number of mass analysis device can be formed by a series of processes. To prevent such areas from being formed on the module substrate 699-1 as much as possible, a large number of blocks in which required coils are arranged on the module substrate 699-1 are first produced (for example, in FIG. 27, the fan-shaped part 684 is one block. In fact, it is preferable to produce the block as a smallest unit of a rectangular shape that includes the fan-shaped portion 684 and that can be easily cut out as a block) and then those blocks are separated from each other and each block is fitted into and attached to the module substrate on which mass analysis device was formed. In this case, the thickness of the part to which the coil block is attached increases. This method enables an effective use of the entire module substrate 699 having a built-in coil. Although the coil shown here is described as a coil for which only a conductive wiring is wound in a spiral shape, this is merely to show that it is a coil, and various coils (inductors) can be used. For example, the coil may be of a package-type in which a coil is internally mounted like a chip inductor. The terminal of the electrode of the chip inductor is exposed to the outside. So, when the chip inductor is inserted into the cavity 694 shown in FIG. 27(*c*), it is easy to connect it with the upper substrate, the lower substrate, and the conductive film wiring 698 in the cavity. Alternatively, the chip inductor can be directly attached to the upper substrate 688 that is disposed on the mass analysis device 683-2.

In the case of a chip inductor, various types of chip inductors, such as those of winding type, deposited type, film-type, those having a ferrite core, a nonmagnetic core, a core of high magnetic permeability, a type having nonmagnetic material and the like can be used depending on their characteristics (inductance, Q Value, etc.). A coil of winding type in which the conductive wiring is exposed is durable against the heat that is produced when a large current flows, so a large magnetic field can be generated. In this case, if the coil is directly attached to the upper and lower substrate(s) 688 and/or 689, air cooling and the like can be easily carried out and the heat resistance can be improved. Even with the coil insertion type shown in FIG. 27(*c*), the coils inside the cavity can be cooled by air or liquid through the opening for cooling, Op formed in the upper and lower substrates.

(The lower surface of the lower substrate 692 of) the module substrate 699-1 with a built-in coil is attached to the upper part of the upper substrate 688 of the mass analysis device having the mass analysis chamber 683-2 and the like. That is, the coil 695 is arranged right above the mass analysis chamber 683-2. That is, the coil 695 of the module substrate 699-1 is disposed at the part that generates the fan-shaped magnetic field. Although only one coil is shown in FIG. 27(*c*), a plurality of coils may be arranged in the width direction (lateral direction in FIG. 27(*c*)) and/or in the depth direction (in the direction of the movement of the ions). For example, assuming that the width of the mass analysis chamber 683-2 is d1, the width of the coil 695 is d2 (in the case of a plurality of coils, the width is the total widths of a plurality of coils, that is, if the width of one coil is b, and m pieces of coils are lined in the width direction, then d2=mb (where gaps between the coils are not considered), the relationship of d2 and d1 is arranged to be d2>d1, while the center of d2 is positioned to be nearly at the center of d1. If the coil is arranged only at the upper part of the mass analysis chamber 683-2, the area to which the perpendicular magnetic field extends in the mass analysis chamber 683-2 is narrow. Therefore, also the module substrate 699-2 with a built-in coil is arranged at the lower part of the mass analysis chamber 683-2. The module substrate 699-2, which is the same as the module substrate 699-1, can be reversed and used. That is, (the upper surface of the lower substrate 692 of) the module substrate 699-2 with a built-in coil is attached to the lower substrate 689 of the mass analysis device having the mass analysis chamber 683-2 and the like. That is, the coil 695 is disposed directly under the mass analysis chamber 683-2. These attachments can be performed by means of room-temperature bonding, high-temperature bonding, diffusion bonding, adhesive, or the like. When an adhesive or the like is used, a nonmagnetic material which does not block the magnetic flux generated by the coil is used. Further, when the substrates 688, 689, and 692 are a glass substrate, a quartz substrate, or the like, they can be attached by electrostatic anodic bonding by placing a Si substrate or a conductive substrate between these substrates. When the substrate is attached and it has an opening, it should be reminded that the opening is not blocked (except for the openings which may be blocked). Since the coil 695 is disposed just under or above the fan-shaped magnetic field region 684 of the mass analysis chamber 683-2, the opening that is required of the upper substrate 688 or the lower substrate 689 of the mass analysis chamber 683-2 may be provided outside the the fan-shaped magnetic field region 684. Alternatively, an opening may be provided on the lateral side of the mass analysis chamber 683-2 or the mass analysis chamber may be widened in the lateral direction so that the opening can be formed in the areas of the upper or lower substrate 688 or 689 where no module substrate 699-1 is placed.

By having the polarity of the coil disposed directly above the mass analysis chamber 683-2 and the polarity of the coil disposed directly under the mass analysis chamber 683-2 to be opposite, a perpendicular magnetic field is generated between the coils. That is, in (the area of the fan-shaped magnetic field of) the mass analysis chamber 683-2, a perpendicular magnetic field is generated. Now the approximate magnetic field of the mass analysis chamber 683-2 is calculated. If a current I flows through a circular coil (number of turns is n) of radius a, the magnetic field on the center axis (the distance b from the center of the coil end) is $H=(nI/2) a^2/(a^2+b^2)^{3/2}$. If a=1 mm and b=1 mm, then $H=1.8 \times nI \times 10^2$ [A/m]. If a=5 mm and b=5 mm, then $H=35 \times nI$ [A/m]. Assuming that the radius of the fan is $R\theta=10$ cm, $m=10^{-27}$ kg, $e=1.6\times10^{-19}$ C, then $B2/V=10^{-6}$, $B=4\pi\times10^{-7}\times H$, and the accelerating voltage V=10 volts, then $H=2.5\times10^3$ [A/m]. If the acceleration voltage V=100 V, then $H=10^4$ [A/m]. From the above, assuming that the number of turns of the coil is 50, a=1 mm, and b=1 mm, and if the acceleration voltage V=10 volts, the current flowing through the coil is 0.28 A, (2) if the acceleration voltage V=100 volts, the current flowing through the coil is 1.2 A, and assuming a=5 mm, b=5 mm, and (3) if the acceleration voltage V=10 volts, the current flowing through the coil is 1.4 A, (4) if the acceleration voltage V=100 volts, the current flowing through the coil is 5.8 A. Therefore, a sufficient magnetic field can be generated even in case of a small coil. Since in the above calculation the magnetic field is based on a single coil provided on one side of the mass analysis chamber, and if a total two coils are provided above and below the mass analysis chamber, the current flowing through the coil may be half of the currents as given above. Since a core to be inserted into the coil is not taken into consideration in the above calculations, and if the core that has a large magnetic permeability is inserted into the coil, the current flowing through the coil can further be decreased greatly so that the coil would have a considerable margin allowance.

As shown in FIG. 27(c), assuming that the height of the mass analysis chamber 683-2 is h1 (equal to the thickness of the main substrate 682), the thickness of the upper substrate 688 is h2, the thickness of the lower substrate 692 of the module substrate 699-1 is h3, the height of the cavity 694 is h4 (equal to the thickness of the substrate 691), and the thickness of the upper substrate 693 is h5, then the total thickness of the mass analysis chamber is h1+2 (h 2+h3+h4+h5) (the thickness of the mass analysis chamber on the lower side of the mass analysis chamber is assumed to be the same as that on the upper side). For example, if h1=1 mm, h2=h3=0.2 mm, h4=1 mm, h5=0.2 mm, then the thickness of the entire mass analysis chamber is 4.2 mm. If h1=10 mm, h2=h3=1 mm, h4=10 mm, h5=1 mm, the mass analysis chamber as a whole has a thickness of 36 mm and its height is very small. Since the size of the ion beam is at its highest 10 nm to 1000 nm, the entire mass analysis chamber has a sufficient space even if h1=1 mm, h2=h3=0.2 mm, h4=1 mm, h5=0.2 mm. In the present invention, as a substrate having a sufficiently uniform thickness can be used, and the substrate is attached and patterned in the LSI process, the size such as this of mass analysis chamber is sufficient. Incidentally, d1 and d2 can be set wide. For example, if h1=1 mm, d1 and d2 can be set such as d 1=1 to 10 mm and d 2=1.1 to 11 mm. In the case of a circular coil, a plurality of coils having a diameter of 1 mm and a height of 1 mm to 5 mm are arranged side by side in the magnetic field region. In particular, since the distance along the direction of the movement of the ion beam becomes long, it is necessary to provide many coils. In the case of the present invention, even with such small coils, the electrodes can be arranged outside and the current can flow in each coil individually such that precise current control (i.e., accurate magnetic field control) is possible. For these controls, LSI chip can be used, to which wiring is connected between the LSI chip and each coil. Incidentally, even if the size of the mass analysis chamber becomes large, it is possible to simulate conditions to see whether the ion beam can be controlled as described above. So, it is possible to arrange many small coils side by side, or also the size of the coil is made larger corresponding to the size of the mass analysis chamber.

FIG. 28 is a diagram showing a mass analysis device that detects ions with ion detection devices that are arranged in multiple directions, which ions were subjected to a force in a magnetic field of the mass analysis chamber. This mass analysis device may be a modification of the mass analysis device shown in FIG. 27(b). FIG. 28(a) shows a mass analysis device that has exits in three directions, i.e., both right and left directions, which form a right angle against the direction of the movement of the incident ion beam 685 that entered the mass detection chamber 683, and an upward direction (the same direction as the incident ion beam 685) (A part of) the mass analysis chamber 684 shown on the right-hand side, which shows the ion selection chamber 683-3, and the ion detection chamber 683-4 are the same as those shown in FIG. 27(a). (A part of) the mass analysis chamber 684 shown on the left-hand side, which shows the ion selection chamber 683-5, and the ion detection chamber 683-6 are substantially symmetrical with those of the mass analysis chamber 683-2 shown on the right-hand side. Therefore, the mass analysis chamber 683-2 is wider than the one that has only the part corresponding to the one side (half) of the mass analysis chamber 683-2, as given above, and the part that generates the magnetic field (where the magnetic field is applied) 684 is also wider. In FIG. 28(a) a part that generates the magnetic field has a rectangular shape. And when ions 685 enter the mass analysis chamber from the extraction electrode/acceleration chamber 683-1 and enter the part that generates the magnetic field (where the magnetic field is applied) 684, they are subjected to a force in the vertical direction and are bent and proceed to the ion selection chamber 683-3 on the right-hand side or the ion selection chamber 683-5 on the left-hand side. The ions 685-1 that have proceeded to the ion selection chamber 683-3 on the right-hand side are detected in the ion detection chambers 683-4, And the ions 685-2 that have proceeded to the ion selection chamber 683-5 on the left-hand side are detected in the ion detection chamber 683-6. When the ions 685 that have a plus and a minus charges enter the ion mass analysis chamber, for example, positive ions can be bent to the right side, negative ions can be bent to the left side, and both plus ions and minus ions can be analyzed simultaneously in one magnetic field 684. By scanning the voltage and the magnetic field, it is possible to simultaneously analyze a wide range of plus ions and minus ions. In addition, by alternately using the left and right ion detection chambers 683-4 and 683-6, the cycle time for measurement can be shortened. For example, since the line that was used for measurement (for example, the left-hand side) is apt to be contaminated, contamination may occur when analyzing continues. So, it is preferable to perform a cleaning by purging (vacuating or gas purging) between the operations. If the mass analysis device has two lines, i.e., right and left lines, cleaning by purging can be performed on one line while measuring is carried out on the other. Or, even if the one line is out of operation, measurement can be carried out on the other.

FIG. 28(a) shows a mass analysis device that has another chamber 683-7 that is arranged in the direction of movement of the incident ions 685. This chamber 683-7 is for making mass analysis of the irons by another method, where it allows the ions 685 to enter and move straight without being affected by a magnetic field. For example, the mass analysis device can be provided with a quadrupole mass analysis chamber and an ion trap mass analysis chamber. An acceleration chamber or an acceleration electrode may be provided so as to give to the ions an appropriate speed and guide the ion beam to the quadrupole mass analysis chamber or the ion trap mass analysis chamber. The advantage of this scheme is that the same sample can be measured using different methods. Therefore, more reliable measurement can be performed. In addition, other open spaces can be used to further provide an ion screening and ion detection chambers. For the mass analysis device of the present invention, where a penetrating chamber (cavity) is formed in the main substrate and other substrates are each attached on the upper and lower sides thereof, a large number of ion detection chambers can be manufactured at the same time and in the same process. So, the manufacturing cost is almost the same as that of the mass analysis device that has one detection chamber.

Following this concept, further, FIG. 28(b) gives a mass mass analysis device mass analysis device mass analysis device analysis device of magnetic field type having many ion detection chambers. The mass detection device comprises a mass analysis chamber 683-2 next to the extraction electrode/acceleration chamber 683-1 or in the direction of the movement of the ion beam 685, where the mass analysis chamber 683-2 has a cavity that expands from the exit of the extraction electrode/acceleration chamber 683-1 or the entrance of the mass analysis chamber 683-2 and the expanded cavity surrounds a part or all of the extraction electrode/acceleration chamber 683-1 The maximum angle formed by the line that extends from the side surface (sidewall) 682-*a* of the main substrate 682 of the extraction electrode/acceleration chamber 683-1 (to the mass analysis chamber 683-2) (shown by a one-dot chain line) and the extended space (cavity) in the right side of the mass analysis chamber 683-2 is given as α1. And the maximum angle formed by the line that extends from the side surface (sidewall) 682-*b* of the main substrate 682 of the extraction electrode/acceleration chamber 683-1 (to the mass analysis chamber 683-2) (indicated by a one-dot chain line) and the extended space (cavity) in the left-hand side of the mass analysis chamber 683-2 is given as α2. In FIG. 28(b), both α1, α2=180 degrees. As can be seen from the FIG., either α1 or α2 may be 0. That is, the mass analysis of ions can be performed in either one of the left and right side spaces. But if both are available, there are advantages in that more accurate and reliable measurements can be performed, the cycle time for measurement can be shortened, and the lifetime of the measuring device can be prolonged. In this embodiment, the mass analysis chamber is made up of a single continuous space, and there is no partition (partition walls). However, if, for example, after the ion detection is performed in the space on the right side and then the ion detection is performed in the space on the left side, and consequently when both spaces of the mass analysis chamber are contaminated, the mass analysis chamber and the ion detection chamber can be cleaned at the same time. So, the cycle time can be shortened and the lifetime of the device can be prolonged.

If the mass analysis chamber has the angles, α1 and α2, and even if they are small it can perform mass analysis by a magnetic field. But, in such a case, the number of ion detection chambers is limited and the area that can be swept by the magnetic field is narrowed. So, it is desired that α1 and α2 are 30° or more. Preferably, they are 45 degrees or more, more preferably 90 degrees or more, further, preferably 120 degrees or more, further, preferably 150 degrees or more, or if they are 180 degrees, the mass analysis chamber can best utilize the capacity as expected from the mass analysis chamber of the present invention. There is a substrate sidewall (partition wall) having a central hole 690-1 between the extraction electrode/acceleration chamber 683-1 and the mass analysis chamber 683-2, and the ion beam 685 passes through the central hole 690-1 and enters the mass analysis chamber 683-2. Within the mass analysis chamber 683-2, there is an area that applies the magnetic field 684 and in which area a magnetic field is applied in the vertical direction (upward and downward) of the mass analysis chamber 683-2 (in the direction of the paper-plane of FIG. 28(b)), so that the ion beam 685 that enters is subjected to a Lorentz force, which bends its orbit. That is, the ion beams draws an orbit that has a radius Rθ that satisfies $m/(ze)=B2R\theta 2/2$ V. A large number of ion detection chambers are arranged around the mass analysis chamber 683-2. FIG. 28(b) shows mass analysis chambers, comprising ion detection chambers, each of which has a rectangular shape, 683-4-1-1 to 683-4-1-*n* on the right side, 683-4-2-1 to 683-4-2-*m* on the upper side, 683-4-3-1 to 683-4-3-*p* on the left side and 683-4-4-1 to 683-4-4-*q* on the lower side, and the total number of ion detection chambers are m+n+p+q.

For example, assuming that the size of the mass analysis chamber is 50 mm×50 mm, the width (including the width of 682-*a, b*) of the extraction electrode/acceleration chamber 683-1 is 5 mm, and that the interval of the ion detection chamber (the width of the ion detection chamber+the width of the partition wall 687) is 0.5 mm, then m=n=p=100, q=90, and the total number of ion detection chambers is 390. Even if there are a large number of ion species in the ion beam, each of them enters any of the ion detection chambers, even under in one magnetic field and one accelerating voltage, they can be identified and measured at one time. Furthermore, by scanning the magnetic field and voltage, it is possible to detect ions each time by using a large number of ion detection chambers, so that more accurate and precise analysis can be performed. In FIG. 28(b), the space (outer shape) of the mass analysis chamber is formed in a rectangular shape, but other shapes such as a polygonal shape and a circular shape can be used. Further, if the entrance of the ion detection chamber is arranged to be perpendicular to the orbit of the ions that were bent, the incident conditions will be the same for of many ions. So, more accurate and precise analysis can be performed. Since the angle of inclination that the incident ions forms with regard to the entrance of the ion detection chamber is known, they can also be compared by calculation. Further, although the magnetic field region 684 is formed in a rectangular shape, it may have a circular shape or other shapes. Such a mass analysis chamber, a magnetic field region, and a large number of ion detection chambers can be manufactured at the same time. Moreover, since the LSI process (photolithography, etching, film formation, alignment at the time of attaching the substrate, etc.) is used, it is possible to manufacture a mass analysis device having extremely high accuracy and precision. Therefore, the accuracy of the mass analysis device is remarkably improved as compared with the conventional devices. Furthermore, since the device itself is also very small, the vacuating system can also be made small, and thus the size of the entire mass analysis device can be made extremely small.

If the upper and lower substrates 693 and 692 are insulating substrates such as a glass substrate, a quartz substrate, an alumina ($Al_2O_3$) substrate, aluminum nitride (AlN) substrate, and the like, and the substrate 691 inserted therebetween is a semiconductor substrate such as a silicon substrate, etc., a cavity (penetrating chamber) can be formed. And an insulating film, a conductive film, a protective film, and the like can be formed in the cavity, on the upper and lower part substrates and the like by various methods that were explained at various parts of this specification. Furthermore, a coil can be formed without forming a cavity. For example, if an insulating film and a conductive film are alternately deposited on a silicon substrate or an insulator substrate and if the conductive film wiring is provided in a circular or polygonal shape, thereby forming a coil of multi-winding while connecting with a via, it is possible to manufacture a large number of high-density minute coils (having small inside diameters). The substrate can also be used as the substrate module 699-1. Also, by inserting a ferromagnetic core of high magnetic permeability at the center of the coil, it is possible to manufacture micro-coils capable of generating a strong magnetic field at high density. For example, its details are described in the patent application (JP2012-134329), the inventor of which is the same as that of the present application and they can be applied to the coils of the present invention.

FIG. 29 is another embodiment of the mass analysis device. The mass analysis device of the present embodiment is of a double converging-type and has an electric field sector generating an electric field and a magnetic field sector generating a magnetic field. That is, in the present embodiment, a mass analysis chamber having a fan-shaped electric field chamber 710 and/or a fan-shaped magnetic field chamber 711 is formed as a penetrating chamber in the main substrate 701, and the upper and lower sides thereof are covered with an upper substrate 702 and a lower substrate 703, thereby forming an airtight space. FIG. 29(*a*) is a plan view showing a cross section that is parallel to the substrate surface. In the fan-shaped electric field chamber 710, the penetrating chamber 704 (704-2) has a fan shape, and the conductive films 707 (707-1, 2) are formed on both side surfaces of the fan-shaped substrate. And a voltage is applied between the conductive film electrodes 707 (707-1 and 707-2), whereby the orbit of the ion beam 709 (indicated by a broken line) is bent. The chamber 704-1 next to the penetrating chamber 704-2 of the fan-shaped electric field chamber 710 is, for example, an extraction electrode/acceleration chamber 307 or an ionization chamber 325 as given in FIG. 19, and a partition wall 705-1 (the sidewall of the substrate) having a central hole 712-1 is set up inbetween, and the ion beam 709 passes through the central hole 712-1 and enters the penetrating chamber 704-2 of the fan-shaped electric field chamber 710. FIG. 29(*b*) shows a cross section (indicated by A1-A2) perpendicular to the side surfaces of the main substrate 701 having the two opposing conductive film electrodes 707 (707-1, 2). An upper substrate 702 and a lower substrate 703 are attached to the upper surface and the lower surface of the main substrate 701, and the penetrating chamber 704-2 is provided. The side surface of the penetrating chamber 704-2 is formed by the main substrate 701 and is substantially perpendicular to the upper substrate 702 and the lower substrate 703. Insulating films 713 are formed on both side surfaces of the penetrating chamber 704-2, and a conductive film 707 is deposited on the insulating film 713. The insulating film 713 and the conductive film 707 can be formed by the various methods that are explained in this specification.

For example, after the divided main substrate 701 is attached to the upper substrate 702 or the lower substrate 703, the penetrating chamber 704-2 is formed. At this time, the side surfaces of the penetrating chamber 704-2 are formed to be substantially vertical. An insulating film 713 is formed on the inner surface of the penetrating chamber 704-2, and a conductive film 707 is further deposited thereon. If the main substrate 701 is an insulated substrate, the insulating film 713 is not necessarily formed. But it may be formed to improve the adhesion of the conductive film 707. Since the upper substrate 702 and the lower substrate 703 are usually insulated substrates, the same applies to these substrates. The conductive film 707 is, for example, made from Cu, Al, Au, Ni, Cr, Ti, W, Mo, silicide, conductive PolySi, conductive C, superconductive film, a laminate thereof, or a composite film thereof, and it can be deposited by a CVD method, a PVD method, a plating method, an electroforming method, or a combination thereof. As shown in FIGS. 29(*a*) and 29(*b*), the conductive film 707 on both sides of the side surfaces of the main substrate 701 is removed by etching, but it can also be formed throughout the side of the side surface. Further, it can be formed partially depending on the parts selected of the surface that are divided. In that case, it is arranged that a voltage can be applied to each conductive film electrode so that the each electric field between the parallel-plate electrodes (curved) is controlled by applying each voltage and the orbit of the ion beam can be accurately controlled.

Even if the main substrate 701 is divided and the conductive film 707 is deposited separately on the upper substrate side and the lower substrate side, the conductive film 707 is deposited on the surfaces of the substrate sidewalls 705-1 and 705-2 that isolate the electric field chamber 704-2 and deposited on the lower surface of the upper substrate 702 or the upper surface of the lower substrate 703. So, the conductive films such as those on electrodes 707-1 and 701-2 on the side surface side of the main substrate 701, the wirings 707-3, 4 on the lower surface of the upper substrate 702 that are to connect to the outer electrodes 716 and 717, and the wiring 707-5, 707-6 on the upper surface of the lower substrate 703 that are to connect to the outer electrodes 717 are removed by photolithography and etching. Thereafter, an insulating film for protecting the conductive film wiring is deposited, and the protective film, etc., on the surface that is to contact and to be bonded to the substrate are removed by etching. Then the main substrate 701 on the side of the upper substrate 702 and the main substrate 701 on the side of the lower substrate 703 side are attached (For example, at the position indicated by an alternate long and short dashed line 718). At this time, so as to have the upper and lower conductive films bonded closely, a conductive film is further deposited on the joint part between the conductive films, or the joint part may be alloyed by adding a metal having a low melting point and melting the metal by heat treatment. Alternatively, when upper and lower main substrates 701 are attached using an adhesive (electrically conductive adhesive) in which a conductive material is dispersed, pressure and heat can be applied to connect the upper and lower conductive films. Furthermore, there is also a method of thermal-compression bonding that bonds the parts of these conductive films such as the following: when anodic electrostatic coupling is effected between the upper and lower main substrates 701 by inserting a glass substrate or the like, a conductive film is to be formed in advance not only on the side surfaces of the glass substrate but also on the upper and lower surfaces where the conductive films are connected to each other (in this case, also a metal with a low melting point may be deposited) and the parts where the conductive films are formed are bonded by thermal-compression bonding. Further, there is also a method such as following: after the upper and lower substrates are attached to each other, an opening is formed in the upper substrate 702 or the lower substrate 703, and gas for selective CVD is introduced therefrom, and then a metal such as W is deposited only on the parts of this conductive film. Also, there is a method of introducing a plating solution and depositing a plating metal only on the parts of this conductive film. The opening that is opened may be used for vacuating. The opening is to be sealed with a low-melting-point glass or the like so as not to impair the required vacuum state of the penetrating chamber 704-2. In the present invention, the voltage can be applied by the electrodes 716 (-1, 2) and 717 (-1, 2) formed on the upper and lower substrates to the conductive film electrodes 707 (707-1, 707-2) formed on the side surfaces of the respective main substrates 701. The electric potentials of the upper and lower conductive film electrodes (716 (-1, 2) and 717 (-1, 2) can be made equal even if sufficient connection is not made on the surfaces that are attached. Therefore, the electric fields of the parallel-plate electrodes 707-1 and 707-2 can be made constant.

On the upper substrate 702, a contact hole 714 that is connected to the conductive film wirings 707-3, 4 is formed and a conductive film is formed in the contact hole 714. Further, the outside electrodes 716-1, 2 are formed on the upper surface of the upper substrate 702. Similarly, on the lower substrate 703, a contact hole 715 that is connected to the conductive film wirings 707-5, 4 is formed and a conductive film is formed in the contact hole 715. Further, the outside electrodes 717-1, 2 are formed on the lower surface of the lower substrate 703. As a result, a voltage can be applied from the outer electrode 716-1 or 717-1 to the parallel-plate electrode 707-1 and from the outer electrode 716-2 or 717-2 to the parallel-plate electrode 707-2.

As another manufacturing method, conductive film wirings 707-3, 4, 5, 6 are formed on the upper substrate 702 or the lower substrate 703, while a penetrating chamber 704-2 is formed in advance in the main substrate 701, and further, the insulating film 713 and the conductive films 707-1 and 707-2 are formed. And also the patterning of the conductive films 707-1 and 707-2 are performed. These films may be formed after the main substrate 701 is attached to another substrate. This substrate will be separated later. Alternatively, the main substrate 701 may be formed as divided and separate pieces. Next, the main substrate 701, on which the penetrating chamber 704-2 and the conductive film patterns 707-1 and 707-2 are formed, is fitted to and attached to the upper substrate 702 or the lower substrate 703 on which the conductive film wirings 707-3 to 70-6 are formed. If another substrate is used, this substrate is separated. For example, in this method the substrate may be attached by means of a softening adhesive (can be peeled off at a certain temperature or higher) or a low-melting-point metal or the like. Thereafter, the other substrate (upper substrate 702 or lower substrate 703) is attached. When the main substrate 701 is divided into a plurality of pieces, the main substrates 701 are sequentially attached to each other, and then the upper substrate and the lower substrate are attached to the main substrates at the last moment or when it is required, or the main substrates 701 are sequentially attached to the upper substrate or the lower substrate In that case, a glass substrate or the like may be interposed therebetween, and it is also necessary to form in advance the penetrating chambers and conductive film patterns on a glass substrate or the like In these cases, so as to firmly connect the conductive films in the penetrating chamber of the attached substrate, a process of depositing the conductive films on the connecting parts by plating method or selective CVD method may be included. In this case, the conductive film can be selectively formed without patterning by a photosensitive film or the like. After patterning the conductive film 707, a protective film (insulating film) can be deposited on the conductive film 707. A protective film (insulating film) can be deposited on the electrode/wiring 716 and a window can be opened at a required position.

As described above, the conductive films 707-1 and 707-2 formed on two parallel side faces of the main substrate 701, which is fan-shaped in plan view and formed substantially perpendicular to the upper and lower substrate surfaces in the vertical direction, are parallel-plate electrodes having an interval k in-between. When voltage V is applied between the electrodes 707-1 and 707-2, an electric field of E=V/k is applied between the parallel-plate electrodes. When the ions 709 move to the center part of the parallel-plate electrodes, the ions are subject to the force F=qE by the electric field E, and the its orbit is bent (q is an electric charge of the ion). Since the electric field E is constant, the orbit of the ion is circular. Assuming that the radius of the circular orbit is r, $r=mv^2/(qE)$. m is the mass of the ion, and v is the velocity of the ion. Therefore, the radii r's of the orbits differ depending on the velocity of the ion, mass of the ion, the voltage between the electrodes, and the charge of the ion. After exiting from the parallel-plate electrodes, no force is applied to the ions, so they moves straight. Next to the electric field chamber 704-2, there is an ion sorting chamber 704-3, in which a substrate sidewall 706 having a central hole 712-3 is provided so that the ions that moved along a circular orbit of a radius rθ, which is the center orbit of the electric field chamber 704-2 can pass through.

The electric field chamber 704-2 and the ion sorting chamber 704-3 are separated by a partition of a substrate sidewall 705-2 having a central hole 712-2, and the ions that exited from the electric field chamber 704-2 pass through the central hole 712-2 and enter the ion sorting chamber 704-3. The ions that moved along a circular orbit of a radius rθ, which is the center orbit of the electric field chamber 704-2, pass through the central hole 712-3 of the substrate sidewall 706. That is, the central hole 712-3 of the substrate sidewall 706 is arranged in the direction in which the ions (center-orbital ion 1) having moved along the circular orbit of a radius rθ, which is the center orbit of the electric field chamber 704-2, are to exit from the parallel-plate electrodes. The ions moving along the other orbits cannot pass through the central hole 712-3 of the substrate sidewall 706 but collide with the sidewall of the substrate sidewall 706, the side surface of the main substrate 701, or the upper substrate or the lower substrate. That is, the size of the central hole 712-3 of the substrate sidewall 706 is so adjusted. In the ion sorting chamber 704-3, if the penetrating chamber on the left side of the substrate sidewall 706 is named 704-3-1 and the penetrating chamber on the right side is named 704-3-2, in the penetrating chamber 704-3-1 on the left side there are also ions other than the center-orbital ion 1 but in the penetrating chamber on the right side in 704-3-2 there are only the center-orbital ion 1. (Of course, by an unexpected leak and the different ions may enter in a small amount.) The substrate sidewall 705-2 separating the electric field chamber 704-2 from the ion sorting chamber 704-3 may be omitted, but by providing this substrate sidewall, some amount of the different ions can also be shielded by this substrate sidewall 705-2. In addition, the electric field chamber 704-2 and the ion sorting chamber 704-3 can be vacuated separately and can be cleaned. Also, since the ions 709 move not only in the center orbit, but they also move in a spread-out state having some breadth, some of these ions also draw a circular orbit of radius rθ by a force of the electric field. So, since these ions (broader center-orbital ion 1) are also the same species as the center-orbital ions 1, the central hole 712-3 of the substrate sidewall 706 is arranged so that the broader center-orbital ions 1 also enter the penetrating chamber 704-3-2 on the right side as much as possible. For example, the central hole 712-3 of the substrate sidewall 706 is arranged on a line connecting the center of the center-orbit with a radius r$\theta$ of the parallel-plates with the position of the ions just before the ion 709 spreads out. Further, the parallel-plate electrodes are made to have a fan shape of 90 degrees, and the adjacent chambers 704-1 and 704-3 are arranged so as to be connected to the fan-shaped electrode chamber 704-2. With having such an arrangement, the convergence point (the convergence point (surface) of the electrostatic field) of the broader center orbit ion 1 come to be positioned near the central hole 712-3 of the substrate sidewall 706, so that most of the center-orbital ions 1 can enter the magnetic field chamber 704-4. Further, the size of the central hole 712-2 of the substrate sidewall 705-2 is made larger than the size of the central hole 712-3 of the substrate sidewall 706, so that the center-orbital ions 1 can enter the ion sorting chamber 704-3.

In the above method, it is possible to pass ions (center-orbital ion 1) having a certain narrow range of kinetic energy, thereby increasing resolution. But this slit (central hole) removes most of the other ions. So, the sensitivity of the ion detection becomes inferior. Therefore, a slit (central hole) may be placed at a position slightly deviated from the convergence point (surface) of this electrostatic field so that other ions can also pass through. This can also be done by adjusting the size of the slit (central hole). The sorted ions (center-orbital ions 1) enter the sorting chamber 704-3-2 and then enter the fan-shaped magnetic field chamber 704-4 next to it. Between the fan-shaped magnetic field chamber 704-4 and the sorting chamber 704-3-2, there is a substrate sidewall 705-3 having a central hole 712-4, and the center-orbital ions 1 passes through the central hole 712-4. The substrate sidewall 705-3 may be omitted, but by providing it, it is possible to separately vacuate the sorting chamber 704-3-2 and the fan-shaped magnetic field chamber 704-4 and to set each of them to have predetermined pressures. In order to measure the pressure, openings may be provided in the upper substrate or the lower substrate, and a pressure sensor may be connected. Also, cleaning and purging can be done separately.

A magnetic field device is disposed above and/or below the fan-shaped magnetic field chamber 704-4, and a fan-shaped magnetic field 708 is applied in a direction perpendicular to the substrate surfaces. The magnetic field chamber 704-4 is a penetrating chamber sandwiched between two fan-shaped side surfaces in the lateral direction and sandwiched between the upper substrate 702 and the lower substrate 703 in the vertical direction. A fan-shaped magnetic field here need not necessary have a fan shape, and all that is required is a vertical magnetic field that is uniformly applied to a predetermined region 708 of the fan-shaped magnetic field chamber 704-4. The structure of the fan-shaped magnetic field chamber 704-4 can be the same as that of the single fan-shaped magnetic field chamber shown in FIG. 27. Further, for example, the upper and lower parts of the fan-shaped magnetic field chamber 704-4 may be sandwiched between a C-type electromagnet, an H-type electromagnet, a window-frame-type electromagnet, a cylindrical type electromagnet, a rectangular-column-type electromagnet or the like. In this case, the polarity of the surface of the electromagnet on the side facing the upper part or the lower part of the electromagnet surface of the magnetic field chamber 704-4 and the polarity of the surface of the opposing electromagnet is reversed. As the thickness (the height, the depth in the longitudinal direction, or the distance between the magnetic poles) of the fan-shaped magnetic field chamber 704-4 of the present invention is very small and the variations in the thickness thereof can be made extremely small, such that the force of the electromagnet can be made larger. As a result, the size of the electromagnet can be reduced. Further, the width (width in the lateral direction) of the fan-shaped magnetic field chamber 704-4 can also be made extremely small, and its variations in size can be made extremely small, so that the lateral size of the electromagnet can be reduced.

FIG. 29(*c*) is a cross sectional view of the mass analysis device of FIG. 29(*a*) at B1-B2 where module substrates 699-1 and 699-2 in which coils are mounted are attached to the upper and lower substrates 702 and 703 of the magnetic field chamber 704-4, This position shown is similar to that in FIG. 27(*c*). The polarity of the coil surface of the coil 695 of the module substrate 699-1 on the side of the upper substrate 702 is opposite to the polarity of the coil surface of the coil 695 of the module substrate 699-2 on the side of the lower substrate 703. The polarity can be easily set by changing the winding direction of the coil or the direction in which the current flows. The axes of the coils 695 are disposed so as to be perpendicular to the substrate surfaces of the main substrate 701, the upper substrate 702 and the lower substrate 703. That is, the axes of the coils 695 are arranged so that they are perpendicular to the upper and lower substrates 692 and 693 of the module substrate 699 and the substrate surface of the coil built-in substrate 691. Then, the coil surfaces (the winding surface of the coil wirings) are disposed so as to be parallel to the upper and lower substrates 692 and 693 of the module substrate 699 and the substrate surface of the coil built-in substrate 691. And, the upper and lower substrates 692 and 693 of the module substrate 699 and the substrate surface of the coil built-in substrate 691 are arranged to be parallel to the substrate surfaces of the main substrate 701 having the magnetic field chamber 704-4 and the upper and lower substrates 702, 703. As a result, magnetic fields generated in the upper and lower coils excite a magnetic field in the upward and downward directions, whereby the magnetic field applies force to the ions 709 that pass through the magnetic field chamber 704-4, in a direction perpendicular to the movement of the ions.

The ions 709 that have passed through the central hole 712-4 of the substrate sidewall 705-3 are subjected to a uniform magnetic field in the region of magnetic field application 708 in the magnetic field chamber 704-4 and bent, thereby forming circular orbits. After exiting from the region of magnetic field application 708, the ions 709 move straight. Next to the magnetic field chamber 704-4 is an ion-drift chamber 704-5, and the ions, after exiting from the ion-drift chamber 704-5, enter the ion detection chamber, passing through the central hole of the substrate sidewall, which hole is a collector slit. Between the magnetic field chamber 704-4 and the ion-drift chamber 704-5, there is a substrate sidewall 705-4 having a central hole 712-5, and the ions are sorted to some extent. In the ion-drift chamber 704-5, the ions 709 move rectilinearly and the collector slit is arranged so that the ions are converged by the collector slit. In this way, by placing the electric field chamber and the magnetic field chamber, the electric field region (the region where the parallel-plate electrodes are disposed) and the magnetic field region (the region where the magnetic field is applied) and the various penetrating chambers so that the directions of the velocity dispersion are opposite, and the widths of the velocity dispersion are the same, in the electrostatic field and the magnetic field, the sensitivity and resolution of ion detection can be enhanced. In some cases, the ion-drift chamber 704-5 can also serve as the ion detection chamber. The electric field chamber does not need to have a fan shape of 90 degrees, and the angle of a fan ε can be freely selected. (For example, 30 degrees<ε<150 degrees) Charged particles that exited from the electric field chamber move straight ahead. Likewise, the magnetic field chamber need not necessarily have a fan shape of 90 degrees, and the angle of the fan δ can be freely selected. (For example, 30 degrees<δ<150 degrees) The charged particles that exited from the magnetic field chamber move straight ahead. The angles of the fans ε and δ may be determined so that the mass analysis device of the double converging type can be formed within the substrates. A plurality of electric field chambers and magnetic field chambers can also be provided. As another application, it is possible to manufacture a mass analysis device having only one or a plurality of electric field chambers or a mass analysis device having only one or a plurality of magnetic field chambers. Even if a plurality of electric field chambers and magnetic field chambers are provided, the mass analysis device of the present invention can be manufactured in one process. Also, since it is possible to connect the substrates as was explained regarding the accelerator, a mass analysis device of large size can be manufactured.

FIG. 30 is a view showing a design guideline of a magnetic field analyzer of single converging fan-type. and a magnetic field analyzer of double converging fan-type. Although these guidelines are derived from general guidelines, these design guidelines can also be applied to an analyzer using the substrate of the present invention. FIG. 30($a$) is a diagram showing design guidelines of a magnetic field analyzer of single converging fan type. The main substrate comprises an ionization chamber 722-1, an ion-drift chamber A 722-2, a magnetic field analyzer chamber 722-3, an ion-drift chamber B 722-4, and an ion detection chamber 722-5. The ionization chamber 722-1 and the ion-drift chamber A 722-2 are separated by a partition of a substrate sidewall 721-1 having a central hole 723-1, and ions generated in the ionization chamber 722-1 spread out through the central hole 723-1 of the substrate sidewall 721-1 and move forward. When the substrate sidewall 721-1 also serves as an extraction electrode, the ions move by being accelerated by the electrode. Thereafter, the ions can be accelerated by the sidewall of the substrate having the central hole. If the position of the central hole 723-1 of the substrate sidewall 721-1 which is the starting point of the spreading-out of the ions is taken as P1, various ions are accelerated and spread out from this point. Even the ions with the same mass-to-charge ratio, m/z, move forward at various angles: for example, the ions 725-1 moving in the center, the ions 725-2 moving bulging outwardly (indicated by a dotted line), the ion 725-3 moving inwardly, and the like. The ion-drift chamber A 722-2 is an area in which accelerated ions move straight forward. The ion-drift chamber A 722-2 and the magnetic field analyzer chamber 722-3 are separated by a partition of the substrate sidewall 721-2 having the central hole 723-2, and vacuating, cleaning and purging can be performed individually. Since the ions exiting from the central hole 723-1 of the substrate sidewall 721-1 are spread out, the size of the central hole 723-2 of the substrate sidewall 721-2 is made larger than the size of the central hole 723-1 of the substrate sidewall 721-1 to facilitate the passage of ions. In some cases, the substrate sidewall 721-2 may be omitted.

In the magnetic field analyzer chamber 722-3, there is a magnetic field region 724, where a vertical magnetic field is applied. So, when the ions enter this region, they move in a circular orbit. If the radius of the circular orbit of the predetermined ion 725-1 is Rθ, the ions 725-2 and 725-3 having the same m/z and having spread out enter the magnetic field region 724 also move in the circular orbit having a radius Rθ. After exiting from the magnetic field region 724, the ions move straight and enter the adjacent ion-drift chamber B 722-4. The magnetic field analyzer chamber 722-3 and the ion-drift chamber B 722-4 are separated by a partition of a substrate sidewall 721-3 having a central hole 723-3. The central hole 723-3 has the size so as also to have the ions 725-2 and 725-3 that have spread out pass through. The spread-out ions 725-1, 2, 3 having the same m/z converge at the convergence point P 3. If the substrate sidewall 721-4 having the central hole 723-4 is arranged at the convergence point P3, only the spread-out ions 725-1, 2, 3 having the same m/z can pass through. The other ions collide with the walls of the substrate sidewall 721-4, the side surface of the main substrate 721, the upper substrate and the lower substrate. Therefore, since the ion-drift chamber B 722-4 becomes contaminated, it is desirable to perform vacuating and also cleaning and purging as appropriate. For this purpose, openings are provided in the upper substrate and the lower substrate of the ion-drift chamber B 722-4, and the vacuating, cleaning and purging are performed through the openings.

If the contamination of the ion-drift chamber B 722-4 is not a serious problem, the substrate sidewall 7213 can also be omitted. Next to the ion-drift chamber B722-4 is an ion detection chamber 722-5, and the ion-drift chamber B722-4 and the ion detection chamber 722-5 are separated by a partition of a substrate sidewall 721-5 having a central hole 723-5. But the ions passing through the convergence point P3 spread out again, so it is necessary to adjust the size of the central hole 723-5 so as not to block the movement of those ions. In some cases, while the substrate sidewall 721-5 is eliminated, an ion detection chamber may be disposed immediately after the substrate sidewall 721-4 that is disposed near the convergence point P3. The substrate sidewall 721-4 may be referred to as a collector slit. If the center point of of the circular orbit having a radius Rθ of the center-orbital ion 725-1 passing through near the center of the magnetic field analyzer chamber 722-3 in the magnetic field region 724 is set as P2, the P1 that is a point where the spreading of the ions starts, P2, and the convergence point P3 are on a straight line (on line m), it is only necessary to arrange each penetrating chamber to satisfy the relationship. Also, the fan-shaped magnetic field region 724 is arranged so as to have a center angle α around P2. Although a can be any angle from 30° to 180°, a is set to 90° in FIG. 30. At this time, the ion-drift chamber A and the ion-drift chamber B are positioned to form an angle of 90 degrees. In the fan-shaped magnetic field region 724, the ions draw a circular orbit, and as described above, each chamber may be designed so as to satisfy an equation, $mv^2/R\theta = Bzev$, where $\frac{1}{2}mv^2 = zeV$ (V is the acceleration voltage). As described above, the width of each chamber can be 100 μm to 1 mm to 20 mm, or more. Also, the height of each chamber is determined by the thickness of the main substrate and can be 100 μm to 1 mm to 20 mm, or more. The thickness of the sidewall of the substrate can be 10 μm to 100 μm to 1 mm or more. The size of the central hole can also be from 10 μm to 100 μm to 1 mm to 10 mm, or more. The length of each chamber may be determined according to the velocity of the ions. If a Si wafer is used as the main substrate, the maximum size of the Si wafer is currently 450 mm in a single crystal. But in the present invention polycrystalline Si and amorphous Si can also be used. So, as a Si wafer, a wafer of 1000 mm square can also be used and the other structure can be formed in conformity with the sizes. Further, since the mass analysis device of the present invention can be manufactured by bonding the components in the longitudinal direction, a device having a desired thickness can be manufactured. But a mass analysis device of a large size can be manufactured by using a technique of bonding in the lateral direction. For example, each chamber is manufactured separately and can be connected in the lateral direction. Furthermore, as it is possible to divide a chamber and connect each of them. So, it is possible to manufacture a large mass analysis device of a desired size.

FIG. 30(b) is a diagram showing design guidelines for magnetic field analyzer of double converging fan-type having an electrostatic field analyzer and a magnetic field analyzer. In this magnetic field analyzer of double converging fan type, also the region formed in the main substrate 731, through which region the ion beam passes, are penetrating chambers formed in the main substrate 731. For these penetrating chambers, at the upper part of the penetrating chamber the upper substrate is attached to, and at the lower part of the penetrating chamber the lower substrate is attached to, the main substrate. And each penetrating chamber is vacuated through the openings provided in the upper substrate and/or the lower substrate, and the pressure is set at the predetermined level. Each penetrating chamber is separated by a partition wall of the substrate having a central hole, and the ion beam passes through the central hole of the partition wall of the substrate and enters each penetrating chamber. The mass analysis device shown in FIG. 30(b) comprises an ionization chamber 732-1 that includes an ion source, an ion-drift chamber A 732-2, an electrostatic field analyzer chamber 732-3, an ion-drift chamber B 732-4, a magnetic field analyzer chamber 732-5, an ion-drift chamber C 732-6, an ion detection chamber 732-7. Between these penetrating chambers, a substrate partition wall 731-1 having a central hole 733-1, a substrate partition 731-2 having a central hole 733-2, a substrate partition wall 731-3 having a central hole 733-3, a substrate partition wall 731-4 having a central hole 733-4, a substrate partition wall 731-5 having a central hole 733-5, a substrate partition 731-6 having a central hole 733-6, and a substrate partition 731-7 having a central hole 733-7 are arranged to separate the penetrating chambers. Ions are generated in the ionization chamber 732-1 and accelerated and spread out from the central hole 733-1 of the substrate sidewall 731-1 that also serves as an acceleration electrode. Although the ions are converged at the starting point P1, they spread out in the ion-drift chamber A 732-2 and enter the electrostatic field analyzer chamber 732-3 through the central hole 733-2 of the substrate sidewall 731-2. In the electrostatic field analyzer chamber 732-3, the ions move in a circular motion owing to the electric field of the parallel-plate electrodes 734-1 and 734-2 of a fan-shape having a radius rθ, which are formed on the parallel side surfaces of the penetrating chamber. The equation of the motion is $mv^2/r=zeE$. ($mv^2/r\theta=zeE$ for the ions passing through the center).) The ions exiting from the central hole 733-1 at the starting point P1 move forward in an expanded breadth and take circular orbits in the electrostatic field analyzer chamber according to the respective kinetic energies. The ions having the same kinetic energy take the circular orbit of the same radius. The ions whose orbits were bent in the electrostatic field analyzer chamber 732-3 pass through the central hole 733-3 of the substrate sidewall 731-3 and enter the adjacent ion-drift chamber B 732-4.

The ions having the same kinetic energy as that of the ions 736-1 passing through the center converge to a point P3, which is the intersection of the line m that connects P1 with P2 and the orbit of the ions 736-1 passing through the center. Here P2 is the center of the curvature formed by the parallel-plate electrodes. If a convergence slit is provided at this convergence point P3 so that only the converged ions pass through it, the resolution can be increased but the ions having the same m/z (736-4, 5) will also be removed. Then the ion-detection sensitivity decreases. For example, if the central hole 733-4 of the substrate sidewall 731-4 is narrowed and disposed at the convergence point P3, the outspread ions 736-4 and 736-5 are also removed.

Therefore, by moving the position of the substrate sidewall 731-4 that is in the ion-drift chamber B 732-4 to the rear side of the point P3 and also by widening the central hole 733-4, the outspread ions 736-4 and 736-5 and converged ions 736-1, 2, 3 can pass. If the substrate sidewall is provided, vacuating, purging and cleaning can be performed independently. But it can be omitted if it were to be used for passing the ions. The outspread ions 736-1 to 736-5 enter the magnetic field analyzer chamber through the central hole 733-5 of the substrate sidewall 731-5 and move in a circular motion by the Lorentz force of the magnet in the magnetic field region 735. Assuming that the orbital radius of a center orbit of the circularly moving ions is Rθ, then $mv^2/R\theta=zevB$. The ions 736-1 to 736-5 having the same m/z and the expanded breadth draw a circular orbit of the same radius Rθ and converge at the convergence point P4 when they exit from the magnetic field region 735. If the substrate sidewall 731-7 having the central hole 733-7 which serves as a collector slit is disposed at the convergence point P4, the ions passing through the central hole 733-7 will be ions having the same m/z. A chamber 732-6 next to the magnetic field analyzer chamber 732-5 is an ion-drift chamber C, and the ions move at a constant speed to a convergence point of ions that have a specific m/z. The ions that have not passed through the central hole 733-7, which is the collector slit, collide with the wall of the substrate sidewall 731-7, the side surface of the main substrate 731, and the like. Gas, powder, and the like generated by these are discharged by a vacuum drawing line in the ion-drift chamber C, or discharged to the outside by cleaning or purging. The ions that have passed through the central hole 733-7, which is the collector slit, enter the ion detection chamber 732-7 and are measured by the ion detector.

The central angle α of the parallel-plate-type electrode of a fan shape can usually be designed easily if the angle is set to 90 degrees. That is, the ion-drift chamber A 732-2 and the ion-drift chamber B 732-4 may be designed to have an angle of 90 degrees. However, the angle is not limited to 90 degrees, and a can be set within the angles of 30 degrees to 120 degrees. Further, the center angle β of the fan-shaped magnetic field region 735 may also be designed in the range of 30 degrees to 180 degrees. Although in the present invention various sizes and shapes can be easily manufactured by a mask projection, the manufacturing depends on the size of the main substrate, so that an optimum layout may be arranged. Since the size of the ion detection chamber 732-7 can be freely designed, it is also possible to arrange a plurality of ion detectors (array detector etc.). This magnetic field analyzer of double converging fan-type is a one having an electric field before the magnetic field (Nier-Jhonson type). But opposite to this, a type having a magnetic field before the electric field may be used. Alternatively, also to arrange two magnetic fields side by side can easily be carried out. Moreover, since it can be manufactured together, there is almost no increase in cost. Furthermore, it can freely be combined with a quadrupole analyzer, ion trap-type, time of flight (TOF)-type and FTICR (Fourier transform-ion cyclotron resonance-type).

The present invention is also applicable to FTICR (Fourier transform-ion cyclotron resonance). FIG. 31 is a diagram showing FTICR of the present invention. FIG. 31(a) is a cross-sectional view of the FTICR in the direction of the movement of the ion which is a direction perpendicular to the substrate surface (magnetic field direction). FIG. 31(b) is a sectional view of the FTICR in the direction perpendicular to the movement of the ions that is perpendicular to the substrate surface (magnetic field direction). An ion source chamber 754-1 and an ICR chamber 754-2 are formed in the main substrate 751. The upper substrate 752 and the lower substrate 753 are attached to the main substrate 751 at the upper and lower parts of these penetrating chambers, respectively. There is a substrate sidewall 751-1 having a central hole 765 between the ion source chamber 754-1 and the ICR chamber 754-2, and the ions 750-1 generated in the ionization chamber are introduced into an ICR (ion cyclotron resonance) chamber 754-2 through the central hole 765 of the substrate sidewall 751-1 serving also as extraction electrodes. The ICR chamber 754-2 is surrounded in the direction of the movement of the ions by the substrate sidewall 751-1 (having the central hole 765) and the side surface 751-2 of the main substrate opposed thereto, and the ICR chamber 754-2, on the the side surface, is surrounded by the substrate sidewall 751-4 (a closed side without a central hole or the like) and a substrate sidewall 751-5 (a closed side without a central hole etc.) of the main substrate 751, and surrounded on the upper and lower sides by the upper substrate 752 and the lower substrate 753.

In the ICR chamber 754-2, opposing trap electrodes A 755-1, -3 (conductive films 755-1, -3 formed on the substrate sidewall 751-1) and a trap electrode B 756-1 (conductive films 756-1 formed on the substrate sidewall 751-2), an opposing ion excitation electrode A 758 formed on the upper substrate 752) and an ion excitation electrode B 757 (a electrode 757 formed on the lower substrate 753), a receiver electrode A 756-2 (a conductive film 756-2 formed on the substrate sidewall 751-4), a receiver electrode B 756-3 (a conductive film 756-3 formed on the substrate sidewall 751-5) are formed. The side surfaces 751-2, 4, 5, and the sidewall 751-1, of the main substrate are the side surfaces of the main substrate 751 which surfaces are substantially perpendicular to the substrate surface of the main substrate 751, the substrate surface of the upper substrate 752, and the substrate surface of the lower substrate 753. Accordingly, the opposing trap electrodes A and B, the opposing receiver electrodes A and B, and the opposing ion excitation electrodes A and B are parallel-plate electrodes, respectively. The conductive film electrodes are connected, through the internal wirings 759 (759-1, 2) and 764 (764-1, 2) or directly, to the outer electrodes 762 (762-1, 2, 3) and 763 (763-1, 2, 3) whereby it is possible to apply a voltage from outside, or to detect the current and the voltage generated internally.

The ions 750-1 that entered from the ion source chamber 754-1 through the central hole 765 of the substrate sidewall 751-1 move from the trapping electrodes A 755-1, 3 to the trapping electrode B 756-1 by the DC voltage applied between the opposing trapping electrodes A and B, The magnetic field B is applied in a direction perpendicular to the trapping electrodes A and B and also the high frequency voltage (frequency ω) applied between the opposing ion excitation electrode A 758 and the ion excitation electrode B 757 cause the ions 750-1 to perform a cyclotron motion in an ICR chamber 754-2 and to form a coherent ion population. At this time, ω=k×(ze B/m). By this ion cyclotron (ICR) motion, an induced current is generated between the receiver electrode A 756-2 and the receiver electrode B 756-3 for detecting the amount of ions. The frequency of each component of the induced current is the same as the frequency w of the ICR. That is, it relates to the mass m of the ion. The induced current is detected as a signal corresponding to time, and then the signal is amplified, digitized, Fourier transformed, and converted into a spectrum corresponding to the frequency. Since the FTICR of the present invention is very small, the external magnetic field B can be small and the electromagnet can also be small. Furthermore, even if a superconducting magnet is used, its size is small so that the volume to be cooled to an extremely low temperature can be reduced. It can also be easily placed inside the coil of a small size.

Next, the process of the mass analysis device of FTICR-type shown in FIG. 31 will be described. The main substrate 751A is divided and a central hole 765 is formed by photolithography and etching. Next, a window is opened at the portions of in the main substrate 751 to form penetrated rooms (chambers) 754 (754-1, 2). These penetrated rooms 754 (754-1, 2) are vertically etched using the Bosch method, the DRIE method, or the like. If the main substrate 751 is a semiconductor substrate such as a Si substrate or a conductor substrate, so as to prevent short-circuit, an insulating film (not shown) is formed on the peripheral surface of the substrate sidewall 751-1, the side surface (751-2, 3, 4, 5) of the main substrate 751. And then after forming the insulating film, the conductive films 755 and 756 are deposited and predetermined patterning is performed to form conductive film electrodes/wirings 755-1, 756-1, 2, 3, and the like. The photosensitive film can be formed by attaching a photosensitive sheet, or coating method, or electrodeposition method, and exposure can be performed by oblique exposure method, oblique rotation exposure method, exposure method with focus of large depth, or the like. The conductive film can be patterned by wet etching or dry etching. Conductive film electrode patterns 758, 759 (759-1, 2), etc. are in advance formed on the upper substrate 752, and conductive film electrode patterns 757, 764 (764-1, 2) etc. are in advance formed on the lower substrate 753 and then the main substrates 751 that were divided are attached to the upper substrate 752 and the lower substrate 753. At this time, since the conductive film pattern and the penetrated room 754 are formed in the main substrate 751, the patterns of the upper substrate 752 and the lower substrate 753 are matched to these patterns. It can be attached using an adhesive, or diffusion bonding, high temperature bonding or room temperature bonding can also be used. If the main substrate 751 is a semiconductor substrate such as Si substrate, or a conductive substrate, and the upper and lower substrates are a glass substrate, a quartz substrate, a sapphire, an alumina substrate, or the like, electrostatic anodic bonding can be used Next, in order to ensure the connection between the conductive film patterns on the upper substrate and the lower substrate and the conductive film patterns on the main substrate side, disposition of the conductive films is performed thereafter, and then patterning may be performed again to form a conductive film on the connection parts. Or a conductive film may be deposited only on the conductive film pattern using a selective conductive film forming method such as a plating method or a selective CVD method, etc. In this case, a second patterning is unnecessary. After forming the conductive film patterns, an insulating film can be formed as a protective film. Next, the divided main substrates 751 are attached to each other. In particular, the substrate sidewalls 751-1, 3, and 751-2, 4, 5, as parts to be aligned, are aligned to the penetrated rooms 754 (754-1, 2). The above-mentioned method can also be used for the attachment. If the main substrate 751 is a semiconductor substrate such as a Si substrate, etc., or a conductive substrate, electrostatic anodic bonding can also be used if a glass substrate or the like is interposed therebetween.

At this time, also a penetrated room, etc., is also formed in advance for a glass substrate or the like to be sandwiched therebetween and the glass substrate is attached while aligning the patterns to each other. By repeating this process several times, a penetrated room having a predetermined depth (height) can be formed. Thereafter, contact holes 760 and 761 are formed in the upper substrate 752 and the lower substrate 753, and conductive films are deposited in the contact holes (plating method, CVD method, PVD method, selective CVD method, coating method of conductive film paste, or the like). Next, electrodes/wirings 762 (762-1, 2, 3, etc.), 763 (763-1, 2, 3, etc.) are formed in the contact holes 760, 761 and at the predetermined parts of the upper substrate 752 and the lower substrate 753. Thereafter, a protective film or the like may be formed and a window may be opened. As a result, the electrodes 762-1 and 763-2 are connected to the trap electrodes 755 and 756-1, the electrodes 762-2 and 763-1 are connected to the ion excitation electrodes 758 and 757, and the electrodes 762-3 and 763-3 are connected to the receiver electrodes 756-2 and 756-3. It is to be noted that the magnetic field B is applied perpendicularly to the trapping electrodes 755, 756-1, and also the ion excitation electrodes 758, 757 and the receiver electrodes 756-2, 756-3 can be exchanged for each other.

In the above process, forming the central hole 765 and forming the penetrated room 754 in the main substrate 751 are described as if they are formed independently by the main substrate. Particularly, about forming the penetrated room 754 and the conductive film, as it is not necessary to consider the base substrate, the etching is easy (over-etching and depositing on the base need not be considered). However, it is also possible to deposit the base substrate on the main substrate 751 and then to perform forming central holes, penetrated rooms, film deposition and patterning. In this case, the base substrate is removed after attaching the upper substrate or the lower substrate. Similarly, it is also possible to perform forming central holes, penetrated rooms, film depositing and patterning after attaching the upper substrate or the lower substrate to the main substrate 751. In this case, it is not necessary to remove the upper substrate or the lower substrate. Further, without forming the conductive film electrodes/wiring patterns 757, 758, 759, 764, which otherwise are to be formed in advance on the upper substrate and the lower substrate, the upper substrate and the lower substrate are attached to the main substrate, and thereafter penetrated rooms, are formed and an insulating film and a conductive film are formed. Since this conductive film can also be formed on the upper substrate and the lower substrate, it is possible to use this as the conductive film electrode/wiring patterns 757, 758, 759, and 764. Alternatively, a concave portion is formed in the parts of the main substrate where the conductive film electrode/wiring patterns 757, 758, 759, 764 are to be arranged using the main substrate alone, and thereafter the upper substrate and the lower substrate are attached to the main substrate, on which concave portion the conductive film electrode/wiring patterns 757, 758, 759, 764 are formed, and then the penetrated rooms, the insulating film, and the conductive film can be formed. In this case, the connection with the conductive film electrodes/wiring patterns 757, 758, 759, and 764 of the upper substrate and the lower substrate is performed when the conductive film on the main substrate side is formed. The method such as a method of forming the conductive film electrode/wiring patterns 757, 758, 759, 764 on the upper substrate and the lower substrate in advance enables to form a thick and strong film of conductive film electrodes/wiring patterns 757, 758, 759, so that it enhances the reliability of the ion excitation electrode to which the high frequency voltage is applied.

FIG. 32 is a diagram showing a structure where the ICR chamber is enlarged. This can also be applied to enlarging the size of various penetrating chambers of other mass analysis devices. The substrate sidewalls (partition walls) 751-1 and the like having the penetrating chambers 754-1 and 754-2 and a central hole 765 (765-1), are formed on the first main substrate 751. The upper substrate 752 on the upper surface of the penetrating chamber 754-2 serving as the ICR chamber and the lower substrate 753 on the lower side, are removed. This removal may be carried out by hollowing them out before attaching the upper substrate 752 or the lower substrate 753 to the main substrate 751, or they may be hollowed out after attachment. It is preferable to vertically etch the portions of the upper substrate 752 and the lower substrate 753 which correspond to the ICR chambers. Further, conductive films 767 (767-1, 2, 3, 4) and 768 (768-1, 2, 3, 4) are deposited on the side surfaces of the portions where the upper substrate 752 and the lower substrate 753 are hollowed out. If these are a semiconductor substrate or a conductive film, an insulating film is formed to prevent a short circuit, and then a conductive film is formed. If a conductive film is also formed on the surfaces of the upper substrate 752 and the lower substrate 753, it is desirable to form the conductive film only on the side surfaces of the portions where the conductive film is removed by using the photolithography method and the etching method and that are hollowed out.

If the upper substrate 752 and the lower substrate 753 are attached to the main substrate 751 and then the upper substrate 752 and the lower substrate 753 are hollowed out, and after forming the penetrated room 754 of the main substrate 751, the penetrated room 754 can be used as a mask (window) for etching the upper substrate 752 and the lower substrate 753. Thereafter, an insulating film and a conductive film are formed and necessary patterning is performed, so that the patterns for the conductive films 767 (767-1, 2, 3, 4) and 768 (768-1, 2, 3, 4) can be formed on side surfaces of the portions where the upper substrate 752 and the lower substrate 753 are hollowed out. At this time, a conductive film is also formed on the side surface around the penetrated room 754-2 of the main substrate 751. If necessary, the conductive film may be formed thick particularly at the connection parts by using a plating method or a selective CVD method. Thereafter, sequentially, the second lower substrate 773 is attached to the first upper substrate 752, the second lower substrate 773 under it is etched away through the hollowed-out portion, and the second main substrate 771 is attached, Then the second main substrate 771 lying under it is etched away from the hollowed-out portion to form a penetrating chamber 779, and a conductive film 774 (774-1, 2, 3, 4) is further formed on the side surface of the penetrating chamber. Next, a second upper substrate 772 on which patterns of the conductive film 776 (776-1, 2, 3, 4, 5) have already been formed is attached and, if necessary, the conductive film is formed on the connection parts of the conductive film by a plating method, by CVD method or the like, to strengthen the connection. Thereafter, a protective film may be placed on the conductive film within the penetrating chamber. Also, a contact hole 777 is formed in the second upper substrate, and a conductive film is formed in the contact hole 777, and further, a conductive film electrode/wiring pattern 778 (778-1, 2, 3, 5) are further formed. The second upper substrate 772 is attached before the conductive film is deposited on the inner surfaces of the penetrating chamber 779 of the second main substrate 771 and then after the conductive film is deposited, the conductive film pattern 774 (774-1, 2, 3, 4) and the conductive film pattern 776 (776-1, 2, 3, 4, 5) may be formed.

Also, about the side of the divided main substrate 751, attachments and film formation and pattern formation are sequentially performed by the same process, where a lower ICR chamber is formed by a process of attaching the third upper substrate 782, the subsequent hollowing-out etching of the upper substrate 782, further attaching the third main substrate 781, forming a penetrating chamber 789, the subsequent film formation and pattern formation, attaching a third lower substrate 783, the subsequent film formation, patterning, and the like. By attaching these two ICRs, that is, upper ICR and lower ICR, the FT-ICR mass analysis device shown in FIG. 31 can be manufactured.

In the above process, the substrates are sequentially attached. But it is possible to prepare a penetrating chamber separately for each substrate and then attach them to each other. That is, a penetrating chamber 779 is formed in the second main substrate 771, the second lower substrate 773 is attached to the second main substrate 771, and the second lower substrate 773 is hollowed out. And also the second upper substrate 772 is attached to them. The conductive film 774 (774-1, 2, 3, 4), the conductive film 775 (775-1, 2, 3, 4), and the conductive film 776 (776-1, 2, 3, 4) are formed. This method of forming is the same as the method performed regarding the first main substrate 751, the first upper substrate 752, and the first lower substrate 753. It should be noted that the contact hole 777 of the second upper substrate 772, the conductive film within the contact hole 777, and the electrode/wiring pattern 778 (778-1, 2, 3, 4, 5) are to be formed in advance, and the second upper substrate 772 may be attached to the second main substrate 771. The upper substrate (first upper substrate) 752 on the upper side of the first main substrate (or its divided upper side) having the penetrating chamber 754 hollowed out and the conductive film pattern formed on the inner surface thereof is attached to the second lower substrate 773 of the second main substrate 771 that has similarly a penetrating chamber 779 hollowed out. For attaching, an adhesive, a room temperature bonding method, a diffusion bonding method, a high temperature bonding method, or the like can be used. If the first upper substrate 752 is an insulator substrate such as a glass substrate or quartz and the second lower substrate 773 is a semiconductor substrate such as a Si substrate, etc., or a conductive substrate, it can be attached by electrostatic anodic bonding. Alternatively, if the second main substrate 771 is a semiconductor substrate such as a Si substrate or a conductive substrate, the second main substrate 771 is attached to the first upper substrate 752 by electrostatic anodic bonding without using the second lower substrate 773. When a protective film is used, the protective film on the part of the conductive film to be connected is removed. Besides increasing the contact area by increasing the size of the connection region or by having the conductive film be thick, for example, at the connection part between the conductive film 767 and the conductive film 775, depositing a conductive film by a plating method or the selective CVD method, or patterning conductive films can be performed. Further, there is a method such as a one of bonding by fusion of heat treating near the melting point, depositing a low melting point alloy (solder etc.) by a plating method, a selective CVD method, or depositing a low melting point alloy (solder etc.) and patterning again the patterned parts of the conductive films and attaching the low melting point alloy, and conducting heat treatment to assist the bonding between the conductive films with a low melting point alloy.

Similarly, a penetrating chamber 789 is formed in the third main substrate 781, the third upper substrate 782 is attached to the third main substrate 781, and the third upper substrate 782 is hollowed out. Also, the third lower substrate 783 is attached to them. A conductive film 784 (784-1, 2, 3, 4), a conductive film 785 (785-1, 2, 3, 4), and a conductive film 786 (786-1) are also formed. This forming method is the same as the method performed regarding the first main substrate 751, the first upper substrate 752, and the first lower substrate 753. By the way, the contact hole 787 of the third lower substrate 783, the conductive film within the hole, and the electrode/wiring pattern 788 (788-1) are formed in advance, and the third lower substrate 783 may be attached to the third main substrate 781. The lower substrate (first lower substrate) 753 on the lower side of the first main substrate (or its divided lower side) having such a penetrating chamber 754 hollowed out and having the conductive film pattern formed on the inner surface thereof is attached to the third upper substrate 782 of the third main substrate 781 having similarly a penetrating chamber 754 hollowed out. The same method of attaching is applied and so is the method of connection between the conductive films. In addition, both the conductive adhesive and the insulating adhesive can also be used, where the conductive adhesive is used for connecting the parts of the conductive films and the insulating adhesive is used for connecting the other parts. They can be treated for patterning and attached separately. Alternatively, a low melting point alloy or the like may be used to bond the parts where the conductive film is connected, and an insulating adhesive may be used to bond the other parts. Alternatively, a conductive adhesive or a low melting point solder alloy may be attached to the parts of the conductive films, and methods of room temperature bonding, diffusion bonding, high temperature bonding, electrostatic anodic bonding, or the like may be used for forming the other parts.

Next, the upper side and the lower side are attached. If the main substrates 751, 771, 781 are a semiconductor substrate such as a Si substrate or a conductive substrate, and even if the transmittance of visible light is low, and if the first to third upper substrates and the first to third substrates are made of material having high transmittance for visible light, such as a glass substrate, an accurate masking alignment can be carried out because the penetrating chamber 769 (754-2, 779, 789, collectively 769) is hollow and has a space therefor. So, while minimizing variations, the conductive films attached to the penetrating chambers and the inner sides thereof can be attached to each other. After the attachments by the heat treatment as described above, plating method, selective CVD method or the like to have the conductive films firmly connect to each other can be carried out. If visible light cannot be used, infrared rays, ultraviolet rays, etc. can be used to attach them. In order to have the pressure of the ICR chamber 769 set to a predetermined low pressure, it can be connected to a vacuum pump through openings for vacuating that are to be provided on the second upper substrate 772 or the third lower substrate 783. Openings for cleaning and purging the inside of the chamber can also be provided. If the ion source chamber 754-1 is at the atmospheric pressure or at relatively high pressure, the required number of intermediate chambers can be provided between the ion source chamber 754-1 and the ICR chamber 769. Then the pressures of these intermediate chambers can be gradually lowered, chamber by chamber so that the pressure of the ICR chamber can be lowered to a desired low pressure. In that case, an acceleration electrode or an extraction electrode (which may have a central hole) for accelerating the ions emitted from the ion source can be provided, or they can be drawn by a pressure difference. As stated above the FTICR mass analysis device having the ion source chamber 754-1, the ion introducing hole 765, and the broad ICR chamber 769 are completed.

In the ICR chamber 769, the conductive film electrodes 755 (755-1, 3), 756 (1, 3, 4), 767 (1, 2, 3, 4), 775 (1, 2, 3, 4), 774 (1, 2, 3, 4), 776 (2, 3, 4, 5), 768 (1, 2, 3, 4), 785 (1, 2, 3, 4) and the like are connected and form the trap electrode 778 (778-2, 3) and the receiver electrode 778 (778-4, 5). In addition, the conductive film electrodes 776 (776-1) and 786 (786-1) form ion excitation electrodes (power sources) 778 (778-1) and 788 (788-1). In the FT-ICR using the substrate of the present invention, the two-dimensional (planar) direction can be enlarged to the same size as the substrate surface, but the height-direction is limited by the substrate thickness. For example, if the main substrate is a Si substrate, the maximum thickness of the Si substrate is about 1 mm, which is the maximum thickness of the substrate normally used, so the height is 1 mm at the maximum. But by stacking and attaching layers, based on the structure and scheme shown in FIG. 32, it is possible to manufacture an ICR chamber of a desired height. (In the case of Si wafer, since a wafer of any thickness can be used, the wafer having a thickness of, for example, 1 cm to 10 cm can also be manufactured, so that a wafer of a substantial height can be manufactured without layers of wafers being stacked. For example, if the thickness of the first main substrate 751 is h4, the thickness of the first upper substrate 752 is h3, the thickness of the first lower substrate 753 is h5, the thickness of the second main substrate 771 is h1, the thickness of the second upper substrate 772 is h8, the thickness of the second lower substrate 773 is h2, the thickness of the third main substrate 781 is h7, the thickness of the third upper substrate 782 is h6, and the thickness of the third lower substrate 763 is h9, the total thickness is the sum of h1 to h 9, and the height of the ICR chamber 769 is the sum of h1 to h 7. For example, if h1=h4=h7=1 mm, h2=h3=h5=h6=h8=h9=0.2 mm, then the total thickness is 4.2 mm and the height of the ICR chamber 769 is 3.8 mm. If h1=h4=h7=3 mm, h2=h3=h5=h6=h8=h9=0.5 mm, the total thickness is 12.0 mm and the height of the ICR chamber 769 is 11.0 mm.

The magnetic field B is directed from the trap electrode A 755 to the trap electrode 756. In order to generate such magnetic field B, the present invention has two methods. One is to place the N pole of the electromagnet or permanent magnet on one side outside the trap electrode of the ICR chamber 754-2 and the S pole on the other side. As a result, a magnetic field B is generated in the direction from the trap electrode A 755 to the trap electrode 756, or to the excitation electrodes 757 and 758. In another method, the ICR chamber 754-2 is disposed inside the coil, where the direction of the axis of the coil is arranged to coincide with the direction from the trap electrode A 755 to the trap electrode 756. FIG. 33 shows FTICR in which the coil of the present invention is arranged. FIG. 33(*a*) is a view of the ICR chamber as seen in the direction in parallel with the direction of movement of the charged particles, and FIG. 33(*b*) is a cross sectional view as seen from the direction of movement of the charged particles in the ICR chamber. The outer periphery of the ICR chamber of the FTICR apparatus shown in FIG. 31 is wound with a coil. That is, the coil is formed on the upper substrate 752, a contact wiring (coil wiring) 766-3 is formed in the upper substrate 752 and connected to the coil wiring 766 (766-1), a coil wiring 766-4 is formed in the main substrate and connected to the coil wiring 766-3 is formed, a contact wiring (coil wiring) 766-5 is formed in the lower substrate 753 and connected to the coil wiring 766-4, and further, a coil wiring 766 (766-2) is formed on the lower surface of the lower substrate 753 and connected to the coil wiring 766-5. In this way, the coil wiring 766 surrounds the periphery of the ICR chamber in a spiral shape.

The coil wirings 766-1 and 766-2 can be formed together with the electrodes 762 and 763. For example, if the upper substrate 752 and the lower substrate 753 are insulators, the coil wirings are wound directly on the electrodes. If the upper substrate 752 and the lower substrate 753 are not insulators, an insulating film such as a $SiO_2$ film or a SiN film is formed on them and thereafter, a conductive film is deposited and patterning is performed. The conductive film is formed by a CVD method, a PVD method, a plating method, a squeegee method, a screen printing method, or a combination thereof. The contact wirings (coil wirings) 766-3 and 766-5 can be formed at the same time as the contact hole wirings 760 and 761. For example, after the contact holes are formed on the upper substrate 752 and the lower substrate 753 if the upper substrate 752 and the lower substrate 753 are insulators, the coil wirings are wound directly on the electrodes. If the upper substrate 752 and the lower substrate 753 are not insulators, an insulating film such as a $SiO_2$ film or a SiN film is formed on them and thereafter, a conductive film is deposited and patterning is performed. The conductive film is formed by a CVD method, a PVD method, a plating method, a squeegee method, a screen printing method, or a combination thereof. For example, after depositing a conductive film of 50 nm to 5000 nm by PVD method, a photosensitive film is formed only inside the contact hole. Then the whole surface is etched (anisotropic dry etching), and after the photosensitive film in the contact hole is removed, a film is formed only in the contact hole by a plating method. As a result, an in-contact-hole coil wiring can be formed. Alternatively, the in-contact-hole coil wiring can also be formed after forming the contact hole, the conductive film is deposited thereon, and the entire surface is plated. At this time, the conductive film is also formed on the upper substrate 752 and the lower substrate 753, but this conductive film can also be used as the coil wiring 766-1 and 2.

Alternatively, the conductive film is formed thick after forming the contact hole. For example, if the contact hole has a diameter of 200 µm, the interior of the contact hole is substantially filled by depositing the conductive film of the thickness of 100 µm or more. The conductive film is also formed on the upper substrate 752 and the lower substrate 753, but this conductive film can also be used as the coil wiring 766-1 and 2. Alternatively, after forming the contact hole, a conductive film can be deposited and further, the interior of the contact hole can be filled with a conductive film (paste) by a squeegee method. At this time, if a gap is provided between the upper substrate 752 and the lower substrate 753, wirings can be formed simultaneously on the upper substrate 752 and the lower substrate 753. Incidentally, if the electrodes 762 and 763 cannot be formed at the positions because of the coil wirings 766-1 and 766, they may be formed outside the coil wirings 766-1 and 766-2 as shown in FIG. 33. If the contact wires 760 and 761 cannot be formed at the positions, they may be formed outside the coil wirings 766-1 and 766-2. For that reason, electrode wirings 758, 757, 759, 764, etc. in the ICR chamber need only be rerouted to some extent. The coil wiring 766-4 in the main substrate can also be formed by the same method.

FIG. 34 shows an FTICR in which the coil of the present invention is arranged differently from that of FIG. 33. In FIG. 34, the second upper substrate 792 is attached to the upper substrate 752 with the support columns 791 (791-1, 2) interposed and attached to the upper substrate 752, and the second lower substrate 794 is attached to the lower substrate 753 with the support columns 793 (793-1, 2) interposed and attached to the lower substrate 794. And thereafter, the FTICR device is cut off from the substrates, and the periphery of the ICR chamber is wound by the coil wirings 795. As the electrodes 762 and 763 can be formed in the spaces 796 and 797 surrounded by the support columns 791 and 793, the second upper substrate 792, and the second lower substrate 794, regardless of the positions of the arrangement of the coils 795, they can be arranged freely. And further, as the spaces 796, 797 can also be sealed, so the electrodes 762 and 763 are not exposed to the external environment. As a commercially available wiring can be used for the coil wirings 795, the size of the wirings can be freely designed and the current to apply can be freely selected. Further, if the coil wirings 795 are covered with an insulating film, there is no need to cover the upper substrate 752, the lower substrate 753, the main substrate 751, the support columns 791 and 793, the second upper substrate 792, and the second lower substrate 794 by an insulator film, even in case they are a conductor or a semiconductor, which is not an insulant. It is possible to attach the upper substrate 752 to the support column 791 in various methods. For example, by, first, attaching a substrate, which is to serve as the support column 791, to the upper substrate 752, then a penetrated room, which is to serve as the space 796, is formed. In this method, when attaching the substrate serving as the support column 791 to the upper substrate 752, since the part of the electrode 762 is of a convex shape, it is sufficient to form in advance a concave at the position of the substrate that serves as the support column 791, which position corresponds to that of the convex part of the electrode, and attach it to the electrode. After forming the space 796, the second upper substrate 792 is attached.

Alternatively, after attaching the substrate serving as the column 791 to the second upper substrate 792, a penetrated room serving as the space 796 is formed, and then the column 791 attached to the second upper substrate 792 is, while being adjusted for alignment with the upper substrate 752, attached to the upper substrate 752. Alternatively, a penetrated room serving as a space 796 is formed in the substrate which serves as the support column 791, and the support column 791 is attached to the upper substrate 752 and the second upper substrate 792. Similarly, on the side of the second lower substrate 794, the support column 793 is attached to the second lower substrate 794 and to the lower substrate 753. Openings are provided in the upper substrate 752, the lower substrate 753, the second upper substrate 792, and the first upper substrate 794 in order to lower the pressure of the ICR chamber or the like, or to purge or clean it. Further, the electrodes 762 and 763 are stretched so that a voltage can be applied from the outside. Thereafter, the substrate is cut in order to manufacture the FTICR device unit by unit. The cutting of the substrate can be performed by a dicing method, a laser cutting method, or the like. The part of the scribing line can be easily cut at the time of the last dining if the substrate is scraped at each step. Thereafter, if necessary, an insulating film or the like is formed outside the device, and the coil wiring 795 is wound around the ICR chamber. In order to generate the required magnetic field, the diameter of the coil wiring, the material of the coil, the number of windings, multiple windings, etc. are selected. Since the ICR device of the present invention is very small, the material of the coil can also be superconductive. Also as the size of the container containing the liquid He or the like, in which the device itself is placed, can be minimized, so that the running cost and the manufacturing cost can also be greatly reduced. As a superconductor, metal superconductor such as a Nb based superconductor and a Mg based superconductor, high temperature superconductive substance such as copper based oxides, and iron based superconductors can be used.

Also, in the case of the structure of the FTICR device shown in FIG. 33, like the one in FIG. 34, after manufacturing the FTICR device, it is possible to remove the electrodes 762 and 763 and to wind the coil wiring so as to surround the ICR chamber. If the ICR chamber has a size 10 mm×40 mm and the size of the whole device is 15 mm×60 mm, 12 pieces can be produced from a 6 inch wafer (150 mm diameter). If the material and the manufacturing costs are 240,000 yen, the price of 1 piece will be 20,000 yen. As the price of the conventional product is 2.4 million yen or more, the present product costs about 1/100 of the conventional product in size and cost. In FIGS. 33 and 34, the coil wiring is wound around the substrate. However, a coil in which the ICR device as shown in FIG. 31 is inserted is manufactured first and, then the ICR chamber is arranged in the coil so that the axis of the coil and the direction of the chamber are aligned. However, in this case, the coil wiring and the ICR device are not in contact with each other, and in some cases the coil wiring is positioned away from the ICR device, so the overall size that includes the coil is larger than those shown in FIGS. 33 and 34.

FIG. 35 is a diagram showing an ionization method different from that described in FIG. 19. This ionization method is a type of matrix-assisted laser desorption ionization method. Through-holes (chambers) 454, 455, 456, 457 and the like are formed in the main substrate 451, and the penetrated room (chamber) 454 is surrounded by a thick main body of the main substrate 451-1 and a partition wall 451-2 having a central hole 481-1. (The side of the side surface is surrounded by the main substrate 451.) The penetrated room (chamber) 454 is a sample chamber, and on the second substrate (upper substrate) 452 or the third substrate (lower substrate) 453, an opening 470 is opened, from which a sample plate (sample plate) 475 is inserted and is brought into contact with the sample back plate 451-1 of the main substrate 451. A vacuum drawing line 468 is opened on the sample back plate 451-1, and an opening is formed in the upper substrate 452 or the lower substrate 453, and the opening is connected to a vacuum pump so that the sample plate 475 can be suctioned. A sample 476 is attached to the center part of the sample plate 475, and the sample 476 is irradiated with laser light 478 from an opening 471 that is opened in the upper substrate 452 or the lower substrate 453. Laser light 471 is introduced from outside and condensed from laser light 478 by a lens 477, and irradiated on a sample 476. For the sample 476, a rapid temperature rise occurs in the matrix because of the irradiation of the laser light 478, and the sample material (matrix) is vaporized and ionized.

A conductive film 459 is formed around the partition wall of the main substrate 451-2 that faces the main substrate 451-1, against which the sample plate 475 is propped, and this conductive film 459 is connected to a contact hole 462 formed on the upper substrate 452 or the lower substrate 453, a conductive film formed in the contact hole 462, and an outside electrode/wiring 464 formed on the upper substrate 452 or the lower substrate 453 connected thereto. When a voltage is applied to the outside electrode/wiring 464, a positive or negative voltage is applied to the conductive film 459. The generated ions are extracted by the voltage of this conductive film (the conductive film 459 is also referred to as an extraction electrode), a part them passes through the central hole 481-1, enters the adjacent low pressure chamber 455, further passes through the central hole 481-2 of the partition wall 451-3 of the main substrate and enters the adjoining ion converging chamber 456, further passes through the central hole 481-3 of the partition wall of the main substrate 451-4 and led to the adjacent penetrated room 457. This penetrated room 457 corresponds to, for example, the extraction electrode in FIG. 19, the acceleration chamber 307 or the mass analysis chamber 308.

Since the sample chamber 454 is in the atmospheric pressure, the adjacent chamber 455 is, for example, a low pressure chamber 455 having a pressure of about 1 torr, wherein the pressure is lowered by a vacuum pump connected to the opening 472 for vacuating that is formed in the upper substrate 452 or the lower substrate 453. A conductive film 460 is formed on the inner surface of the adjacent chamber 456. This conductive film 460 is connected to a contact hole 465 formed on the upper substrate 452 or the lower substrate 453, a conductive film formed in the contact hole 465, and an outside electrode/wiring 466 formed on the upper substrate 452 or the lower substrate 453 connected thereto. Voltage is applied to this conductive film 460 from the outside electrode/wiring 466, where the same sign (positive or negative) of voltage as that of the ion beam 479 is applied, and the ion beam 479 is converged. If the conductive film 460 is divided into several regions so that a voltage can be applied to each region, the ion beam 479 can be converged and its orbit can be adjusted by adjusting these voltages. Accordingly, since the position of the ion beam entering the adjacent chamber 457 can be adjusted, the ion beam can pass through the central hole 481-3 more accurately, and moreover, almost all the ion beams 479 can be guided to the mass analysis chamber. Thus sensitivity of the ion detection be improved. Also in the ion converging chamber 456, an opening 473 for a vacuum drawing line is formed in the upper substrate 452 or the lower substrate 453, and the ion converging chamber 456 can be set in a low-vacuum state. For example, the pressure of the ion converging chamber 456 is in $10^{-3}$ to $10^{-4}$ torr. (It should be noted that the pressure of the mass analysis chamber is, for example, in $10^{-5}$ to $10^{-6}$ torr.)

A conductive film 458 may be formed on the side surface of the sample back plate 451-1 of the main substrate. This conductive film 458 is connected to a contact hole 461 formed on the upper substrate 452 or the lower substrate 453, a conductive film formed in the contact hole 461, and an outside electrode/wiring 463 formed on the upper substrate 452 or the lower substrate 453 connected thereto. The sample plate 475 is a conductor, and a voltage is applied from the conductive film 458. If the laser beam 478 is irradiated on the sample 476, various ions are generated, but the ions having the same potential as the voltage applied to the sample plate 475 come out from the sample. When a voltage opposite to the voltage of the sample plate 475 is applied to the conductive film 459, the ions having the same sign as the voltage of the sample plate 475 are almost attracted to the conductive film 459 and pass through the central hole 481-1.

Since heat is generated by ion irradiation, the sample chamber 454 becomes hot. Therefore, a concave portion 469 is formed near the sample back plate of the main substrate wall 451-1, against which the sample plate is propped, and the concave portion 469 is cooled. For this cooling, for example, cooling water, cooling gas can be used. Also, a similar concave portion may be formed around the sample chamber 454 for cooling, and it is also possible to cool the sample chamber from the side of the upper substrate 452 or the lower substrate 453. Incidentally, as the conductive film 458 is also a good conductor of heat, the heat of the sample plate 475 can be effectively absorbed. In particular, since the sample plate 475 is closely attached to the conductive film 458 by the vacuum drawing line 468, the electrical connection and the heat transfer are also improved.

FIG. 36 is a diagram showing an embodiment of another ionization method. An upper substrate (second substrate) 502 and a lower substrate (third substrate) 503 are attached to the upper and lower surfaces of the main substrate (first substrate) 501, respectively, and the penetrating chamber 504 (504-1, 504-2, 504-3) penetrating the upper substrate (second substrate) 502 to the lower substrate 503 (third substrate) is formed on the main substrate 501. Reference number 504-1 denotes an ionization chamber, and a spray gas introducing line 516 for introducing a spray gas is connected to the ionization chamber 504-1. Next to the ionization chamber 504-1 is an extraction electrode/acceleration chamber 504-2, which is separated by a substrate partition 501-2 having a central hole 505-1. The extraction electrode/acceleration chamber 504-2 is a penetrating chamber that is separated by a substrate sidewall 501-2 having a central hole 505-1, and that is separated by a substrate partition wall 501-4 having a central hole 505-2, from the adjacent chamber 504-3. In the extraction electrode/acceleration chamber 504-2, a substrate sidewall 501-3 serving as an extraction electrode having a central hole 505-3 is arranged. A conductive film electrode wiring 508 is formed on the surface of the substrate sidewall 501-3, and it is also formed on the upper surface of the lower substrate 503 and is connected to an outer electrode 511 through the contact 510 of the lower substrate 503, which electrode is formed on the lower surface of the lower substrate 503.

If the spray gas introducing line 516 is formed near the center of the main substrate 501, it can be manufactured by the same process as the central hole 505. However, if the size is different from that of the central hole 505, photolithography and etching may be performed separately. The spray gas introducing line 516 is connected to the entrance of the opening of the spray gas introducing line 518 opened in the upper substrate 502 or the lower substrate 503 through another spray gas introducing line 517. After the entrance of the opening of the spray gas introducing line 518 is opened by photolithography method + etching method or the like, the spray gas introducing line 517 can be formed by subsequently etching the main substrate 501 with the opening portion masked. The upper substrate or the like may be attached to the main substrate after forming the spray gas introducing line 517 in advance on the main substrate 501 and/or forming the entrance of the opening of the spray gas introducing line 518 in the upper substrate or the like. Alternatively, an opening may be formed in the upper substrate 502 or the lower substrate 503, and the opening may be used for a spray gas introducing line.

A spray gas (also referred to as an atomized gas or a nebulizer gas) containing the sample liquid or the sample gas is introduced through the entrance of the opening of the spray gas introducing line 518 and the spray gas 525 is introduced into the ionization chamber 504-1. A conductive film 506 is formed on the inner surface of the ionization chamber 525. And a contact hole 512 (the upper substrate 502 side), and/or a contact hole 510 (the lower substrate 503 side), a conductive film formed on them, electrode/wiring 513 (on the upper substrate 502 side) and/or the electrode/wiring 511 (on the lower substrate 503 side), are connected to the conductive film 506, so that a voltage can be applied to the conductive film 506 by the electrode/wiring 511 or 513, whereby the ions are ionized so as to have the same sign as the voltage applied to the spray gas 525 that was introduced into the ionization chamber 525. The conductive film 509 on the upper substrate 502 or the lower substrate 503 can be formed even before it is attached to the main substrate 501. That is, after forming the conductive film 509 on the upper substrate 502 or the lower substrate 503, the main substrate 501 having penetrated rooms or concave portions may be aligned and then attached Similarly, about the conductive film 509 on the side surface of the main substrate, after forming the conductive film on the side surface of the main substrate 501 having the penetrated rooms or the concave portions, the upper substrate 502 or the lower substrate 503 can be attached to the main substrate 501. The main substrate 501 may be divided into two or more pieces and formed separately from the upper substrate 502 and the lower substrate 503 are and then these may be fitted and attached to each other. A conductive film 526 is formed also on the inner surface of the spray gas introducing line 516, and a voltage can be applied thereto. In that case, since the spray gas is ionized also within the spray gas introducing line 516, the ionization is carried out more efficiently. As a method of forming the conductive film 526 on the inner surface of the spray gas introducing line 516, as described in the present specification, the main substrate 501 is divided and a half of the concave portion 516 is formed there. And then a conductive film 526 is formed on the surface of the concave portion 516, and the divided parts may be bonded vertically. A conductive film can also be formed on the inner surface of the spray gas introducing line 517.

As a method of forming, for example, a conductive film can be formed by a CVD method, a PVD method, or a plating method after forming the spray gas introducing line 517. These conductive films are the films such as Cu, W, Mo, Ni, Cr, Al, Au, Ti, high concentration poly Si, conductive carbon (including conductive nanotubes, graphene) etc., or composite films or deposited films thereof. A high voltage (for example, 100 V to 10 KV) is applied to the ionization chamber 504-1 and ions are generated, such that heat is also generated. The main substrate 501 is, for example, made of silicon or the like, and the upper substrate 502 and the lower substrate 503 are made of, for example, glass, quartz or the like, and the conductive film and the insulating film also can bear the temperature of over 300° C. However, if this high temperature is transferred to the mass analysis chamber it will affect the characteristics. So, it is desirable to prevent the temperature from rising as much as possible. Since this mass analysis device is small, it is easy to cool the whole device by applying cold air, but it is desirable to cool particularly the part that tends to be heated. Since the ionization chamber 504-1 and the like is heated relatively to a high temperature, a concave portion 519 is to be formed in the main substrate 501 around the ionization chamber 504-1, etc. And the ionization chamber 504-1 etc., can be cooled by introducing cooling water into the concave portion 519. The concave portion 519 may be formed by first forming the opening 521 in the upper substrate 502 or the lower substrate 502 and then ny etching the main substrate 501 through the opening 521. Or after forming the concave portion 519, the upper substrate 502 or the lower substrate 502 can be attached to the main substrate 501. The opening 521 may be formed before or after the upper substrate 502 or the lower substrate 502 is attached to the main substrate 501.

By applying a high frequency voltage to the electrode 513 or 511, the gas present in the ionization chamber 504-1 can be converted into a plasma (ionized). At this time, since the gas can be converted into a plasma even at a low pressure equal to or less than the atmospheric pressure (for example, 1 torr to 100 torr), an opening for vacuating is provided in the upper and lower substrates 502 and 503 of the ionization chamber 504-1 to depressurize the ionization chamber 504-1 to a low pressure. Alternatively, a high voltage (for example, 100V to 10 KV) is applied between the conductive film 508 of the partition wall of the extraction electrode 501-3 and the conductive films 506 and 509 in the ionization chamber 504-1 so as to also ionize gas and mist in the ionization chamber 504-1. In this case, preferably partition wall 501-2 is omitted. Also in the ionization chamber of FIG. 36, as in FIG. 37, the conductive films 506 and 509 can be used as heaters. In this case, it is also possible to ionize gas and mist in the ionization chamber 504-1 by applying a high voltage between the conductive films 506, 509 on the heater side and the extraction electrode side.

The ions ionized in the ionization chamber 504-1 are drawn by the substrate sidewall 501-3 having the central hole 507 formed in the adjacent chamber sandwiching the partition wall 501-2 having the central hole 505-1, and pass through the central hole 507, and further passes through the central hole 505-2 of the partition wall 501-4 having the central hole 505-2 and move as an ion beam 528 to the adjoining penetrating chamber 504-3. A contact hole 510 and an electrode/wiring 511 are formed on the conductive film 508 in the extraction electrode/acceleration chamber 504-2, and voltage can be applied externally. For example, if a reverse voltage potential that is opposite to that of the ions is applied to the ions, the ions are drawn and accelerated, resulting in an ion beam 528 passing through the central hole 507. An acceleration electrode (having a central hole) or a converging electrode may further be provided in the extraction electrode/acceleration chamber 504-2. Alternatively, the ion converging chamber 456 of FIG. 35 may be provided in front of and behind the extraction electrode/acceleration chamber 504-2 to converge the ions. The adjacent chamber 504-3 is, for example, a mass analysis chamber (308 in FIG. 19). The partition wall 501-2 between the ionization chamber 504-1 and the extraction electrode/acceleration chamber 504-2 may be omitted if there is no problem when drawing the ions with the extraction electrode 501-3. For example, when positive ions are generated, a positive voltage is applied to the conductive films 506 and 526. Because of the positive voltage applied to the conductive film 506 of the ionization chamber 504-1, the generated positive ions are converged near the center. The converged positive ions are drawn by the extraction electrode 501-3 to which the negative voltage is applied. At this time, the size of the central hole 505-1 of the partition wall 501-2 is adjusted so as to have the ions be easily drawn by the extraction electrode 501-3. For example, the size of the central hole 505-1 can be smaller than that of the central hole 507 to enable the ions to easily pass through the central hole 505-1 of the extraction electrode 501-3. Although the pressure of the ionization chamber 504-1 is near the atmospheric pressure, the pressure in the extraction electrode/acceleration chamber 504-2 can be lowered by the partition wall 501-2. For example, a vacuum-drawing line 522 (522-1) can be provided between the partition wall 501-2 and the partition wall 501-3 of the extraction electrode for vacuating.

The method described in FIG. 36 is a kind of electrospray ionization (ESI) method. Since the electrospray ionization (ESI) method is an atmospheric pressure ionization method, the ionization chamber 504-1 has the atmospheric pressure, but an opening can be provided in the upper substrate 502 or the lower substrate 503 of the ionization chamber 504-1 to discharge the air from ionization chamber 504-1 to the extent that it does not influence the ionization. It is also possible to clean the ionization chamber 504-1 by providing another opening and purging it with nitrogen or drying it. A vacuum drawing line 522 (522-2) is provided for vacuating a chamber on the right-hand side of the extraction electrode/acceleration chamber 504-2 (between the partition wall 501-3 and the partition wall 501-4).

In FIG. 36, the upper electrode 509 and the lower electrode 506 are separated and a conductive film electrode is not formed on the side surface, so that so-called parallel-plate electrodes are formed, and as a high frequency voltage is applied between the upper electrode 509 and the lower electrode 506 the plasmas are produced, thereby ionizing the spray gas 525 that are let off from the central hole 516. In particular, when the distance between the upper electrode 509 and the lower electrode 506 is as small as 500 μm to 1 mm to 2 mm, a high electric field is generated between the upper electrode 509 and the lower electrode 506, so that plasma are easily produced. When the distance between these electrodes is 2 mm or more, plasmas are produced corresponding to the increase of the magnitude of the high frequency voltage. If the upper electrode 526 and the lower electrode 526 formed on the inner surface of the central hole 516 are separated to form parallel-plate electrodes, the distance between these electrodes will be less than the distance between the electrode 509 formed on the upper substrate 502 and the electrode 506 formed on the lower substrate 503. If the upper electrode 526 and the lower electrode 526 which are formed on the inner surface of the central hole 516 and are separated from each other are connected to the electrode 509 formed on the upper substrate 502 and the electrode 506 formed on the lower substrate 503 are connected on their respective side surfaces, the ions can be converted to a plasma in the central hole by applying a lower voltage, which voltage is high frequency voltage applied between the upper electrode 526 and the lower electrode 526, which are formed and separated on the inner surface of the central hole 516. Since the pressure of the penetrating chamber 504-1 can also be lowered, it is easy to set the conditions for generating plasmas.

FIG. 37 is a diagram for explaining the atmospheric pressure chemical ionization method. The same reference numbers are used to denote the same materials and the like as in FIG. 36. The part where the spray gas 525 enters is a heating chamber 504-6, and next to the heating chamber 504-6 there is an ionization chamber 504-7 which is separated by a partition 501-6 having a central hole 505-1. Conductive films 506 and 509 are deposited on the inner surface of the heating chamber 504-6. These conductive films 506 and 509 are thin film resistors, and the electrodes 511-1, 511-2 (contact holes are 510-1, 510-2) and the electrodes 513-1, 513-2 (Contact holes 512-1 and 512-2) are connected to them, having resistive elements between them. If current is passed between the electrodes 511-1 and 511-2 and/or between the electrodes 513-1 and 513-2, the thin film resistor 509 generates heat. The heating chamber 504-6 is heated to, for example, about 300° 500° C., the spray gas 525 is vaporized into the solvent and sample molecules and enters the ionization chamber 504 through the central hole 505-1 (In some cases the substrate sidewall 501-6 may not exists). If the thin film resistor 526 is also formed on the spray gas introducing lines 516 and 517 and heat is generated by running a current, the vaporization of the spray gas 525 to the solvent and to the sample molecule is improved.

In the ionization chamber 504-7, electrodes, each with a pointed end (sharpened) (pointed electrodes) 529 and 530 are arranged facing each other. The electrode 529 is disposed on the lower substrate 503 and is connected to the outside electrode/wiring 511-3 through the contact hole 510-3. The electrode 530 is disposed on the upper substrate 502 side and is connected to the outside electrode/wiring 513-3 through the contact hole 512-3. When a voltage is applied between them, discharge occurs and the evaporated solvent molecules are ionized into reactive ions, and the transfer of protons occurs between the reactive ions and the sample molecules (ionization reaction), and the sample molecules are protonated or deprotonated and become ions. These ions pass through the central hole 505-2 of the partition wall 501-4 and are drawn to the extraction electrode arranged in the adjacent chamber 504-8. That is, the adjacent chamber 504-8 is an extraction electrode/acceleration chamber, which is similar to the extraction electrode/acceleration chamber 504-2 in FIG. 36, whereby, the ion beam 528 is introduced into the mass analysis chamber or the like. Since the temperatures of the heating chamber 504-6 and the ionization chamber 504-7 will rise, preferably concave portions 519 are formed in the surrounding area of main substrate 501, so that the heat from these chambers is prevented from leaking outside by the cooling water and cooling gas. In FIG. 37, the exit of the spray gas introducing line 516 is described as facing the central hole 505-1 of the partition wall 501-6 (for example, front side or rear side of the paper plane of FIG. 37) and the pointed electrodes 529, 530. Preferably the exit of the spray gas introducing line 516 is provided on the side surface of the heating chamber 504-6, so that it does not face the central hole 505-1 or the pointed electrode 529, 530, so as not to have a non-vaporized mist enter the ionization chamber 504-7, or attach to the pointed electrodes 529 and 530 thereby lowering the electric field voltage of the ionization chamber. Further, a mist or gas discharge port may be provided on the upper and lower substrates 502 or 503 of the heating chamber 504-6, or it may be discharged in a small amount by a pump through the gas discharge port. Also, at the time of maintenance, purging including drying and the like may be performed with N2 or the like using this discharge port. Similarly, the ionization chamber 504-7 may be provided with a discharge port, and/or an opening for purging or vacuating.

A method of forming the pointed electrodes 529 and 530 will be described below. FIG. 38 is a view showing a method for manufacturing an ionization chamber having pointed electrodes. As shown in FIG. 38(a), the photosensitive film 543 is patterned so as to reduce h25 of a part of the main substrate 541, which has a thickness of h25 and attached to the lower substrate 542 to a thickness h25. A film (for example, an insulating film such as $SiO_2$) that enhances the attachment between the main substrate 541 and the photosensitive film 543 or serves as an etching stopper may be stacked between the main substrate 541 and the photosensitive film 543. Using this pattern 543 as a mask, a concave portion 544 having a thickness h 26 of the main substrate is formed (FIG. 38(b)). Next, the photosensitive film 545 (545-1) is patterned for forming the substrate sidewall 541-1 of the main substrate 541 having the thickness h 25. At the same time, the photosensitive film 545 (545-2) is patterned in the concave portion 544 for leaving the portion of the main substrate of forming the steeple 541-3 (FIG. 38(c)) Using the photosensitive film 545 (545-1, 2) as a mask, the main substrate 541 is etched to form a penetrated room 546 that reaches the lower substrate 542. In the case where the main substrate 541 is a Si substrate and the lower substrate is a glass substrate or a quartz substrate, they can be firmly attached by electrostatic anodic bonding. So, even if the Si substrate is etched at a high speed and nearly vertically, the conditions of the dry etching can be selected which does not etch the glass substrate 542 too much even if over-etching occurs. By this etching, the substrate partition wall 541-1 having the thickness h 25, the portion of the main substrate 541-2 that was not etched, and the parts at which the pointed electrode 541-3 are to be formed are formed. (FIG. 38(d)).

Next, the photosensitive film 547 is patterned, and the photosensitive film 547-1 is patterned on a portion of the main substrate 541, such as the substrate sidewall 541-1, which is not to be etched. At this time, so as not to etch the side surfaces of the substrate sidewall 541-1, the side surfaces of the substrate sidewall 541-1 are also covered with the photosensitive film 547-1. At the same time, the photosensitive film 547-2 is patterned so that the pointed electrode 541-3 is formed on the portion of the main substrate 541-2 where the pointed electrode 541-3 is to be formed (FIG. 38(e)). Using this photosensitive film 547-2 as a mask, the main substrate 541-2 is etched. This etching is the etching which also performs side-etching. This etching is performed under such conditions that the amount of the side etching and the amount of the etching in the vertical direction are controlled. Namely, this side etching method is the one, where when the vertical etching is performed by the amount of h26, the amount of the side etching that is performed is h 27. Therefore, assuming that the width (diameter) of the photosensitive film 547-2 is 2×h 27 and h 27=h 26, and when the main substrate 541-3 is etched in the vertical direction by h 26 and the lower substrate 542 is exposed, the etched pattern 541-3 has a conical shape whose tip is a spire. {FIGS. 38(f), (g)}

Next, a conductive film is deposited and patterned, as shown in FIG. 38(h), to form a conductive film pattern 548 covering the entire conical main substrate 541-3 and a wiring pattern 549 connected to the conductive film pattern 548 and extending over the lower substrate. The wiring pattern 549 is connected, through the contact hole 550 formed in the lower substrate 542 and through the conductive film formed there, to the conductive film electrode/wiring 551 formed on the lower surface of the lower substrate 542. The same pattern are formed on the side of the upper substrate 540, and as shown in FIG. 38(i), when the substrate sidewall 552 (552-1) on the upper substrate 540 and the substrate sidewall 541 (541-1) on the lower substrate 542 are superimposed, an ionization chamber in which a conical pointed electrodes face each other can be formed. Needless to say, not only the substrate sidewall 552 (552-1) and the substrate sidewall 541 (541-1) are superimposed, but also the main substrates 552 and 541 formed in the same height are superimposed. As described in the present specification, various methods for attaching the main substrates 552 and 541 to each other, such as a method using an adhesive, a room temperature bonding, a diffusion bonding, a high temperature bonding, and an electrostatic bonding can be used. Particularly when the main substrate is a Si substrate or a conductive substrate, it can be firmly attached by electrostatic anodic bonding by sandwiching a glass substrate or a quartz substrate 553 between them.

In FIG. 38, a pair of pointed electrodes is shown, but by providing a plural pairs of pointed electrodes, the discharge regions can be increased. So, the ionization efficiency is increased. It is necessary to over-etch the main substrate 541-2 to a certain extent when producing the pointed electrode. So, if a perfectly pointed electrode is produced, h27 becomes smaller than h26, and the heights h27 of the pointed electrode varies to some extent. Therefore, the distance between the tips of the pointed electrodes after attaching the upper and lower substrates also vary slightly, and thus the discharge voltages also vary. However, since voltages can be individually applied to the respective electrodes, and when a large number of pointed electrodes are formed, by changing the voltages stable discharges can be realized.

In FIG. 38, after the upper substrate or the lower substrate is attached to the main substrate, then the pointed electrode is formed using the main substrate. However, it is also possible to attach the pointed electrode to the upper substrate or the lower substrate in advance, and then produce the ionization chamber as given in FIG. 38(g) by attaching the main substrate having the concave portion. In this case, the entire pointed electrode can be made a conductive electrode, and an electrode that is resistant to high voltage can be manufactured. Further, by attaching the upper substrate or the lower substrate to the main substrate, the portion of the main substrate where the pointed electrode is to be formed is completely removed by etching (in other words, changing it to a penetrating chamber in FIG. 38(b)). Then a pointed electrode can be mounted to a predetermined position with a mounting device. If the pointed electrode as a whole is a conductor, contact holes can be formed in the upper and lower substrates just below the pointed electrode, so that the conductive film 548 or 549 does not need to be formed. Further, without forming the concave portion 544 as shown in FIG. 38(b), the pointed electrode may be formed and the height h27 of the pointed electrode may be adjusted during the side etching. Particularly if the opposing electrode is not a pointed electrode, but a parallel-plate electrode, it is advantageous because a relatively large distance can be placed between the pointed electrode and the parallel-plate electrode, Further, an ionization chamber having the structure as shown in FIG. 38(g) is manufactured, where the main substrate with a height h26 is first used to form the pointed electrode and the sidewall of the substrate (the height at this time is smaller than h25), and then by attaching a substrate such as another main substrate or glass substrate, etc., having a required height, to the part to which a substrate sidewall etc., is to be attached.

In FIG. 38, although the pointed electrode is formed both on the upper and lower substrates, it is possible to ionize the vaporized gas by causing discharge (corona discharge or the like) even if one of them is a parallel-plate electrode. In this case, the parallel-plate electrode can be formed on the upper substrate or the lower substrate like the conductive film 549 shown in FIG. 38(h). But it is also possible to form a conductive film pattern on the upper substrate or the lower substrate in advance, or first a flat plate electrode is attached, which is attached to the main substrate having penetrated rooms, and thereafter, the lower substrate side and the upper substrate side can be attached as shown in FIG. 38(f). In this case, it is also possible to form a plurality of pointed electrodes.

In FIG. 37, the ions generated in the ionization chamber 504-7 enter the adjacent chamber 504-8, which is, for example, an extraction electrode chamber, where the ions 528 that were generated are drawn by the extraction electrode. However, since the ionization chamber 504-7 is separated from the adjacent chamber 504-8 by the substrate sidewall plate 501-4 having the central hole 505-2, the drawing force of the ions is not so strong. Therefore, a conductive film electrode is formed on the main substrate sidewall facing the substrate sidewall plate 501-4, and the voltage having the same sign (positive or negative) as that of the ions to be admitted to the adjacent chamber 504-8 can be applied so as to push out and to eject ions having a desired sign to the adjacent chamber 504-8. In FIG. 37, the substrate sidewall plate 501-6 is opposed to the substrate sidewall plate 501-4. But as there is a central hole 505-1, the area of the conductive film formed on the side surface of the substrate sidewall plate 501-6 is small, such that in some cases the force for pushing out the ions may be weak. Alternatively, if the substrate sidewall plate 501-6 is not provided, the opposing part is the substrate sidewall 501-1. But because the distance is too far, the force for pushing ions is weakened. Therefore, the adjacent chamber 504-8 is not disposed at the position that is opposed to the substrate sidewall plate 501-6. For example, the relationship in the positions of the adjacent chamber 504- to the substrate sidewall plate 501-6 is at 90 degrees. In this case, the substrate sidewall (in the ionization chamber 504-7, it is in the position that is in the direction perpendicular to the paper surface of FIG. 37) faces the adjacent chamber 504-8, and the conductive film electrode is formed on the whole side surface of the substrate sidewall. Therefore, the force to push out the ions is sufficient, and most of the generated ions enter the adjacent chamber 504-8.

In FIG. 19, a solid sample is irradiated to generate ions and neutral particles. (In this case, laser irradiation and the like is not necessarily required if ionization is sufficient.) FIG. 39 shows an embodiment in which continuous flow (CF)-FAB ionization, which is one type of fast atom bombardment method (FAB), is applied to the present invention. The main substrate 561 is attached to the upper substrate 562 and the lower substrate 563, the penetrating chambers 564-1, 564-2, 5 64-3 and the like are formed. The penetrating chambers 564-1 and 564-2 are separated by a substrate sidewall 561-3 having a central hole 565-1, and the penetrating chambers 564-2 and 564-3 are separated by a substrate sidewall 561-10 having a central hole 565-4. The penetrating chamber 564-1 is an ionization chamber, and a sample introducing hole 566 is formed in the center of the substrate sidewall 561-1 on the side surface thereof, and a vertical sample introducing hole 567 leading to it is formed. The sample introducing hole 566 can be formed in the same way as the central hole 565-1, etc. The vertical sample introducing hole 567 has an opening 568-1 that is formed in the upper substrate and is connected to it.

The component to be detected enters, together with a mobile-phase substance, the ionization chamber 564-1 from the sample introducing opening 568-1, through the vertical direction sample introducing hole 567 and the sample introducing hole 566. As the mobile-phase substance, an organic solvent or an organic solvent/water in which a highly viscous liquid (matrix) such as glycerin, etc., is added in a concentration of 0.1 to a few % is used. At the exit part 573 of the sample introducing hole 566, the organic solvent and water vaporize, and the matrix having the component to be detected as dissolved state seeps out to the side surface of the substrate at the exit part 573 of the sample introduction hole 566. At this time, the component to be detected is concentrated in the matrix by evaporation of the solvent or the like. An opening 568-2 is opened in the upper substrate of the ionization chamber, etc., and a neutral fast atom beam 571 such as Xe or Ar that was accelerated to several kV by an FAB gun 570 arranged above is irradiated on the matrix 574. Owing to the kinetic energy of the fast atoms, the matrix, solvent molecules, etc., that is left without being vaporized are ionized, and the transfer of protons and electrons occurs between the ions and the component to be detected. As a result, positive and negative ions are generated in the component to be detected. The generated ions enter the extraction electrode/acceleration chamber 564-2 next to the ionization chamber 564-1, are accelerated and converged, and are guided to the adjacent chamber 564-3 as an ion beam 575. This adjacent chamber 564-3 is, for example, a mass analysis chamber. A plurality of accelerating electrodes, converging electrodes 561-4, 5, etc., is arranged in the extraction electrode/acceleration chamber 564-2, and the openings for vacuating 568-3 are opened here and there, and the extraction electrode/acceleration chamber 564-2 is depressurized to a low pressure. The accelerating electrode and converging electrodes 561-4 and 561 are the substrate sidewalls having the central holes 565-2 and 3, etc., and a conductive film is formed around the sidewalls, and a voltage can be applied. The ionization chamber 564-1 may also be provided with an opening for vacuating on the upper substrate or the like so as to be depressurized to a low pressure. Furthermore, by placing the ionization chamber, including the ion gun itself, in the vacuum box, it is possible to lower the pressure of the ionization chamber. Further, if the main substrate side surface that is irradiated by the atomic beam 571 generates heat, a cooling chamber may be provided on the backside thereof. On the side surface of the main substrate irradiated by the atomic beam 571, a conductive film can be formed in addition to various insulating films, and the heat generated or the like can be promptly transferred to the outside. The ionization method shown in FIG. 39 is called a CF-FAB method, and when this invention is used, the ionization chamber can be made very small, and can be easily manufactured, and it also enables accurate measurement.

<Collision cell> In the mass analysis device, in order to improve the accuracy and the sensitivity of analysis, a plurality of multipole electrode chambers comprising a plurality of quadrupole that are arranged along the ion beam axis is also in practical use, whereby the ions emitted from the four (multiple) electrode chambers of the first sector are taken into the four (multiple) electrode chambers of the next sector, which increased the efficiency of incorporation into the four (multiple) electrode chambers of the next sector. Among them, below the collision cell manufactured using the present invention is described. In the quadrupole mass analysis chamber described in this specification, a collision cell introduces a collision gas or reaction gas such as Ar, $N_2$, $O_2$, $NH_3$ or the like through the opening provided in the upper substrate or the lower substrate from outside and have these introduced gases collide with the ion beam that enters from the first sector to generate product ions by having the ions dissociated or reacted. A high frequency voltage (a DC bias voltage may be applied) applied to the quadrupole electrode is applied to these product ions, which are sent to the four (quadrupole) electrode chamber or the like, of the next sector. Therefore, according to the present invention, it is very easy to change the quadrupole electrode chamber to a collision cell. That is, the introduction port introducing the collision gas and the reaction gas and the discharge port (the discharge port is connected to the vacuum pump) discharging them are formed.

Because gas is introduced into the collision cell, the pressure of the cell becomes higher than that of the penetrating chamber (e.g., mass analysis chamber) of the first sector or the next sector. So, in order not to influence as much as possible the penetrating chambers of the first sector or the next sector, a penetrating chamber may be further provided between these penetrating chambers, and a vacuum drawing line may be connected to the penetrating chamber provided for vacuating it. Further, it is possible to adjust the in-flow in and out-flow of the gas by making larger or smaller the central hole (through which the ion beam passes) provided in the partition wall between those penetrating chambers, or by adjusting the length of the penetrating chamber. If the central hole (through which the ion beam passes) provided in the partition wall between the penetrating chambers is made smaller, so as not to have the ion beam collide with the partition wall the ion beam may be converged by providing an electrode on the partition wall itself. Alternatively, a partition wall (substrate sidewall) having a central hole for converging ion beam may be separately arranged in front of the penetrating chamber. In the present invention, even if a plurality of penetrating chambers, partition walls and conductive films are provided, the process is almost the same, so that there is not much increase in the man-hours for manufacturing or in manufacturing cost. (Although the area increases slightly, it is not a problem because the increase is small.) Therefore, as a precautionary measure, a penetrating chamber, a partition wall, or a conductive film partition wall (which may be called an ion (accelerating or converging) lens) can be provided, and a voltage is applied from the outside if necessary. But if it is not necessary, no voltage is applied.

<Ion Trap Type Mass Analysis Device> Next, the present invention can also be applied to an ion trap-type mass analysis device. FIG. 40 is a diagram showing a method for manufacturing an ion trap-type mass analysis device. A main substrate 601 is attached to a support substrate 602. As the support substrate 602, various substrates such as an insulator substrate of glass, ceramic, plastic or the like, a semiconductor substrate such as a Si substrate, a conductor substrate of Cu, Al, Fe or the like can be used. A method of attaching the support substrate 602 to the main substrate 601 is performed by using an adhesive or low melting point solder (metal) so that it can be separated from the main substrate 601, as will be described later. In the case of an adhesive, one which can be peeled off by ultraviolet irradiation or one which can be desorbed by applying heat can be used. A photosensitive film 603 is formed on the surface of the main substrate 601 that is attached to the support substrate 602, and a window is opened in the region where the ion trap-type mass analysis device is to be formed. (FIG. 40(a)) Next, the main substrate 601 is etched in the portion where a window is opened to a predetermined thickness to form a concave portion 604 for the main substrate 601. This predetermined thickness is approximately equal to the radius of the ring electrode of the ion trap-type mass analysis device (FIG. 40(b)) (the thickness of main substrate is h31, and the predetermined thickness is h32).

Next, the photosensitive film 603 is removed, the photosensitive film 605 is applied (or attached) again, and the portions 605-3, -4, which are to be kept as the substrate sidewall and the main substrate, and ring electrode forming patterns 605-1 and 605-2 of the ion trap-type mass analysis device are formed by photolithography. The ring electrode forming patterns 605-1 and 605-2 of the trap-type mass analysis device are formed in the concave portion 604 of the main substrate 601. At this time, as shown in FIG. 40(k), the photosensitive film patterns 605-1 and 605-2 are linked and forms a circular pattern. (It is noted that even a square or rectangular pattern can form a quadrupole electric field by adjusting the voltage condition of the trap-type mass analysis device (FIG. 40(c)). Next, the main substrate 601 is etched using the photosensitive film pattern 605 as a mask. At this time, some portions of the main substrates 601-1, 2, 3 are maintained (thickness h33). Etching of the main substrate 601 is performed by isotropic etching, using wet etching or dry etching method so that side etching is performed. Or etching along the crystal axis of silicon by alkali wet etching, and also etching in the lateral direction are performed. Various methods of etching are known to easily control to maintain a constant thickness h33. For example, if a high-concentration P-type diffusion layer is formed in advance in a silicon substrate (it can be done by a substrates-bonding method), it will work as an etching stopper. (FIG. 40(d)) FIG. 40(e) shows an illustration in which the photosensitive film 605 is removed. Next, the portion 606-2 of the main substrate 601-2, which is to be a hollow central portion of a ring electrode, is removed by etching. This etching is performed by vertical (anisotropic) etching after the photosensitive film is formed and the window is opened only at this portion. At this time, the main substrates 601-4, 601-7, 601-1, 601-3 and the like are not etched. The portions 601-5 and 601 that form the ring electrode may be etched to some extent as long as the height can be controlled (Characteristics can be adjusted by changing voltage) (FIG. 40(f)).

Next, a conductive film is deposited on the main substrate 601 to form a conductive film pattern 607. Unnecessary conductive film is removed by etching while the portions (601-5, 6) that are to form a ring electrode and the wiring parts that are connected to the portions are left un-etched. If the main substrate is a semiconductor substrate such as Si substrate, or the like, first an insulating film is formed and then a conductive film is formed. The conductive film is a metal film of Cu, W, Mo, Cr, Ti, Al, Au or the like, an alloy film or a deposited film thereof, and they are deposited by CVD method, PVD method, plating method, electroforming method or the like. (FIG. 40(g)) Next, the upper substrate or the lower substrate 608 to which an end cap electrode 609 is attached is aligned and attached to the main substrate 601. (FIG. 40(h)) This attachment may be carried out by using an adhesive, or if the upper substrate or the lower substrate 608 is made of glass or quartz, and the main substrate is Si substrate or the like, connection by the electrostatic anode diameter may be performed. Thereafter, the support substrate 602 is removed. There are various methods for removing this support substrate. For example, if the support substrate 602 and the main substrate 601 are attached with a thermosoftening adhesive or a low melting point alloy (softening temperature or melting point T1), or if the main substrate 601 and the upper and lower substrates are attached with a curable adhesive or electrostatic anodic bonding (curing temperature or an electrostatic anodic bonding temperature T2), first the adhesive or the like, of T1>T2 is to be selected. Then the main substrate 601 is attached to the upper and lower substrates at the temperature T2, and the substrate 602 and the main substrate 601 are separated by raising the temperature to T1 or higher. (FIG. 40(i))

Next, a groove (central hole) 610 serving as a passage for the ion beam is formed in the main substrate 601. As the height of the main substrate 601-4 and 601-7 is h31, the main substrates 601-4 and 601-7 are attached to the upper and lower substrates 608 but the main substrates 601-5 and -6, which are to become ring electrodes, are not attached to the upper and lower substrates 608. However, since the ring electrode wiring 607 extends to the main substrates 601-4 and 601-7, contact holes 611 are opened at these parts of the upper and lower substrates 608, and conductive films are formed in the contact holes, and further, electrode wirings 612 are formed on the upper and lower substrates 608. At the same time, a contact hole 611 and an electrode wiring 612, which are electrically connected to the end cap electrode 609, are formed. Thereafter, the upper substrate side and the lower substrate side are attached to complete the ion trap portion. When attaching the substrates, a glass substrate or the like may be interposed between the main substrates. The ring electrodes 601-5 and 601-6 are formed in one piece, and the upper and lower conductive films 607 are attached and connected to each other. In addition, the ring electrodes 601-5 and 601-6 are supported by 601-3 and 601-4, which makes them to appear to be unstable. But the thickness h33 of the portions 601-3 and 601-4 can be adjusted, and these portions can be manufactured by materials that do not affect the ion trapping characteristics and that can be appropriately formed as supporting portions. And further they can be formed in a way that they are connected in part to the upper and lower substrates 608. So, the supporting strength is sufficient. Further, in FIG. 40, the parts of the ring electrodes 601-5 and 601-6 are thinned. However, if no problem occurs in the ion trapping characteristics even if these parts are not thinned, it is not necessary to thin the parts of the ring electrodes 601-5 and 601-6. In such a case, the ring electrode 601-5 and 601-6 can be directly attached to the upper and lower substrates 608, which further can increase the supporting strength. Further, in this case, since the contact hole and the electrode wiring can also be taken out directly from the ring electrodes, there is no need to provide 601-3 and 601-4, and an independent ring electrode can be formed. (FIG. 40(*j*))

As described above, by the present invention, an ion trap-type mass analysis device can be manufactured by a simple process. This ion trap-type mass analysis device is composed of one ring electrode 601-5, 6 and two opposing end cap electrodes 609-1, 609-2. A high frequency high voltage is applied to the ring electrodes 601-5, 6, and an ion capturing space 615 is formed by a quadrupole electric field in a space (ion trap space 613) that is surrounded by the ring electrodes 601-5, 6 and the pair of end cap electrodes 609-1 and 609-2 and ions are captured in the ion capturing space 615. An appropriate auxiliary AC voltage is applied to the end cap electrodes 609-1 and 609-2 corresponding to the desired mode of analysis at that time. The charged particles (ions, electrons) enter through the passage on the left side of the central hole 610 formed in the ring electrode 601-5 and the main substrate 601-4 connected thereto (charged particle G 1). The charged particle G 1 is accelerated by the extraction electrode and enters, for example, from the ionization chamber on the left side of the substrate 601-4 having the central hole 610. The charged particle G 1 exits from the central hole 610 of the ring electrode 601-5 moves to the ion trapping space 613 (charged particle G 2) and is captured in the ion capturing space 615 by the ion trapping electric field. The ions captured in the ion capturing space 615 are suitably swept (charged particles G3) and enter the central hole 610 of the opposing ring electrode 601-6 and further pass through the central hole 610 of the substrate 601-7 connected thereto (charged particle G4). For example, they move to the adjacent ion detection chamber, where the ion quantity is counted.

Further, a target gas (Ar, Xe, $N_2$, $NH_3$, $O_2$, etc.) is introduced into the ion trapping chamber 613 from the opening 617 provided in the upper substrate 608 or the like, and the ions are decomposed or reacted by causing the ions to collide with the target gas, which ions has the mass number of a specific range and have been collected at the center of the ion trap chamber by the electric field formed inside the ion trap chamber. That is, a collision cell can also be formed. After sufficient dissociation and decomposition are performed, the voltage applied to the electrodes 601-5, 6, 609-1, 2 is changed, and an electric field for discharging the ions is formed inside the ion trap chamber 615 to eject the ions. The ions exiting from the ion trap chamber are led to the mass analyzer and the ion detector. Further, if the openings for vacuating 616 are formed in the upper and lower substrates 608, the ion trap chamber can be set to a desired level of vacuum.

In the ion trap-type mass analysis device shown in FIG. 40, the charged particle G enter the ion trap chamber 613 through the central hole 610 of the ring electrode 601-5 and further pass through the central hole 610 of the ring electrode 601-6 and exit from the ion trap chamber 613. But they can also pass through the end cap electrode 609. FIG. 41 is a view showing an ion trap-type mass analysis device in which the charged particles pass through an end cap electrodes 609. As the same processes can be used as are shown in FIG. 40(*a*) to FIG. 40(*i*), Figures corresponding to FIG. 40(*h*) and thereafter of FIG. 40, are shown in FIG. 41. Particularly, the parts that are different from those of FIG. 40 will be described in detail. In FIG. 41(*h*), an opening 614 is formed in the upper substrate 608, and a passage 618 is formed in the end cap electrode 609. When the end cap electrode 609 is attached to the upper substrate 608, the opening 614 and the passage 618 are attached so that they match. As a result, the opening 614 and the passage 618 make a passage that leads in a direction perpendicular to the substrate surface of the upper substrate 608. All others details are the same as those described in FIG. 40(*h*), FIG. 40(*i*), and FIG. 4(*j*). In FIG. 40(*j*), when attaching the upper substrate 608-1 side to the lower substrate 608-2 side, the upper passages 614-1 and 618-1 and the lower passages 614-2 and 618-2 are aligned so that they are on one straight line. It is preferable that the center line thereof passes through the center of the ion capturing space 615.

Next, as shown in FIG. 41(*k*), the second upper substrate 620 to which the second main substrate 619 is attached, is formed, thereby forming G penetrating chamber 621. An ionization chamber and an extraction electrode are arranged in the penetrating chamber 621. Each component is arranged so that the generated ions pass through passages 614-1 and 618-1. The support column 619-1 and 619-2 of the second main substrate 619 having the penetrating chambers 621 attached to the second upper substrate 620 having these functions are attached to the (first) upper substrate 608-1. They are aligned and attached to each other so that the ions generated in the penetrating chamber 621 pass through the passages 614-1 and 618-1 and enter the ion trap chamber 613.

Next, the second lower substrate 623, to which the third main substrate 622 is attached, is manufactured, and the penetrating chamber 624 is formed. An ion detection chamber is arranged in the penetrating chamber 624. Each component is arranged so that the ions ejected from the ion trap chamber 613 through the passages 614-2 and 618-2 to the penetrating chamber 624 enter the detection chamber. The support columns 622-1 and 622-2 of the third main substrate 622 having the penetrating chambers 624 attached to the second lower substrate 623 having these functions are attached to the (first) lower substrate 608-2. They are aligned and attached to each other so that the ions are ejected and that pass through the passages 614-2 and 618-2 enter the ion detection chamber.

In the ion trap-type mass analysis device shown in FIG. 40, the charged particles (ions) advance in parallel to the substrate surface, but in the case of the ion trap-type mass analysis device of FIG. 41 the charged particles (ions) advance perpendicularly to the substrate surface. If the size (height) of each chamber that has one main substrate is insufficient, the number of layers of the main substrates required may be attached, with each substrate having a required thickness. In this way, an ion trap-type mass analysis device that can move ions through a passage opened in the end cap electrodes can be manufactured. In the ion trap-type mass analysis device shown in FIGS. 40 and 41, the ring electrodes 601-5 and 601-6 are separated from the upper substrate and the lower substrate 608. But they may be formed in a way they are attached to each other without being separated. In that case, the ion trap space is surrounded by the ring electrodes 601-5 and 601-6. Therefore, the occupied area (volume) of the ring electrodes can be small. And the ring electrode manufacturing process can be simplified.

FIG. 48 is a view showing ion trap-type mass analysis device formed in the vertical direction as in FIG. 41. In ion trapping shown in FIG. 48, the ring electrode is not afloat but fastened. This ion trap-type mass analysis device comprises a substrate region B having an ion trap chamber, a substrate region A having an ionization chamber and an extraction electrode chamber, and a substrate region C having an ion detection chamber. In the substrate region A a penetrating chamber 914-2 serving as an extraction electrode chamber is arranged at the center, and penetrating chambers 914-1, 914-3 serving as ionization chambers for supplying ions to the extracted electrode chamber 914-2 are arranged. The extraction electrode chamber 914-2 and the ionization chamber 914-1 are separated by a substrate sidewall plate 911-3 having a central hole 915-1. The extraction electrode chamber 914-2 and the ionization chamber 914-3 are separated by a substrate sidewall plate 911-4 having a central hole 915-2. Ionization chambers using any of the various ionization methods described herein can be adopted. Also a sample supply chamber can be connected to this ionization chamber. Although two ionization chambers are provided here, one ionization chamber may be sufficient, or three or more ionization chambers may be connected to the extraction electrode chamber 914-2. Alternatively, externally generated ions may be introduced into the extraction electrode chamber 914-2.

The extraction electrode chamber 914-2 has a function of accelerating ions and sending them to the ion trap chamber at a certain speed. The upper surface of the main substrate 911 is attached to the upper substrate 912, and the lower surface of the main substrate 911 is attached to the lower substrate 913. Disk-shaped electrodes 917-1 and 917-2, of which centers are bored, are formed on the lower substrate 913 and an insulating film 918 is formed between the disc-shaped electrodes 917-1 and 917-2. If necessary, an insulating film 918 is also formed on the disk-shaped electrodes 917-1 and 917. If a voltage having a sign opposite to that of the ions is applied to the disc-shaped electrodes 917-1 and 917-2, the ions are drawn out from the opening 919 opened in the center of the disk-shaped electrodes 917-1 and -2, accelerated, and enter the ion trap chamber 904. If an ejecting electrode 916 is formed on the upper substrate 912 just above the disc-shaped electrodes 917-1 and 917, and if the voltage of the same sign as that of the ions is applied to the protruded electrode 916, the ions are pushed out and enter the opening 919. With this ejecting electrode 916, the movements of ions into the opening 919 can be improved.

The substrate region B is different from that of FIG. 41 in that the ring electrodes are each attached to the upper and lower substrates. That is, a penetrating chamber 904 whose center portion is narrowed is formed in the main substrate 901, and the substrate sidewalls 901-1 and 901-2 are tapered. There are various methods for forming this structure. For example, if a Si substrate is attached to a support substrate, and Si etching is performed from the upper side after it is masked with a photoresist, etc. Then half of the penetrating chamber having inclined surfaces of a tapered shape can be produced. The angle of this taper can be controlled by changing etching conditions. Subsequently, when the support substrate is removed and the same ones are attached together (for example, at a one-dot chain line M), the substrate region B having the penetrating chamber 904 having the shape shown in FIG. 48 can be manufactured. The conductive films 905 (905-1, 2) that are to become a ring electrode are deposited on the side surfaces of the substrate sidewalls 901-1 and 901-2 of the main substrate 901. If the main substrate 901 is a conductive film or a semiconductor substrate such as Si substrate, an insulating film is first deposited on the main substrate 901 and then a conductive film is deposited. Here, the ring electrode 905 (905-1, 905) has a substantially circular cross section on the surface that is parallel to the substrate surface and is made of a single electrode.

An end cap electrode 906 is formed on the upper substrate 902, and is disposed in a penetrating chamber 904, which is an ion trap chamber. An end cap electrode 908 is formed on the lower substrate 903, and is disposed in the penetrating chamber 904, which is an ion trap chamber. An opening 907 is formed in the center of the end cap electrode 906 and the upper substrate 902 of the substrate region B and the lower substrate 913 of the substrate region A are attached so that the axes of the opening 907 and the opening 919 are aligned. Therefore, the ions moving through the openings 919 and 907 are trapped in ion capturing space 910 that is at the center of the ion trap chamber 904.

The substrate region C has a penetrating chamber 924, which is an ion detection chamber, and an upper substrate 922 is attached to the upper surface of the main substrate 921, and a lower substrate 923 is attached to the lower surface of the main substrate 921. Parts 921-3, -4 of the main substrate 921 are left on the upper substrate 922. An opening 928 is opened in the center part, and around the peripheries of the parts 921-3,-4, in particular, the side surface of the opening 928 the conductive films 925-1 and 925-2 are formed. The opening 928 on the side of the upper substrate 922 has a shape of a hole. But the opening on the parts 921-3 and 921 of the main substrate have a shape of groove formed by parallel plates, and the conductive films formed on the side surfaces of the parts 921-3,-4, forms parallel-plates electrodes. The parts 921-5, 6 of the main substrate are left in the penetrating chamber 924 and their surfaces are parallel to each other and a space 924-2 is formed by the surfaces that are parallel. A secondary electron emission material film 926 (926-1, 2) is formed on the surface of the parts 921-5, 6 of the main substrate (when the main substrate is a semiconductor or a conductor, via an insulating film) and conductive films (on the top and bottom) are formed at both ends. Regarding the substrate region B and the substrate region C, the lower substrate 903 of the substrate region B and the upper substrate 922 of the substrate region C are attached so that the axes of the opening 909 and the opening 928 are aligned.

The ions trapped in the ion capturing space 910 are attracted by the electric potential of the end cap electrode 908 and enter the opening 928 of the substrate region C through the opening 909. Since the conductive film electrodes 925-1 and 925-2 formed on the side surfaces of the opening portion 928 of the substrate region C formed by the main substrate 921-3 and 4 are parallel plates electrodes, the orbits of the ions can be bent by adjusting the voltage. Accordingly, the bent ions collide with the secondary electron emitting material film 926-2 of the lower electrode and emit electrons e's. The emitted electrons e's are attracted by the electric field of the upper electrode and collide with the secondary electron emission material film 926-1 and emit the electrons e's. The emitted electrons e's are attracted by the lower electric field and collide with the secondary electron emission material film 926-2, and emit electrons e's. Since the number of electrons emitted by the collision is much larger than the number of electrons before the collision, the number of electrons increases as collision is repeated. The last electrons emitted after colliding with the edge of the secondary electron emitting material film collides with a conductive film formed on the side surface (inner surface) of the sidewall on the right end part of the substrate 921-2 of the penetrating chamber 924 (924-3) and generates current. By measuring this current, the quantity of the ions can be obtained.

The space 924-2 can be used as a central hole, in which a secondary electron emitting material film is formed on its inner surface. If conductive films are each formed at both ends of them and a (high) voltage is applied to the conductive films and if ions are introduced into the central hole 924-2 and caused to collide, similarly secondary electrons are emitted, whereby a change in the current can be measured by the conductive film electrode 927. In the substrate region C, the region of the lower main substrate 921-6 is larger than the region of the upper main substrate 921-5. But in the case of forming a central hole, since the upper and lower layers are attached to each other, one on top of the other, the difference of the sizes will not cause any particular problem. In this way, an ion trap-type mass analysis device of vertical-type having a plurality of ionization chambers can be manufactured. In the figures, wirings connected to the conductive films, contact wirings or outside electrodes are not shown. But since the wirings can be designed so as to be rerouted, the outside electrodes can be arranged at the desired locations. Also, neither gas inlet holes nor openings for vacuum drawing lines are described, but they can also be arranged at the desired positions.

<electron multiplier> The ion beam sorted in the mass analysis 308 enters the ion detection room 309. Various kinds of systems can be used as the ion detection systems arranged in the ion detection room. Here we explain about the secondary electron multiplier of a parallel plate type or a pipe shaped channel type. The ion detection room 309 is the penetrated room formed in the main substrate and is partitioned by the substrate side wall plate (substrate partition(ed) wall plate) 301-5. The upper portion of the penetrated room 309 is adhered to the upper substrate 302, and the lower portion of the penetrated room 309 is adhered to the lower substrate 303, and the side of the side surface of the penetrated room 309 is surrounded by the main substrate 301. The electrode 333 is formed on the lower surface of the upper substrate 302, and the electrode 332 is formed on the upper surface of the lower substrate 303. These electrodes 332 and 333 are constructed from the secondary electron emissive materials. The secondary electron emissive materials are the materials to emit easier electrons by getting the energy when the charged particles such as ions or electrons, etc. are impacted to them. There are MgO, Mg, Au, Pt, BeO, Cr, PoliSi, Al, Al2O3, TiN, and these compounds as the secondary electron emissive materials.

In the case of the parallel plate type, two sides of the main substrate 301 can be parallel plate electrodes by forming the secondary electron emissive materials on the side surfaces of the main substrate 301. (In that case, an insulating film is desirable sandwiched.) In the pipe shaped channel type secondary electron multiplier, the secondary electron emissive materials may be continuously connected as the electrode 333 on the lower surface of the upper substrate 302, the electrode 332 on the upper surface of the lower substrate 303, and the electrode formed on two side surfaces of the main substrate 301. Also, similarly to the substrate side wall having the central hole, the substrate side wall having the central hole is formed, and the electrodes consisted of the secondary electron emissive materials formed in the parallel plate type, or the electrodes consisted of the secondary electron emissive materials formed continuously on the inner surface of the central hole, and the secondary electron multiplier can be made.

Contact hole 323 (the conductive film is formed inside it) is formed in both edge of the electrodes 332, 333, outside electrodes 324 (324-1, 2, 3, 4) are formed in outside of the upper substrate 302, and the lower substrate 303. When high direct voltage is applied between the outside electrodes 324-1, 3 of the electrodes 332, 333 in the side of the entrance of the ion beam 331 and the outside electrodes 324-2, 4 of the electrodes 332, 333 in the side of the exit, the ion beam 331 impacts to the electrodes 332 or 333 consisted of the secondary electron emissive materials as shown by the arrow sign, secondary electron 334-1 is emitted, and the secondary electron 334-1 impacts to the electrodes 332 or 333 facing, and secondary electron 334-2 is emitted, and final secondary electron 334-$n$ is collected using collector 335 by multiplying electrons with electronic avalanche. The collector 335 is the portion where the secondary electron 334-$n$, come out of the output edge portion of the electrodes 332 and 333 consisted of the secondary electron emissive materials impacts, for example, is conductive film formed on the side surface of the main substrate 301-6 that is the final edge in the longitudinal of the ion detection room 309. The collector 335 connects the outside electrode 324-5 through contact hole 323. Since direct voltage to lead the secondary electron 334-$n$ is applied between the output edge portion electrodes 324-2, 4 consisted of the secondary electron emissive materials in the ion detection room 309 and the collector electrodes 324-5 connecting to the collector 335, the secondary electrons 334-2 are almost collected to the collector 335 and collector current is detected through the collector electrode 324-5.

In the parallel plate type, since the inclined electric field can be formed by displacing the both edges of the electrodes 332 and 333 each other, and the motion of electrons can be made near cycloidal motion, the collector current can increase.

FIG. 42 is the diagram showing the ion detection room where many dynodes using the present invention are arranged. FIG. 42(*a*) is the cross sectional schematic diagram in the parallel direction to the substrate surface, FIG.

42(b) is the cross sectional schematic diagram in the vertical direction to the substrate surface. The neighbor room of the ion detection room 637 is the mass analysis room, these rooms are partitioned by the substrate side wall (partitioned wall) 631-2-1 and 631-3-1 (these are one continuous side wall, and have the central hole 630 (630-1)), and the ion detection room 637 becomes a low pressure by vacuumizing through the opening portion 647 for vacuumizing opened in the upper or lower substrate 641, 642. The ion beam 630 entering the ion detection room and going out the mass analysis room passes the central hole 630 (630-2) of the substrate side wall (partitioned wall) 631-2-2 and 631-3-2 (these are one continuous side wall) having the central hole 630 (630-2). The conductive films 633-1 and 633-2, which constructs the parallel plate electrodes on the right and left side wall plate of the central hole 630 (630-2), are formed. One electrode 633-1 connects to the outside electrode 646-0 through the contact hole (conductive film is deposited in it) 645 opened in the upper substrate 641, and the other electrode 633-2 connects to the outside electrode 644-0 through the contact hole (conductive film is deposited in it) 643 opened in the lower substrate 642. Electric field generates between the parallel plate electrode 633-1 and 633-2 and the ion beam 639 is curved in the orbital by applying voltage to the outside electrodes 644-1 and 646-1. If parallel plate electrodes are formed in the central hole, since the distance is small and the large electric field generates even small voltage, the ion beam can be curved easily. Accordingly if a small voltage may not be applied, the conductive film 633-1 and 633-2 for the parallel plate electrodes may be formed in a part of the side surface 631-2 and 631-3 of the main substrate 631. The conductive film is, for example, Cu, Al, W, etc.

Plural main substrate 631-2-3-1 to 631-2-3-*n* (in the side of the side surface 631-2 of the main substrate) and 631-3-3-1 to 631-3-3-*m* (in the side of the side surface 631-3 of the main substrate), which are projected from the side surface of the main substrate in the right and the left to the inside of the ion detection room 637, are formed in the ion detection room 637, and the secondary electron emissive material films 632 (632-1, . . . , 632-*n*) and 635 (635-1, . . . , 635-*m*) via insulating film (for example, SiO2 film, SiNxOy film, SiNx film) are formed on the convex portion 631-2-3-1 to 631-2-3-*n* and 631-3-3-1 to 631-3-3-*m*. After the secondary electron emissive material film is deposited using, for example, CVD method, PVD method, or plating method, it is formed using photolithography method and etching method, the insulating film covers at least the surface of the convex portion 631-2-3-1 to 631-2-3-*n* and 631-3-3-1 to 631-3-3-*m* from the side surface 631-2 and 631-3 of the main substrate. Since the secondary electron emissive material films are semiconductor or conductor, they are not made conduct each other in the neighbor portions. Accordingly, insulating film (SiO2 film, etc.) is ordinarily deposited between the main substrate 631 and the secondary electron emissive material 632, the unnecessary portions are etched and removed using photolithography method and etching method so that the secondary electron emissive material films formed on the convex portions 631-2-3-1 to 631-2-3-*n* and 631-3-3-1 to 631-3-3-*m* do not conduct electrically each other. Next conductive film is deposited, and the conductive film wiring patterns 634 (634-1, . . . , 634-*n*) and 636 (636-1, . . . , 636-*m*) are formed so that they contacts with a part of the secondary electron emissive material films 632 formed the convex portion 631-2-3-1 to 631-2-3-*n* and 631-3-3-1 to 631-3-3-*m*. The above process can be performed simultaneously with the formation of the conductive film 633-1 and 633-2 for the parallel plate electrode.

The convex portions 631-2-3-1 to 631-2-3-*n* and 631-3-3-1 to 631-3-3-*m* are can be formed when the penetrated room (the ion detection room) 637 is formed. For the pattern formation of the secondary electron emissive material films 632, the photosensitive film pattern is formed on the almost vertical side surface to the surface of the main substrate 631, and though the secondary electron emissive material films 632 and the conductive film 633 need be etched and removed by the mask the pattern, after the photosensitive film pattern is formed using an method to expose using the photosensitive sheet and as electro casting resist method, the process can be performed using an isotropic etching (dry or wet). For the exposure method can be performed using inclined irradiation exposure method or inclined rotating exposure method, if focus depth is deep, vertical irradiation can be available. Electron radiation exposure method can be used. Since thick resist film can be exposed in the case of the exposure method of deep focus depth, the photosensitive film can be formed using coating method. Since these conductive film patterns 633, 634, 636 are formed on the lower surface of the upper substrate 641 and on the upper surface of the lower substrate 642, the contact holes 645 and 643 in the upper substrate 641 and the lower substrate 642 to the portions, and conductive films are formed in the contact holes, and on them conductive film electrode wiring 646 (646-0, 1, . . . *n*, n+1) and conductive film electrode wiring 644 (644-0, 1, . . . , *m*) are formed. Thus voltage can be applied to the conductive pattern 633, 634, 636.

After the ion beam 639 enters the ion detection room 637, since the ion beam 639 can be curved in the orbital by the electric field generating in the parallel plate electrodes 633 (633-1, 2) mentioned above, it can be irradiated to the secondary electron emissive material film of the nearest concave portion 631-2-3-1. Particularly if the reverse voltage to the charge of the ion beam is applied to the secondary electron emissive material film 632-1 connecting to the conductive film 634-1 through the conductive film 634-1, the ion beam can be irradiated getting the energy additionally. If voltage is applied to the secondary electron emissive material film 632-1, the parallel plate electrode 633 (633-1, 2) may not be equipped. Well, if the parallel plate electrode 633 (633-1, 2) is equipped, the ion beam can be irradiated to the given portion by controlling the voltage. The secondary electrons 640 are emitted by impacting the ion beam 639 to the secondary electron emissive material film 632-1.

If plus voltage is applied to the secondary electron emissive material film 635-1 formed in the concave portion 635-3-3-1 formed in the facing side surface 631-3 from the conductive film 636-1 (the voltage need be set at more plus side than electric potential in the secondary electron emissive material film 632-1 so that the secondary electro do not return, and the voltage conditions may be set at the optimized value with measuring), almost the secondary electrons emitted from the secondary electron emissive material film 632-1 enter the secondary electron emissive material film 635-1 and the secondary electrons are emitted additionally. By this repeated, major amounts of secondary electrons 640-*p* are emitted by multiplied from the secondary electron emissive material film 632-*n* formed on the concave portion 631-2-3-*n* of the final stage, they are collected to the collector conductive film 638. Voltage can be applied to the collector conductive film 638 from outside electrode wiring 646-(*n*+1) through contact 645, if the voltage is in more plus side than the potential of the secondary electron emissive material film 632-*n*, almost the secondary electrons are irradiated to the collector conductive film 638, and the current generated by the secondary electrons can be detected.

For example, in the case where incident ions 639 are plus, the ions 639 are curved to the side of the main substrate 631-2 by applying minus voltage to the parallel plate electrode 633-1, also minus voltage (for example, −aV) may be applied to the secondary electron emissive material film 632-1. In addition, the secondary electrons 640-1 impact to the secondary electron emissive material film 635-1 by applying voltage (for example, (−a+b) V) of more a little plus side than −aV to the secondary electron emissive material film 635-1 that is impacted next. Thus applying the voltage (fore example, bV) of more a little plus side than the dynode in the front stage to the dynode in the next stage, voltage of cV is applied to the secondary electron emissive material film 632-n in the final stage (for example, c=−a+n×2b). Additionally, by applying the voltage of (c+d)V to the collector 638, secondary electrons 640-p emitted from the secondary electron emissive material film 632-n collect almost to the collector 639. Though the values of a, b, c and d may be determined from actual measurement, since the ion detection room 637 of the present invention is very small and can be made very accurately using LSI process, high electric field can be get even if the values of a, b, c and d are small. For example, if the distance between the secondary electron emissive material films formed on the substrate side surfaces 631-2 and 3 is 1 mm, and a=10V-500V, n=10, m=9, we can select a=0.5V-25V, c=0V, d=1-50V. Also, if the distance between the secondary electron emissive material films formed on the substrate side surfaces 631-2 and 3 becomes longer, for example, the above value may be set by multiple number.

FIG. 42(b) is the cross sectional schematic diagram in longitudinal direction (vertical direction to the substrate surface) of the ion detection room 637, and a part of the structure in the cross sectional direction (vertical direction to the paper surface) are shown by overlapping. For example, Though the parallel plate electrode 633(633-1, 2), the contact holes 643, 645m, and the electrode wiring 644-0, 646-0 are not necessarily arrange at the same level, all structures are drawn to understand their relation. Well, the transparent patterns are used relating to the portions that are not arranged in the same cross sectional position. Since such relation is known at soon, they are adopted in the other portions. Though the area of the collector 638 is drawn as the same size as the ion detection room 637, since the size in the lateral direction (the longitudinal direction in FIG. 42(a)) can be taken larger, if the area 637-A where the collector 638 is arranged is extended in the lateral direction and the area of the collector 638 are extended, more secondary electrons 640-p can be caught.

FIG. 42(c) is the cross sectional schematic diagram of A-A' portion in FIGS. 42(a) and (b), and the diagram seen from the right and left direction of FIGS. 42(a) and (b). Though the dashed line shows a boarder line between the side surface 631-2 of the main substrate 631 and the concave portion 631-2-3 that becomes the dynode portion, since they are the same main substrate and the boarder line is not seen, the dashed line 647 is drawn by extending the main substrate side surface in the portion where the concave portions do not exist in the cavity that becomes the ion detection room in the other portions. Similarly the dashed line 6478 shows the boarder line between the side surface 631-3 of the main substrate 631 and the concave portion 631-3-m that becomes the dynode portion. The secondary electron emissive material film 632 and 635 are respectively deposited on the surface of the concave portion 631-2-3 and the concave portion 631-3-m from the lower surface of the upper substrate 641 to the upper surface of the lower substrate 642. The conductive film 636 is deposited additionally on the surface of the secondary electron emissive material film 632 from the lower surface of the upper substrate 641 to the upper surface of the lower substrate 642. Thus since the conductive film 636 and the secondary electron emissive material film 632 contact in the wide area, though the case where the secondary electron emissive material films 632, 635 are the conductive films is not surprising, in the case where the secondary electron emissive material films 632, 635 are the semiconductor film, the sufficient voltage is applied to the secondary electron emissive material films 632 from the conductive film 636. Of course, the portion where the concave portion exists is narrower than the concave portion does not exist. Well, insulating film is formed between the secondary electron emissive material films 632, 635 and the main substrate 631, they can be made conduct each other, additionally insulating film can be formed as passivation film on the conductive film 636 and the secondary electron emissive material films 632, 635. Since small patterns such as contact hole or via, etc. may not be formed in the penetrated room, accurate patterning in the portion that becomes the convex portion such as the penetrated room is not needed and it is easy to form them.

FIG. 42(d) is the cross sectional schematic diagram of B-B' portion in FIGS. 42(a) and (b), and the diagram seen from the right and left direction of FIGS. 42(a) and (b). The conductive film 633 (633-1, 2) for the parallel plate electrode in the right and left sides of the inner surface of the central hole 630-2 is formed. These conductive films 633 (633-1, 2) are extended to the upper substrate 641 or the lower substrate 642 as written in FIGS. 42(a) and (b), the voltage can be applied from the outside electrode wiring 646-0 or 644-1. The main substrate 631 is divided in the upper and lower portions as explained above, the central hole 630 and the conductive film 633 can be formed by adhered respectively to the upper substrate 641 and the lower substrate 642, and they may be stuck. The portion stuck (adhesion portion) is shown by the dashed line 649.

It is easy to irradiate the ion beam 639 at the constant angle to the pattern of the secondary electron emissive material films 632 when the shape of the concave portion 631-2-3-1 to n and 631-3-3-1 to m formed almost vertically in the thickness direction of the main substrate 631 as shown in FIG. 42(a). Additionally since the secondary electrons are easy to enter the inclined surface facing at almost the constant angle in the incident angle, the design and the condition selection are easy. Inclined angle of the concave portion 631-2-3-1 that is dynode portion where the ion beam is irradiated and that is nearest in the side of the entrance of the ion beam 639 is $\alpha 1$, inclined angle $\beta 1$ of the concave portion 631-3-3-1 that is dynode portion facing where the secondary electrons coming out of them are irradiated, inclined angle is $\alpha n$ of the concave portion 631-2-3-n that is dynode portion of n numbers in the side of the side surface 631-2 of the main substrate 631, inclined angle is $\beta m$ of the concave portion 631-3-3-m that is dynode portion of m numbers in the side of the side surface 631-3 of the main substrate 631. Then the inclined angle may be 10 digree $<\alpha 1, \ldots, \alpha n < 45$ degree, 10 digree$<\beta 1, \ldots, \beta m < 45$ degree. Irradiated angle of ion beam, emission rate of the secondary electrons and irradiation angle are easy to control by selecting the above value. Well, if the inclined angle becomes smaller, the ion detection room need become longer. If the inclined angle becomes larger, the ion detection room can be shorter.

A surface shape of the concave portions 631-2-3-1 to n and 631-3-3-1 to m can be curved shape. For example, the main substrate is divided in two portions in the upper and lower, when respective the concave portions 631-2-3-1 to n and 631-3-3-1 to m are formed, the concave portions 631-2-3-1 to n and 631-3-3-1 to m are etched in the curved shape or in the inclined shape using wet etching or dry etching that can control etching speed of the etching in the lateral direction (or side etching) and the etching in the longitudinal direction (or thickness direction of the main substrate), and these may be adhered in the center portion. If the surface shape of the concave portions 631-2-3-1 to n and 631-3-3-1 to m becomes such the inclined face or the curved face, since the secondary electrons, etc. can be concentrated on the surface of the concave portions 631-2-3-1 to n and 631-3-3-1 to m, more secondary electrons can generate.

FIG. 43 shows one embodiment of the method to make the parallel plate electrodes shown in FIG. 42. The difficulty in the method of the parallel plate electrodes 633-1, 2 is to form the electrodes in the side surface of the central hole 630-2. In FIG. 43, only state near the parallel plate electrodes shown in FIG. 42. In FIG. 43, the main substrate is divided into half portions of the upper and lower portions. FIG. 43(a)-(e) are plane diagrams (parallel to the surface of the main substrate), and FIG. 43(f)-(k) are the vertical cross section to the plane diagram. The photosensitive film pattern 653 is formed on the surface of the main substrate 651 adhered to the lower substrate 652, and the portion forming the central hole is opened (FIG. 43(e)), the convex portion 654 that becomes the central hole is formed from the opening portion in the main substrate 651. The depth of the convex portion 654 is about half of the depth of the real central hole (the central hole 630-2 in FIG. 42). The central hole 654 should be etched as vertically as possible since the parallel plate electrode is made in the side surface of the central hole 654. FIG. 43(g) shows the state where the photosensitive film pattern 653 is removed.

Next the window of the photosensitive film 655 in the portion that becomes the ion detection room is opened. The photosensitive film 655-2 is a pattern forming the substrate side wall having the central hole 654, and the photosensitive film 655-3 is the pattern forming side surfaces of the substrate 651 in the portion that becomes the ion detection room, and the opening portion is the portion that becomes the ion detection room. (FIG. 43(b)) The main substrate 651 in the portion that becomes the ion detection room is etched using these photosensitive film patterns as mask. These etching may be vertical etching or taper etching. When the substrates in the upper and the lower are fitted later, the upper surface may be made with the size controlled. FIG. 43(c) shows the state after the main substrate 651 in the portion that becomes the ion detection room is etched and the photosensitive film 655 is removed, and there the main substrate 651-2, 3 that become the side surface of the ion detection room, and the substrate side wall 651-1 having the central hole 654-1, and the lower substrate 652 that becomes the lower surface of the ion detection room are shown. The portions in the longitudinal direction (the travelling direction of the ion beam in the central hole) may be made larger than the real central hole 654-1 by considering the etching deviation and the mask moving deviation.

Next insulating film is formed on the main substrate 651, (the insulating film is not written, when the main substrate is insulator, the insulating film may not be deposited.) and conductive film 656 is deposited, and photosensitive film pattern 657-1 to make the parallel plate electrodes and photosensitive film patterns 657-2, 3 to make wiring are formed. Since these photosensitive film patterns are formed on the step portions, the patterning is performed using photosensitive sheet film, electrocasting resist film, large focus depth exposure method, inclined exposure method, rotating exposure method. (FIG. 43(d)) The conductive film pattern 656 is etched using the photosensitive pattern as mask, and the conductive film patterns 656 (656-1, 2, 3) are formed. FIG. 43(e) is the plane diagram after the photosensitive film pattern 657 is removed, and the conductive films 656-1 are the electrodes formed on the right and left side surfaces of the central hole 654-1, and the conductive films 656-2, 3 are wiring patterns formed in the lower substrate 652. A-A' cross section in FIG. 43(e) is FIG. 43(h), and the conductive film electrode 656-1 is formed on the right and left side surface of the central hole 654 formed in the central portion of the side wall 651-1 of the main substrate 651. B-B' cross section in FIG. 43(e) is FIG. 43(i), and the conductive film electrode 656-1 is formed on the side surface of the central hole 654, and the conductive film electrode 656-1 connects to the wiring patterns 656-2, 3 formed in the lower substrate at the step of the side wall 651-1. Though the conductive film 656 is formed using PVD method or PVD method, then the conductive film 656 becomes thinner at the step, but since the conductive film is deposited thickly using plating method or selective CVD method, etc., their films are connected electrically sufficiently. Additionally since the step is tapered if taper etching is performed when the main substrate 651 is etched, their conductive films are connected sufficiently. Well, insulating film between the conductive film 656 and the main substrate is not written in FIG. 43(i).

The same portions are formed in the side of the upper substrate 658, and the ion detection room where the side surfaces formed in the central hole become the electrodes of the parallel plate electrodes is formed by adhering the lower substrate 652 and the upper substrate 658. After adhering the side of the lower substrate 652 and the side of the upper substrate 658, the contact holes 659 (659-1, 2) and 660 (660-1, 2) are formed, and the conductive film is formed in the contact holes, and the electrode wirings 661 (661-1, 2) and 662 (662-1, 2) connecting to their contact holes are formed. (These contact holes and electrode wirings are formed before adhered.) The connection between the conductive film wirings 656-2 and 4, and the connection between the conductive film wirings 656-3 and 5, and the connection between the conductive film wirings 656-1 (656-1-1, 2) formed on the side surface of the central hole 654 are performed when they are adhered, for example, by pressure bonding. Or they can also be adhered using the adequate thermal treatment, or fusion method When they are adhered using the adhesive agency, if they are pressed and bonded using the adhesive agency containing dispersed conductive particles, only the portions where the conductive films exist can be connected. Since the parallel plate electrodes are formed on the side surface of the central hole using the simple process as mentioned above and the voltage can be freely applied from the outside of the ion detection room, the orbital of the ion beam can be changed under the given conditions. Since the electrodes can be separated on the way of the central hole, the voltage can be applied to the respective electrodes, and the orbital of the ion beam can be changed in front stage of the parallel plate electrodes and the back stage of the parallel plate electrodes respectively, the ion beam can be controlled more accurately. Additionally since the parallel plate electrodes can be formed easily in the upper and lower portions of the central hole (The photosensitive patterns are formed in the upper and lower portions of the central hole, the conductive film in the side surfaces may be etched and removed.), the ion beam can be controlled in the upper and lower directions. Accordingly since the ion beam can be controlled in the right and left directions and in the upper and lower directions while the controls in the right and left directions and the control in the upper and lower directions are performed, the ion beam can be irradiated to the desirable portions of the dynodes or channel electrodes.

FIG. 44 is the diagram showing the embodiments applying the central hole of the invention to channel type secondary electron multiplier. The side wall 671-3 having the central hole 674-3 of length L in the ion detection room 677 is formed. The ion detection room 677 is a cavity room where a part or all of the main substrate between the upper substrate 672 and the lower substrate 673 are hollowed in the sate where the upper substrate 672 and the lower substrate 673 and the main substrate 671 are adhered. The ion detection room 677 has the substrate side wall (partition wall) 671-1 separating between the ion detection room 677 and the neighbor room and having the central hole 674-1, wherein the neighbor room, for example, the mass analysis room where the ion beam 678 entering, the parallel plate type electrode 676-1-1, which make the ion beam impact to the given inner surface of the central hole 674-3 of the channel type secondary electron multiplier 680 by curving the ion beam 678, the substrate side wall 671-2 having the central hole 674-2 where the ion beam travel, the channel type secondary electron multiplier 680, the collector electrode 676-4 where the secondary electrons 679-n emitted from the channel type secondary electron multiplier 680 irradiate, the substrate side wall 671-4 making collector electrode film deposit and supporting the collector electrode 676-4. In the present invention, the collector electrode can be deposited using the same process as the other conductive film. For example, penetrated room 677 is formed in the main substrate adhered to the lower substrate 673 or the upper substrate 672, after that, if the main substrate is conductive substrate (for example, Fe series, Cu series, Al series, conductive C series) or semiconductor substrate (for example, Si series, C series, compound series), after insulating film (for example, SiOx, SiOxNy, SiNy) is deposited, conductive film (for example, Ti series, Cu series, Al series, conductive C series, W series, Silicide series, conductive poly-Si series, Mo series, Ni series, Au series, Ag series) is deposited, and the desirable patterning may be performed. After that, the side of the upper substrate and the side of the lower substrate may be adhered. Though the collector electrode 676-4 is drawn as formed in the side surface 671-4 of the substrate side wall 671 to the travelling direction of the ion beam 678, it may be formed as catching most secondary electrons 679-n. For example, the central portion of the substrate side surface 671-4 may be put a dent. This can be made by isotropic etching or side-etching controlled when the side wall side surface 671-4 (half portion divided) is formed. Also, we can simply make the side surface 671-4 of the substrate side wall 671 incline to the travelling of the ion beam 678. Additionally the ion detection having the collector electrode (the ion detection room from coming out of the area 680 that becomes the secondary electron multiplier) may be made by extending in the direction of the main substrate side surface (right angle to the thickness direction of the main substrate and the right angle direction to the paper of FIG. 44).

Though the parallel plate electrode 676-1 (675-1-1, 2) in FIG. 44 is the electrode formed in the central hole similarly to FIG. 43, it is different from FIG. 43 in the point that the electrodes are the parallel electrodes to the surface of the upper substrate 672 and the lower substrate 673 and the main substrate. (The electrodes shown in FIG. 43 are formed in the vertical direction to the surface of the upper substrate 672 and the lower substrate 673 and the main substrate.) Though the formation method is as written previously, after conductive film 676-1-1 is formed, the bottom surface side of the central hole 674-2 is covered by the photosensitive film, and the photosensitive film in the side of the side surface is removed, the conductive film in the side of the side surface may be etched and removed using their patterns as mask. Or without using the substrate side wall, the upper electrode is formed on the lower surface of the upper substrate 672, and the lower electrode is formed in the lower substrate 673, thus the parallel plate electrode can be made. In that case, after the main substrate 671 is adhered to the upper substrate 672 or the lower substrate 673, the penetrated room is formed, after that, insulating film and conductive film are formed, and the photosensitive film is patterned and the upper electrode is formed on the lower surface of the upper substrate 672, and the lower electrode is formed on the upper surface of the lower substrate 673, thus the structure of the parallel plate electrode can be constructed, or after the upper electrode and the lower electrode are respectively formed in the upper substrate 672 and the lower substrate 673, the main substrate 671 where the penetrated room or the convex portion is formed previously is adhered to them (the patterns of the upper electrode and the lower electrode are fitted to the penetrated room or the concave portion), thus the structure of the parallel plate electrode can be constructed. (in the case of the concave portion, after adhered, the main substrate need be etched and removed so that they become the perfect penetrated room.) If the distance between the upper electrode and the lower electrode of the central hole is d, since electric field e=V/d, the ion orbital can be changed by changing d and/or V. Namely when the amount of changing of the ion orbital is obtained at the same value, if d is small, the application voltage V may be small. When d become largest, it becomes the case where the main substrate does not the side wall, then d almost equals to the thickness of the main substrate. (Really, the thickness of insulating film and conductive film need be considered.)

Next we explain about the secondary electron multiplier 680. If we use the present invention, the channel type secondary electron multiplier can be made by the simple process. Namely the substrate side wall 671-3 having the central hole 674-3 of length L is formed. The main substrate 671 is divided into 2 portions, and the concave portion (depth d/2, width e) is made similarly to the previous explanation. If vertical etching method is used, the cross section becomes the concave portion of rectangular geometry, and if side etching method is used, the cross section becomes the inclined concave portion (trapezoidal geometry may be called). (there is a case of a little curved shape.) Next the substrate side wall 671-3 of the main substrate 671 is formed. (This length becomes the channel length of the secondary electron multiplier.) Namely the main substrate 671 except the substrate side wall 671-3, etc. (other substrate side wall patterns are contained) is etched, and the ion detection room 677 of the penetrated room is formed. After that, insulating film and secondary electron emissive material 675 are deposited in the concave portion 674-3, substrate side wall 671-3 and the penetrated room, etc., next the secondary electron emissive material 675 in the area except the concave portion 674-3 and the side surface portions (and the upper substrate 672, in the lower substrate 673, the necessary portions in the side surface of the penetrated room 677 of the substrate 671) of both edges of the substrate side wall 671-3 is etched as shown in FIG. 44. Next the conductive film 676 is deposited, wiring 676-2 (676-2-1, 2) and 676-3 (676-3-1, 2), the other wiring 676-1 (676-1-1, 2) and the collector electrode 676-4, etc. are formed so that they contact with the both edge portions of the secondary electron emissive material 675. After that, passivation film (for example, SiOx, SiOxNy, SiNy) protecting the conductive film 676 may be formed. After that, the side of the upper substrate and the side of the lower substrate are adhered.

FIG. 44(*b*) is the cross sectional schematic diagram of A-A' portion in FIG. 44(*a*) after adhesion. The central hole 674-3 is surrounded by the insulating film 681 and the secondary electron emissive materials 675 deposited on the insulating film 681. The secondary electrons travel with multiplying through the cavity portion 674-3. Namely ion beam 678 impacts the secondary electron emissive materials 675 near entrance formed in the cavity (called channel), there secondary electrons 679-1 generate. Voltage V is applied between the electrodes 676-2 (676-2-1, 2) in the side of the entrance of the secondary electron multiplier 680 and the electrodes 676-3 (676-231, 2) in the side of the exit of the secondary electron multiplier 680, (here the voltage in the side of the entrance makes more minus than the voltage in the side of the exit. For example, when the voltage in the side of the exit is 0V, and the voltage in the side of the entrance is −P0V (Po>0), as approaching to the side of the exit, since the secondary electron multiplier becomes more plus side voltage, the number of electrons emitted increases while electrons impact the secondary electron emissive materials in succession. In the exit, if the voltage of the collector 676-4 is set at the more plus side than that of the electrode 676-3 (675-3-1, 2) in the side of the exit, (for example, the voltage in the side of the exit is 0V, the collector voltage is Q0V (Q0>0)) the last secondary electrons **679-*n* are collected to the collector 676-4, and the collector current can be detected. Since the shape of the central hole 674-3 can be changed optionally when the concave portion is etched, we can select the optimized shape. If the side surface of the concave portion or the secondary electron emissive materials in the lower and upper portions is removed, the parallel plate shaped electrode of the secondary electron emissive materials can be formed. If the secondary electron emissive materials are deposited on the upper substrate, the lower substrate, and the side surface (vertical direction to the paper face in FIG. 44) of the main substrate 671, the channel type (the parallel plate type and pipe type (the secondary electron emissive materials connect inside) can be made) secondary electron multiplier with depth d (almost the same as the thickness of the main substrate 671) and width e (almost half width of the side surface) can be made Additionally though it is difficult to increase channel depth d (thickness direction of the main substrate) gradually, since it is easy to increase channel width e (the side surface direction of the main substrate, namely the vertical direction to the paper face of FIG. 44) gradually in the travelling direction of the charged particles, the inclined electric field can be easily made. Accordingly, the inclined electric field can be realized even if the channel length L is not lengthened much. Though the ion beam can be controlled in the upper and lower (method of FIG. 44) and in the right and left (methods of FIG. 42, FIG. 43) by applying the electric field using the parallel electrodes, since the secondary electrons generated are drawn by the electric field by corresponding to the position of the secondary electron emissive materials impacted firstly in the secondary electron multiplier 680, if the structure of the secondary electron multiplier 680 is the parallel plate type, the structure of the electrode can multiply the secondary electrons without problems even if the structures of the electrode are upper and lower type or right and left type. Or even if the parallel plate electrodes changing the ion beam orbital do not exist, if the ion beam directly enter the secondary electron multiplier 680**, the ion beam is drawn by the electric field and impact the secondary electron emissive materials and thus the secondary electrons generate, after that, the secondary electrons are drawn and thus the multiplication of the secondary electrons can be realized. If the parallel plate electrodes, since the ion beam can be irradiated to the desirable portion of the secondary electron emissive materials, the secondary electron multiplier can be lessen in length and width (d and e).

FIG. 45 shows one embodiment of the cross section (vertical direction to substrate surface) of the mass analyzer using Si substrate (more than 4 inches) where the glass substrate adhered to the upper and lower surface. The present mass analyzer includes the sample feeding portion, ionization portion, drawing electrode portion, mass analysis portion, and ion detection portion. Sample gas or sample solution supplied from the sample feeding portion is atomized or gasified in the exit of the sample feeding portion, and are ionized in the ionization portion where high electric field is applied. The ions generated are extracted by extraction electrode in the extraction electrode and acceleration electrode portion, and accelerated and decelerated and focused and enter the mass analysis portion having electric field room and magnetic field room, and are selected corresponding to value of m/z (mass charge ratio, m: mass, z: charge) in the mass analysis portion, and are emitted to the ion detection room. In the ion detection room, amount of ions is detected as current by electron-multiplying the ion charge. The present invention is multi substrate type device of the mass analyzer (GC-MS, LC-MS) combining with gas chromatograph and liquid chromatograph, etc. (Of course, the present invention can apply to solid sample.) Name of each part in FIG. 45 is as follows. Though their numbers may be overlapped with the number in the other figures, here they are these names.

Si substrate, 1-1 first Si substrate side wall (plate) (side partition wall (plate)), 1-2 second substrate side wall (plate), 1-3 third substrate side wall (plate) (for extraction electrode), 1-4 forth substrate side wall (plate), 1-5 fifth substrate side wall (plate), 1-6 sixth substrate side wall (plate), 1-7 seventh substrate side wall (plate) (for multiplier formation), 1-8 eighth substrate side wall (plate), 2 upper substrate, 3 lower substrate, 4 penetrated room, 4-1 ionization room, 4-2 extraction electrode room, 4-3 mass analysis room (electric field room), 4-4 mass analysis room (magnetic field room), 4-5 ion detection room, 5 contact wiring (upper substrate), 6 contact wiring (lower substrate), 7 outside electrode (on upper substrate), outside electrode (on lower substrate), 9 upper side conductive film electrode wiring, 10 lower side conductive film electrode wiring, 9-1 ionization room upper electrode, 10-1 ionization room lower electrode, 9-2 substrate side wall (plate) conductive film electrode (extraction electrode), 10-2 substrate side wall (plate) conductive film electrode, 9-3 substrate side wall (plate) conductive film electrode (upper side), 10-3 substrate side wall (plate) conductive film electrode (lower side), 9-4 multiplier applying electrode (upper side), 9-5 multiplier applying electrode (upper side), 10-4 multiplier applying electrode (lower side), 10-5 multiplier applying electrode (lower side), 11 central hole, 11-1 central hole (sample inlet), 11-2 central hole (second substrate side wall (plate)), 11-3 central hole (for extraction electrode), 11-4 central hole (forth substrate side wall (plate)), 11-5 central hole (fifth substrate side wall (plate)), 11-6 central hole (sixth substrate side wall (plate)), 11-7 central hole (for multiplier), 12 secondary electron emissive material film, 13 sample inlet (longitudinal hole), 14 opening portion (upper substrate), 15 cooling hole, 16 opening portion (lower substrate), 17 sample inlet line, A sample (liquid, gas), A-1 spray gas, B-1 coil (upper side), B-2 coil (lower side)

The sample feeding portion and the ionization portion apply an electrospray ionization (ESI) method to the present invention. Since the liquid (sample liquid) containing a target substance (sample) is used as sample. Accordingly it is one of liquid chromatograph (LC)—ESI method. The sample liquid enter from arrow A. Since the central hole (sample inlet tube) 11-1 becomes capillary, the sample liquid extends at the portion where it enters the ion detection room, it atomizes (gasifies) (It is shown by sign A, also called spray gas.) Since conductive film 9-7, 10-7 for heating can be also formed in the central hole (sample inlet tube) 11-1, the sample can be heated. Or hot liquid or gas is flowed in the concave portion 15, and thin film resister is formed and heated electrically, and the temperature of the central hole 11-1 can increase.

High voltage of 2000V-4000V can be applied from the outside electrodes 7-1 and 8-1 to the conductive film electrode 9-7 and 10-7 in the inner surface of the central hole 11-1 that is the capillary. (Facing electrode is the conductive film electrode 10-2-1 on the substrate side wall plate 1-2.) Thus the sample liquid passes the central hole 11-1 of the capillary, and it becomes liquid drop (spray gas) A-1 charged in the exit 18 of the ionization room 4-1, and it is emitted to the penetrated room 4-1. The penetrated room 4-1 can be heated using a pat of the conductive film electrode 9-1 and 10-1, and the opening portion 16 is opened in the upper and lower substrates and connected to pump, and the solvent gasified can be soon exhausted. Also since the central hole 11-1 can be heated as mentioned already, the gasification of the sample liquid A can be assisted. Thus the charged liquid drop (spray gas) is atomized and dried, and the sample is ionized.

Electron ionization (EI) is explained base on FIG. 47. The ionization room 34-1 is the penetrated room formed in Si substrate 31 where the upper substrate 32 and the lower substrate 33 are adhered to the upper and lower surface of Si substrate, and sample gas is introduced from the opening portion 42, and the ionization room 34-1 is vacuumized from the opening portion 43 and becomes low pressure. Filament 41 of W, etc. film is formed on the lower substrate, and the current is passed from the outside electrodes 38-1 and 38-1-2, and the filament 41, and the filament 41 is heated, and thermal electrons (e) generate. The thermal electrons (e) fly to electron trap electrode 39-1-2 formed on the upper substrate surface facing. (Ionization voltage 50V-100V) The sample gas G introduced into the ionization room 34-1 is ionized by the thermal electrons. (M+e-→M+2e-) The generated ions are pushed out from the conductive film electrode (repeller electrode) 40-1 formed on the side surface of the substrate side wall 31-1, and they are sent to the extraction electrode acceleration electrode room 34-2 from the ionization room. The ions are accelerated by the extraction electrode acceleration electrode 40-2-1 in the extraction electrode acceleration electrode room 34-2, and they enter the next mass analysis room showed in FIG. 45, etc. If necessary, the electrodes are lined up, the ions are accelerated and focused.

Electromagnet coil B-5 is arranged on the outside of the upper substrate. (Lower side N pole) Electromagnet coil B-4 is arranged on the outside of the lower substrate. (Upper side N pole) Thus the ionization room is sandwiched by the electromagnets, by this the thermal electrons e drawn out of the filament 41 travel to the trap electrode 39-1-2 while they move spirally, the ionization efficiency can be increase by increasing impacting time and chance with the sample gas molecules. The extraction electrode room 4-2 is partitioned with the ionization room 4-1 by Si substrate side wall plate 1-2 having the central hole 11-2. The conductive film electrode 10-2-1 of Si substrate side wall plate 1-2 is grounded, and the reverse charged voltage to the ions is applied to the conductive film electrode 10-2-2 of Si substrate side wall plate 1-3. The ions generated in the ionization room enter the extraction (pulling) electrode room 4-2 through the central hole 11-2 of Si substrate side wall plate 1-2, and they are extracted (pulled out) and accelerated by the conductive film electrode 10-2-2 of the extraction electrode, and they are emitted to the next room through the central hole 11-3 of Si substrate side wall plate 1-3. The opening portion 14 for vacuumizing is formed in the extraction electrode room 4-2, and the room is kept at the given pressure. Also, the opening portion 14 except the opening portion 14 for vacuumizing is formed, and inert gas such as Ar, etc. is introduced from it, and the extraction electrode room 4-2 can be cleaned. Additionally if necessary, the substrate side wall plates (conductive film is also formed) having the central holes that have the same structure as the extraction electrodes are arranged in the extraction electrode room 4-2, the ions can be accelerated by applying reverse voltage to the ions, or the ions can be decelerated and focused by applying the same voltage to the ions.

The ions selected in the mass analysis room enter the ion detection room 4-5 through the central hole of the substrate side wall plates 1-6. If the voltage between both edges of the substrate side wall plates 1-7 (the back side is plus to the front side) is applied, the inclined electric field is formed in the length L direction of the secondary electron emissive material film 12-1 and 12-2. FIG. 46 is one sample of completed drawing of the final product (only main body) of the present invention made in wafer. Namely the mass analyzer including the sample supply portion, the ionization portion, the extraction electrode acceleration electrode portion, the mass analysis portion (the electric field portion (the electric field portion (quarter sector), the magnetic field portion (quarter sector), the ion detection portion is made in Si wafer (4 inches to 8 inches, and more larger them) where the glass substrate is adhered to the upper and lower. And vacuum system is equipped outside. The sample supply portion can be arranged numerously, the liquid sample, etc. is connected to the sample supply of the device from outside, and can be controlled using controlling and analyzing LSI. When the super conductive magnets are used in the magnetic field portion, the substrate case is equipped in the portion using them, the portion can be cooled till ultralow temperature. The mass analysis device of the present invention is the size where they can be made in 4 inches –10 inches-more than 10 inches wafer, thus it can be made very cheaply. The mass analysis device of the present invention is very small (for example, the main body size: less than 6 inches wafer (50 cm3), weight: less than 130 g), and since manufacturing in block, manufacturing cost is less than 100000 yen (in the main body size 6 inches wafer). Since each functional portion can be made collectively and very accurately, and much more accurately compared to the other compared to other parts assembly type, detection accuracy can be realized in more then the conventional type. Also, since the mass analysis device of the present invention is very small and very light, it can be portable and measured in-situ.

Also, if the present invention is applied to the accelerator, for example, linear accelerator, synchrotron, microtron, cyclotron, etc., the conventional super large accelerator can make ultra small. For example, the conventional synchrotron of diameter 100 m can make the synchrotron of diameter less than 10 m, and the conventional linac of length 30 km can make the linac of length less than 1 km. As mentioned above, manufacturing cost is much reduced for the mass analyzer and the accelerator of the present invention, and can be less than 1000000 Yen as medical devises, thus all the cancer patient can be cured cheaply. Even if the descriptions written in each of the embodiments described above are not described in the other embodiments, it goes without saying that they can be applied in all embodiments when they are mutually compatible. Additionally, the above embodiments are examples, they can be performed by changing variously within the scope not to extend beyond the inventive gist, and it goes without saying that the right scope of the present invention should be not limited by the above embodiments

INDUSTRIAL APPLICABILITY

These inventions are not limited to just the accelerator and the mass analyzer, are applied to the individual element or part or system constructing them. These inventions are also applied to all devices using the acceleration system, for example ion implantation device.

What is claimed is:

1. A mass spectroscope, comprising:
a main substrate having a first face and a second face,
a first substrate adhered to the first face of the main substrate,
a second substrate adhered to the second face of the main substrate,
a plurality of cavities penetrating from the first face of the main substrate to the second face of the main substrate,
at least one of the cavities penetrating from the first face of the main substrate to the second face of the main substrate is a mass spectroscopic cavity, and
a voltage or magnetic field generator configured to make orbits of charged particles change in the mass spectroscopic cavity for performing mass analysis.

2. The mass spectroscope according to claim 1,
wherein the cavities include at least two adjacent cavities penetrating from the first face to the second face, and the two adjacent cavities are a first cavity and a second cavity, and the second cavity is the mass spectroscopic cavity,
wherein the first cavity and the second cavity are partitioned by a main substrate wall plate of the main substrate,
a pathway of the main substrate wall plate connects the first cavity and the second cavity, and
the charged particles enter the mass spectroscopic cavity from the first cavity through the pathway of the main substrate wall plate.

3. The mass spectroscope according to claim 2,
the mass spectroscope is an Ion Cyclotron Resonance mass spectroscope,
wherein the mass spectroscopic cavity is the second cavity penetrating from the first face of the main substrate to the second face of the main substrate, and the charged particles enter the mass spectroscopic cavity and move with a cyclotron motion in the mass spectroscopic cavity,
wherein the mass spectroscopic cavity has a side wall for a trap electrode, the side wall for a trap electrode being a side wall of the main substrate where the charged particles moving with a cyclotron motion impact, and
the side wall for the trap electrode is disposed in a travelling direction of the charged particle and faces the main substrate wall plate having the pathway,
wherein a first electrode is disposed on the side wall for the trap electrode and the first electrode captures the charged particle,
wherein a second electrode is disposed on the first substrate and a third electrode is disposed on the second substrate in the mass spectroscopic cavity, and the charged particles are excited by a voltage applied between the first and second electrodes, and
wherein a magnetic field is applied in a substantially parallel direction relative to a direction from the main substrate wall plate having the pathway to the side wall for a trap electrode.

4. The mass spectroscope according to claim 3,
wherein the magnetic field is generated by a coil spirally wound around an outer side of the mass spectroscopic cavity.

5. The mass spectroscope according to claim 1,
wherein the mass spectroscope is a quadrupole mass spectroscope and the mass spectroscopic cavity is a quadrupole mass spectroscopic cavity, and
the mass spectroscopic cavity is surrounded by the first substrate and the second substrate in a substantially vertical direction relative to the first face of the main substrate and/or the second face of the main substrate,
wherein the first substrate has a first face and a second face, and the second substrate has a first face and a second face, and
the second face of the first substrate is adhered to the first face of the main substrate, and the first face of the second substrate is adhered to the second face of the main substrate,
wherein two quadrupole electrodes are disposed on the second face of the first substrate, and two quadrupole electrodes are disposed on the first face of the second substrate, and
the orbits of the charged particles change by a high-frequency voltage or a direct voltage applied to the quadrupole electrodes.

6. The mass spectroscope according to claim 1,
wherein the mass spectroscope is a magnetic sector mass spectroscope and the mass spectroscopic cavity is a magnetic sector mass spectroscopic cavity, and
the magnetic sector mass spectroscopic cavity penetrates from the first face of the main substrate to the second face of the main substrate,
wherein at least one electromagnet is disposed outside of the first substrate and/or outside of the second substrate in the magnetic sector mass spectroscopic cavity, and
wherein the orbits of the charged particles in the mass spectroscopic cavity change by a magnetic field generated in a substantially vertical direction relative to the first face of the main substrate and/or the second face of the main substrate in the mass spectroscopic cavity by the at least one electromagnet.

7. The mass spectroscope according to claim 1,
wherein the mass spectroscope is an electric sector mass spectroscope and the mass spectroscopic cavity is an electric sector mass spectroscopic cavity, and
the electric sector mass spectroscopic cavity penetrates from the first face of the main substrate to the second face of the main substrate,
wherein the electric sector mass spectroscopic cavity is surrounded by side faces of the main substrate in a substantially vertical direction relative to the first face of the main substrate and/or the second face of the main substrate, and
wherein electrodes are disposed on the side faces of the main substrate in the electric sector mass spectroscopic cavity, and the orbits of the charged particles in the electric sector mass spectroscopic cavity change by a voltage applied to the electrodes.

8. The mass spectroscope according to claim 1,
wherein the mass spectroscope is a double-focusing mass spectroscope having at least one magnetic sector mass spectroscopic cavity room and at least one electric sector mass spectroscopic cavity,
wherein the magnetic sector mass spectroscopic cavity penetrates from the first face of the main substrate to the second face of the main substrate,
wherein at least one electromagnet is disposed outside of the first substrate and/or outside of the second substrate in the magnetic sector mass spectroscopic cavity,
wherein the orbits of the charged particles in the mass spectroscopic cavity change by a magnetic field generating in a substantially vertical direction relative to the first face of the main substrate and/or the second face of the main substrate in the mass spectroscopic cavity by the at least one electromagnet,
wherein the electric sector mass spectroscopic cavity penetrates from the first face of the main substrate to the second face of the main substrate,
wherein the electric sector mass spectroscopic cavity is surrounded by side faces of the main substrate in a substantially vertical direction relative to the first face of the main substrate and/or the second face of the main substrate, and
wherein electrodes are disposed on the side faces of the main substrate in the electric sector mass spectroscopic cavity, and the orbits of the charged particles in the electric sector mass spectroscopic cavity change by a voltage applied to the electrodes.

9. An accelerator, comprising:
a main substrate having a first face and a second face,
a first substrate adhered to the first face of the main substrate,
a second substrate adhered to the second face of the main substrate,
linear acceleration system that accelerates or decelerates charged particles and/or a focusing system that focuses the charged particles,
a plurality of cavities penetrating from the first face of the main substrate to the second face of the main substrate, at least two of the cavities being adjacent cavities,
a main substrate wall plate of the main substrate partitioning the adjacent two cavities,
a pathway of the main substrate wall plate connecting the adjacent two cavities, and
an electrode on the main substrate wall plate
wherein the charged particles enter one of the adjacent two cavities from the other of the adjacent two cavities through the pathway,
wherein the charged particles are accelerated or decelerated by a high-frequency voltage or a direct voltage applied to the electrode on the main substrate wall plate,
wherein the focusing system is disposed in a first cavity of the cavities penetrating from the first face of the main substrate to the second face of the main substrate, and
the focusing system has four-pole magnets, and
a first of the four-pole magnets is disposed outside of the first substrate adhered to the first face of the main substrate in the first cavity which the charged particles pass through, and
a second of the four-pole magnets is disposed outside of the second substrate adhered to the second face of the main substrate in the first cavity, and
the third and fourth of the four-pole magnets are disposed outside of both side faces of the main substrate in the first cavity which the charged particles pass through.

10. The accelerator according to claim 9,
the accelerator further comprises at least one annular orbit,
wherein the annular orbit is a second cavity of the cavities penetrating from the first face of the main substrate to the second face of the main substrate, and
the charged particles passing through the linear acceleration system and/or the focusing system enter the annular orbit, and
wherein at least one electric magnet is disposed outside of the first substrate adhered to the first face of the main substrate in a curved path of the annular orbit, at least one electric magnet is disposed outside of the second substrate adhered to the second face of the main substrate in a curved path of the annular orbit, and the charged particles travel along the curved path by a magnetic field generated with the electric magnets.

11. The accelerator according to claim 10, the annular orbit has a linear acceleration system,
wherein the linear acceleration system of the annular orbit comprises plural cavities penetrating from the first face of the main substrate to the second face of the main substrate, and at least two of the plural cavities are adjacent to one another, and
the two adjacent cavities of the plural cavities are partitioned by a second main substrate wall plate of the main substrate, and
the second main substrate wall plate has a second pathway connecting the two adjacent cavities of the plural cavities, and
the charged particles enter one of the two adjacent cavities of the plural cavities from the other of the two adjacent cavities of the plural cavities through the second pathway, and
wherein the charged particles are accelerated or decelerated by a high-frequency voltage or a direct voltage applied to a second electrode on the second main substrate wall plate.

12. The accelerator according to claim 11, there are n annular orbits, where n is an integer of 2 or more,
wherein an (i+1)th annular orbit is disposed outside of an ith annular orbit, and the (i+1)th annular orbit is connected to the ith annular orbit through a third cavity of the cavities penetrating from the first face of the main substrate to the second face of the main substrate, and
the charged particles exit from the ith annular orbit and enter the (i+1)th annular orbit through the third cavity, where i is an integer of 1 to n.

13. The accelerator according to claim 9 further comprising a charged particle generator that generates the charged particles,
wherein the charged particle generator includes a second main substrate having a first face and a second face,
another first substrate adhered to the first face of the second main substrate, and
another second substrate adhered to the second face of the second main substrate,
wherein the charged particle generator includes a charged particles generating cavity that generates the charged particles, and
the charged particles generating cavity penetrates from the first face of the second main substrate to the second face of the second main substrate, and
wherein the charged particles generated in the charged particles generator enter the linear accelerator through another cavity of the cavities penetrating from the first face of the second main substrate to the second face of the second main substrate.

14. A charged particle generator that generates charged particles, comprising:
a main substrate having a first face and a second face,
a first substrate adhered to the first face of the main substrate,
a second substrate adhered to the second face of the main substrate, and
a charged particles generating cavity that generates the charged particles, the charged particles generating cavity penetrating from the first face of the main substrate to the second face of the main substrate.

15. The charged particles generator according to claim 14,
wherein a sample is disposed in the charged particles generating cavity,
a laser is configured to irradiate the sample through an opening in the first substrate; so that the sample is decomposed into decomposed particles, and
one ionized beam selected from the group consisting of a laser, an electron beam, a radiation light, and an X-ray is configured to irradiate the decomposed particles so that the charged particles are generated by the irradiation of the ionized beam in the charged particles generating cavity.

16. The charged particles generator according to claim 14,
wherein a sample board is placed into the charged particles generating cavity via a first opening in the first substrate,
the sample board has a first face and a second face,
a sample is attached on the first face of the sample board,
the second face of the sample board is secured to a wall of the main substrate,
a voltage is applied to the sample board,
a laser is configured to irradiate the sample through an opening in the first or second substrate so that the sample is decomposed into decomposed particles, and some of the decomposed particles are charged particles, and
the charged particles having the same electric charge as an electric charge of the sample board are released from the sample board.

17. The charged particles generator according to claim 14,
wherein conductive films are formed in the charged particles generating cavity, and the conductive films are divided into at least a first conductive film area and a second conductive film area that are electrically isolated from each other, and
a sample liquid or gas is introduced into the charged particles generating cavity from an inlet in the first substrate, the second substrate and/or the main substrate wall, and
wherein the sample liquid or gas is ionized in the charged particles generating cavity by an electric field generated by a voltage applied between the first conductive film area and the second conductive film area.

18. The charged particles generator according to claim 17, wherein an electric magnet is disposed outside of the charged particles generating cavity so that a magnetic field is applied in the charged particles generating cavity.

* * * * *